United States Patent
Lee et al.

(10) Patent No.: US 10,797,247 B2
(45) Date of Patent: Oct. 6, 2020

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Bumsung Lee, Cheonan-si (KR); Sunhee Lee, Hwaseong-si (KR); Soungyun Mun, Cheonan-si (KR); Daesung Kim, Yongin-si (KR); Jungcheol Park, Yongin-si (KR); Yunsuk Lee, Seongnam-si (KR); Seungwon Yeo, Daejeon (KR); Junghwan Park, Hwaseong-si (KR); Wonsam Kim, Hwaseong-si (KR); Yeon Hee Choi, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 390 days.

(21) Appl. No.: 15/836,306

(22) Filed: Dec. 8, 2017

(65) Prior Publication Data

US 2018/0102486 A1    Apr. 12, 2018

Related U.S. Application Data

(63) Continuation-in-part of application No. 14/808,058, filed on Jul. 24, 2015, now Pat. No. 9,917,257.

(30) Foreign Application Priority Data

Jul. 24, 2014 (KR) .................. 10-2014-0093922
May 14, 2015 (KR) .................. 10-2015-0067007
Apr. 20, 2017 (KR) .................. 10-2017-0050859

(51) Int. Cl.
*H01L 51/00* (2006.01)
*C07D 495/04* (2006.01)
(Continued)

(52) U.S. Cl.
CPC ...... *H01L 51/0072* (2013.01); *C07D 491/048* (2013.01); *C07D 495/04* (2013.01);
(Continued)

(58) Field of Classification Search
CPC ............. C07D 491/048; C07D 495/04; C07D 519/00; C09K 11/06; C09K 2211/1018;
(Continued)

(56) References Cited

U.S. PATENT DOCUMENTS

| | | |
|---|---|---|
| 5,843,607 A | 12/1998 | Hu et al. |
| 2010/0187977 A1 | 7/2010 | Kai et al. |

(Continued)

FOREIGN PATENT DOCUMENTS

| | | |
|---|---|---|
| CN | 105473593 A | 4/2016 |
| JP | 11-162650 A | 6/1999 |

(Continued)

OTHER PUBLICATIONS

The Notice of Allowance dated Dec. 27, 2018 for corresponding JP 2018-505670, 2 pages.
Korean Office Action for corresponding KR 10-2018-0111996, dated Mar. 25, 2020, twelve pages.

*Primary Examiner* — Dawn L Garrett
(74) *Attorney, Agent, or Firm* — Vorys, Sater, Seymour & Pease LLP; Mih Suhn Koh

(57) ABSTRACT

Provided are an organic electric elements, and electronic devices thereof, wherein high luminous efficiency, low driving voltage and the improved lifetime of the organic electronic element are achieved by using the compound of the present invention as a phosphorescent host material.

12 Claims, 3 Drawing Sheets

(51) Int. Cl.
  *C07D 519/00* (2006.01)
  *C07D 491/048* (2006.01)
  *C09K 11/06* (2006.01)
  *H01L 51/52* (2006.01)
  *H01L 51/50* (2006.01)
  *H01L 27/32* (2006.01)

(52) U.S. Cl.
  CPC ............ *C07D 519/00* (2013.01); *C09K 11/06* (2013.01); *H01L 51/0052* (2013.01); *H01L 51/0059* (2013.01); *H01L 51/0061* (2013.01); *H01L 51/0067* (2013.01); *H01L 51/0071* (2013.01); *H01L 51/0073* (2013.01); *H01L 51/0074* (2013.01); *C09K 2211/1018* (2013.01); *H01L 27/32* (2013.01); *H01L 51/001* (2013.01); *H01L 51/0081* (2013.01); *H01L 51/0085* (2013.01); *H01L 51/5016* (2013.01); *H01L 51/5056* (2013.01); *H01L 51/5072* (2013.01); *H01L 51/5088* (2013.01); *H01L 51/5096* (2013.01); *H01L 51/5206* (2013.01); *H01L 51/5221* (2013.01)

(58) Field of Classification Search
  CPC ... H01L 27/32; H01L 51/001; H01L 51/0052; H01L 51/0059; H01L 51/0061; H01L 51/0067; H01L 51/0071; H01L 51/0072; H01L 51/0073; H01L 51/0074; H01L 51/0081; H01L 51/0085; H01L 51/5016; H01L 51/5056; H01L 51/5072; H01L 51/5088; H01L 51/5096; H01L 51/5206; H01L 51/5221
  See application file for complete search history.

(56) References Cited

U.S. PATENT DOCUMENTS

2013/0069049 A1\* 3/2013 Park ..................... C07D 487/04
  257/40
2016/0028020 A1 1/2016 Lee et al.

FOREIGN PATENT DOCUMENTS

| KR | 10-2008-0085000 A | 9/2008 |
| KR | 10-2009-0057711 A | 6/2009 |
| KR | 10-2011-0018340 A | 2/2011 |
| KR | 10-2013-0021350 A | 3/2013 |
| KR | 10-2013-0083817 A | 7/2013 |
| KR | 10-2014-0043224 A | 4/2014 |
| KR | 10-2014-0073412 A | 6/2014 |
| KR | 10-2014-0126610 A | 10/2014 |
| KR | 10-2014-0134947 A | 11/2014 |
| KR | 10-2014-0136722 A | 12/2014 |
| KR | 10-2015-0007476 A | 1/2015 |
| KR | 10-2015-0032447 A | 3/2015 |
| KR | 10-2015-0135109 A | 12/2015 |
| KR | 10-2015-0141147 A | 12/2015 |
| KR | 10-2016-0012066 A | 2/2016 |
| KR | 10-2016-0022784 A | 3/2016 |
| KR | 10-2016-0050517 | 4/2016 |
| KR | 10-2017-0122115 A | 11/2017 |
| KR | 10-1921680 B1 | 2/2019 |
| WO | 2013/105747 A1 | 7/2013 |
| WO | 2014/076917 A1 | 5/2014 |
| WO | 2015/037965 A1 | 3/2015 |
| WO | 2015/142036 A1 | 9/2015 |
| WO | 2015/178731 A1 | 11/2015 |
| WO | 2017/188655 A1 | 11/2017 |
| WO | 2017/188676 A1 | 11/2017 |

\* cited by examiner

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This application is a continuation in part of U.S. patent application Ser. No. 14/808,058 filed on Jul. 24, 2015, now published as a U.S. Pub. No. US 2016/0028020, which is incorporated herein by reference in their entirety

BACKGROUND

Technical Field

The present invention relates to compounds for organic electric elements, organic electric elements comprising the same, and electronic devices thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed there between. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

In the case of a polycyclic compound containing a heteroatom, the difference in properties according to the material structure is so large that it is applied to various layers as a material of an organic electric element. In particular, it has characteristics of different band gaps (HOMO, LUMO), electrical characteristics, chemical properties, and physical properties depending on the number of rings, fused positions and the type and arrangement of heteroatoms, therefore application development for layers of various organic electric elements using the same has been progressed.

As a representative example thereof, in the following Patent Documents 1 to 4, the performance of the 5-membered cyclic compound in the polycyclic compound has been reported depending on the hetero type, arrangement, substituent type, fused position, and the like.

Patent Document 1: U.S. Pat. No. 5,843,607
Patent Document 2: Japanese Laid-Open Patent Publication No. 1999-162650
Patent Document 3: Korean Published Patent Application No. 2008-0085000
Patent Document 4: US Patent Publication No. 2010-0187977
Patent Document 5: Korean Published Patent Application No. 2011-0018340
Patent Document 6: Korean Published Patent Application No. 2009-0057711

Patent Documents 1 and 2 disclose an embodiment in which the indolecarbazole core in which the hetero atom in the 5-membered cyclic compound is composed only of nitrogen is used, and an aryl group substituted or unsubstituted in N of indolocarbazole is used. However, in the prior invention 1, there exists only a simple aryl group substituted or unsubstituted with an alkyl group, an amino group, an alkoxy group, or the like as a substituent so that the effect of the substituents of the polycyclic compounds was very poor to prove, and only the use as a hole transport material is described, and the use thereof as a phosphorescent host material is not described.

Patent Documents 3 and 4 disclose a compound in which pyridine, pyrimidine, triazine or the like containing an aryl group and N is substituted for an indolecarbazole core having a hetero atom N in the same 5-membered cyclic compound as in the above Patent Documents 1 and 2, however only the use examples for phosphorescent green host materials are described, and the performance for other heterocyclic compounds substituted for indolecarbazole core is not described.

In Patent Documents 5, Nitrogen, oxygen (O), sulfur (S), carbon and the like are described as heteroatom in the 5-membered cyclic compound, however there are only examples using the same heteroatom in the performance measurement data, the performance characteristics of a 5-membered cyclic compound containing a different heteroatom could not be confirmed.

Therefore, the patent document does not disclose solutions to low charge carrier mobility and low oxidation stability of a 5-membered cyclic compound containing same heteroatom. When the 5-membered cyclic compound molecules are generally laminated, as the adjacent π-electrons increase, they have a strong electrical interaction, and this is closely related to the charge carrier mobility, particularly, the same 5-membered cyclic compound of type has an edgetoface morphology as an order of arrangement of molecules when molecules are laminated, otherwise a different 5-membered cyclic compound with different heteroatoms has an antiparallel cofacial π-stacking structure in which the packing structure of the molecules is opposite to each other, so that the arrangement order of the molecules becomes face-to-face morphology. It is reported that the steric effect of the substituent substituted on the asymmetrically arranged hetero atom N as the cause of this laminated structure causes relatively high carrier mobility and high oxidation stability (*Org. Lett.*2008, 10, 1199).

In Patent Document 6, an example of using as a fluorescent host material for various polycyclic compounds having seven or more membered cyclic compounds has been reported.

As described above, the fused positions, the number of rings, the arrangement of heteroatoms, and characteristic change by type of the polycyclic compounds have not yet been sufficiently developed.

Particularly, in a phosphorescent organic electric element using a phosphorescent dopant material, the LUMO and HOMO levels of the host material have a great influence on the efficiency and life span of the organic electric element, this is because the charge balance control in the emitting layer, the quenching of the dopant, and the reduction in efficiencyand life span due to light emission at the interface of the hole transport layer can be prevented, depending on whether electron and hole injection in the emitting layer can be efficiently controlled.

For fluorescent and phosphorescent host materials, recently we have been studying the increase of efficiency and life span of organic electric elements using TADF (thermal activated delayed fluorescent), exciplex, etc., particularly, and many studies have been carried out to identify the energy transfer method from the host material to the dopant material.

Although there are various methods for identifying the energy transfer in the emitting layer for TADF C thermally activated delayed fluorescent) and exciplex, it can be easily confirmed by the PL lifetime (TRTP) measurement method.

The TRTP (Time Resolved Transient PL) measurement method is a method of observing a decay time over time after irradiating the host thin film with a pulsed light source, and therefore it is possible to identify the energy transfer method by observing the energy transfer and the lag time. The TRTP measurement can distinguish between fluorescence and phosphorescence, an energy transfer method in a mixed host material, an exciplex energy transfer method, and a TADF energy transfer method.

There are various factors affecting the efficiency and life span depending on the manner in which the energy is transferred from the host material to the dopant material, and the energy transfer method differs depending on the material, so that the development of stable and efficient host material for organic electric element has not yet been sufficiently developed. Therefore, development of new materials is continuously required, and especially development of a host material for an emitting layer is urgently required.

SUMMARY

Currently, OLED devices are being developed in the direction of lowering the power consumption and increasing the color purity. In order to solve one or more of the above-mentioned problems in prior art, an aspect of the present invention is to provide a compound into which a Sub having excellent electron characteristics is introduced, and capable of lowering driving voltage, increasing luminous efficiency, improving color purity and lifetime of device, an organic electric element comprising the same, and an electronic device thereof.

In accordance with an aspect of the present invention, the compound represented by the following formula 1 is provided.

[Formula 1]

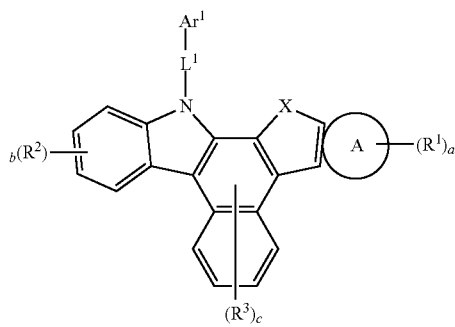

$Ar^1 =$ 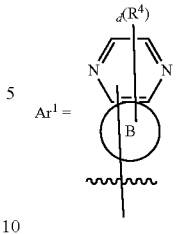

In another aspect of the present invention, organic electric elements comprising the compound represented by the formula 1 above and electronic devices including the organic electric element are provided.

According to the embodiments of the present invention, luminous efficiency, heat-resistance, and lifetime of the organic electric elements can be improved and a driving voltage of the organic electric elements can be lowered because the electron transfer ability and the thermal stability are improved, and electron injection from the ETL is facilitated, resulting in a LUMO energy level that is easy to balance charge in the a light emitting layer by using a specific compound as a material of the organic electric device, wherein the specific compound has an aromatic ring additionally fused to the existing core and a sub-substituent having a strong ET characteristic.

DETAILED DESCRIPTION

Figure 1:
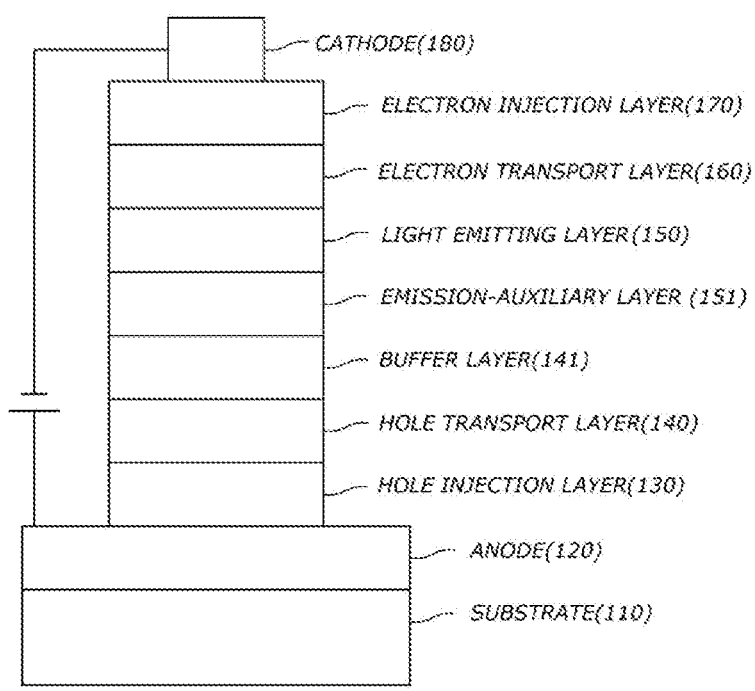
FIG. 1 illustrates an example of an organic light emitting diode according to an embodiment of the present invention.
Figure 2:
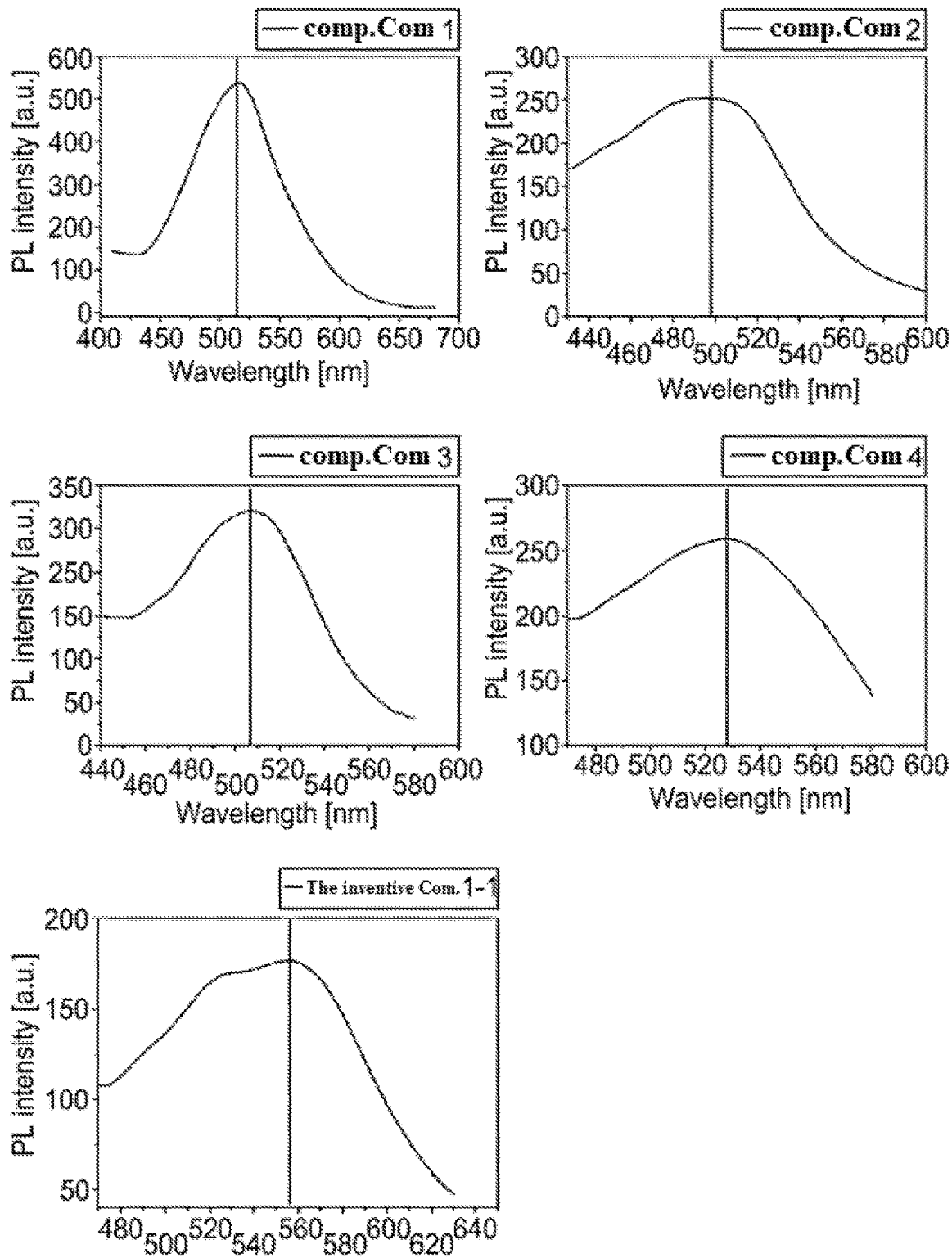
FIG. 2 shows the PL results of comparative compounds 1 to 4 and compound 1-1 of the present invention.
Figure 3:
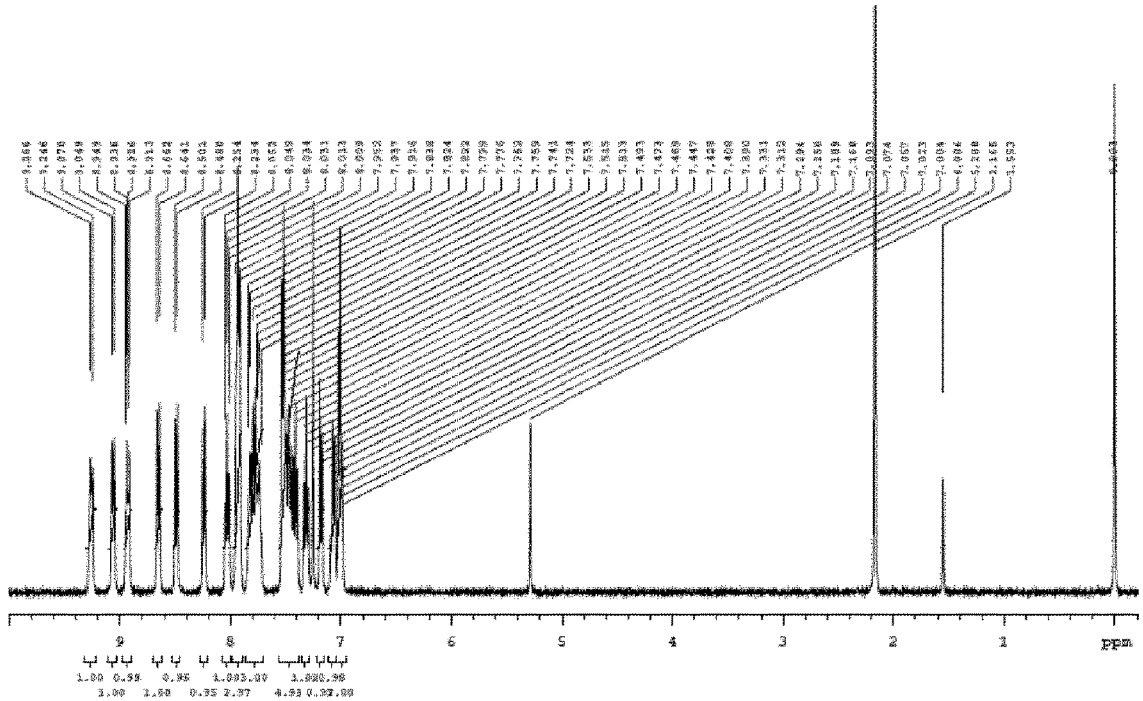
FIG. 3 shows the 1H NMR results of compound 1-1 of the present invention.

Hereinafter, some embodiments of the present invention will be described in detail. In the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "heteroalkyl", as used herein, means alkyl substituted one or more of carbon atoms consisting of an alkyl withhetero atom.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

Unless otherwise stated, the term "alkenoxyl group", "alkenoxy group", "alkenyloxy group" or "alkenyloxy group", as used herein, means anoxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an arylgroup. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of heteroatoms. Unless otherwise stated, the term "heteroaryl group" or "heteroarylene group", as used herein, means a $C_2$ to $C_{60}$ aryl containing one or more of heteroatoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include $SO_2$ instead of carbon consisting of cycle. For example, "heterocyclic group" includes compound below.

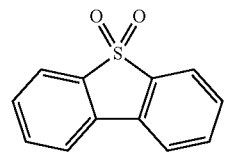 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the formulas used in the present invention are as defined in the index definition of the substituent of the following formula.

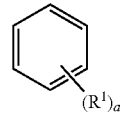

Wherein, when a is an integer of zero, the substituent $R^1$ is absent, that is, hydrogen atoms are bonded to all the carbon constituting the benzene ring, and chemical formulas or compounds may be written without explicitly describing the hydrogen. In addition, one substituent $R^1$ is bonded to any carbon of the carbons forming the benzene ring when "a" is an integer of 1, substituents $R^1$ are bonded, for example, as followings when "a" is an integer of 2 or 3, substituents $R^1$ are bonded to the carbon of the benzene ring in a similar manner when "a" is an integer of 4 to 6, and R¹s may be the same or different from each other when "a" is an integer of 2 or more.

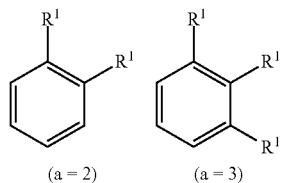

Unless otherwise expressly stated, the terms "ortho", "meta", and "para" used in the present invention refer to the substitution positions of all substituents, and the ortho position indicates the position of the substituent immediately adjacent to the compound, for example, when benzene is used, it means 1 or 2 position, and the meta position is the next substitution position of the neighbor substitution position, when benzene as an example stands for 1 or 3 position, and the para position is the next substitution position of the meta position, which means 1 and 4 position when benzene is taken as an example. A more detailed example of the substitution position is as follows, and it can be confirmed that the ortho-, and meta-position are substituted by non-linear type and para positions are substituted by linear type.

[Example of Ortho-Position]

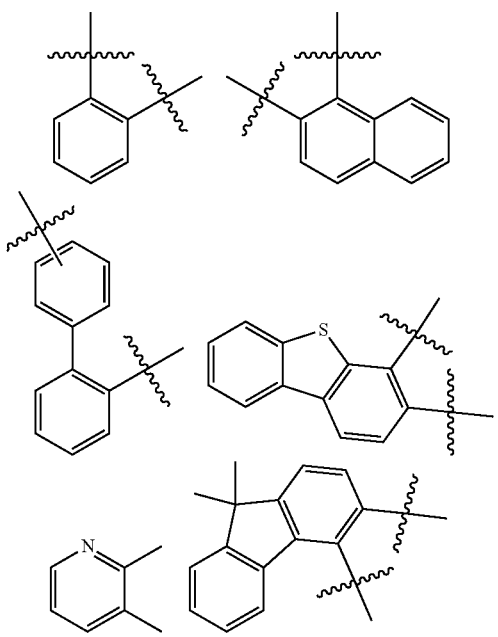

[Example of Meta-Position]

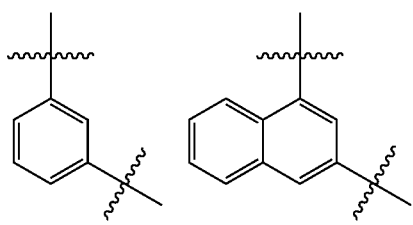

-continued

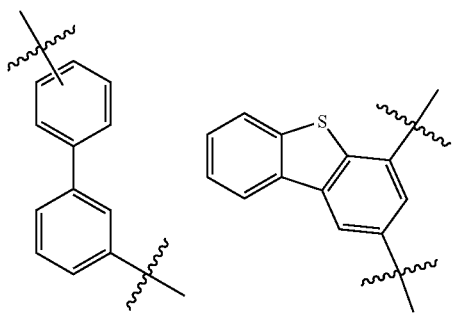

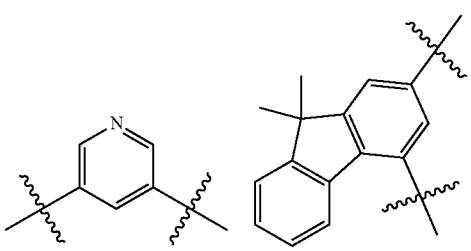

[Example of Para-Position]

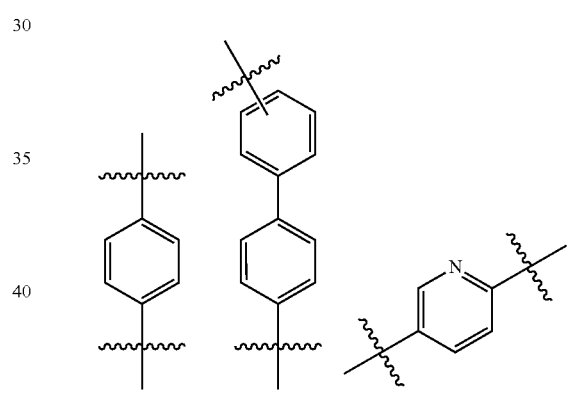

Hereinafter, a compound according to an aspect of the present invention and an organic electric element comprising the same will be described.

The present invention provides a compound represented by the following Formula 1.

[Formula 1]

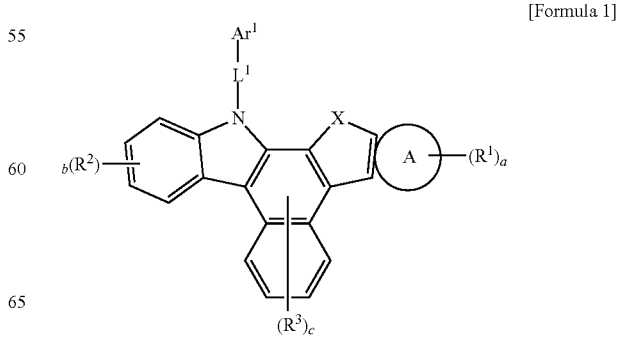

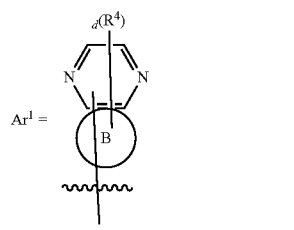
wherein,
1) A ring is $C_{10}$ aryl group,
2) B ring is selected from the group consisting of the following formulas B-1 to B-16:
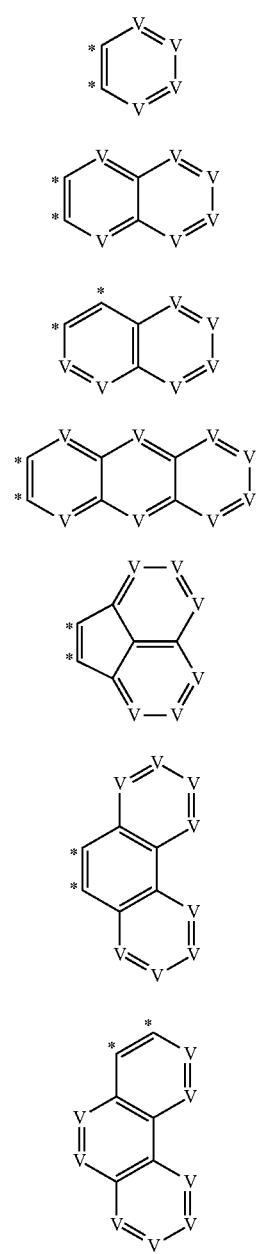
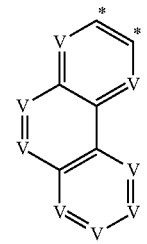
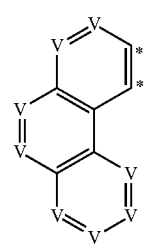
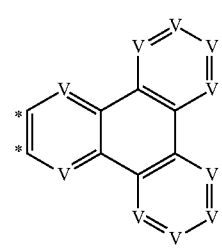
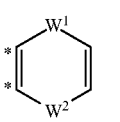
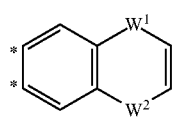
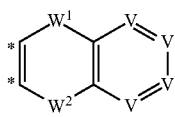
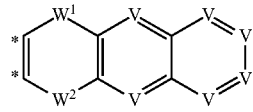
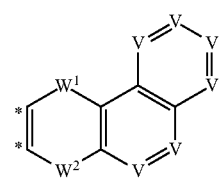

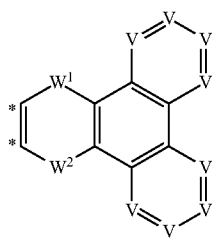

B-16 in formulas B-1 to B-1, "*" indicates the position to be condensed with pyrazine comprising two Ns, 1) $W^1$ and $W^2$ are each independently a single bond, S or O, 2) V is N or C, 5) X is O or S, 6) a is an integer of 0 to 6, b and c are each an integer of 0 to 4, d is an integer of 0 to 11, and 7) $R^1$, $R^2$, $R^3$ and $R^4$ are the same or different from each other, and are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group and -L'-N($R^a$)($R^b$).

Where $R^1$ to $R^4$ are an aryl group, preferably $R^1$ to $R^4$ may be each a $C_6$-$C_{30}$ aryl group, more preferably a $C_6$-$C_{18}$ aryl group. Where $R^1$ to $R^4$ are a heterocyclic group, preferably $R^1$ to $R^4$ may be each a $C_2$~$C_{40}$ heterocyclic group, more preferably a $C_2$~$C_{30}$ heterocyclic group, more preferably a $C_2$~$C_{20}$ heterocyclic group.

In case a, b and c are 2 or more, $R^1$, $R^2$ and $R^3$ are each in plural and are the same or different, and a plurity of $R^1$, a plurity of $R^2$, or a plurity of $R^3$ may be bonded to each other to form a ring.

8) L' is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group, $R^a$ and $R^b$ are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

9) $L^1$ is each independently selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group.

The aryl group, fluorenyl group, arylene group, heterocyclic group, fused ring group, alkyl group, alkenyl group, alkoxyl group, and aryloxy group may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, -L'-N($R^a$)($R^b$), a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic grou, a $C_3$-$C_{20}$ cycloalkyl group, a $C_7$-$C_{20}$ arylalkyl group, and a $C_8$-$C_{20}$ arylalkenyl group, and these substituents may be linked each other to form a ring, wherein 'ring' comprises a $C_3$-$C_{60}$ aliphatic ring, a $C_6$-$C_{60}$ aromatic ring, a $C_2$-$C_{60}$ heterocyclic group or the combination thereof, and comprises a saturated or unsaturated ring.

Formula 1 above may be represented by any one of Formulas 2 to 4 below:

[Formula 2]

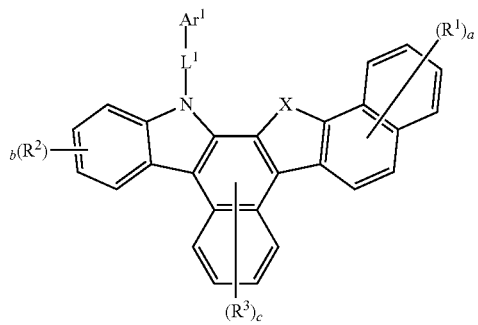

[Formula 3]

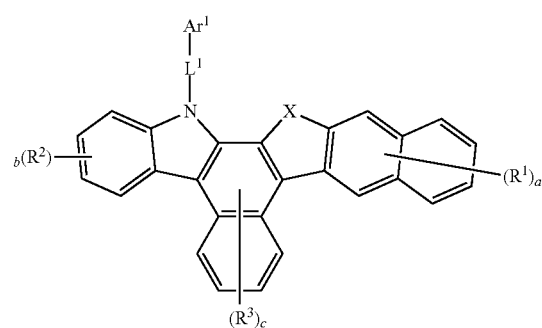

[Formula 4]

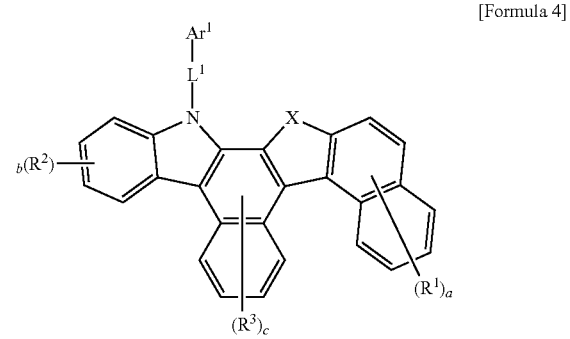

In Formulas 2 to 4, X, $L^1$, $Ar^1$, $R^1$, $R^2$, $R^3$, a, b and c are the same as defined above.

Further, Formula 1 above may be represented by any one of Formulas 5 to 7 below:

[Formula 5]
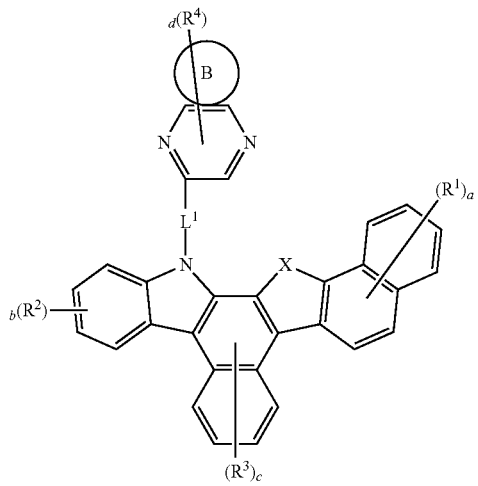
[Formula 6]
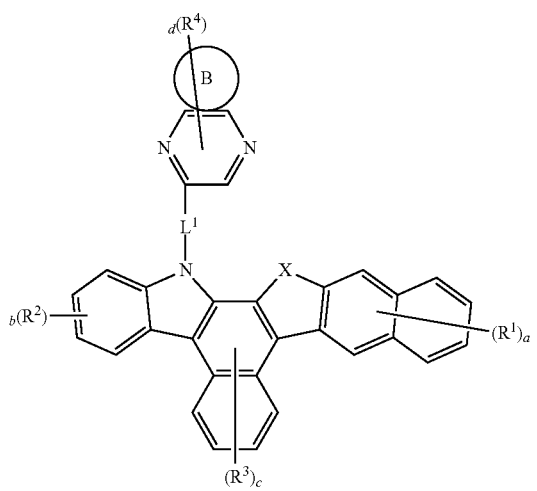
[Formula 7]
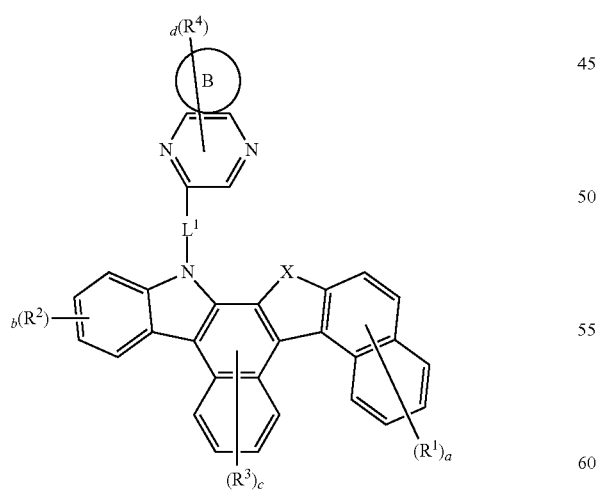
In Formulas 5 to 7, X, $L^1$, $Ar^1$, $R^1$, $R^2$, $R^3$, $R^4$, a, b, c, d, B ring are the same as defined above.
One embodiment of the present invention provides the compound of which the chemical structure $Ar^1$ of the formula 1 comprising the pyrazine is represented by any one of the following Formulas C-1 to C-22.
C-1
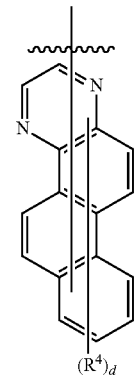
C-2
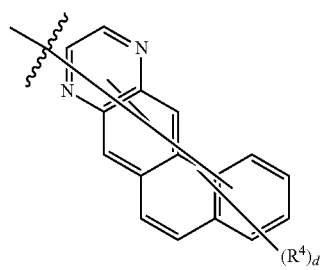
C-3
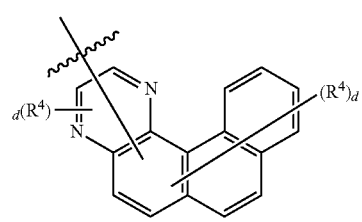
C-4
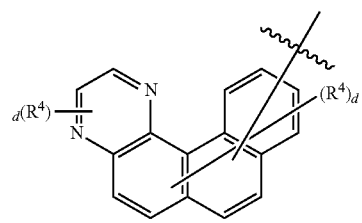
C-5
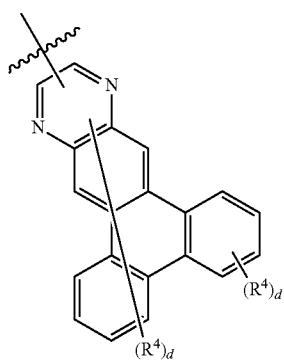

C-6
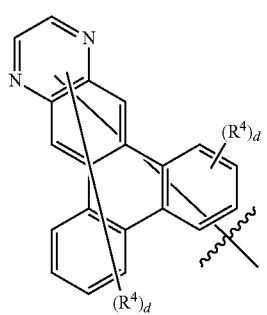
C-7
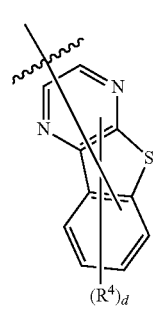
C-8
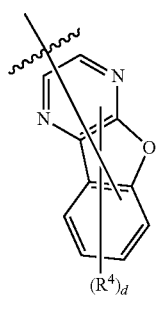
C-9
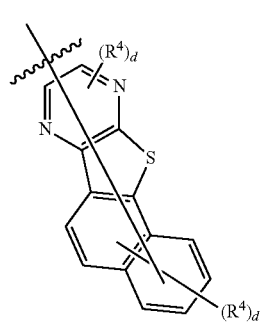
C-10
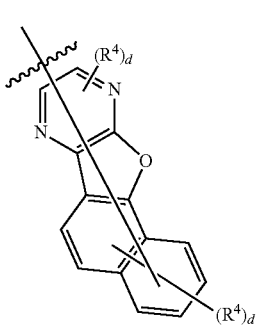
C-11
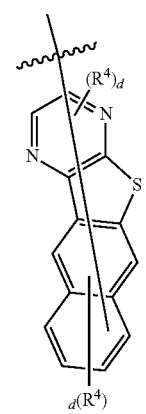
C-12
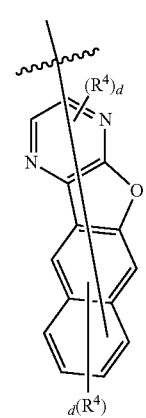
C-13
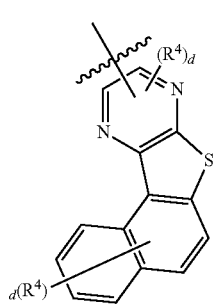
C-14
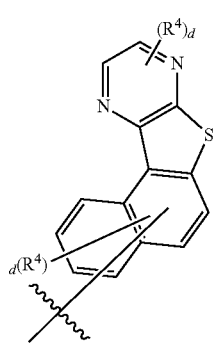

C-15
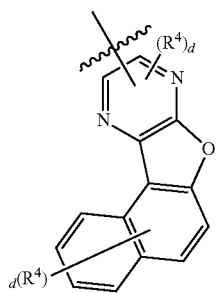
C-16
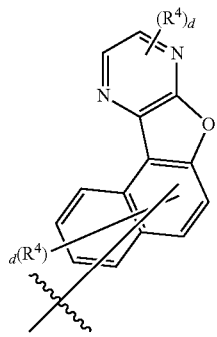
C-17
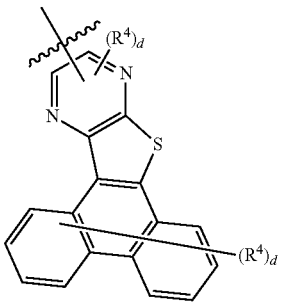
C-18
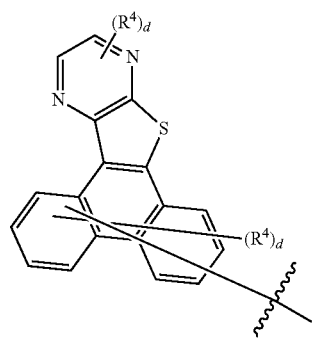
C-19
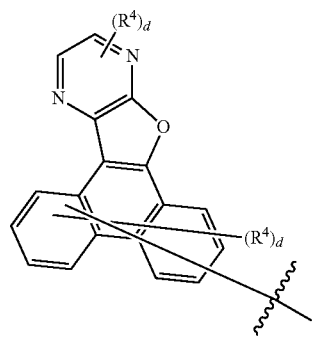
C-20
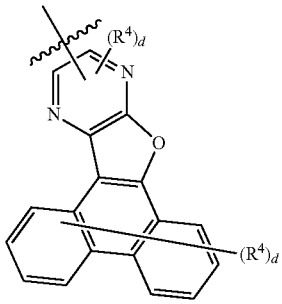
C-21
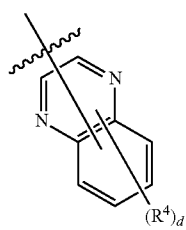
C-22
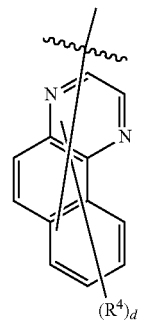
In Formulas C-1 to C-22, $R^4$ is the same as defined above, and d is an integer of 0~11.
The present invention comprises the compound wherein $R^4$ in the above formula 1 is represented by any one of the following formulas R-1 to R-10.
<R-1>
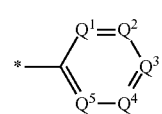
<R-2>
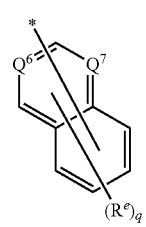
<R-3>
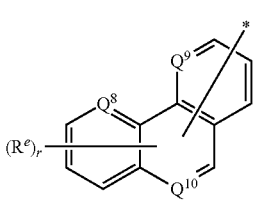

-continued

<R-4>
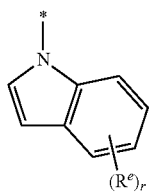

<R-5>
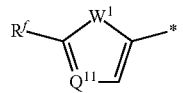

<R-6>
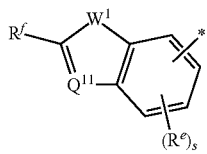

<R-7>
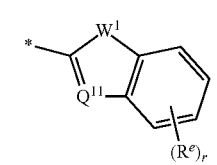

<R-8>
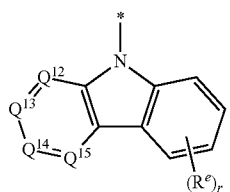

<R-9>
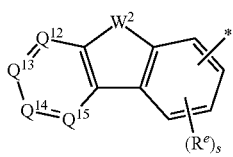

<R-10>
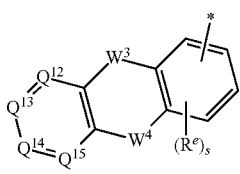

In Formulas R-1 to R-10,

1) $Q^1$ to $Q^{15}$ are each independently $CR^g$ or N,

2) $W^1$ is S, O or $NR^h$,

3) $W^2$ to $W^4$ are each independently S, O, $NR^h$ or $CR^iR^j$,

4) $R^e$ is selected from the group consisting of hydrogen, deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and when these substituents are adjacent, they may be linked each other to form a ring, 5) $R^f$ and $R^g$ are each independently selected from the group consisting of hydrogen, deuterium, a $C_6$-$C_{20}$ aryl group, a fluorenyl group, a fused ring group of a $C_3$-$C_{20}$ aliphatic ring and a $C_6$-$C_{20}$ aromatic ring, a $C_2$-$C_{20}$ heterocyclic group containing at least one heteroatom selected from O, N, S, Si, and P, a $C_1$-$C_{20}$ alkyl group, a $C_2$-$C_{20}$ alkenyl group, a $C_2$-$C_{20}$ alkynyl group, and a $C_1$-$C_{30}$ alkoxyl group, 6) $R^h$, $R^i$ and $R^j$ are each independently selected from the group consisting of a $C_6$-$C_{20}$ aryl group, a $C_2$-$C_{20}$ heterocyclic group containing at least one heteroatom selected from O, N, S, Si, and P, a $C_1$-$C_{20}$ alkyl group, a $C_2$-$C_{20}$ alkenyl group, a $C_1$-$C_{20}$ alkoxyl group and a fluorenyl group, $R^i$ and $R^j$ may be linked each other to form a spiro compound together with C to which they are bonded, 7) q is each independently an integer of 0 to 5, 8) r is each independently an integer of 0 to 4, 9) s is each independently an integer of 0 to 3, when q, r and s are each 2 or more, $R^e$ is each the same or different, "*" indicates the position to be bonded, When $R^e$ to $R^j$ are an aryl group, preferably $R^e$ to $R^j$ may be each a $C_6$-$C_{30}$ aryl group, more preferably a $C_6$-$C_{18}$ aryl group. When $R^e$ to $R^j$ are a heterocyclic group, preferably $R^e$ to $R^j$ may be each a $C_2$~$C_{40}$ heterocyclic group, more preferably a $C_2$~$C_{30}$ heterocyclic group, more preferably a $C_2$~$C_{20}$ heterocyclic group.

Specifically, the compound represented by Formula 1 may be any one of the following compounds.

1-1

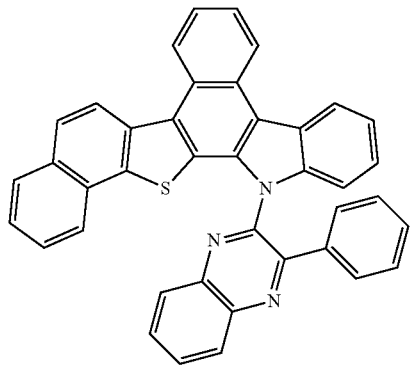

1-2

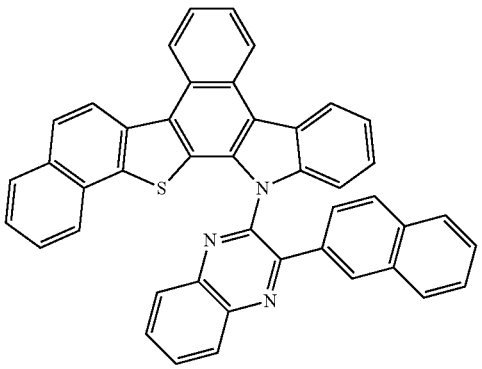

-continued
1-3
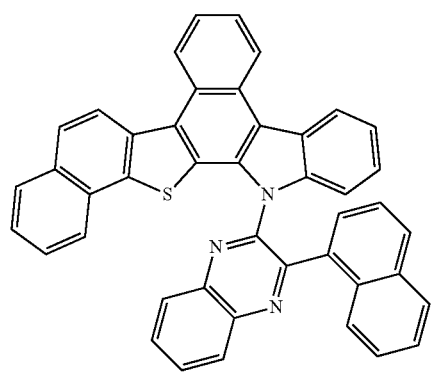
1-4
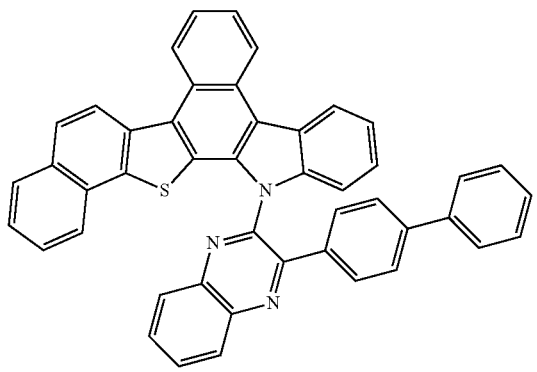
1-5
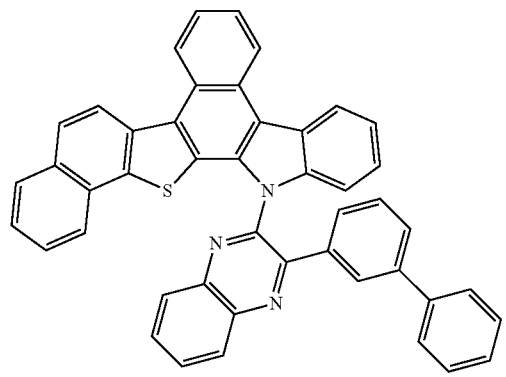
1-6
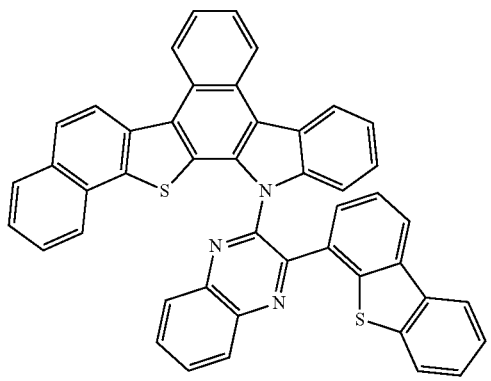
1-7
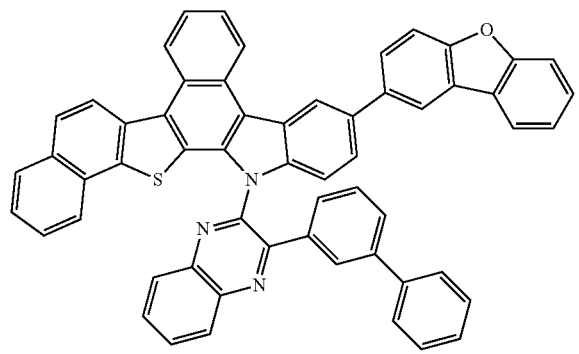
1-8
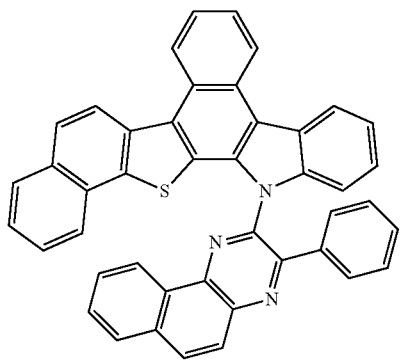
1-9
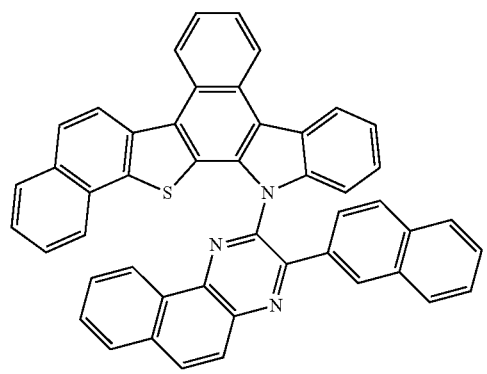
1-10
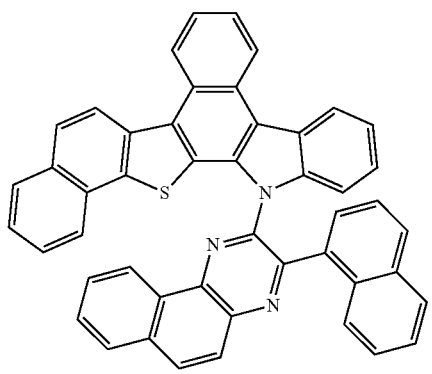

-continued
1-11
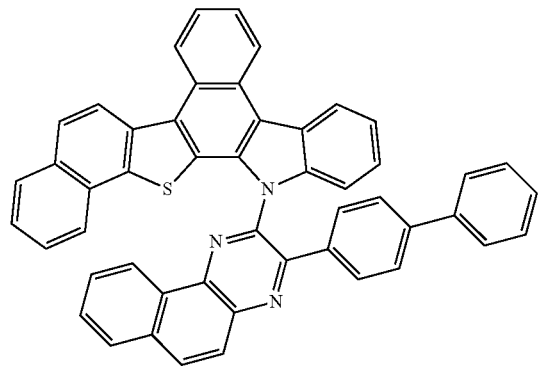
1-12
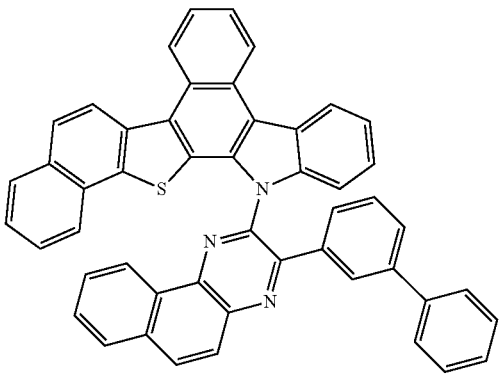
1-13
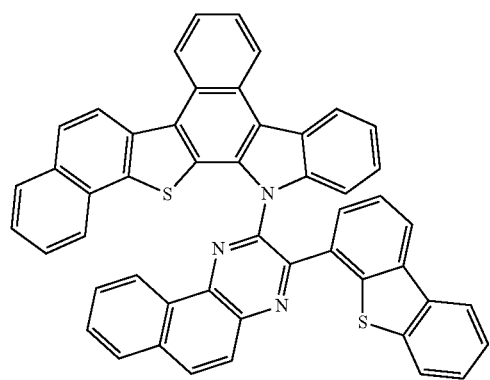
1-14
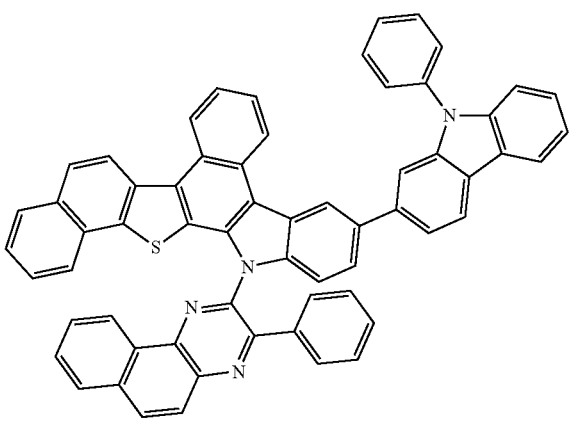
1-15
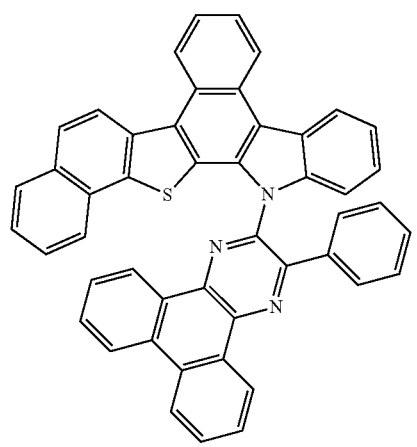
1-16
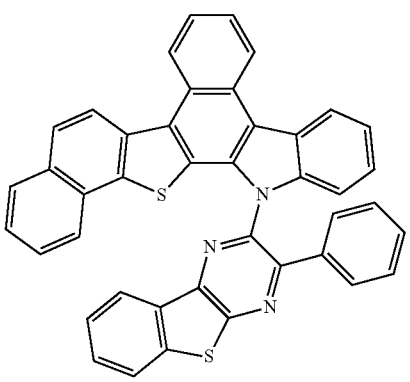
1-17
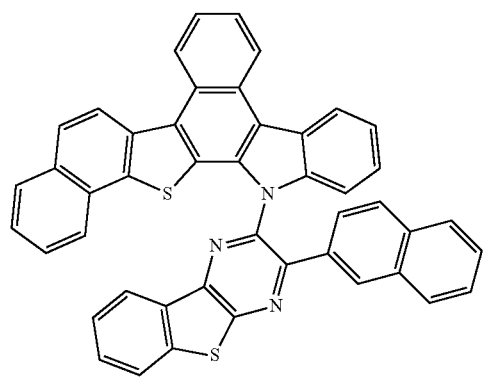
1-18
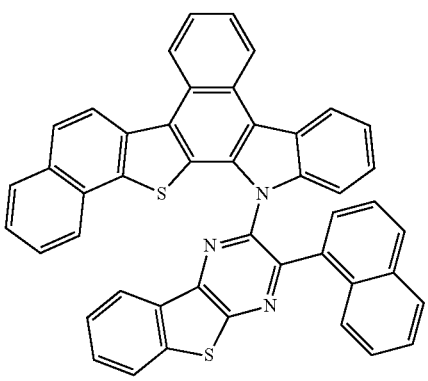

-continued
1-19
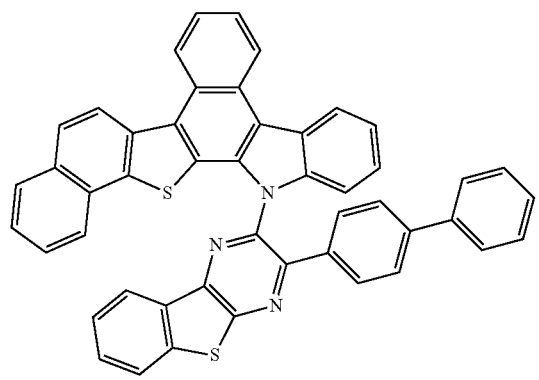
1-20
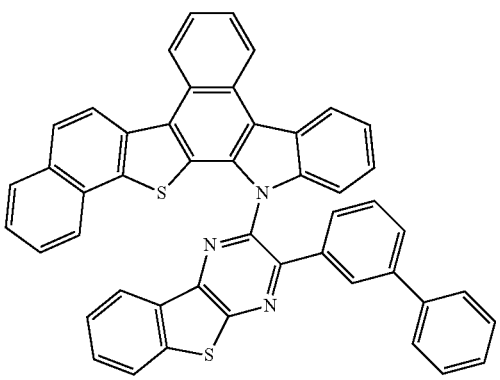
1-21
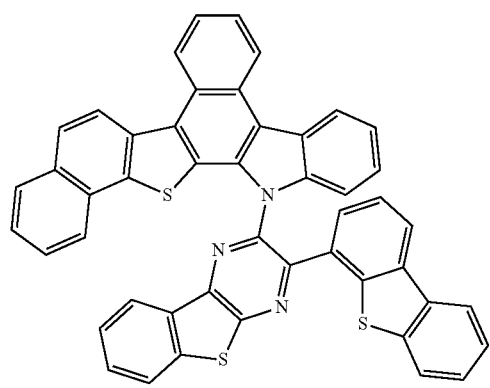
1-22
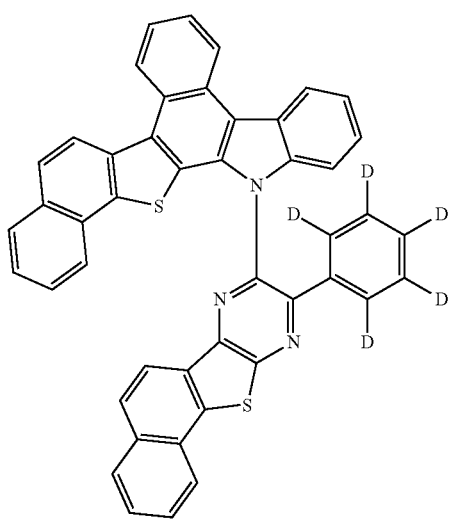
1-23
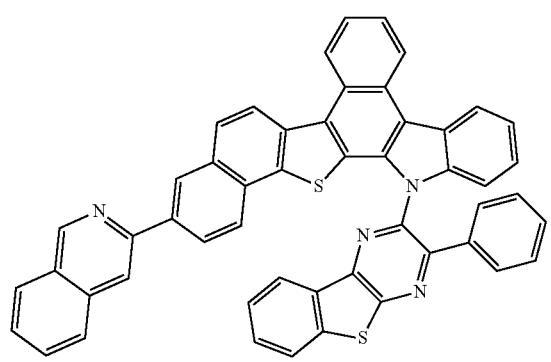
1-24
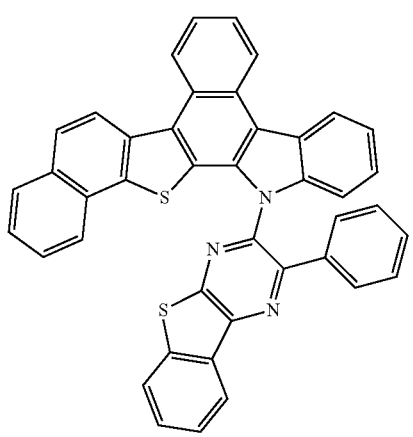

-continued
1-25
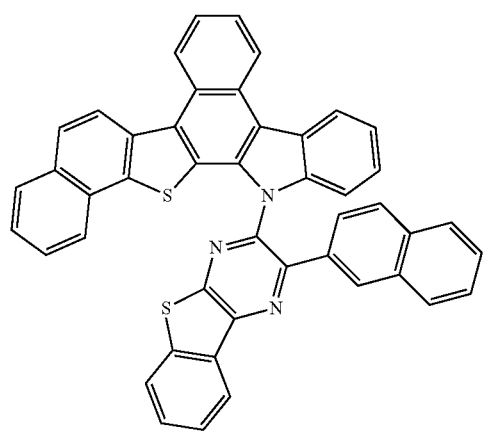
1-26
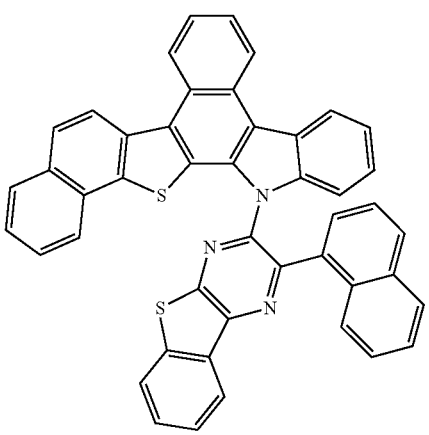
1-27
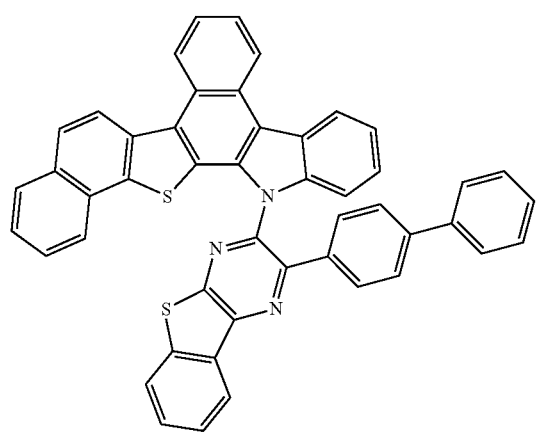
1-28
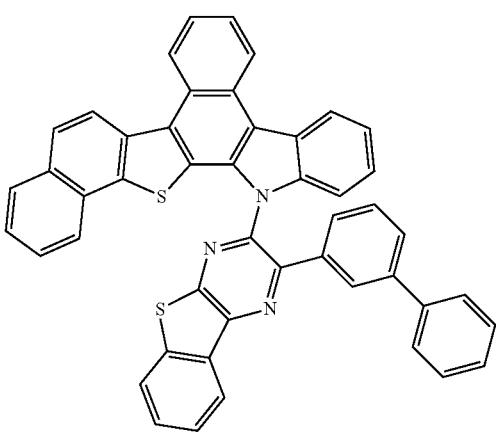
1-29
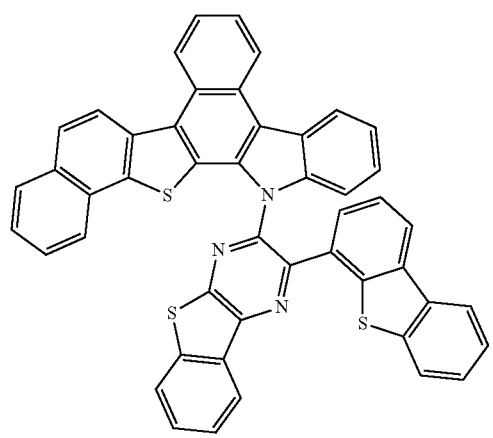
1-30
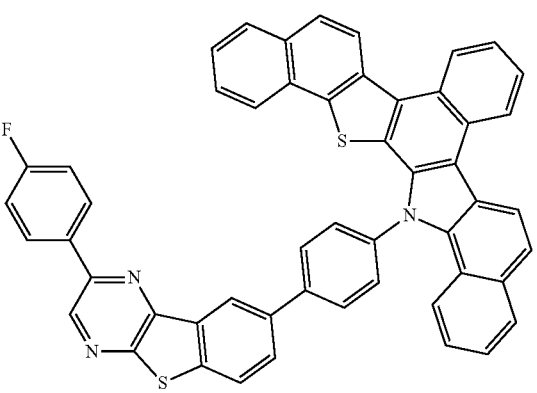

-continued
1-31
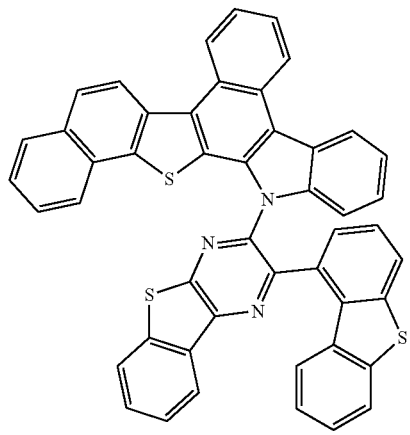
1-32
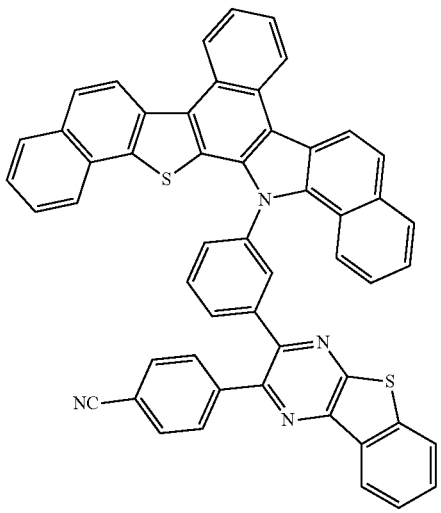
1-33
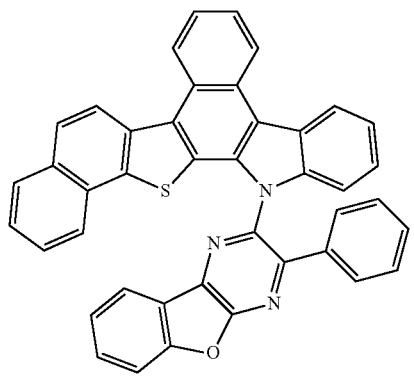
1-34
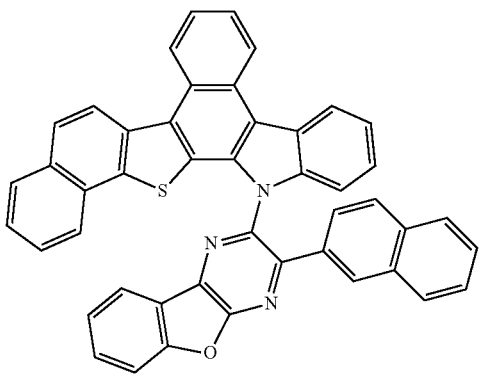
1-35
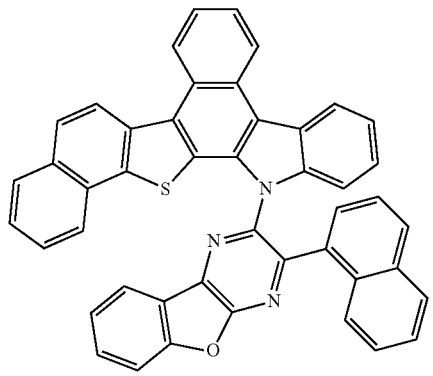
1-36
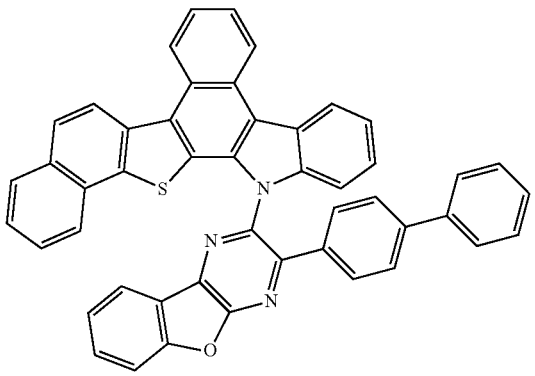
1-37
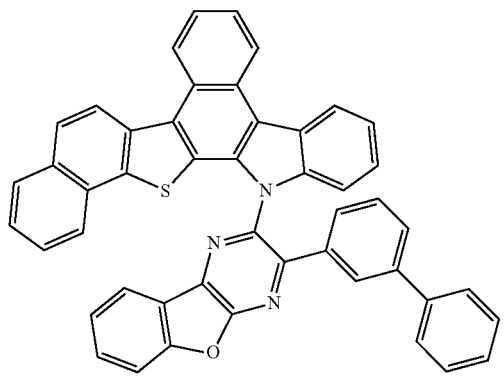
1-38
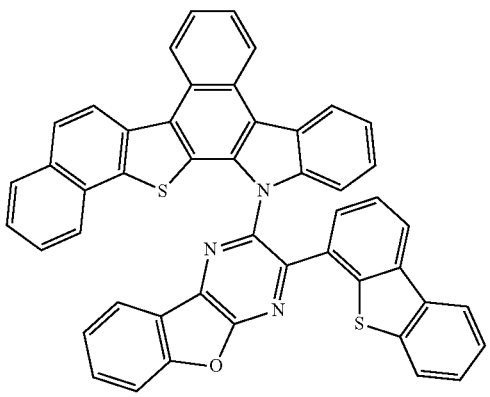

-continued
1-39
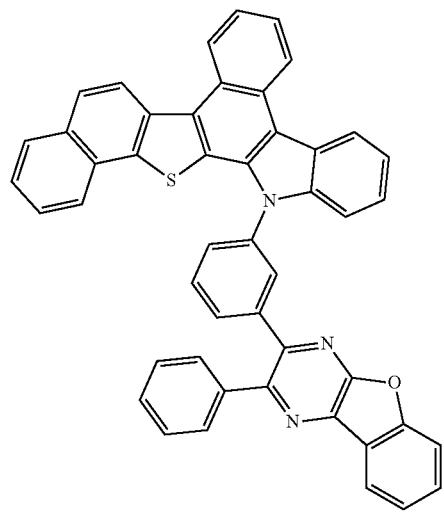
1-40
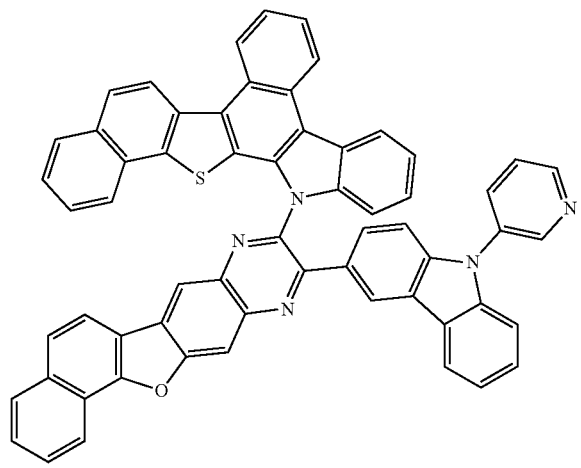
1-41
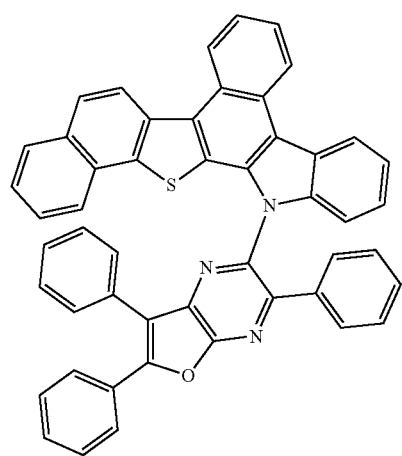
1-42
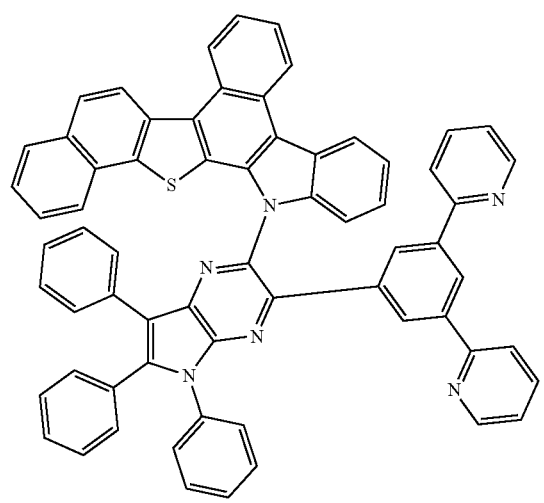
1-43
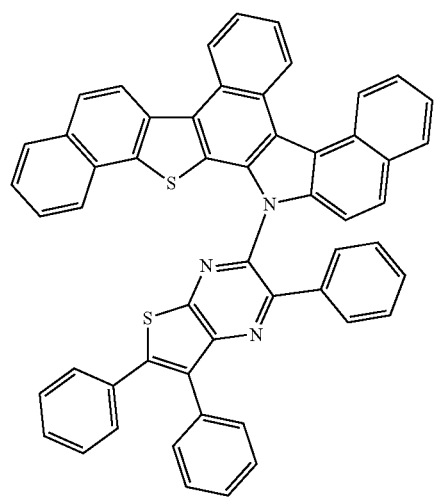
1-44
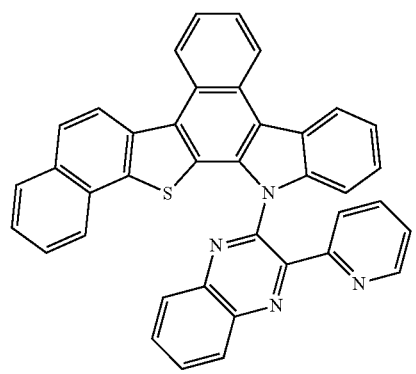

1-45
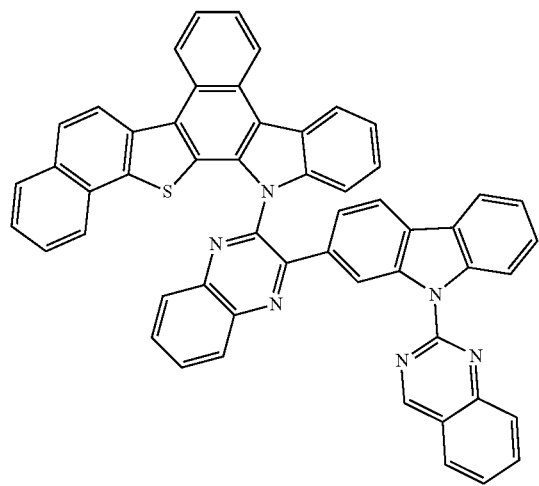
2-1
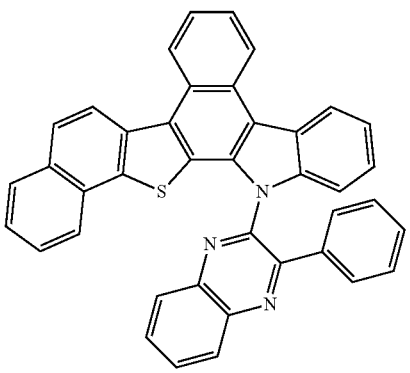
2-2
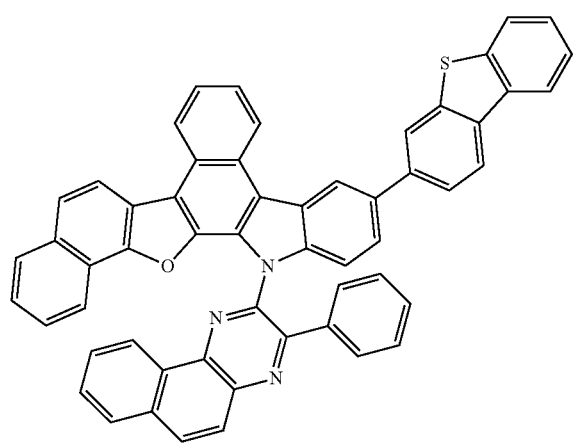
2-3
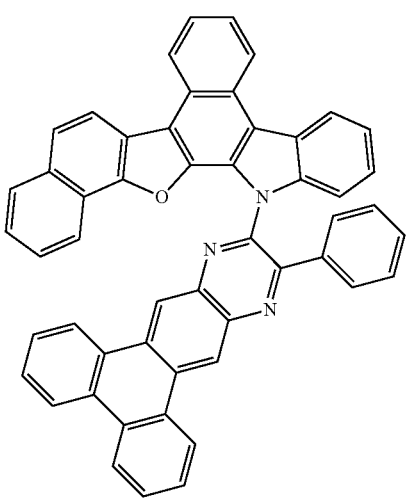
2-4
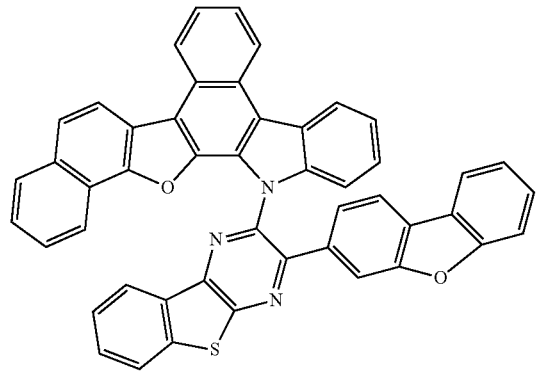
2-5
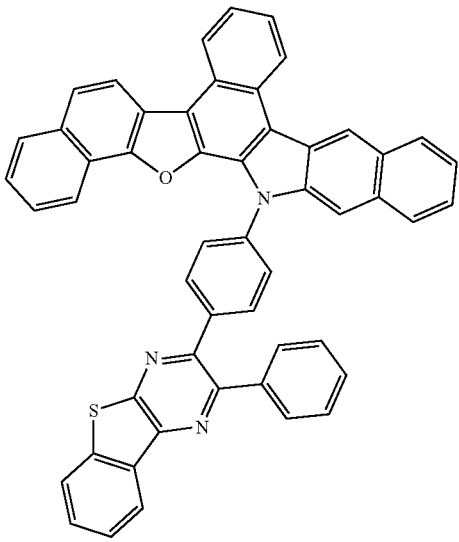

2-6
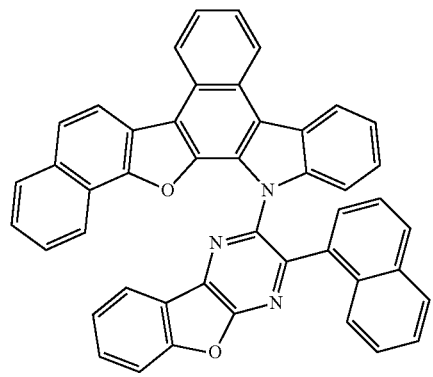
2-7
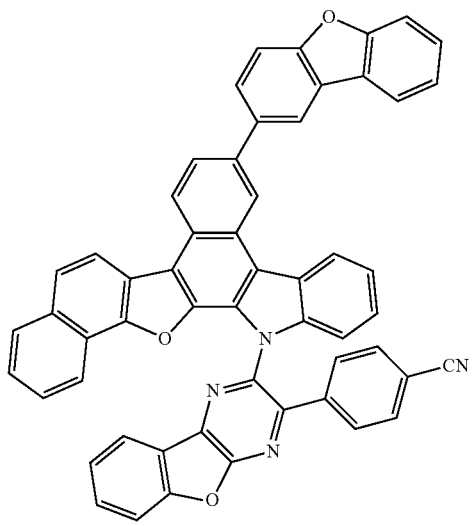
2-8
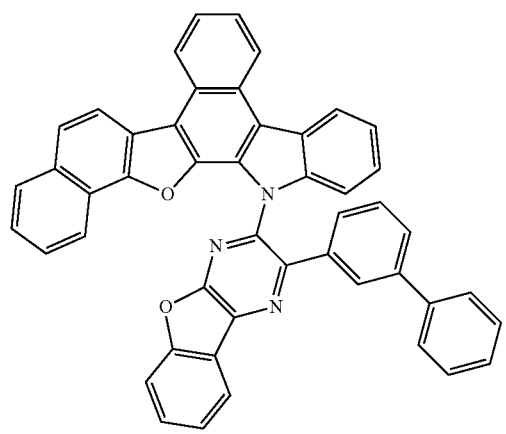
2-9
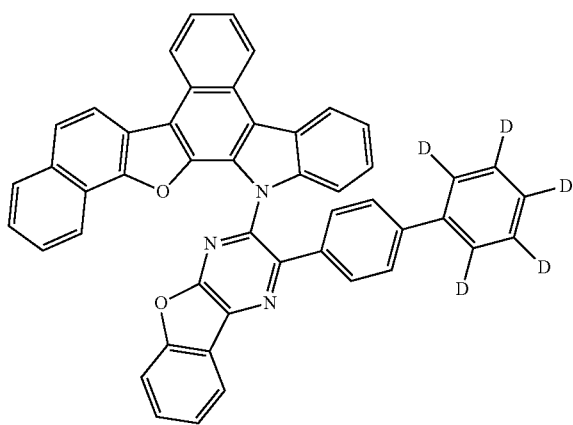
2-10
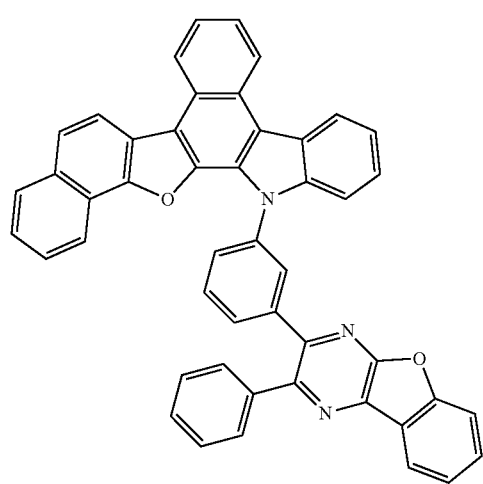
3-1
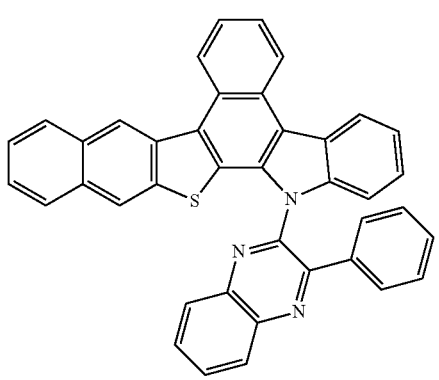

-continued
3-2
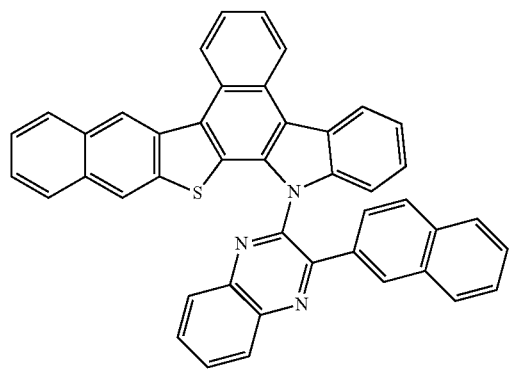
3-3
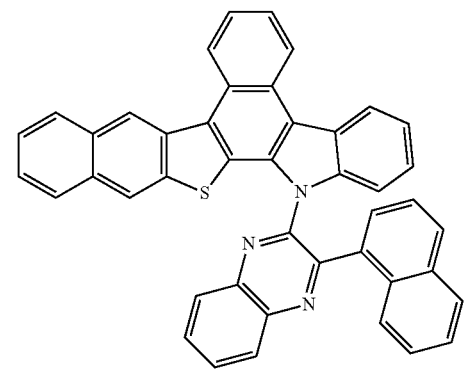
3-4
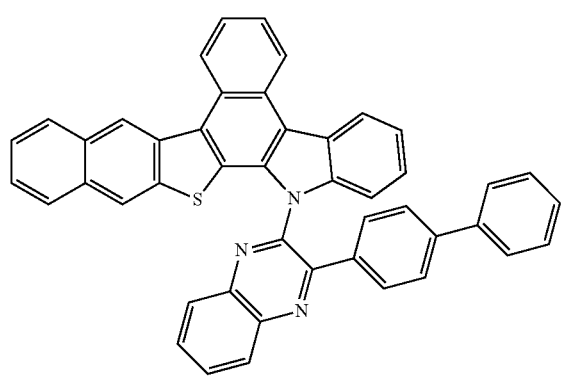
3-5
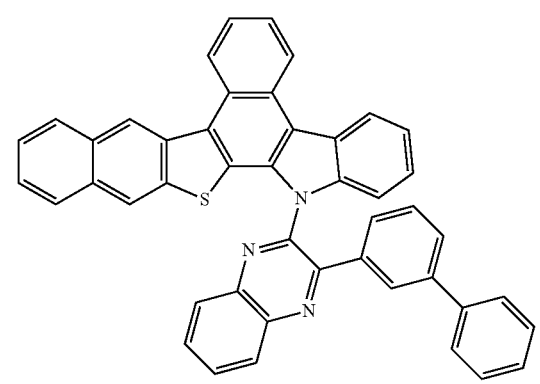
3-6
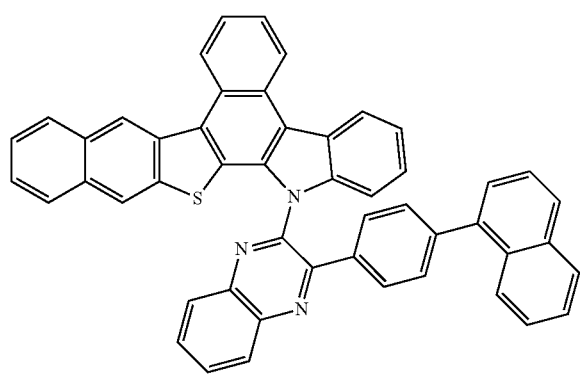
3-7
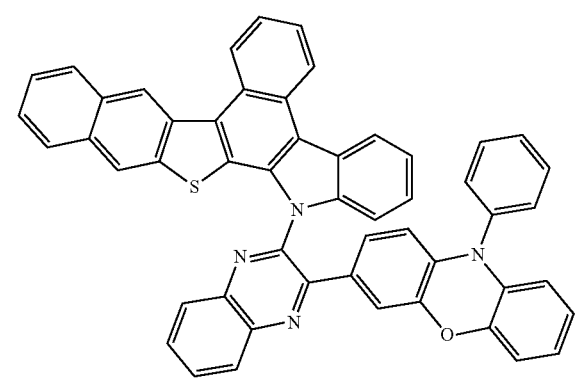
3-8
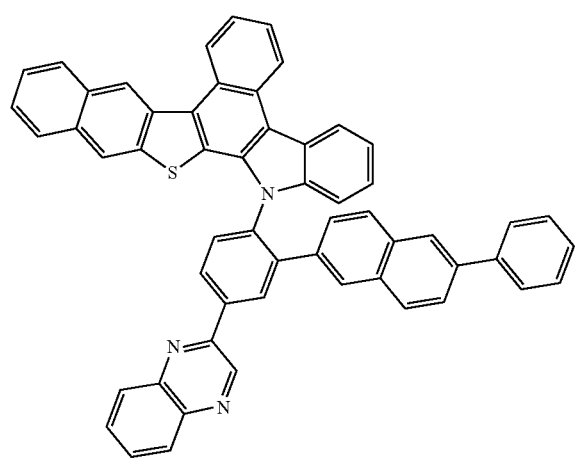
3-9
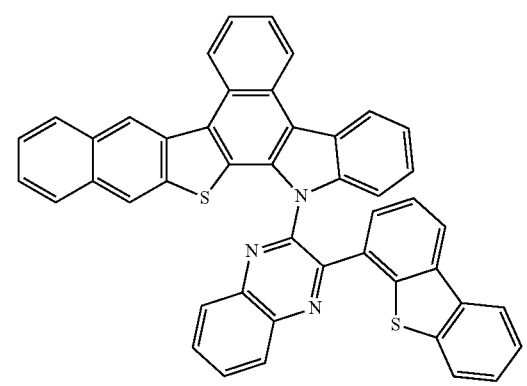

-continued
3-10
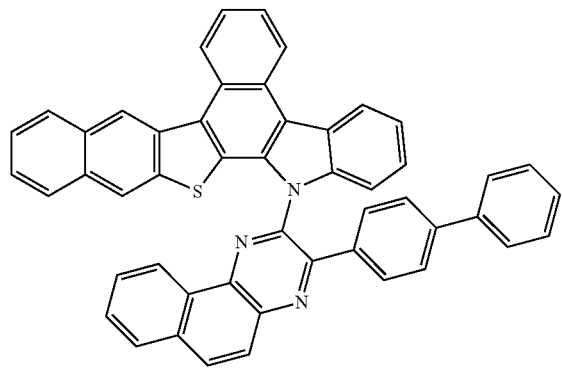
3-11
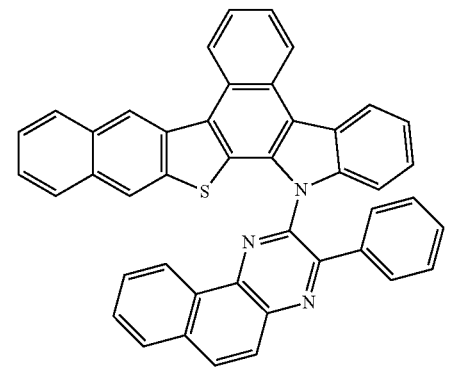
3-12
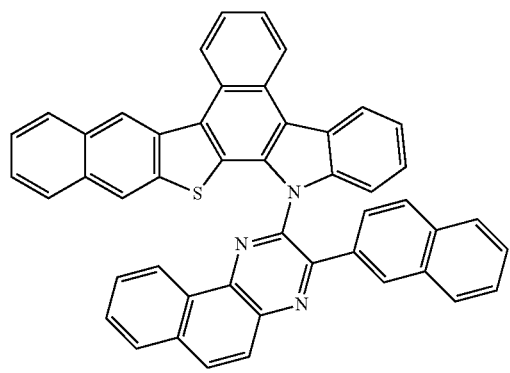
3-13
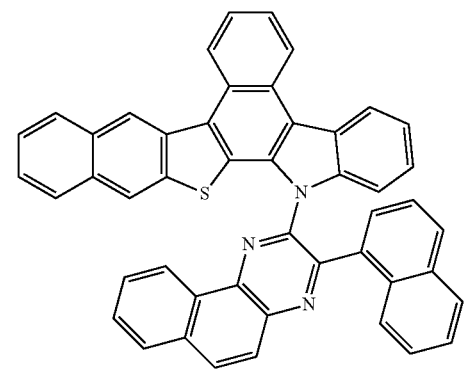
3-14
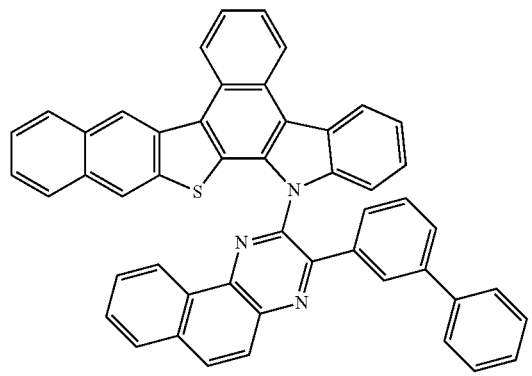
3-15
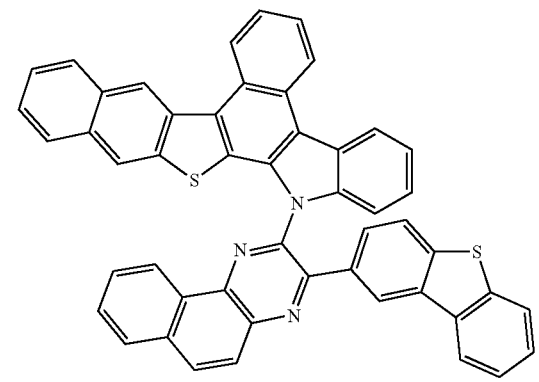
3-16
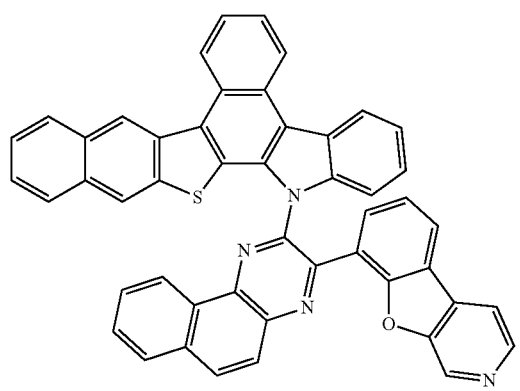
3-17
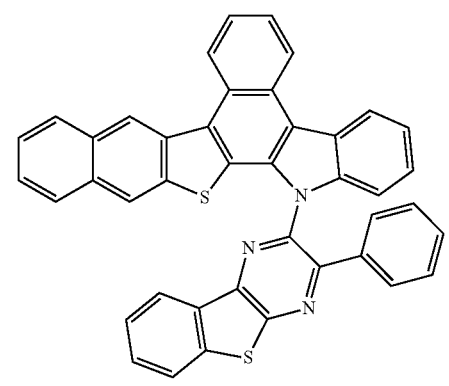

-continued
3-18
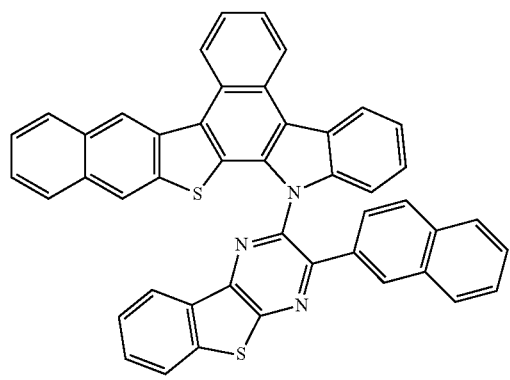
3-19
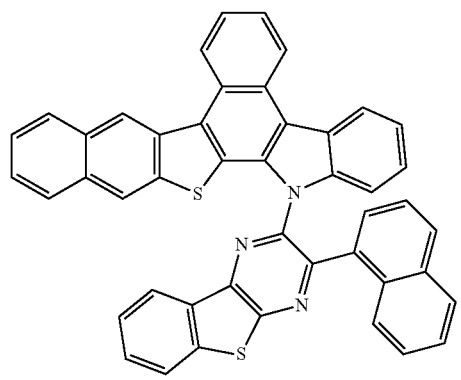
3-20
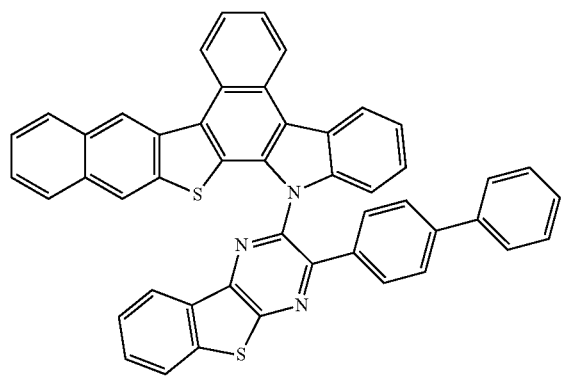
3-21
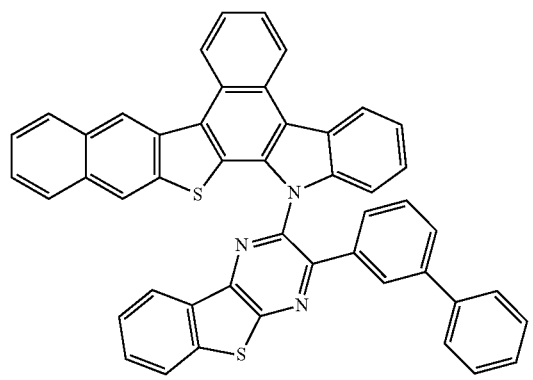
3-22
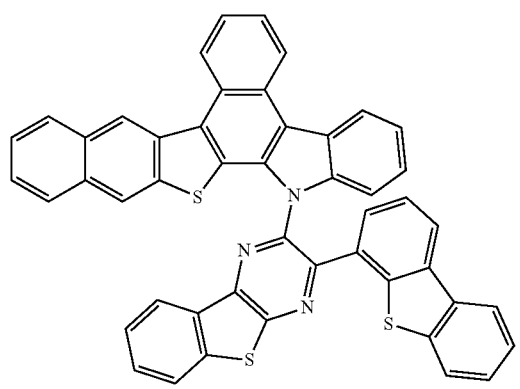
3-23
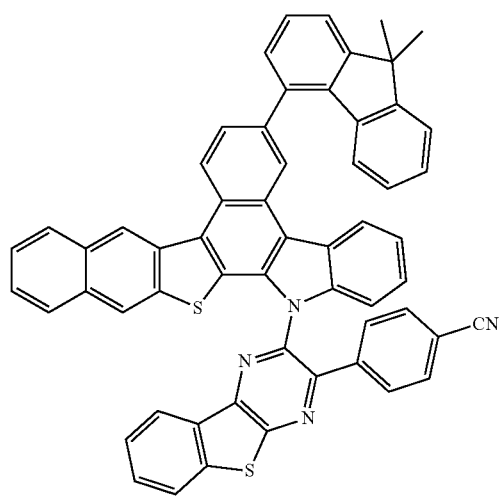

-continued
3-24
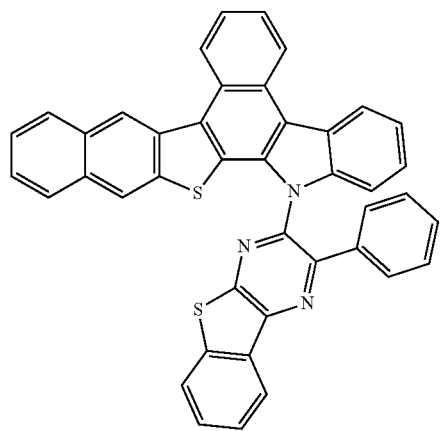
3-25
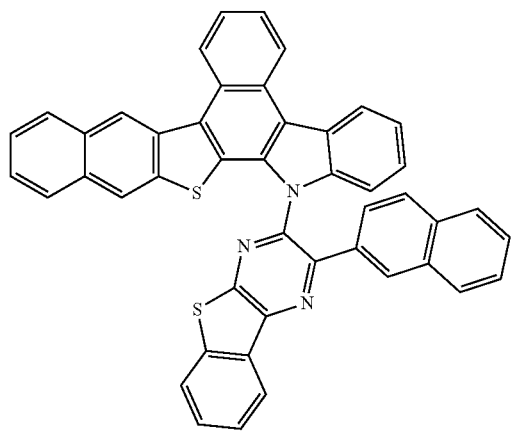
1-26
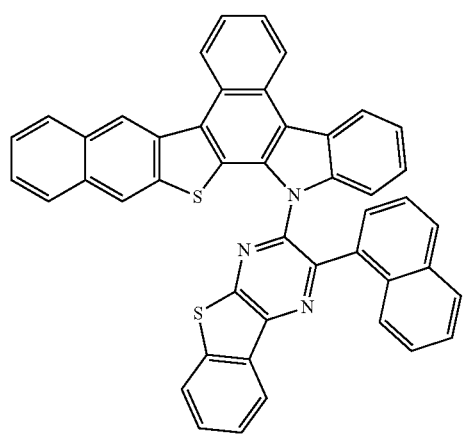
1-27
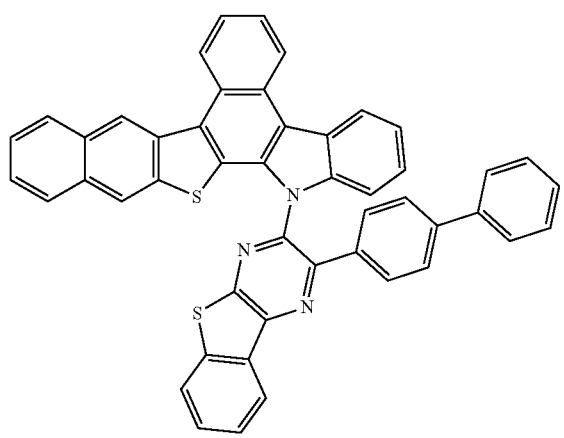
3-28
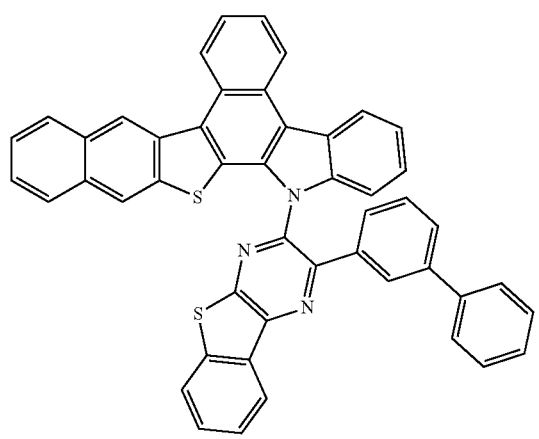
3-29
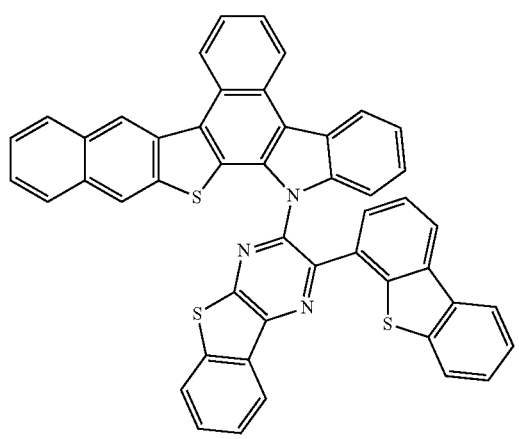

-continued
3-30
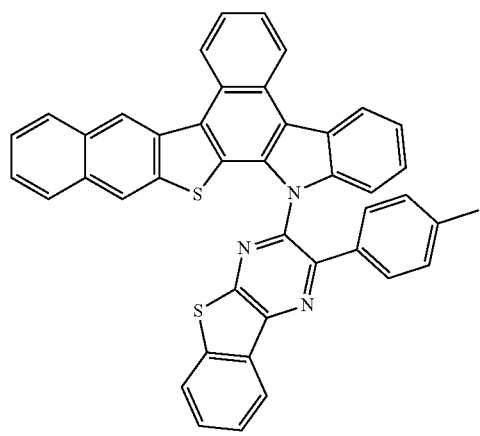
3-31
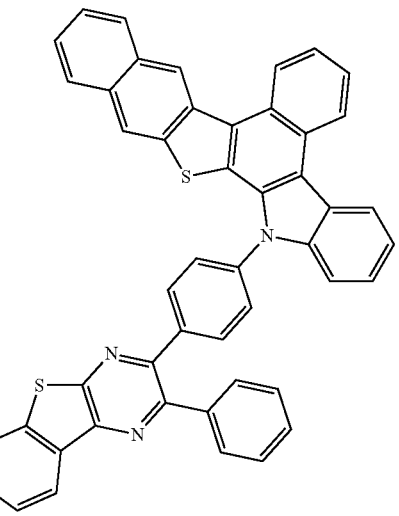
3-32
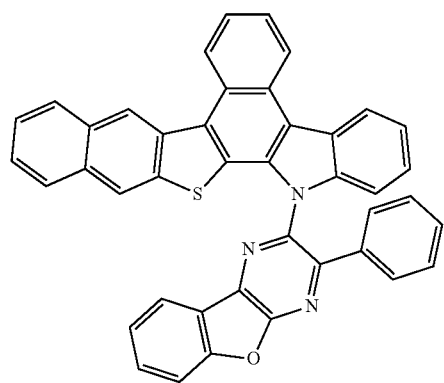
3-33
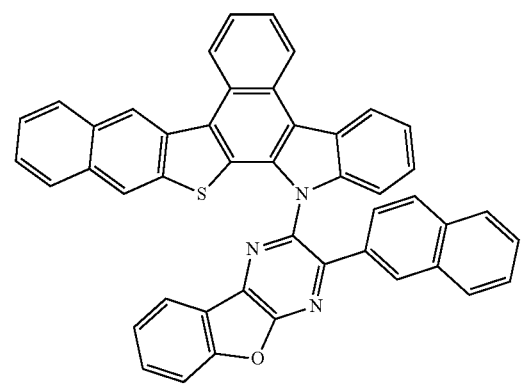
3-34
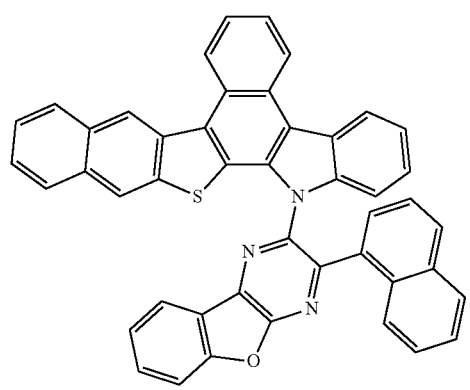
3-35
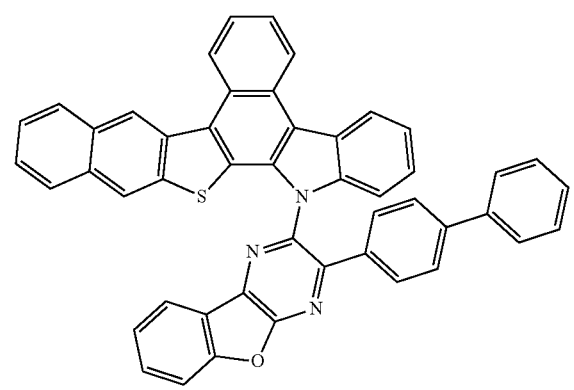

-continued
3-36
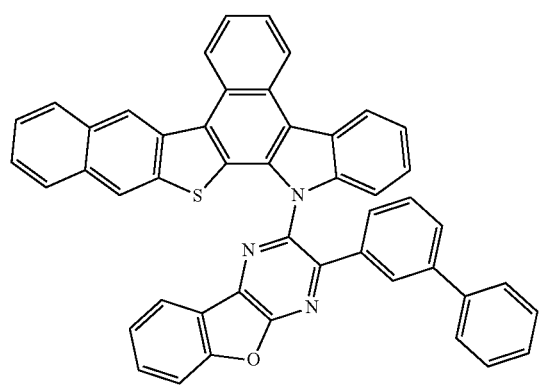
3-37
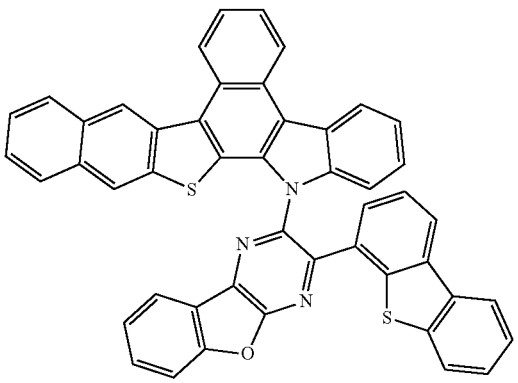
3-38
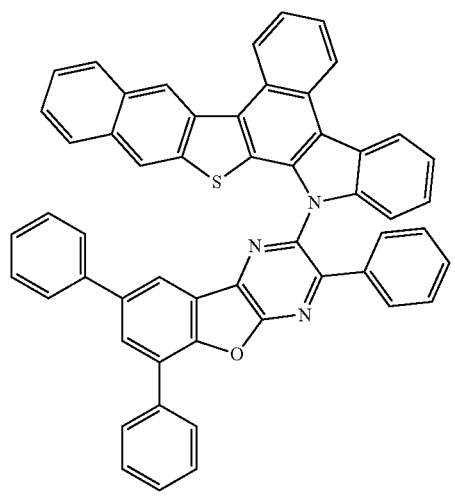
3-39
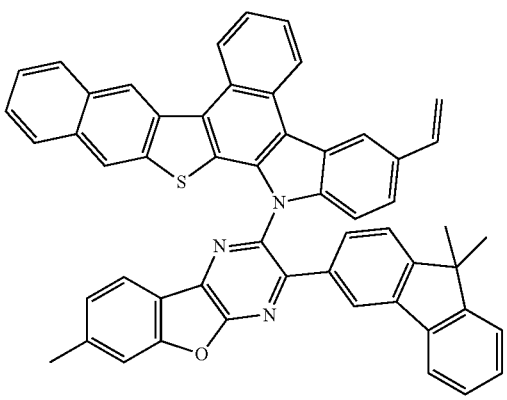
3-40
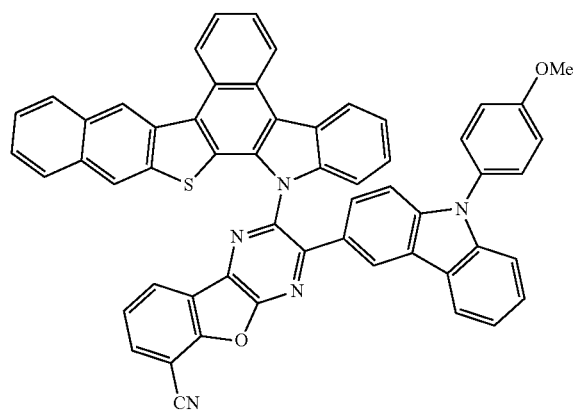
3-41
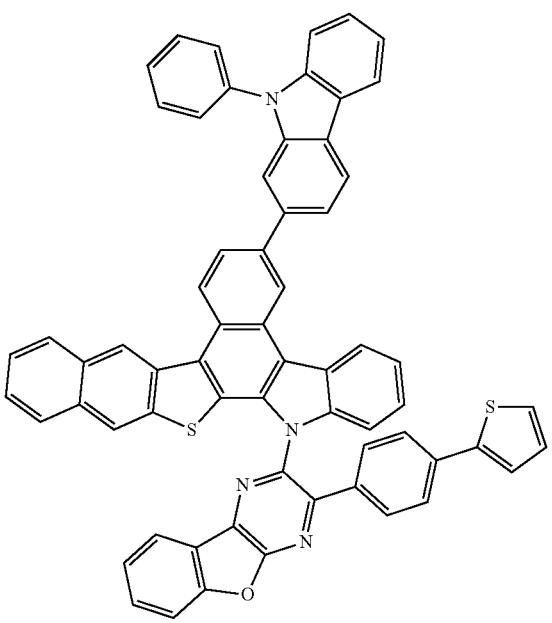

-continued
3-42
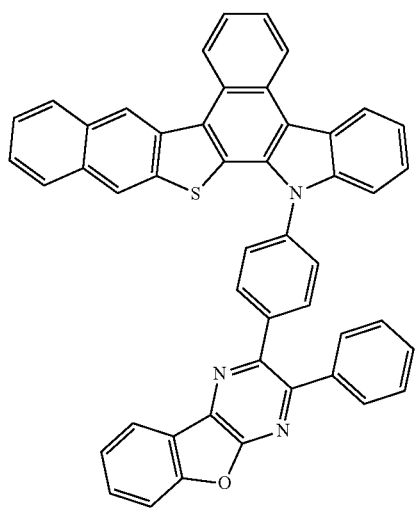
3-43
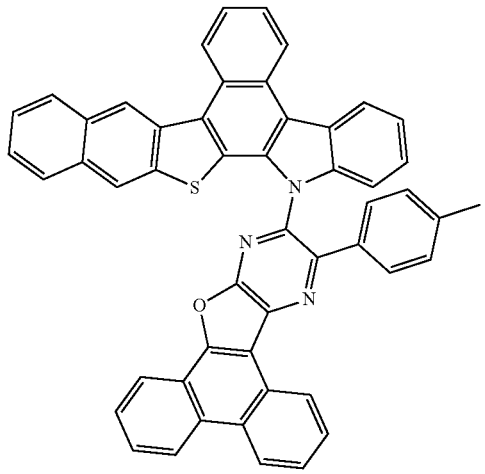
3-44
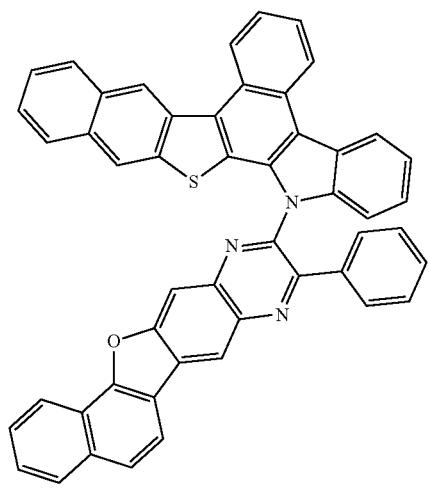
3-45
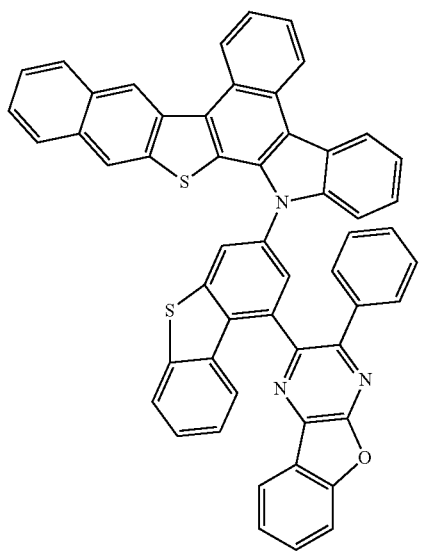
4-1
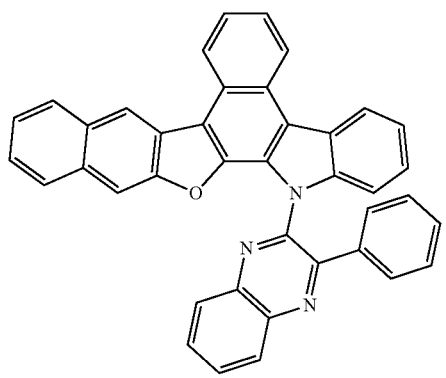
4-2
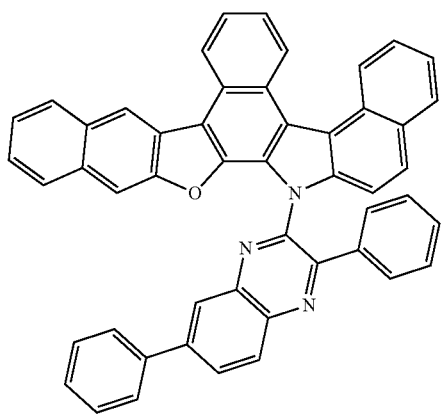

4-3
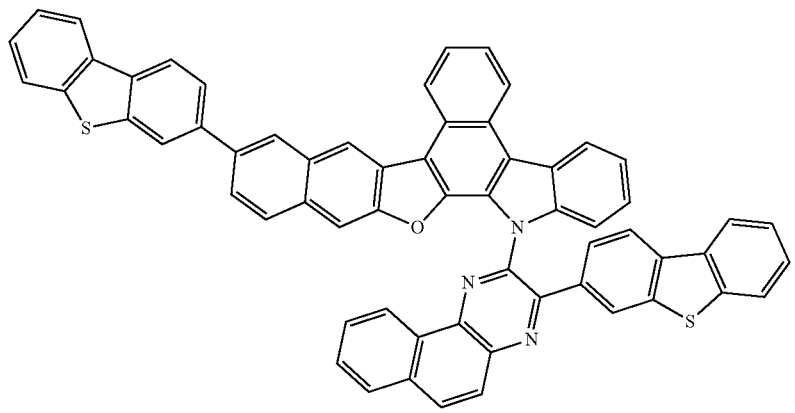
4-4
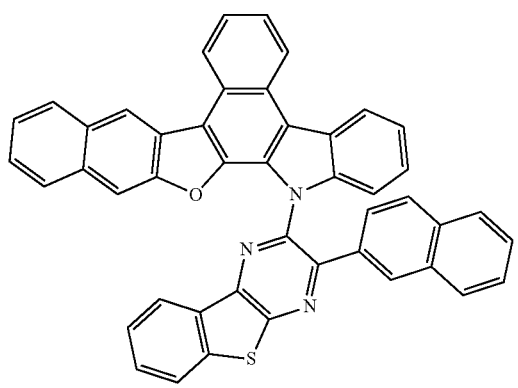
4-5
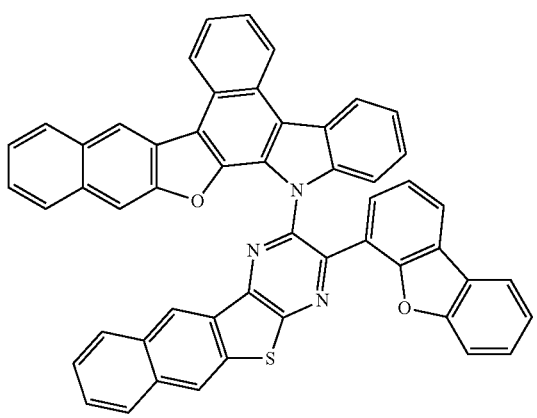
4-6
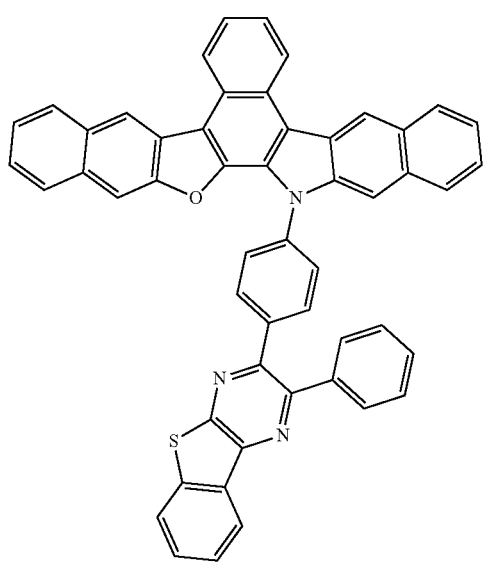
4-7
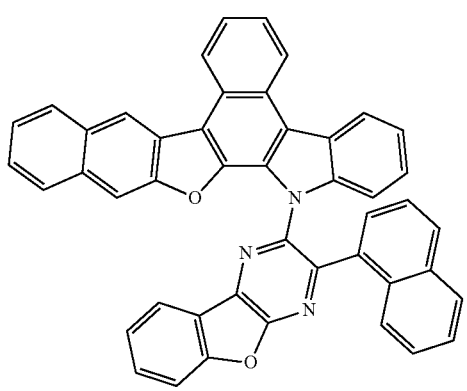

-continued
4-8
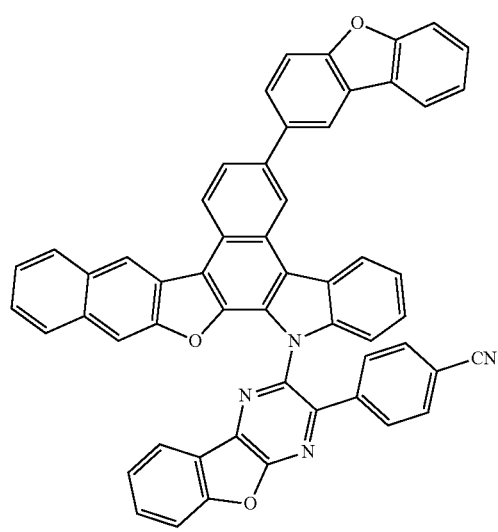
4-9
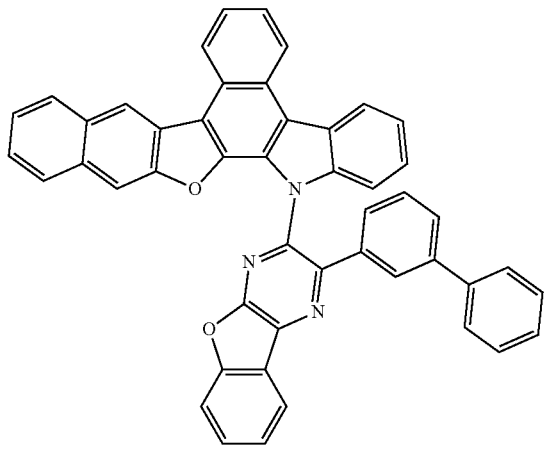
4-10
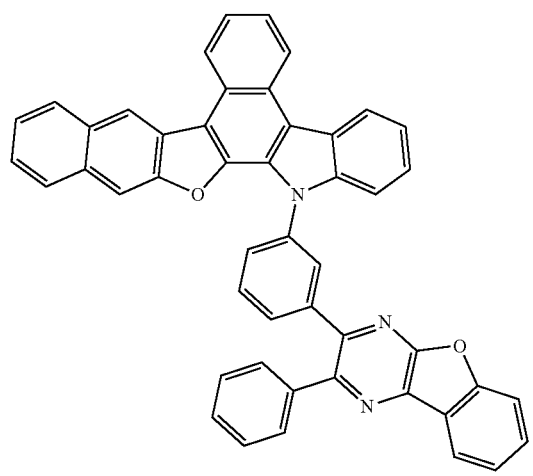
5-1
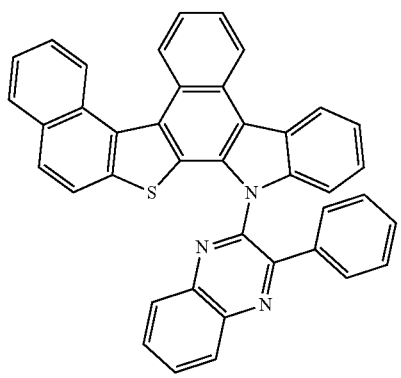
5-2
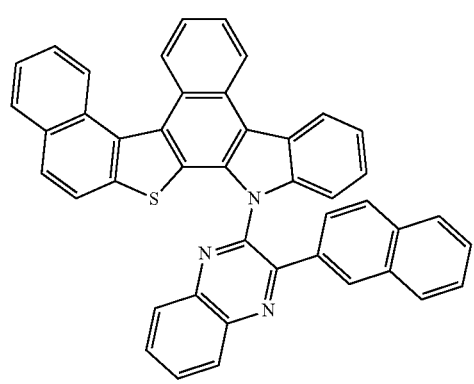
5-3
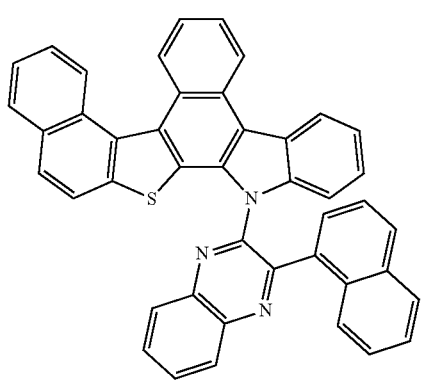

-continued
5-4
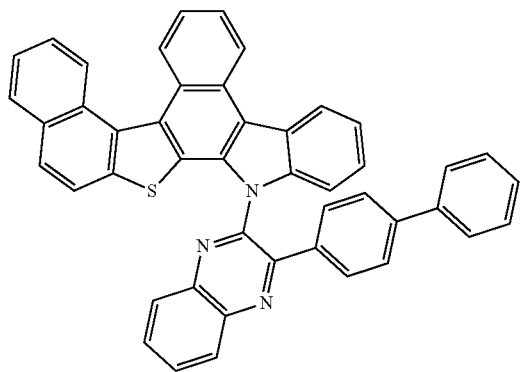
5-5
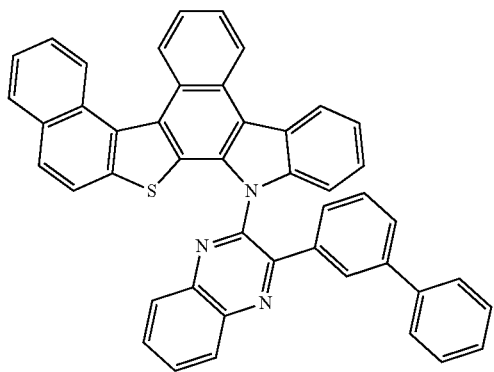
5-6
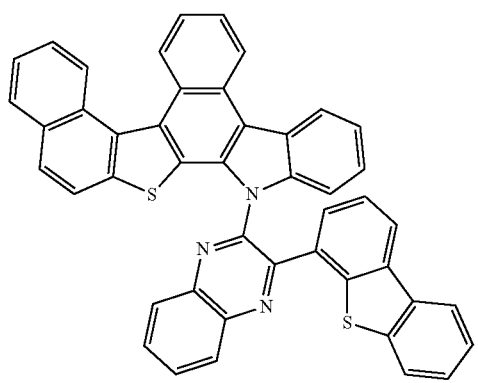
5-7
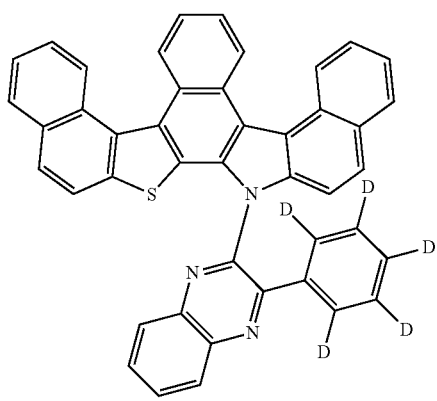
5-8
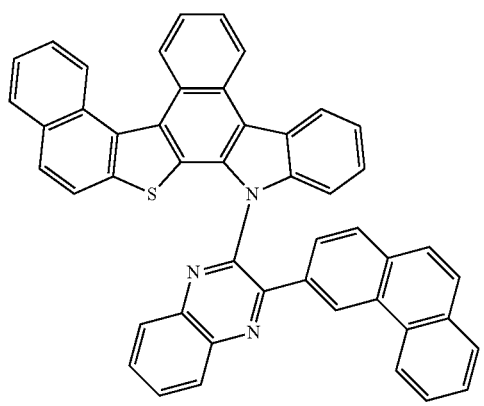
5-9
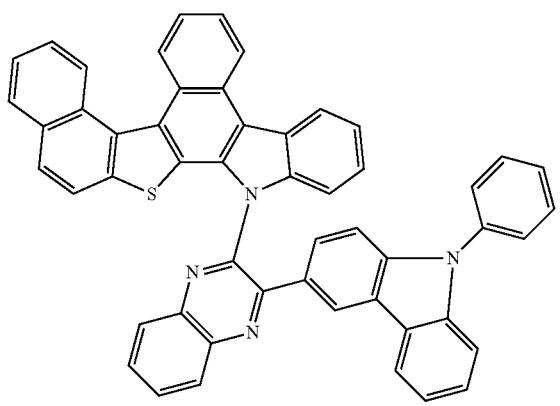

-continued
5-10
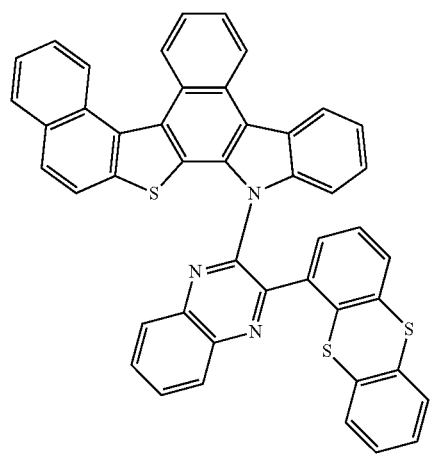
5-11
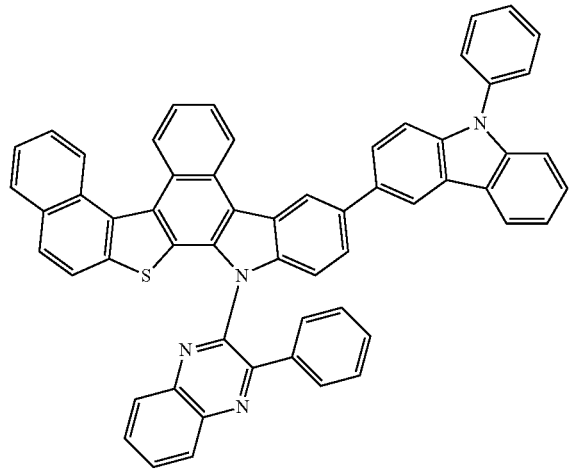
5-12
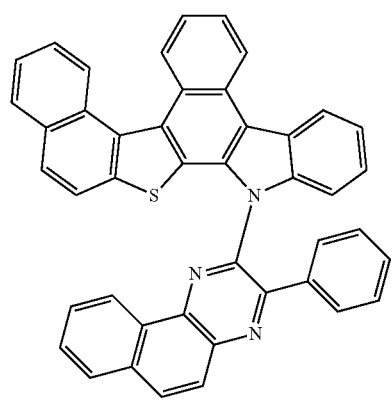
5-13
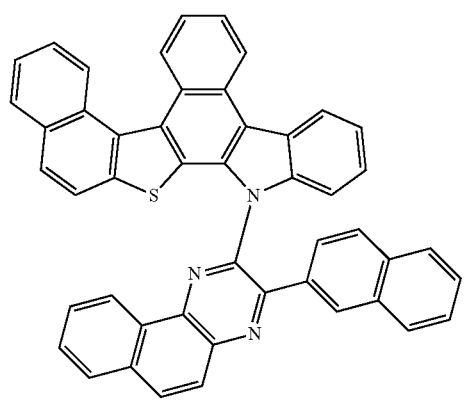
5-14
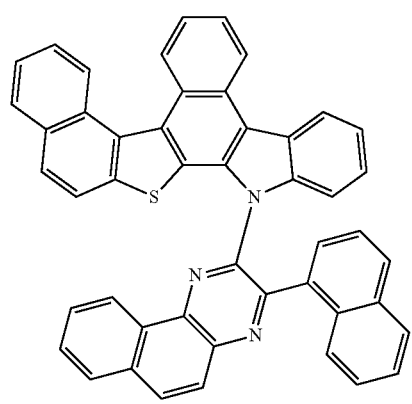
5-15
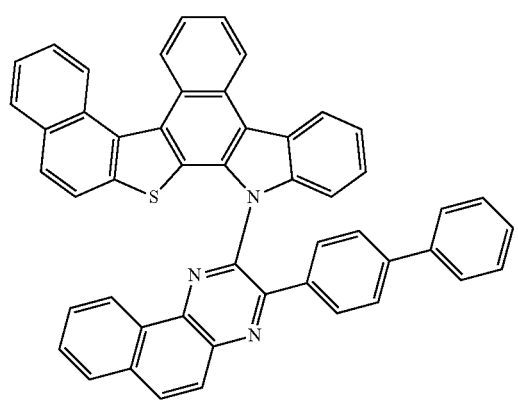

-continued
5-16
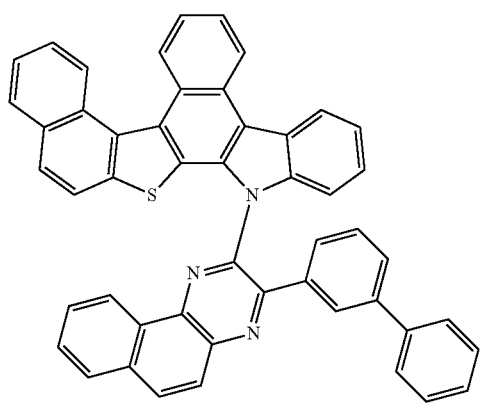
5-17
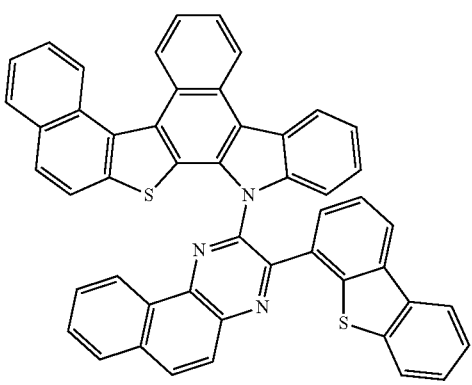
5-18
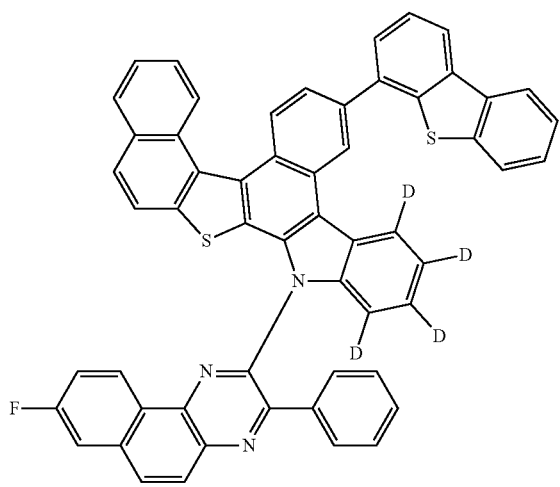
5-19
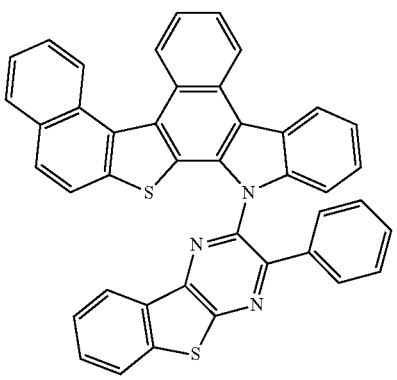
5-20
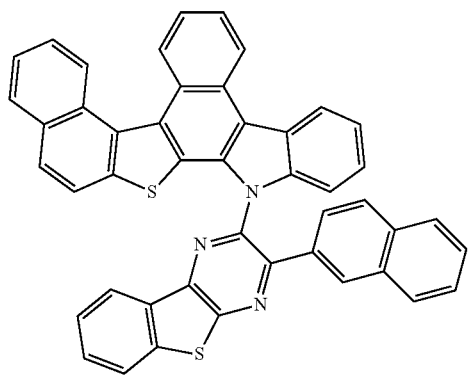
5-21
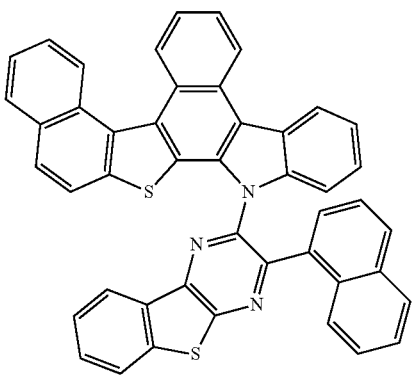
5-22
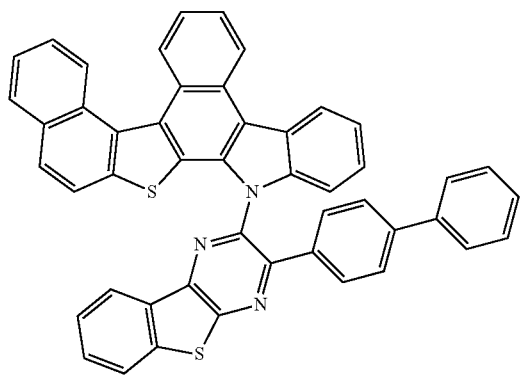
5-23
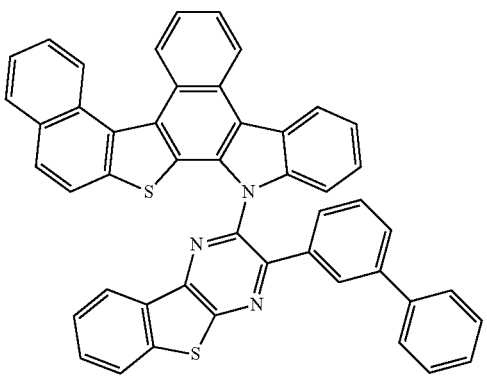

-continued
5-24
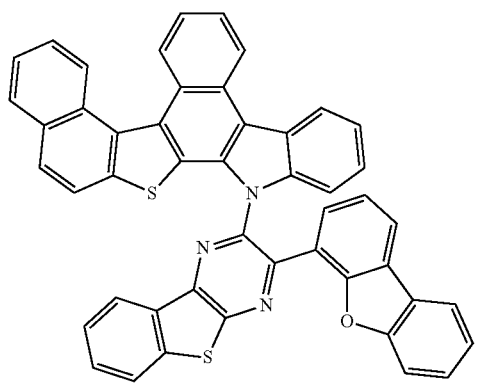
5-25
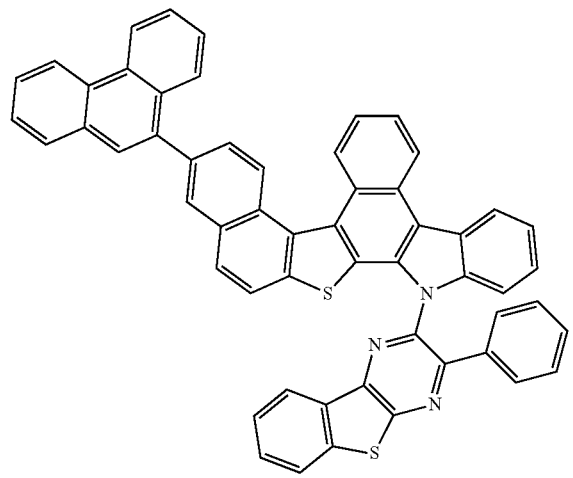
5-26
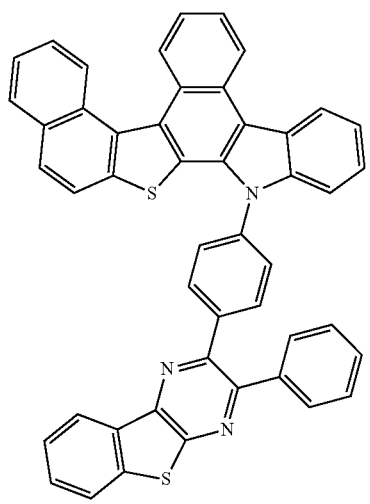
5-27
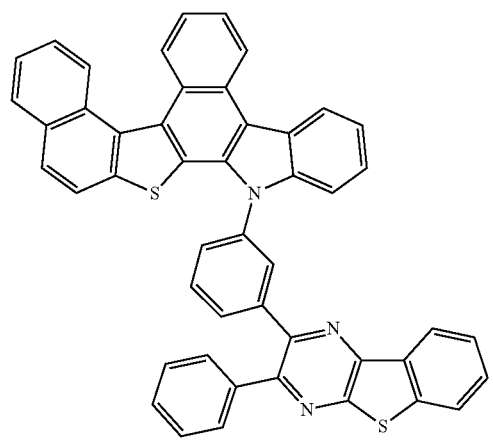
5-28
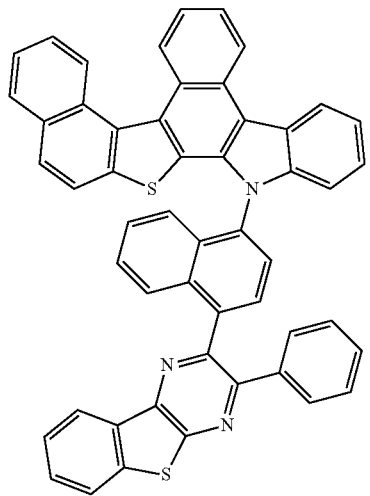
5-29
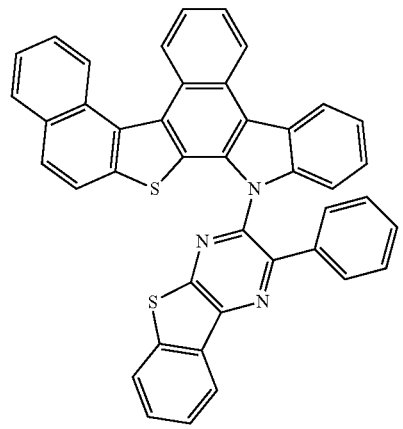

-continued
5-30
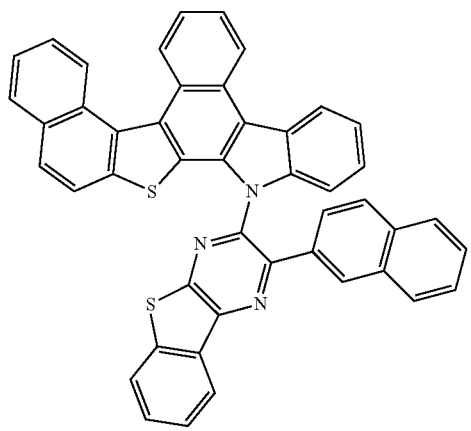
5-31
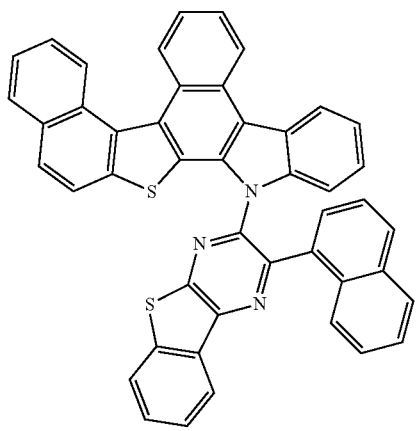
5-32
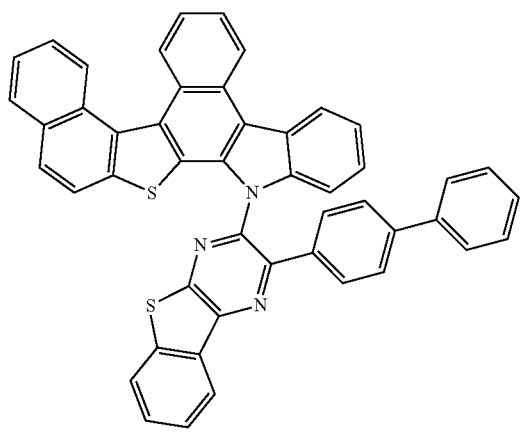
5-33
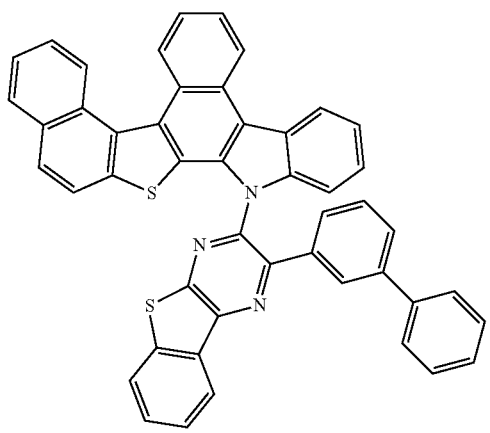
5-34
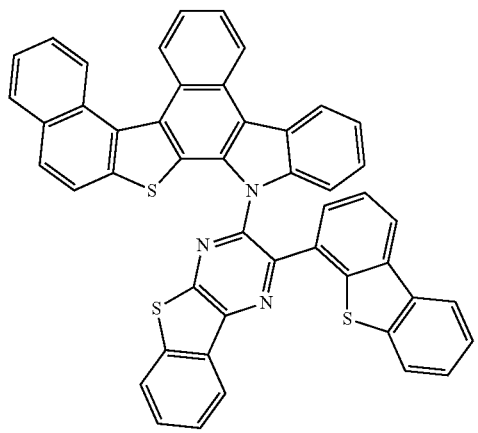
5-35
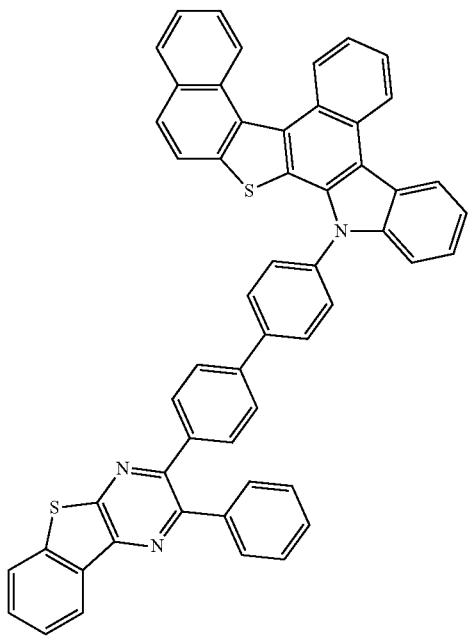

5-36
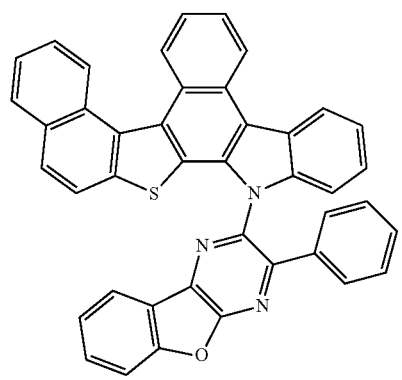
5-37
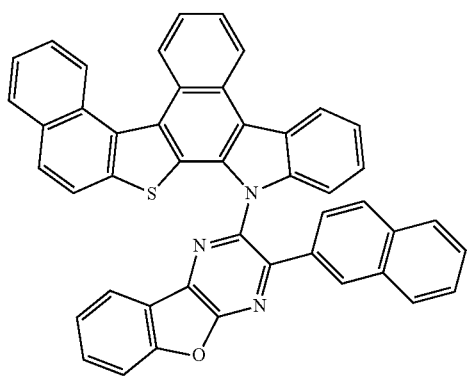
5-38
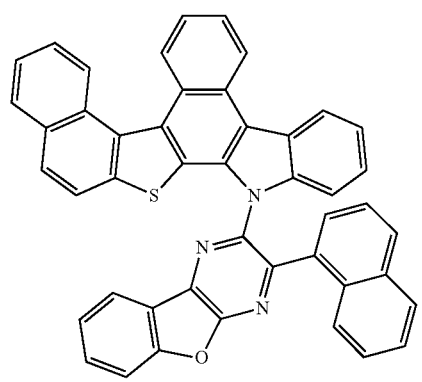
5-39
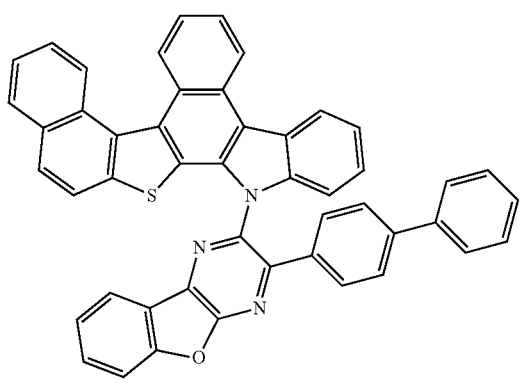
5-40
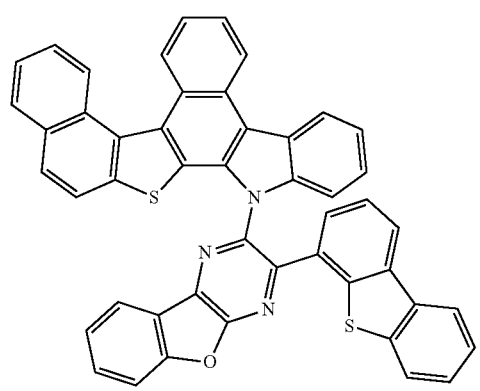
5-41
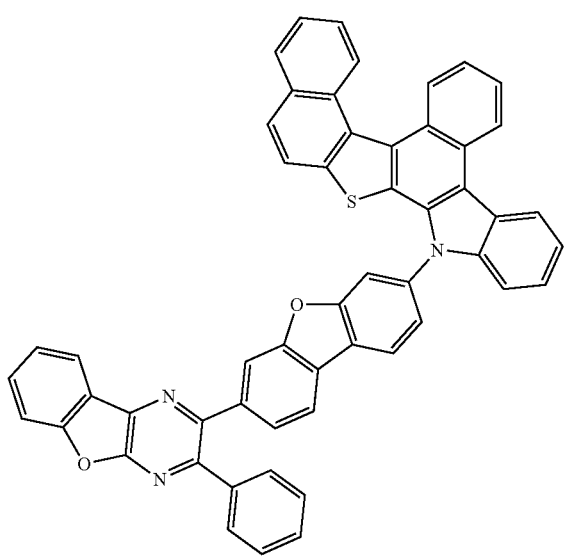

-continued
5-42
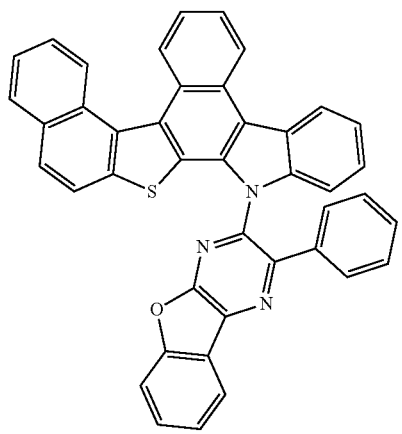
5-43
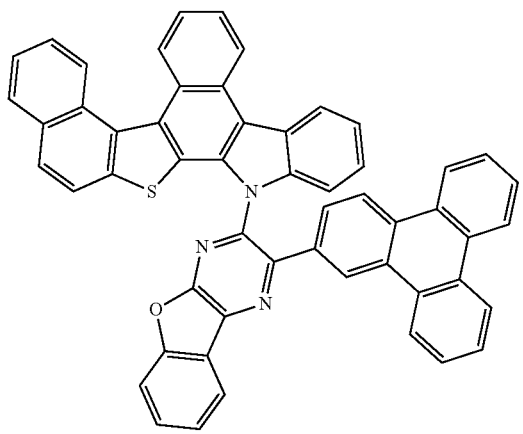
5-44
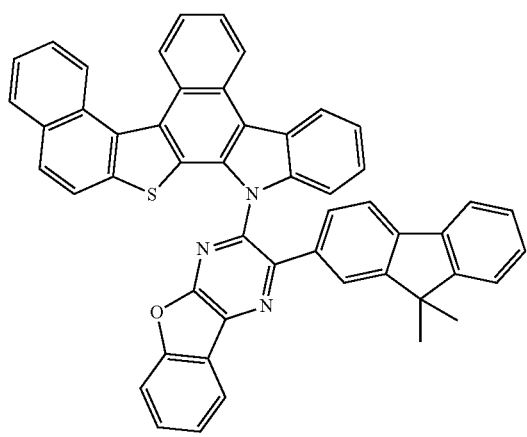
5-45
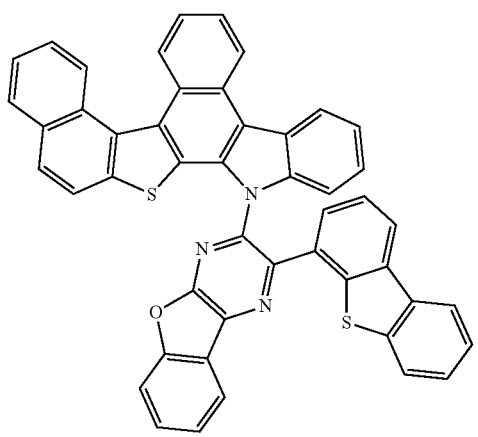
6-1
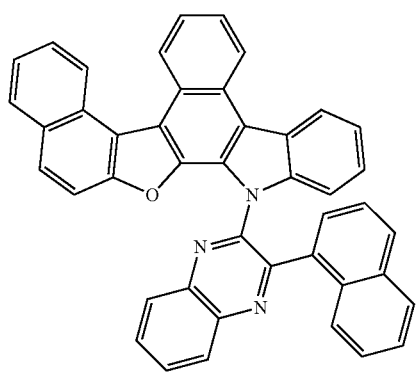
6-2
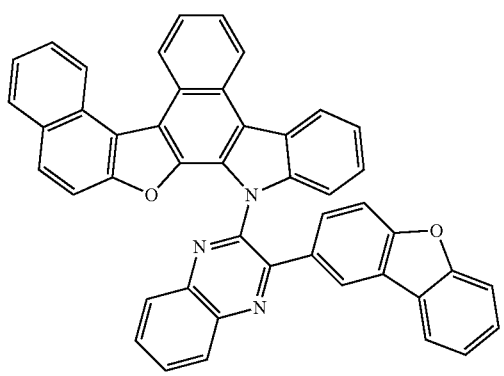

-continued
6-3
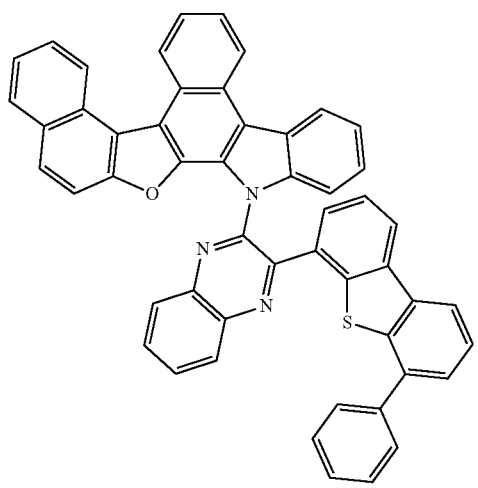
6-4
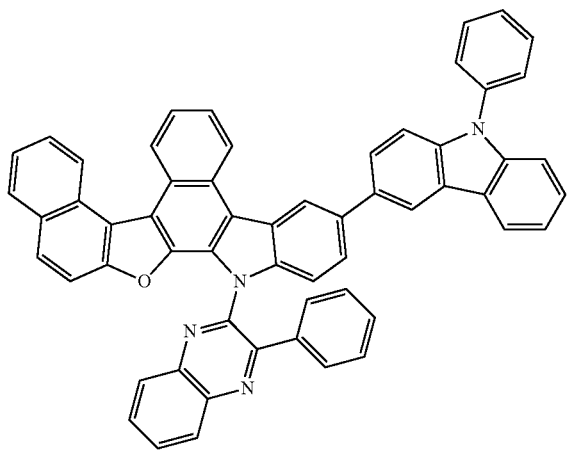
6-5
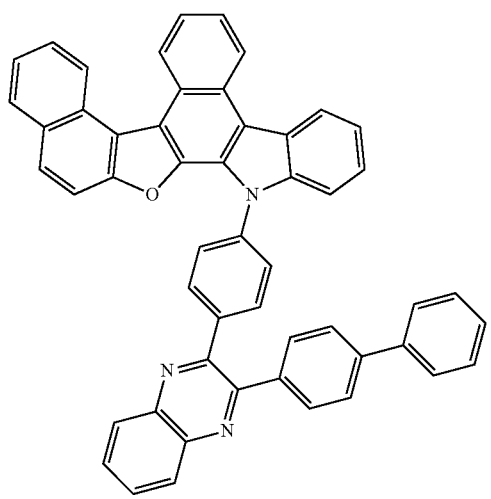
6-6
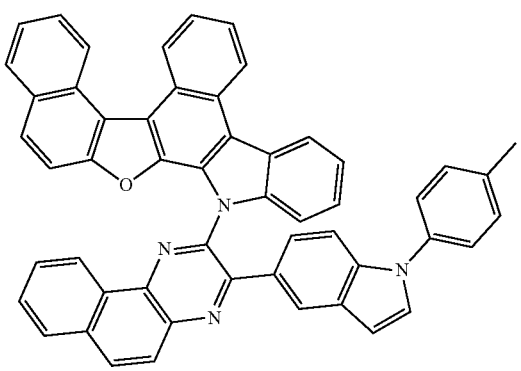
6-7
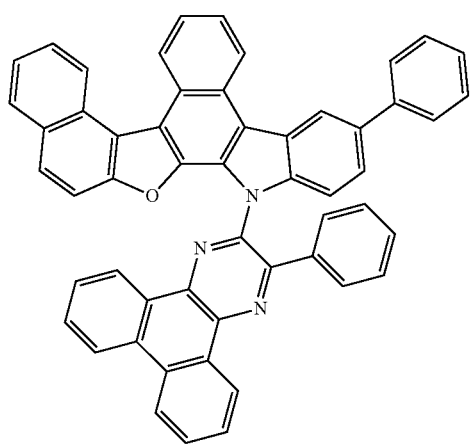
6-8
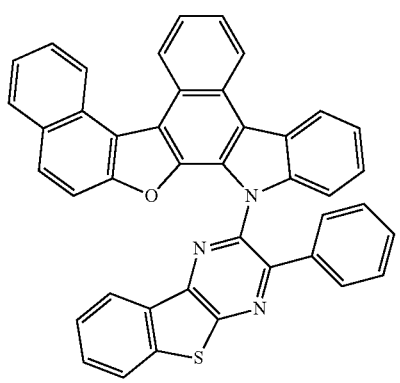

-continued
6-9
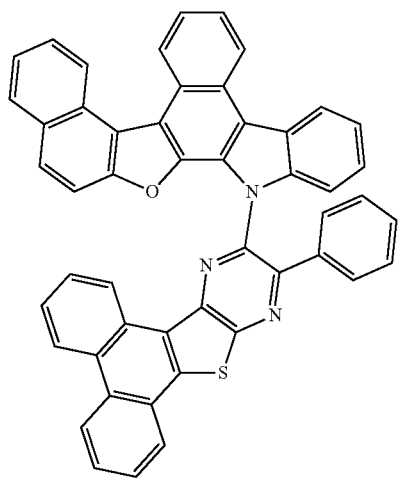
6-10
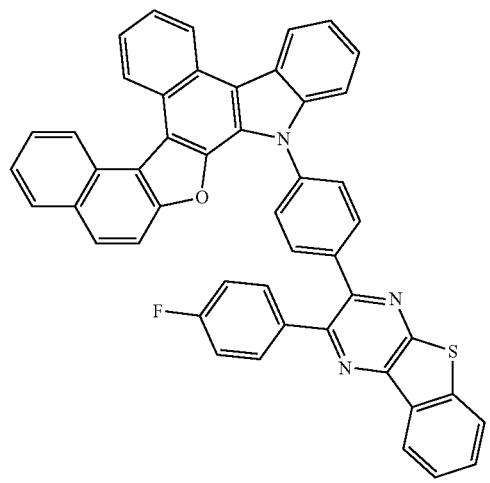
6-11
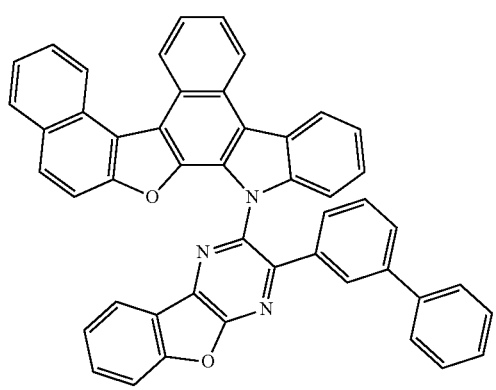
6-12
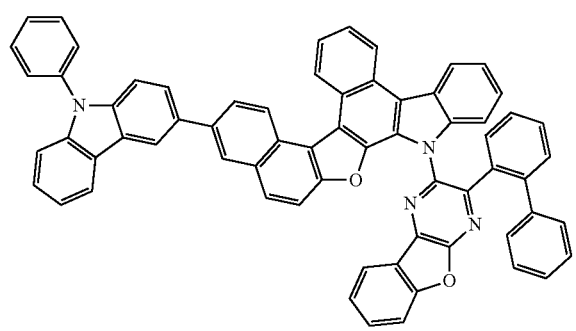
6-13
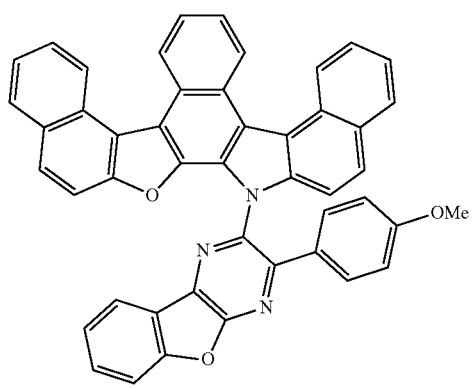
6-14
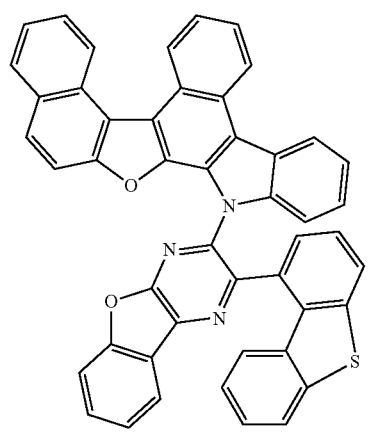

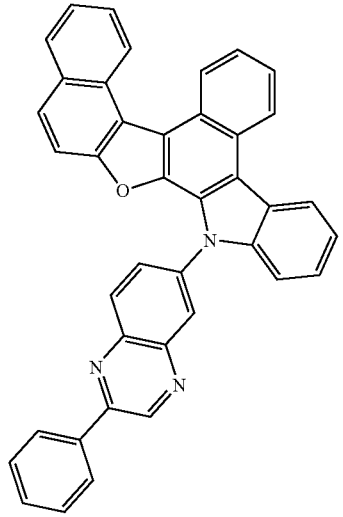

6-15

Referring to FIG. 1, an organic electric element 100 according to an embodiment of the present invention includes a first electrode 120 formed on a substrate 110, a second electrode 180, and an organic material layer between the first electrode 110 and the second electrode 180, wherein the organic material layer contains compound represented by Formula 1. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, the remaing layers except the light emitting layer 150 may not be formed. The organic material layer may further include a hole blocking layer, an electron blocking layer, an emission-auxiliary layer 151, an electron transport auxiliary layer, a buffer layer 141, etc., and the electron transport layer 160 and the like may serve as a hole blocking layer.

Although not shown, the organic electric element according to an embodiment of the present invention may further include at least one protective layer or one capping layer formed on at least one of the sides the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the electron transport layer (160), and the electron injection layer (170) is formed thereon, and then depositing a material usable as a cathode thereon can manufacture an organic electroluminescent device according to an embodiment of the present invention.

In addition, an emission auxiliary layer (151) may be further formed between the hole transport layer (140) and the emitting layer (150), and an electron transport auxiliary layer may be further formed between the emitting layer (150) and the electron transport layer (160).

The present invention may further include a light efficiency enhancing layer formed on at least one of the opposite side to the organic material layer among one side of the first electrode, or one of the opposite side to the organic material layer among one side of the second electrode.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

The compound represented by Formula 1 may be comprised in the organic material layer, and in at least one layer of a hole injection layer, a hole transport layer, an emission auxiliary layer and the emitting layer, and the compound may be included as a single compound or a mixture of two or more different kinds.

As another specific example, the present invention provides an organicelectric element wherein the emitting layer of the organic material layeris a phosphorescent light emitting layer. For example, compound of the present invention may be used as material of a light emitting layer 150, a hole transport layer 140 and/or an emission-auxiliary layer 151, preferably, as host material of a light emitting layer 150, more preferably, as phosphorescent red host material.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R(Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the present invention provides an electronic device including a display device which includes the above described organic electric element, and a control unit for controlling the display device.

Another embodiment of the present invention provides an electronic device including the organic electric element, wherein the organic electric element may be any one of an organic light emitting diode, an organic solar cell, an organic photo conductor, an organic transistor, and an element for monochromatic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula 1 and 2 according to the present invention and preparation examples of the organic electric element will be described in detail by way of example, but are not limited to the following examples of the invent ion.

Synthesis Example

The compound (final products) according to the present invention can be synthesized by reacting according to the following method, but are not limited thereto.

<Reaction Scheme 1>

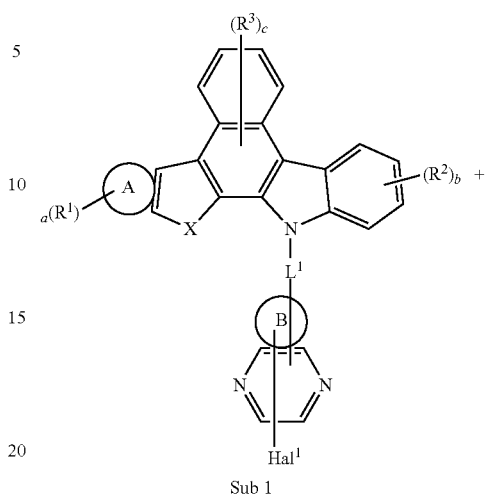

Sub 1

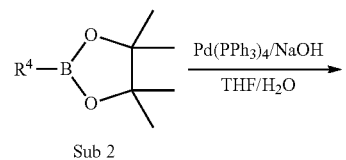

Sub 2

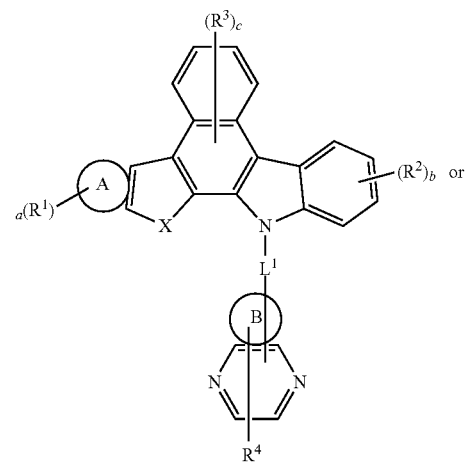

Final Product

-continued

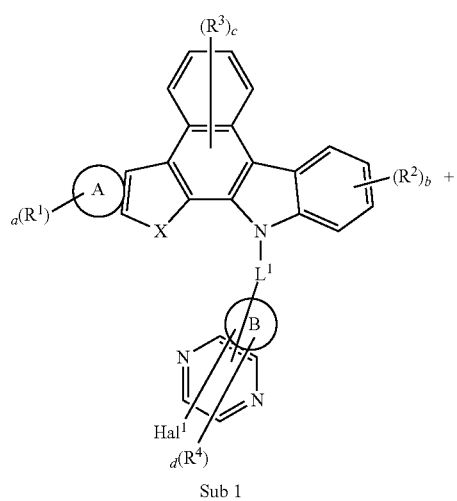
Sub 1

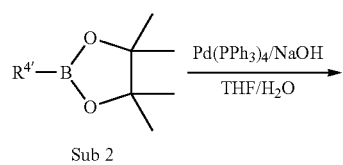
Sub 2

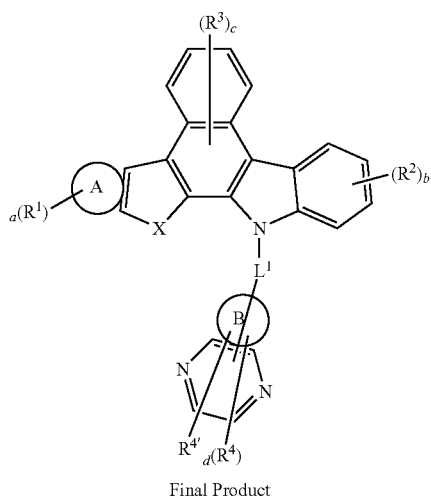
Final Product

Hal¹ = Cl, Br

R⁴' can be the same as the definition of R⁴, and R⁴' meanses a substituent which is the same as R⁴ or different from R⁴.

I. Synthesis of Sub 1

Sub 1 of the Reaction Scheme 1 can be synthesized according to, but not limited to, the reaction route of the following Reaction Scheme 2 and Reaction Scheme 3.

<Reaction Scheme 2>

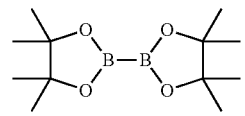

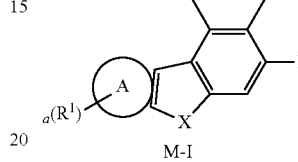
M-I

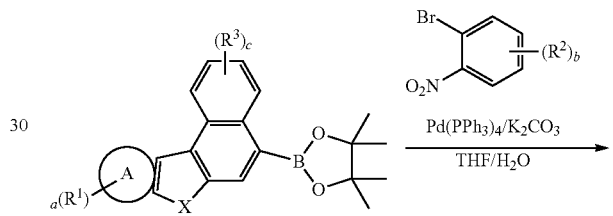
Sub 1-I

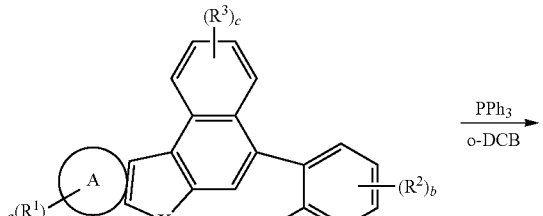
Sub 1-II

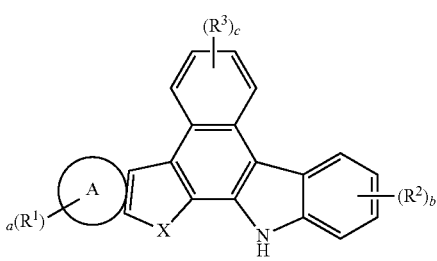
Sub 1-III

<Reaction Scheme 3>
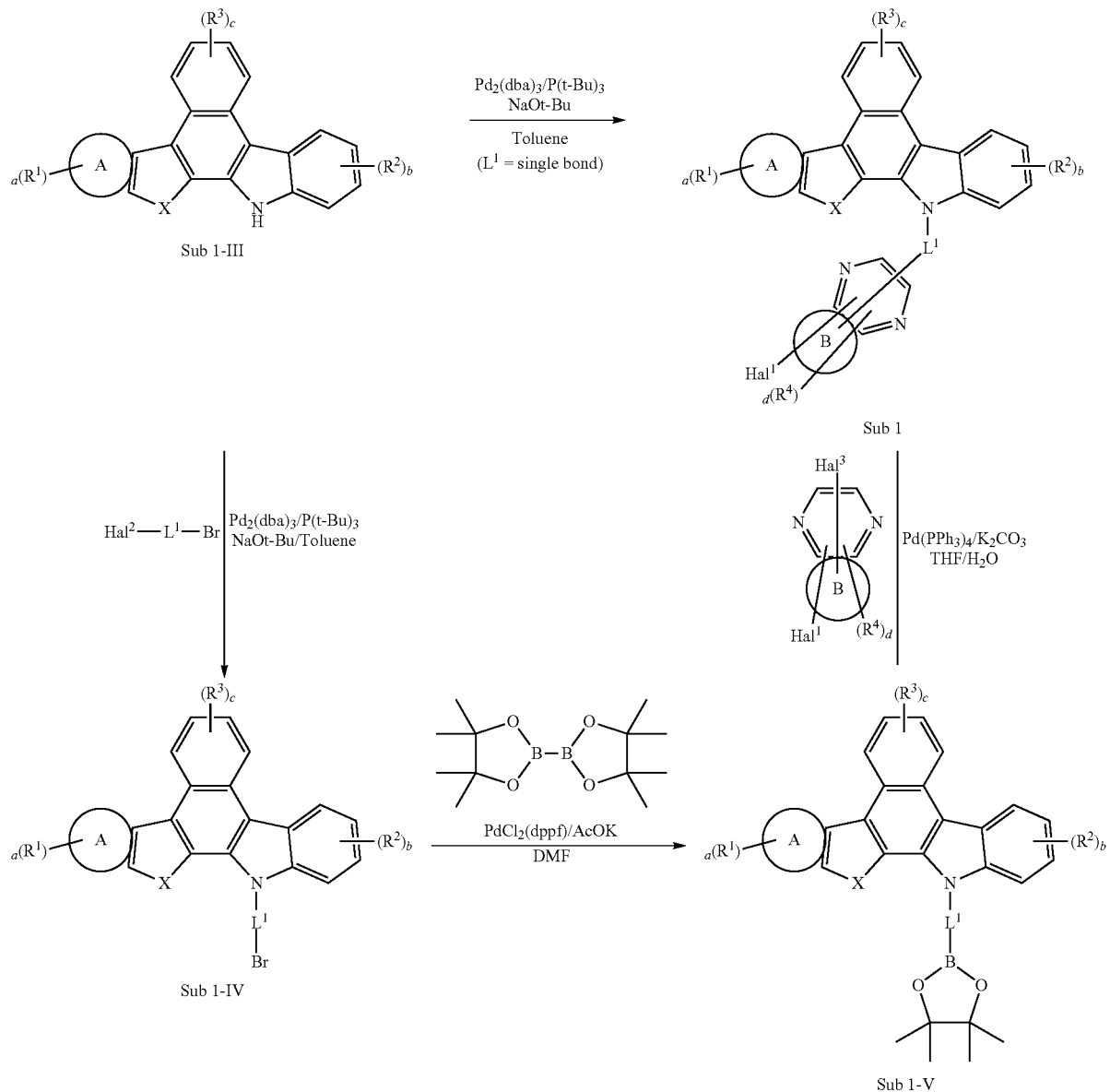
Hal² = I, Br
Hal¹, Hal³ = Cl, Br
In the above reaction scheme 1, the reactants of
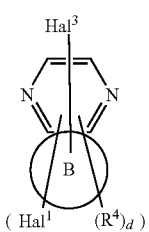
were synthesized by referring to four literatures as follows.
1) The synthesis method disclosed in Korean Patent No. 10-1488560 (Registered on Feb. 3, 2013) filed by Doosan Corporation was used, (See Reaction Scheme A)
<Reaction Scheme A>
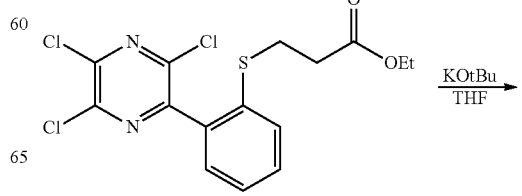

-continued

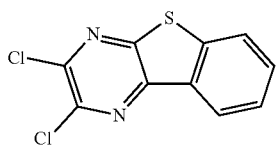

2) The synthesis method disclosed in international published patent PCT/EP2015/068240 (First priority Filing date: Aug. 8, 2014) filed by BASF was used. (See Reaction Scheme B)

<Reaction Scheme B>

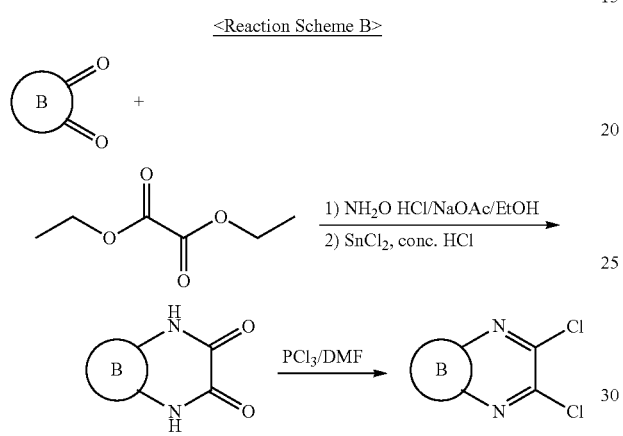

3) The synthesis method disclosed in Chinese Publishe Patent No. 2016-10316704 filed by Soochow University (filed on May 15, 2013) was used. <See Reaction Scheme C>

<Reaction Scheme C>

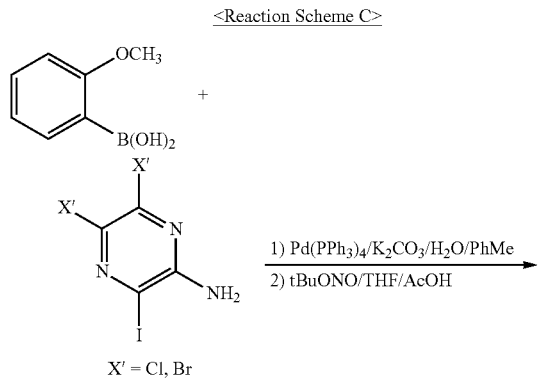

X' = Cl, Br

4) The synthesis method disclosed in Korean Laid-Open Patent Publication No. 2015-0130953 (First priority Filing date: Dec. 5, 2014) filed by LG Display Co., Ltd. was used. <See Synthesis of compound 6>

Synthesis Examples of compounds comprised in Sub 1 are as follows.

Synthesis Example of M-I

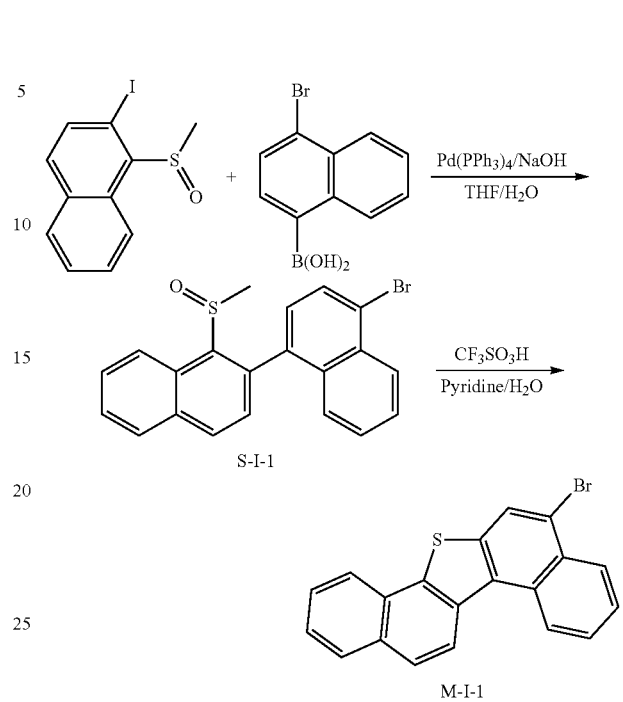

1) Synthesis of S-I-1

(4-bromonaphthalen-1-yl)boronic acid (28 g, 111.6 mmol) was dissolved in THF (491 ml) in a round bottom flask, then 2-iodo-1-(methylsulfinyl)naphthalene (35.28 g, 111.6 mmol), Pd(PPh$_3$)$_4$ (1.93 g, 1.67 mmol), NaOH (6.70 g, 167.40 mmol) and water (246 ml) were added and stirred at 80° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 30 g (yield: 68%) of the product.

2) Synthesis of M-I-1

S-I-1 (30 g, 75.89 mmol) obtained in the above synthesis was added into a round bottom flask together with triflic acid (100.7 ml, 1138.35 mmol) and stirred at room temperature for 24 hours. Then, a pyridine aqueous solution (1329 ml, pyridine:H$_2$O=1:5) was slowly added dropwise, refluxed and stirred for 30 minutes. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 21.8 g (yield: 79%) of the product.

Synthesis of M-I-2

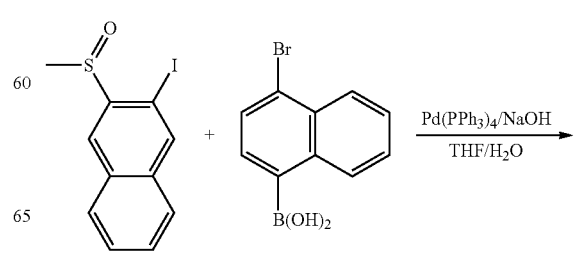

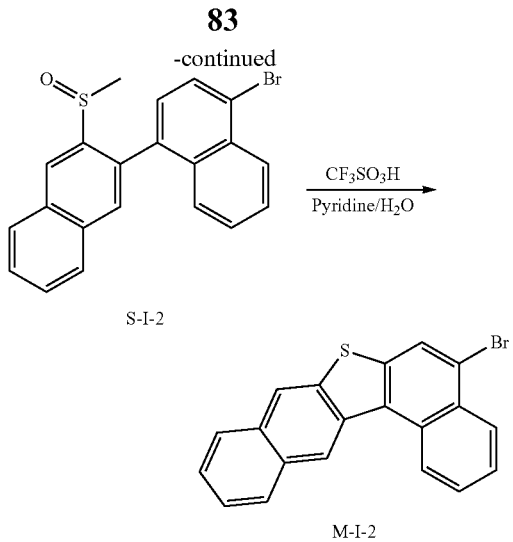

S-I-2

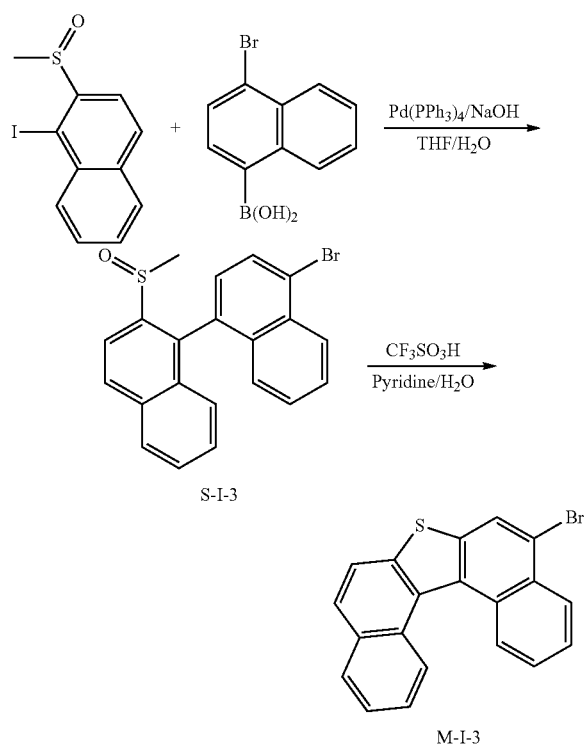

S-I-3

M-I-3

1) Synthesis of S-I-2

30.16 g (yield: 66%) of the product was obtained by using (4-bromonaphthalen-1-yl)boronic acid (29 g, 115.59 mmol), THF (509 ml), 2-iodo-3-(methylsulfinyl)naphthalene (36.54 g, 115.59 mmol), Pd(PPh$_3$)$_4$ (2 g, 1.73 mmol), NaOH (6.94 g, 173.38 mmol), and water (254 ml) in the same manner as described above for the synthesis of S-I-1.

2) Synthesis of M-I-2

20.1 g (yield: 73%) of the product was obtained by using S-I-2 (30 g, 75.89 mmol) obtained in the above synthesis, triflic acid (100.7 ml, 1138.35 mmol), pyridine aqueous solution (1329.6 ml, pyridine: H$_2$O=1:5) in the same manner as described above for the synthesis of M-I-1.

Synthesis of M-I-3

1) Synthesis of S-I-3

30.77 g (yield: 63%) of the product was obtained by using (4-bromonaphthalen-1-yl)boronic acid (31 g, 123.56 mmol), THF (543 ml), 1-iodo-2-(methylsulfinyl)naphthalene (31 g, 123.56 mmol), Pd(PPh$_3$)$_4$ (2.14 g, 1.85 mmol), NaOH (7.41 g, 185.34 mmol), and water (272 ml) in the same manner as described above for the synthesis of S-I-1.

2) Synthesis of M-I-3

20.7 g (yield: 75%) of the product was obtained by using S-I-3 (30 g, 75.89 mmol) obtained in the above synthesis, triflic acid (100.7 ml, 1138.35 mmol), pyridine aqueous solution (1329.6 ml, pyridine: H$_2$O=1:5) in the same manner as described above for the synthesis of M-I-1.

Synthesis of M-I-4

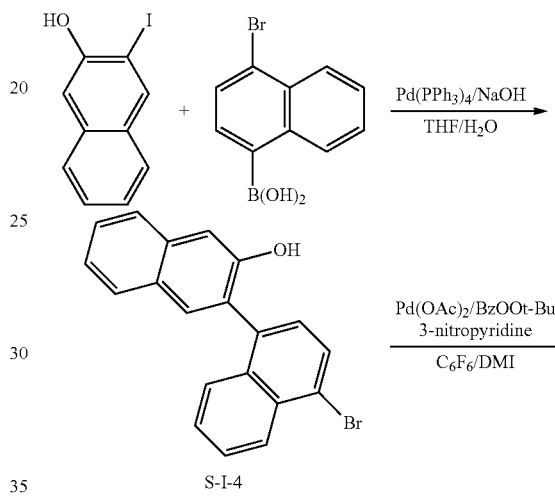

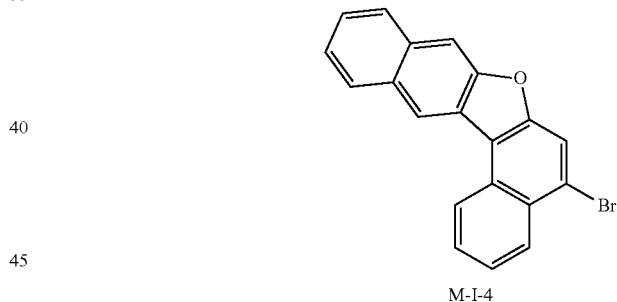

S-I-4

M-I-4

1) Synthesis of S-I-4

30.29 g (yield: 64%) of the product was obtained by using (4-bromonaphthalen-1-yl)boronic acid (34 g, 135.52 mmol), THF (596 ml), 3-iodonaphthalen-2-ol (36.60 g, 135.52 mmol), Pd(PPh$_3$)$_4$ (2.35 g, 2.03 mmol), NaOH (8.13 g, 203.28 mmol), and water (298 ml) in the same manner as described above for the synthesis of S-I-1.

2) Synthesis of M-I-4

The starting material S-I-4 (30 g, 85.90 mmol) was added into a round bottom flask together with Pd(OAc)$_2$ (1.93 g, 8.59 mmol), 3-nitropyridine (1.07 g, 8.59 mmol) and dissolved in C$_6$F$_6$ (128.9 ml) and DMI (85.9 ml). Then, tert-butyl peroxybenzoate (33.37 g, 171.81 mmol) was added and stirred at 90° C. When the reaction was completed, the reaction product was extracted with CH$_2$Cl$_2$ and water, and then the organic layer was dried with MgSO$_4$ and concentrated. Then, the concentrate was passed through silica gel column and recrystallized to obtain 21.18 g (yield: 71%) of product.

Synthesis of M-I-5

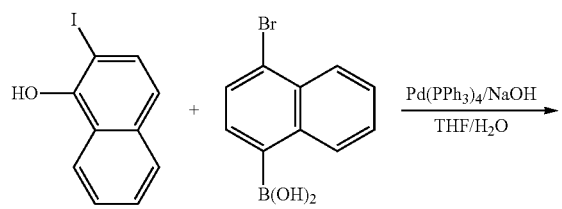

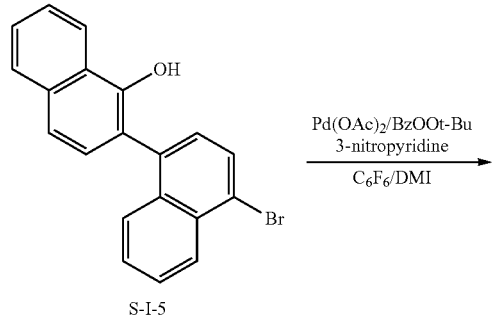

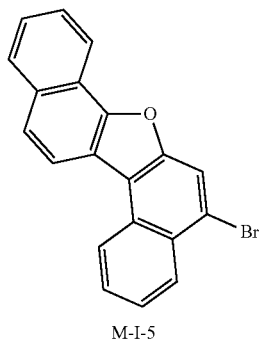

M-I-5

1) Synthesis of S-I-5

30.21 g (yield: 62%) of the product was obtained by using (4-bromonaphthalen-1-yl)boronic acid (35 g, 139.50 mmol), THF (614 ml), 2-iodonaphthalen-1-ol (37.68 g, 139.50 mmol), Pd(PPh$_3$)$_4$ (2.42 g, 2.09 mmol), NaOH (8.37 g, 209.26 mmol), and water (307 ml) in the same manner as described above for the synthesis of S-I-1.

2) Synthesis of M-I-5

22.07 g (yield: 74%) of the product was obtained by using S-I-5 (30 g, 85.90 mmol) obtained in the above synthesis, Pd(OAc)$_2$ (1.93 g, 8.59 mmol), 3-nitropyridine (1.07 g, 8.59 mmol), C$_6$F$_6$ (128.9 ml), DMI (85.9 ml), tert-butyl peroxybenzoate (33.37 g, 171.81 mmol) in the same manner as described above for the synthesis of M-I-4.

Synthesis of M-I-6

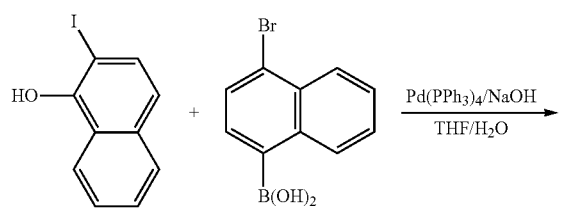

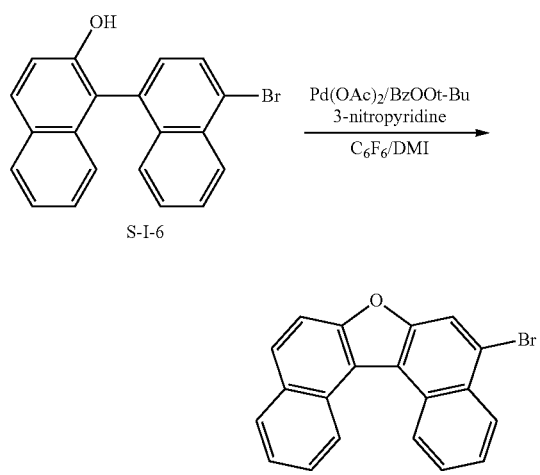

1) Synthesis of S-I-6

31.67 g (yield: 65%) of the product was obtained by using (4-bromonaphthalen-1-yl)boronic acid (35 g, 139.50 mmol), THF (614 ml), 1-iodonaphthalen-2-ol (37.68 g, 139.50 mmol), Pd(PPh$_3$)$_4$ (2.42 g, 2.09 mmol), NaOH (8.37 g, 209.26 mmol), and water (307 ml) in the same manner as described above for the synthesis of S-I-1.

2) Synthesis of M-I-6

22.67 g (yield: 76%) of the product was obtained by using S-I-6 (30 g, 85.90 mmol) obtained in the above synthesis, Pd(OAc)$_2$ (1.93 g, 8.59 mmol), 3-nitropyridine (1.07 g, 8.59 mmol), C$_6$F$_6$ (128.9 ml), DMI (85.9 ml), tert-butyl peroxybenzoate (33.37 g, 171.81 mmol) in the same manner as described above for the synthesis of M-I-4.

1. Synthesis example of Sub 1-1

<Reaction Scheme 4>

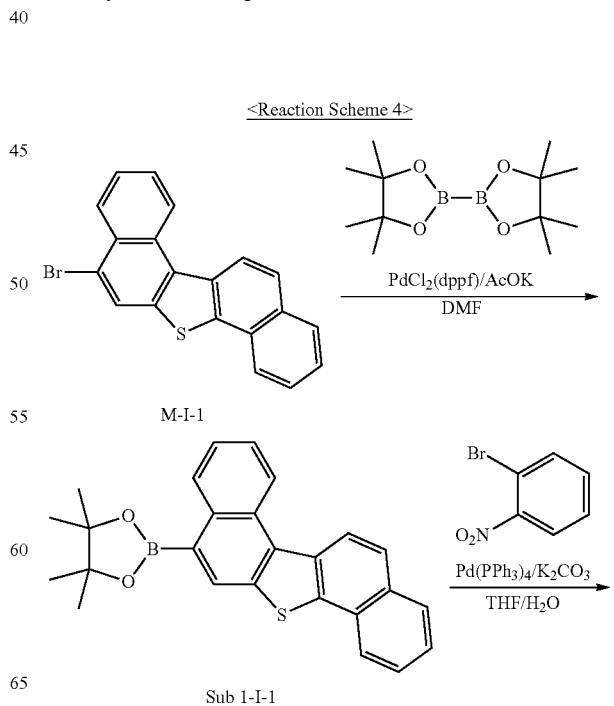

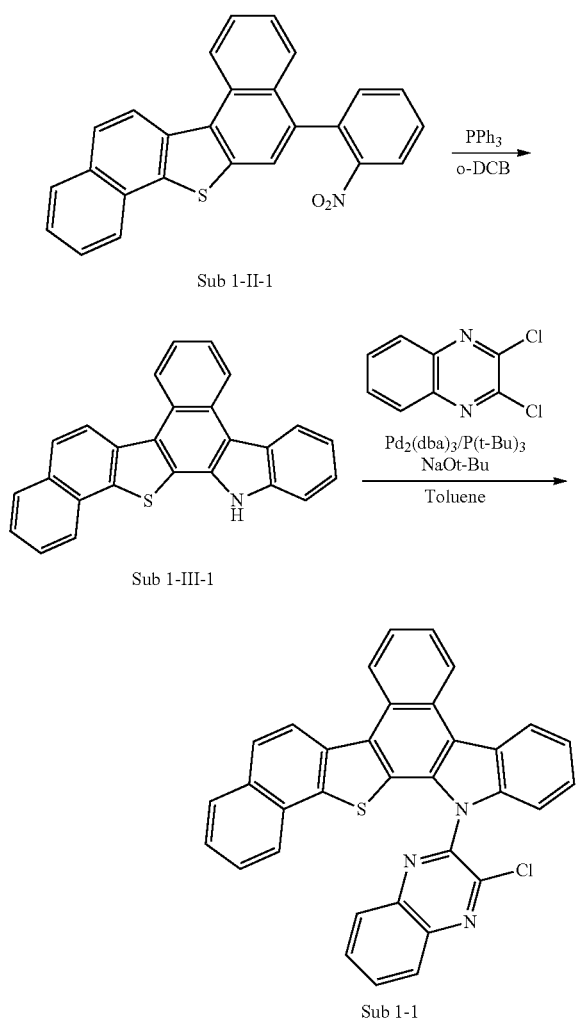

Sub 1-II-1

Sub 1-III-1

Sub 1-1

(1) Synthesis of Sub 1-I-1

The starting material M-I-1 (70 g, 192.69 mmol) was dissolved in DMF (1214 ml) in a round bottom flask, and then Bis(pinacolato)diboron (53.83 g, 211.96 mmol), Pd(dppf)Cl$_2$ (4.23 g, 5.78 mmol), KOAc (56.73 g, 578.08 mmol) were added and stirred at 90° C. When the reaction was completed, DMF was removed by distillation and the reaction product was extracted with CH$_2$Cl$_2$ and water. Then, the organic layer was dried with MgSO$_4$ and concentrated. Then, the concentrate was passed through silica gel column and recrystallized to obtain 64.05 g (yield: 81%) of the product.

(2) Synthesis of Sub 1-II-1

Sub 1-II-1 (63.2 g, 154.02 mmol) obtained in the above synthesis was dissolved in THF (216 ml) in a round bottom flask, and then 1-bromo-2-nitrobenzene (34.22 g, 169.42 mmol), Pd(PPh$_3$)$_4$ (4.23 g, 4.62 mmol), K$_2$CO$_3$ (44.40 g, 462.06 mmol), water (108 ml) were added and stirred at 80° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 45.59 g (yield: 73%) of the product.

(3) Synthesis of Sub 1-III-1

Sub 1-II-1 (45.50, 112.22 mmol) obtained in the above synthesis was dissolved in o-dichlorobenzene (224 ml) in a round bottom flask, and then triphenylphosphine (88.30 g, 336.65 mmol) was added and stirred at 200° C. When the reaction was completed, o-dichlorobenzene was removed by distillation and, and then the reaction product was extracted with CH$_2$Cl$_2$ and water. Then, the organic layer was dried with MgSO$_4$ and concentrated. Then, the concentrate was passed through silica gel column and recrystallized to obtain 31.85 g (yield: 76%) of the product.

(4) Synthesis of Sub 1-1

Sub 1-III-1 (30 g, 80.33 mmol) obtained in the above synthesis was dissolved in toluene (843 ml) in a round bottom flask, and then 2,3-dichloroquinoxaline (15.99 g, 80.33 mmol), Pd$_2$(dba)$_3$ (1.1 g, 1.2 mmol), P(t-Bu)$_3$ (0.81 g, 4.02 mmol), NaOt-Bu (11.58 g, 120.49 mmol) were added and stirred at 100° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 17.65 g (yield: 41%) of the product.

2. Synthesis example of Sub 1-4

<Reaction Scheme 4>

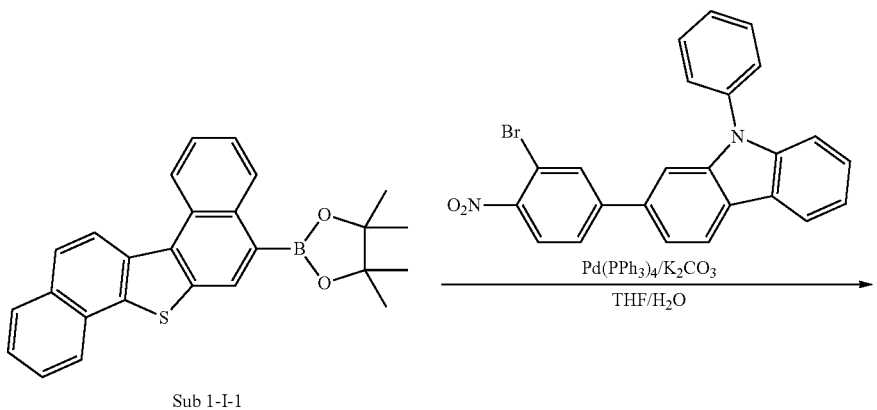

Sub 1-I-1

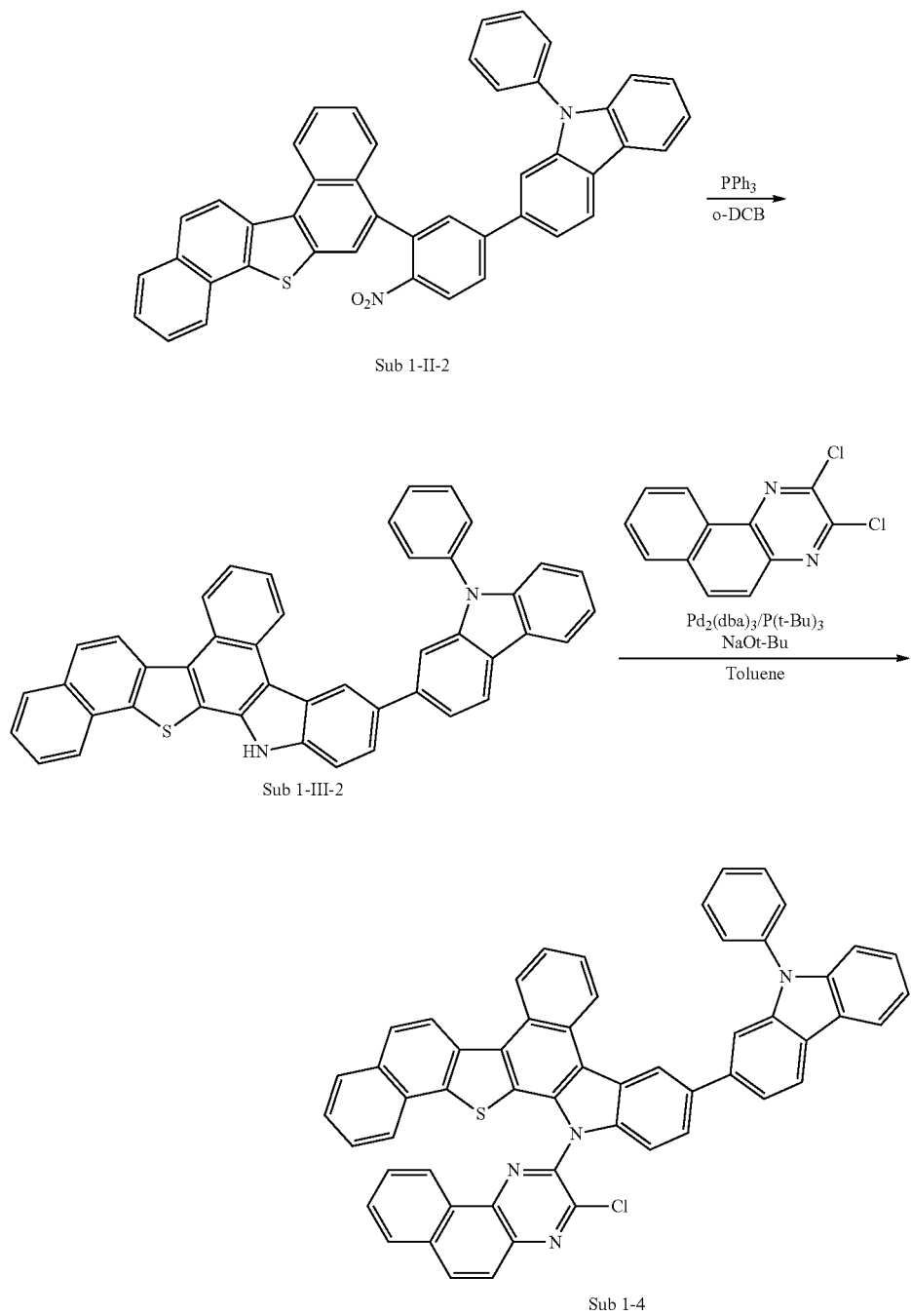

(1) Synthesis of Sub 1-II-2

2-(3-bromo-4-nitrophenyl)-9-phenyl-9H-carbazole (44.29 g, 99.92 mmol), Pd(PPh$_3$)$_4$ (3.46 g, 3.00 mmol), K$_2$CO$_3$ (41.43 g, 299.75 mmol), THF (440 ml), water (220 ml) were added to Sub 1-I-1 (41 g, 99.92 mmol) obtained in the above synthesis, and then 47.82 g (yield: 74%) of the product was obtained by carring out in the same manner as described above for the synthesis of Sub 1-II-1.

(2) Synthesis of Sub 1-III-2

Triphenylphosphine (57.18 g, 218.01 mmol), o-dichlorobenzene (145 ml) were added to Sub 1-II-2 (47 g, 72.67 mmol) obtained in the above synthesis, and then 28.15 g (yield: 63%) of the product was obtained by carring out in the same manner as described above for the synthesis of Sub 1-III-1.

(3) Synthesis of Sub 1-4

2,3-dichlorobenzo[f]quinoxaline (12.48 g, 50.10 mmol), Pd$_2$(dba)$_3$ (1.25 g, 1.37 mmol), P(t-Bu)$_3$ (0.74 g, 3.64 mmol), NaOt-Bu (13.13 g, 136.64 mmol), toluene (228 ml) were added to Sub 1-III-2 (28 g, 45.55 mmol) obtained in the above synthesis, and then 15.07 g (yield: 40%) of the product was obtained by carring out in the same manner as described above for the synthesis of Sub 1-1.

3. Synthesis example of Sub 1-10

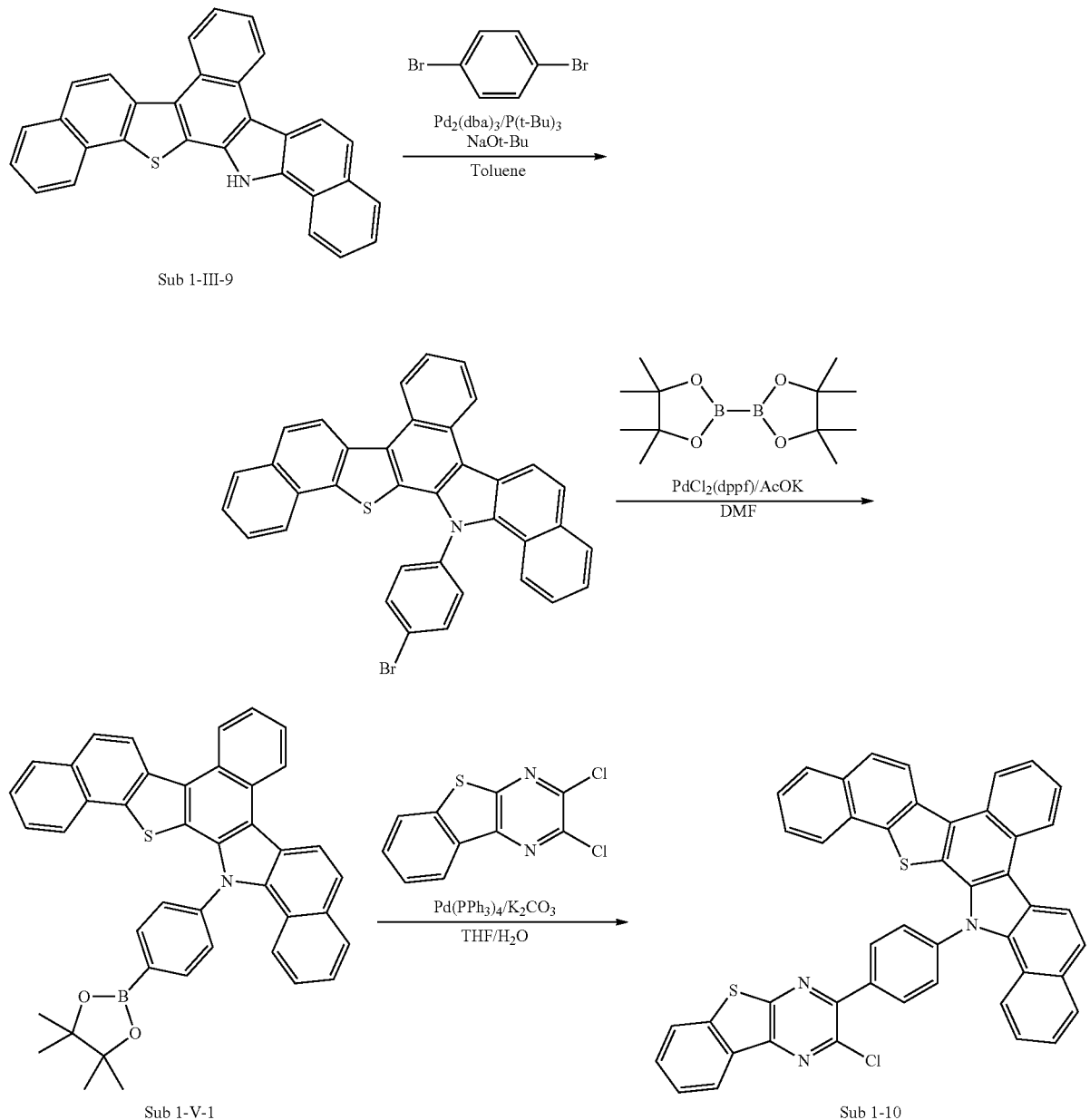

(1) Synthesis of Sub 1-IV-1

1,4-dibromobenzene (17.16 g, 72.72 mmol), $Pd_2(dba)_3$ (0.91 g, 0.99 mmol), $P(t-Bu)_3$ (0.67 g, 3.31 mmol), NaOt-Bu (9.53 g, 99.17 mmol), toluene (694 ml) were added to Sub 1-III-9 (28 g, 66.11 mmol) obtained in the above synthesis, and then 27.16 g (yield: 71%) of the product was obtained by carring out in the same manner as described above for the synthesis of Sub 1-1.

(2) Synthesis of Sub 1-V-1

Sub 1-IV-1 (27.16 g, 46.95 mmol) obtained in the above synthesis was dissolved in toluene (140 ml) in a round bottom flask, and Bis(pinacolato)diboron (13.11 g, 51.64 mmol), $Pd(dppf)Cl_2$ (1.03 g, 1.41 mmol), KOAc (13.82 g, 140.84 mmol) were added, then, stirring at 120° C. was followed. When the reaction was completed, DMF was removed by distillation, and the reaction product was extracted with $CH_2Cl_2$ and water, and then the organic layer was dried with $MgSO_4$ and concentrated. Then, the concentrate was passed through silica gel column and recrystallized to obtain 22.03 g (yield: 75%) of product.

(3) Synthesis of Sub 1-10

2,3-dichlorobenzo[4,5]thieno[2,3-b]pyrazine (8.98 g, 35.21 mmol), $Pd(PPh_3)_4$ (0.61 g, 0.53 mmol), $K_2CO_3$ (7.30 g, 52.82 mmol), THF (155 ml), water (77.47 ml) were added to Sub 1-V-1 (22.03 g, 35.21 mmol) obtained in the above synthesis, and then 9.61 g (yield: 38%) of the product was obtained by carring out in the same manner as described above for the synthesis of Sub 1-II-1.

4. Synthesis example of Sub 1-24
<Reaction Scheme 4>
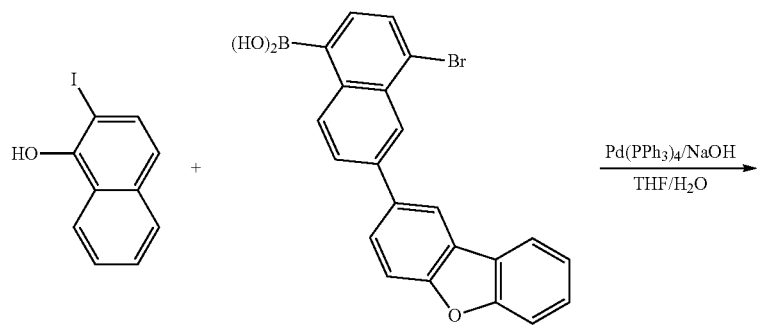
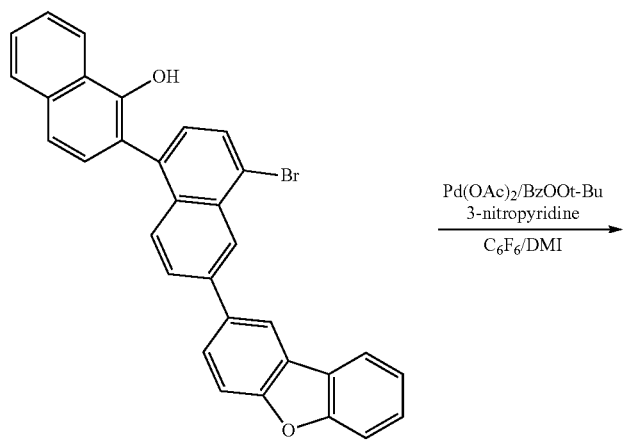
S-I-7
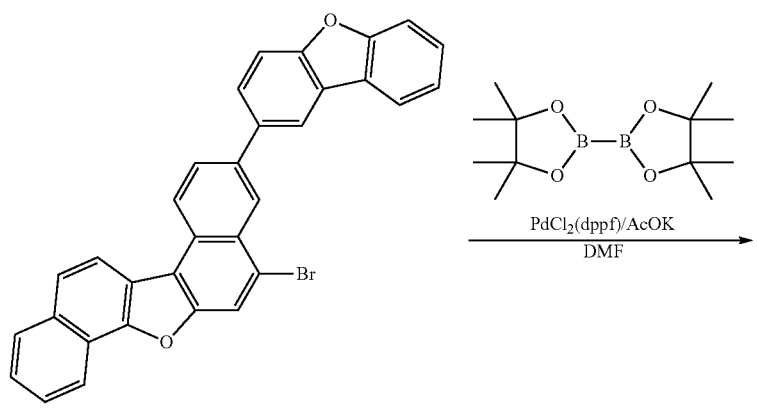
M-I-7

-continued
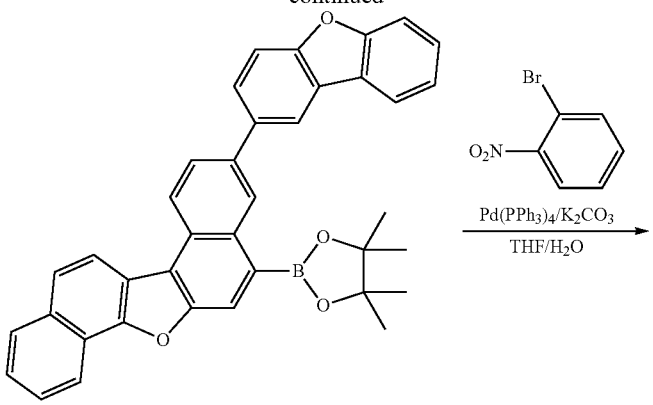
Sub 1-I-3
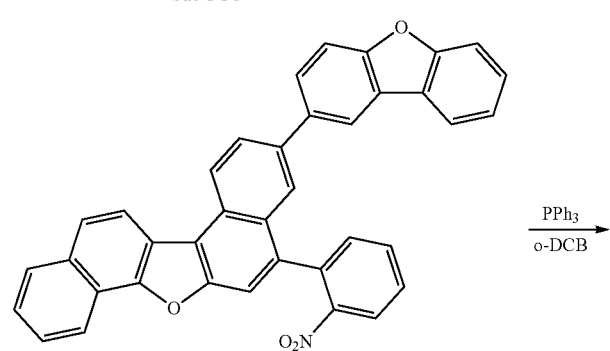
Sub 1-II-3
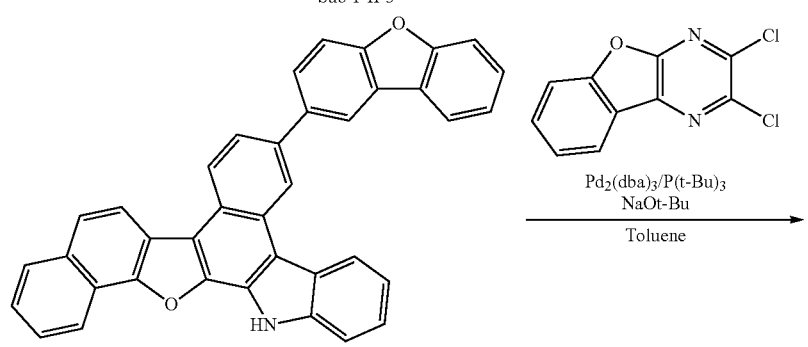
Sub 1-III-3
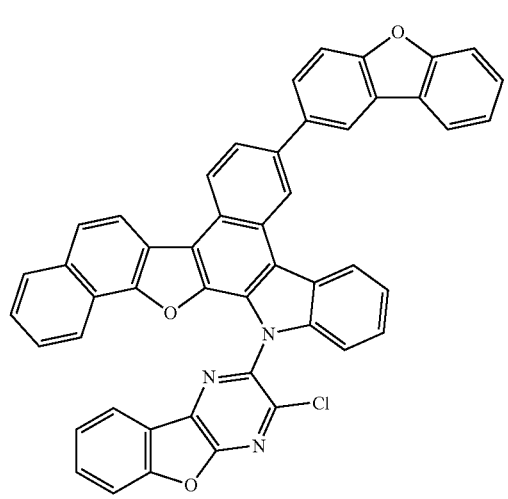
Sub 1-24

1) Synthesis of S-I-7

86.51 g (yield: 70%) of the product was obtained by using (4-bromo-6-(dibenzo[b,d]furan-2-yl)naphthalen-1-yl)boronic acid (100 g, 239.77 mmol), THF (1055 ml), 2-iodonaphthalen-1-ol (64.75 g, 239.77 mmol), Pd(PPh$_3$)$_4$ (4.16 g, 3.60 mmol), NaOH (14.39 g, 359.65 mmol), and water (527 ml) in the same manner as described above for the synthesis of S-I-1.

2) Synthesis of M-I-7

The starting material S-I-7 (86 g, 166.86 mmol) was added into a round bottom flask together with Pd(OAc)$_2$ (3.75 g, 16.69 mmol), 3-nitropyridine (2.07 g, 16.69 mmol) and dissolved in C$_6$F$_6$ (250 ml) and DMI (167 ml). Then, tert-butyl peroxybenzoate (64.82 g, 333.71 mmol) was added and stirred at 90° C. When the reaction was completed, the reaction product was extracted with CH$_2$Cl$_2$ and water, and then the organic layer was dried with MgSO$_4$ and concentrated. Then, the concentrate was passed through silica gel column and recrystallized to obtain 62.53 g (yield: 73%) of product.

3) Synthesis of Sub 1-I-3

51.86 g (yield: 76%) of the product was obtained by using M-I-7 (62.50 g, 121.74 mmol) obtained in the above synthesis, DMF (609 ml), Bis(pinacolato)diboron (34.01 g, 133.91 mmol), Pd(dppf)Cl$_2$ (2.67 g, 3.65 mmol), KOAc (35.84 g, 365.22 mmol) in the same manner as described above for the synthesis of Sub 1-V-1.

4) Synthesis of Sub 1-II-3

1-bromo-2-nitrobenzene (18.67 g, 92.42 mmol), Pd(PPh$_3$)$_4$ (3.2 g, 2.77 mmol), K$_2$CO$_3$ (38.32 g, 277.27 mmol), THF (407 ml), water (203 ml) were added to Sub 1-I-3 (51.8 g, 92.42 mmol) obtained in the above synthesis, and then 43.13 g (yield: 84%) of the product was obtained by carring out in the same manner as described above for the synthesis of Sub 1-II-1.

5) Synthesis of Sub 1-III-3

Triphenylphosphine (60.9 g, 232.19 mmol), o-dichlorobenzene (155 ml) were added to Sub 1-II-3 (43 g, 77.4 mmol) obtained in the above synthesis, and then 31.61 g (yield: 78%) of the product was obtained by carring out in the same manner as described above for the synthesis of Sub 1-III-1.

6) Synthesis of Sub 1-24

2,3-dichlorobenzofuro[2,3-b]pyrazine (15.88 g, 66.41 mmol), Pd$_2$(dba)$_3$ (1.66 g, 1.81 mmol), P(t-Bu)$_3$ (0.98 g, 4.83 mmol), NaOt-Bu (17.41 g, 181.11 mmol), toluene (302 ml) were added Sub 1-III-3 (31.61 g, 60.37 mmol) obtained in the above synthesis, and then 18.41 g (yield: 42%) of the product was obtained by carring out in the same manner as described above for the synthesis of Sub 1-1.

5. Synthesis example of Sub 1-41

<Reaction Scheme 4>

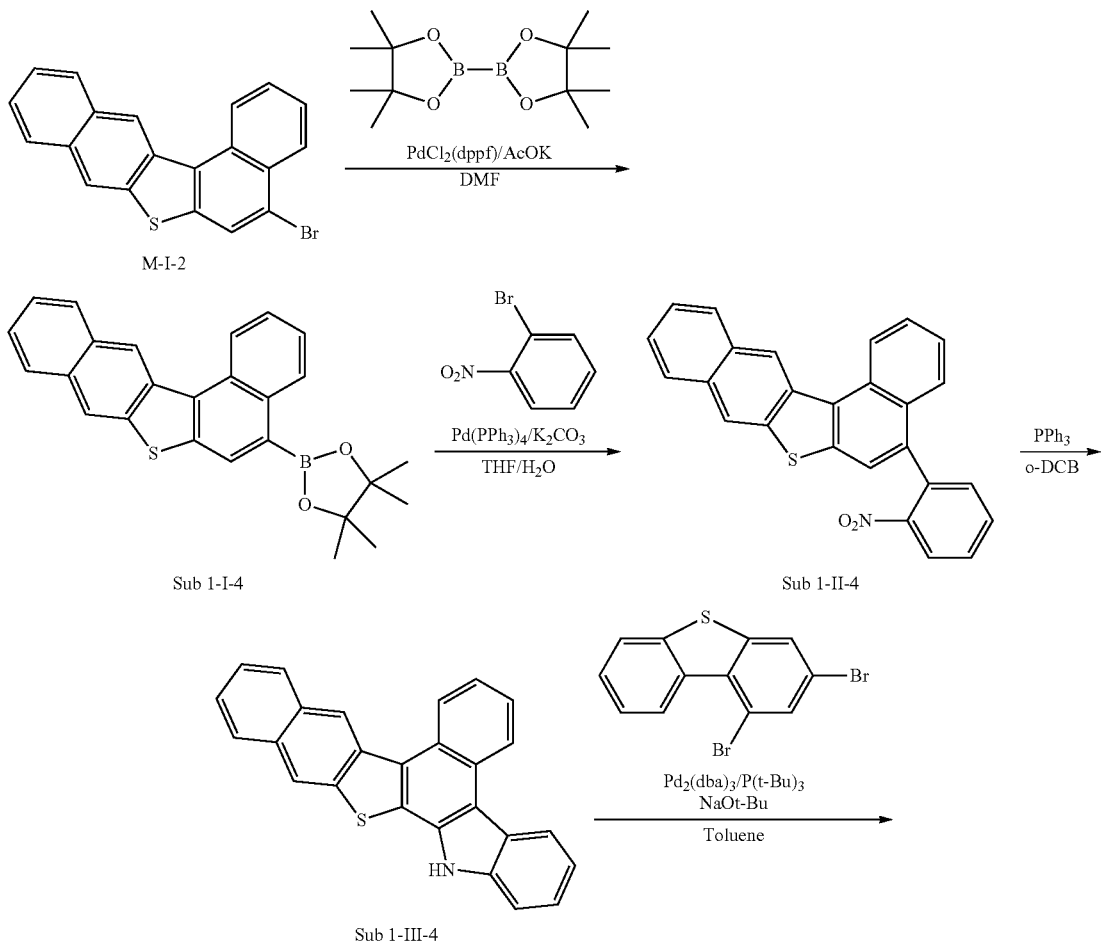

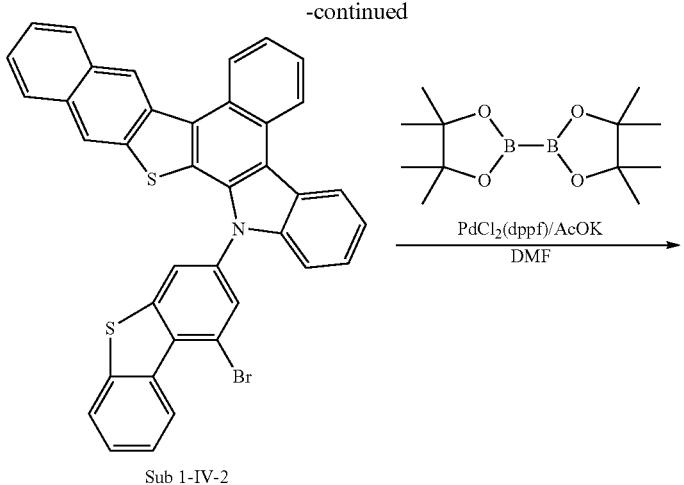

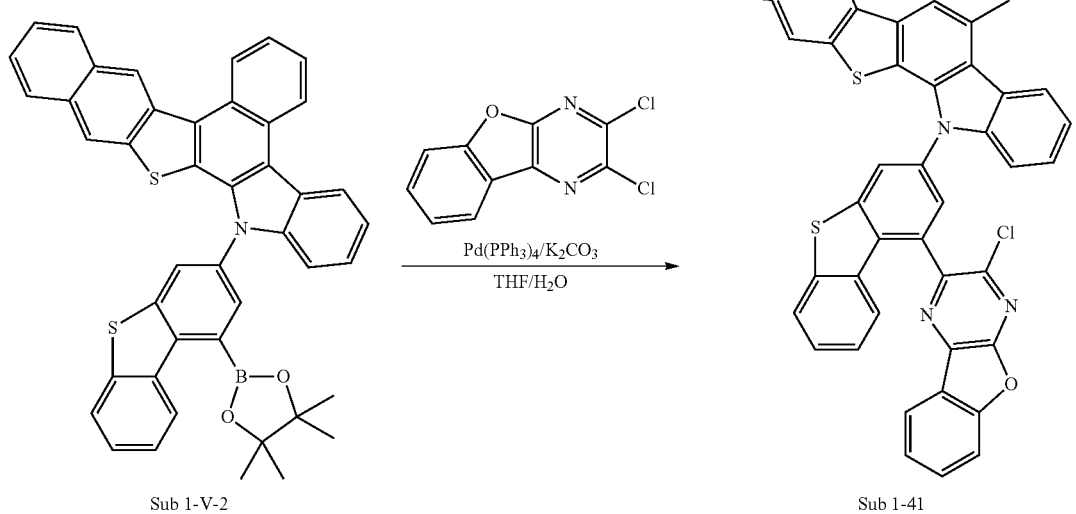

1) Synthesis of Sub 1-I-4

93.70 g (yield: 79%) of the product was obtained by using M-I-2 (105 g, 289.04 mmol) obtained in the above synthesis, DMF (1445 ml), Bis(pinacolato)diboron (80.74 g, 317.95 mmol), Pd(dppf)Cl$_2$ (6.34 g, 8.67 mmol), KOAc (85.10 g, 867.12 mmol) in the same manner as described above for the synthesis of Sub 1-V-1.

2) Synthesis of Sub 1-II-4

1-bromo-2-nitrobenzene (45.78 g, 226.64 mmol), Pd(PPh$_3$)$_4$ (7.86 g, 6.80 mmol), K$_2$CO$_3$ (93.97 g, 679.92 mmol), THF (997 ml), water (498 ml) were added to M-I-4 (93 g, 226.64 mmol) obtained in the above synthesis, and then 76.27 g (yield: 83%) of the product was obtained by carring out in the same manner as described above for the synthesis of Sub 1-II-1.

3) Synthesis of Sub 1-III-4

Triphenylphosphine (147.49 g, 562.31 mmol), o-dichlorobenzene (375 ml) were added to Sub 1-II-4 (76 g, 187.44 mmol) obtained in the above synthesis, and then 53.20 g (yield: 76%) of the product was obtained by carring out in the same manner as described above for the synthesis of Sub 1-III-1.

4) Synthesis of Sub 1-IV-2

1,3-dibromodibenzo[b,d]thiophene (48.54 g, 141.91 mmol), Pd$_2$(dba)$_3$ (1.95 g, 2.13 mmol), P(t-Bu)$_3$ (1.44 g, 7.10 mmol), NaOt-Bu (20.46 g, 212.87 mmol), toluene (1490 ml) were added to Sub 1-III-4 (53 g, 141.91 mmol) obtained in the above synthesis, and then 32.42 g (yield: 36%) of the product was obtained by carring out in the same manner as described above for the synthesis of Sub 1-1.

5) Synthesis of Sub 1-V-2

25.09 g (yield: 73%) of the product was obtained by using Sub 1-IV-2 (32 g, 50.42 mmol) obtained in the above synthesis, DMF (252 ml), Bis(pinacolato)diboron (14.09 g, 55.47 mmol), Pd(dppf)Cl$_2$ (1.11 g, 1.51 mmol), KOAc (14.85 g, 151.27 mmol) in the same manner as described above for the synthesis of Sub 1-V-1.

6) Synthesis of Sub 1-II-4

2,3-dichlorobenzofuro[2,3-b]pyrazine (8.77 g, 36.67 mmol), Pd(PPh$_3$)$_4$ (0.64 g, 0.55 mmol), K$_2$CO$_3$ (7.60 g, 55.01 mmol), THF (161 ml), water (80 ml) were added to Sub 1-V-2 (25 g, 36.67 mmol) obtained in the above synthesis, and then 11.40 g (yield: 41%) of the product was obtained by carring out in the same manner as described above for the synthesis of Sub 1-II-1.

6. Synthesis example of Sub 1-18

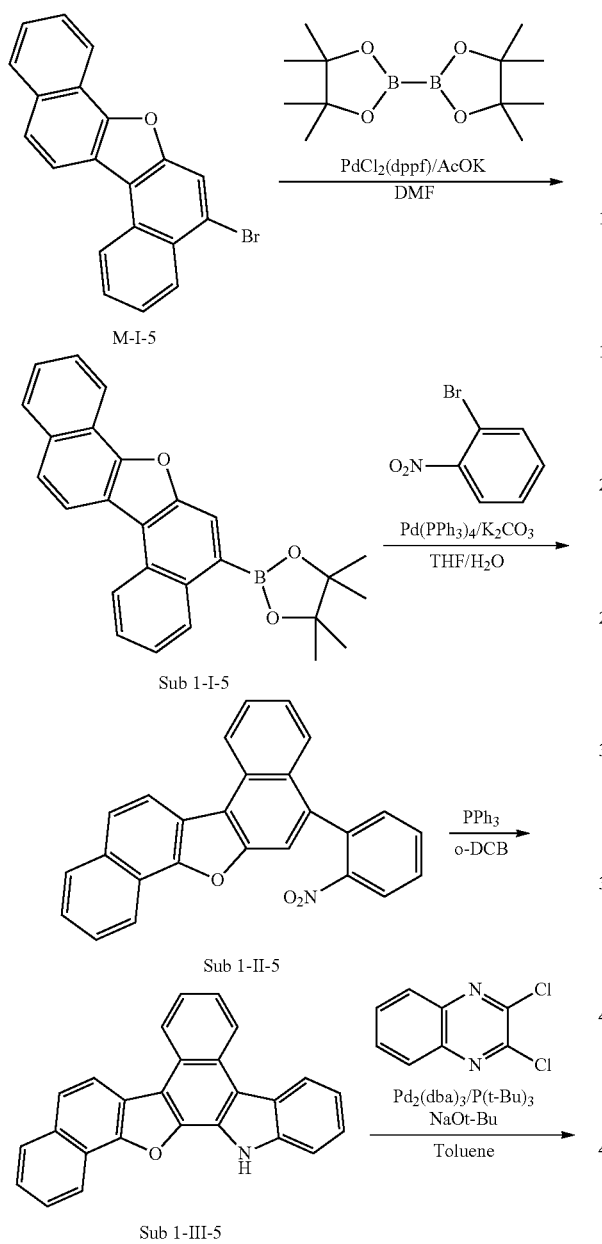

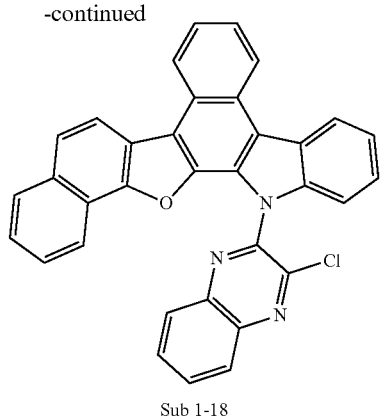

Sub 1-18

1) Synthesis of Sub 1-I-5

17.91 g (yield: 83%) of the product was obtained by using M-I-5 (19 g, 54.72 mmol) obtained in the above synthesis, DMF (274 ml), Bis(pinacolato)diboron (15.29 g, 60.19 mmol), Pd(dppf)Cl$_2$ (1.20 g, 1.64 mmol), KOAc (16.11 g, 164.17 mmol) in the same manner as described above for the synthesis of Sub 1-V-1.

2) Synthesis of Sub 1-II-5

1-bromo-2-nitrobenzene (8.71 g, 43.12 mmol), Pd(PPh$_3$)$_4$ (1.49 g, 1.29 mmol), K$_2$CO$_3$ (17.88 g, 129.35 mmol), THF (189 ml), water (95 ml) were added to M-I-5 (17 g, 43.12 mmol) obtained in the above synthesis, and then 14.61 g (yield: 87%) of the product was obtained by carring out in the same manner as described above for the synthesis of Sub 1-II-1.

3) Synthesis of Sub 1-III-5

Triphenylphosphine (29.30 g, 111.71 mmol), o-dichlorobenzene (74 ml)triphenylphosphine (29.30 g, 111.71 mmol), o-dichlorobenzene (74 ml) were added to Sub 1-II-5 (14.5 g, 37.24 mmol) obtained in the above synthesis, and then 10.65 g (yield: 80%) of the product was obtained by carring out in the same manner as described above for the synthesis of Sub 1-III-1.

4) Synthesis of Sub 1-18

2,3-dichloroquinoxaline (5.85 g, 29.38 mmol), Pd$_2$(dba)$_3$ (0.40 g, 0.44 mmol), P(t-Bu)$_3$ (0.30 g, 1.47 mmol), NaOt-Bu (4.23 g, 44.07 mmol), toluene (308 ml) were added to Sub 1-III-5 (10.5 g, 29.38 mmol) obtained in the above synthesis, and then 11 g (yield: 72%) of the product was obtained by carring out in the same manner as described above for the synthesis of Sub 1-1.

7. Synthesis example of Sub 1-44

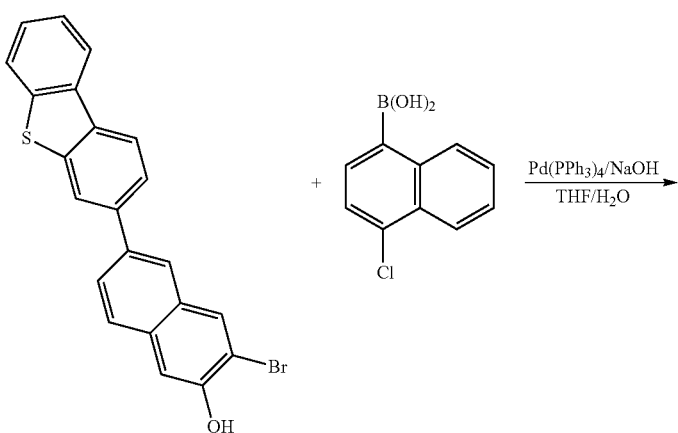

-continued
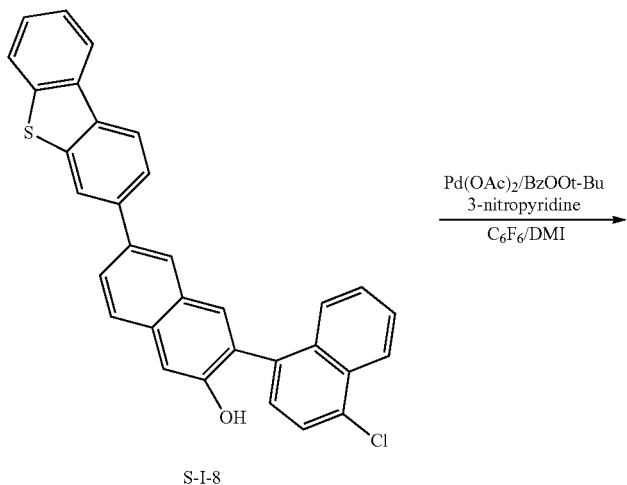
S-I-8
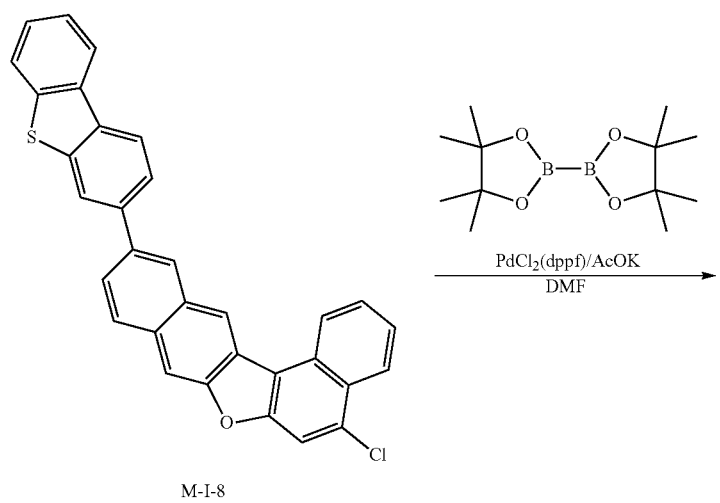
M-I-8
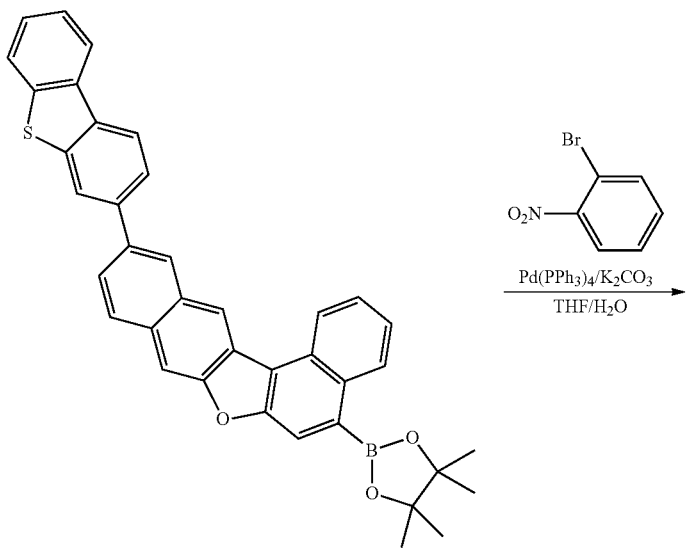
Sub 1-I-6

-continued
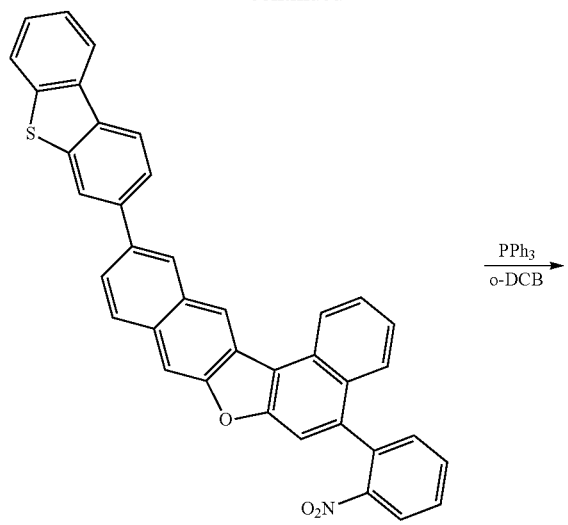
Sub 1-II-6
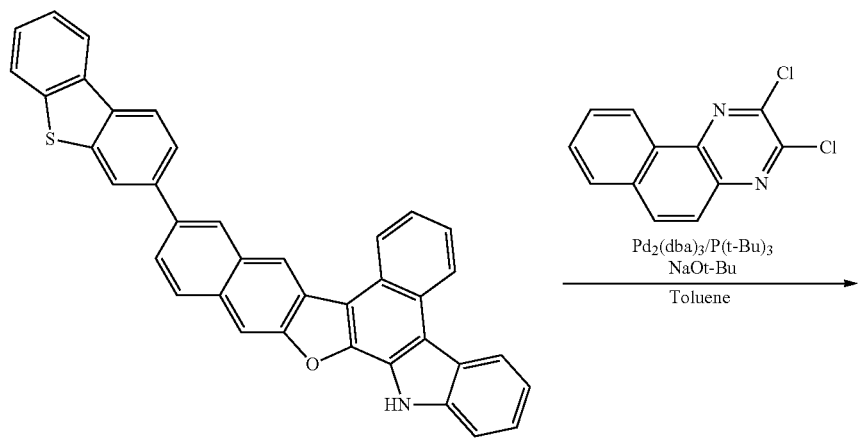
Sub 1-III-6
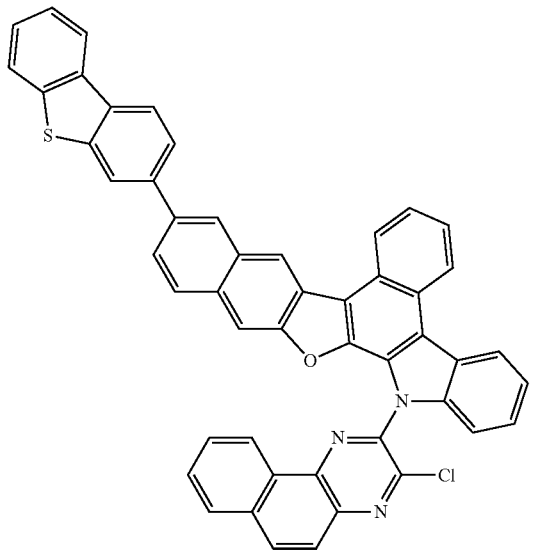
Sub 1-44

1) Synthesis of S-I-8

(4-chloronaphthalen-1-yl)boronic acid (31.07 g, 150.5 mmol), THF (662 ml), 3-bromo-6-(dibenzo[b,d]thiophen-3-yl)naphthalen-2-ol (61 g, 150.5 mmol), Pd(PPh3)4 (2.61 g, 2.26 mmol), NaOH (9.03 g, 225.75 mmol), water (331 ml) were added to Sub 1-V-1 (22.03 g, 35.21 mmol) obtained in the above synthesis, and then 51.31 g (yield: 70%) of the product was obtained by carring out in the same manner as described above for the synthesis of Sub S-I-1.

2) Synthesis of M-I-8

S-I-8 (51 g, 104.72 mmol), Pd(OAc)2 (2.35 g, 10.47 mmol), 3-nitropyridine (1.30 g, 10.47 mmol) were dissolved in C6F6 (157.1 ml) and DMI (104 ml) and tert-butyl peroxybenzoate (40.68 g, 209.44 mmol) was added, and then, 36.57 g (yield: 72%) of the product was obtained by carring out in the same manner as described above for the synthesis of M-I-8.

3) Synthesis of Sub 1-I-6

34.23 g (yield: 80%) of the product was obtained by using M-I-8 (36 g, 74.23 mmol) obtained in the above synthesis, DMF (371 ml), Bis(pinacolato)diboron (20.73 g, 81.65 mmol), Pd(dppf)Cl2 (1.63 g, 2.23 mmol), KOAc (21.85 g, 222.68 mmol) in the same manner as described above for the synthesis of Sub 1-V-1.

4) Synthesis of Sub 1-II-6

1-bromo-2-nitrobenzene (11.91 g, 58.97 mmol), Pd(PPh3)4 (2.04 g, 1.77 mmol), K2CO3 (24.45 g, 176.92 mmol), THF (259 ml), water (129 ml) were added to Sub 1-I-6 (34 g, 58.97 mmol) obtained in the above synthesis, and then 27.64 g (yield: 82%) of the product was obtained by carring out in the same manner as described above for the synthesis of Sub 1-II-1.

5) Synthesis of Sub 1-III-6

Triphenylphosphine (37.85 g, 144.32 mmol), o-dichlorobenzene (96 ml) were added to Sub 1-II-6 (27.5 g, 48.11 mmol) obtained in the above synthesis, and then 20.25 g (yield: 78%) of the product was obtained by carring out in the same manner as described above for the synthesis of Sub 1-III-1.

6) Synthesis of Sub 1-44

2,3-dichlorobenzo[f]quinoxaline (9.23 g, 37.06 mmol), Pd2(dba)3 (0.51 g, 0.56 mmol), P(t-Bu)3 (0.37 g, 1.85 mmol), NaOt-Bu (5.34 g, 55.59 mmol), toluene (389 ml) were added to Sub 1-III-6 (20 g, 37.06 mmol) obtained in the above synthesis, and then 11.15 g (yield: 40%) of the product was obtained by carring out in the same manner as described above for the synthesis of Sub 1-1.

8. Synthesis example of Sub 1-52

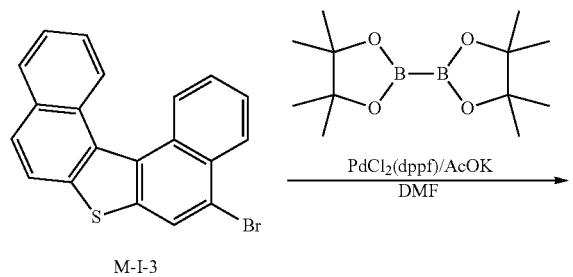

M-I-3

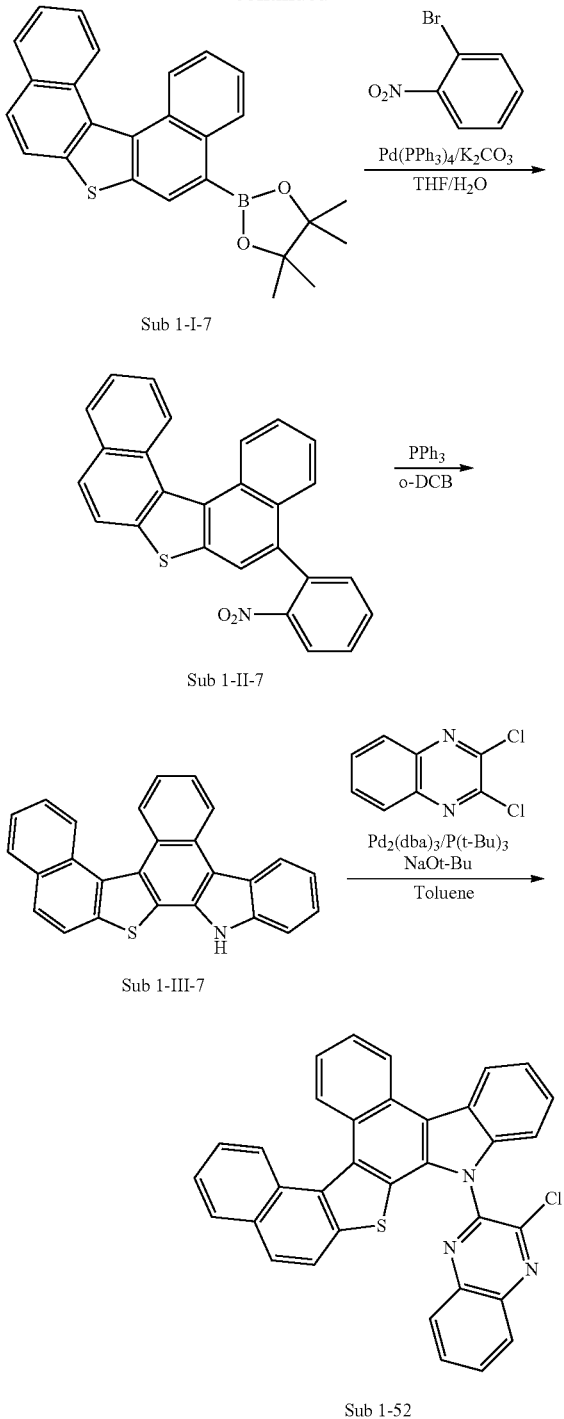

1) Synthesis of Sub 1-I-7

20.38 g (yield: 82%) of the product was obtained by using M-I-3 (22 g, 60.56 mmol) obtained in the above synthesis, DMF (302 ml), Bis(pinacolato)diboron (16.92 g, 66.62 mmol), Pd(dppf)Cl2 (1.33 g, 1.82 mmol), KOAc (17.83 g, 181.68 mmol) in the same manner as described above for the synthesis of Sub 1-V-1.

2) Synthesis of Sub 1-II-7

1-bromo-2-nitrobenzene (9.6 g, 47.52 mmol), Pd(PPh3)4 (1.65 g, 1.43 mmol), K2CO3 (19.70 g, 142.56 mmol), THF (209 ml), water (105 ml) were added Sub 1-I-7 (19.5 g, 47.52 mmol) obtained in the above synthesis, and then 16.38 g (yield: 85%) of the product was obtained by carring out in the same manner as described above for the synthesis of Sub 1-II-1.

3) Synthesis of Sub 1-III-7

Triphenylphosphine (31.05 g, 118.38 mmol), o-dichlorobenzene (79 ml) were added to Sub 1-II-7 (16 g, 39.46 mmol) obtained in the above synthesis, and then 12.08 g (yield: 82%) of the product was obtained by carring out in the same manner as described above for the synthesis of Sub 1-III-1.

4) Synthesis of Sub 1-52

2,3-dichloroquinoxaline (6.40 g, 32.13 mmol), Pd$_2$(dba)$_3$ (0.44 g, 0.48 mmol), P(t-Bu)$_3$ (0.33 g, 1.61 mmol), NaOt-Bu (4.63 g, 48.20 mmol), toluene (337 ml) were added to Sub 1-III-7 (12 g, 32.13 mmol) obtained in the above synthesis, and then 11.71 g (yield: 68%) of the product was obtained by carring out in the same manner as described above for the synthesis of Sub 1-1.

9. Synthesis example of Sub 1-64

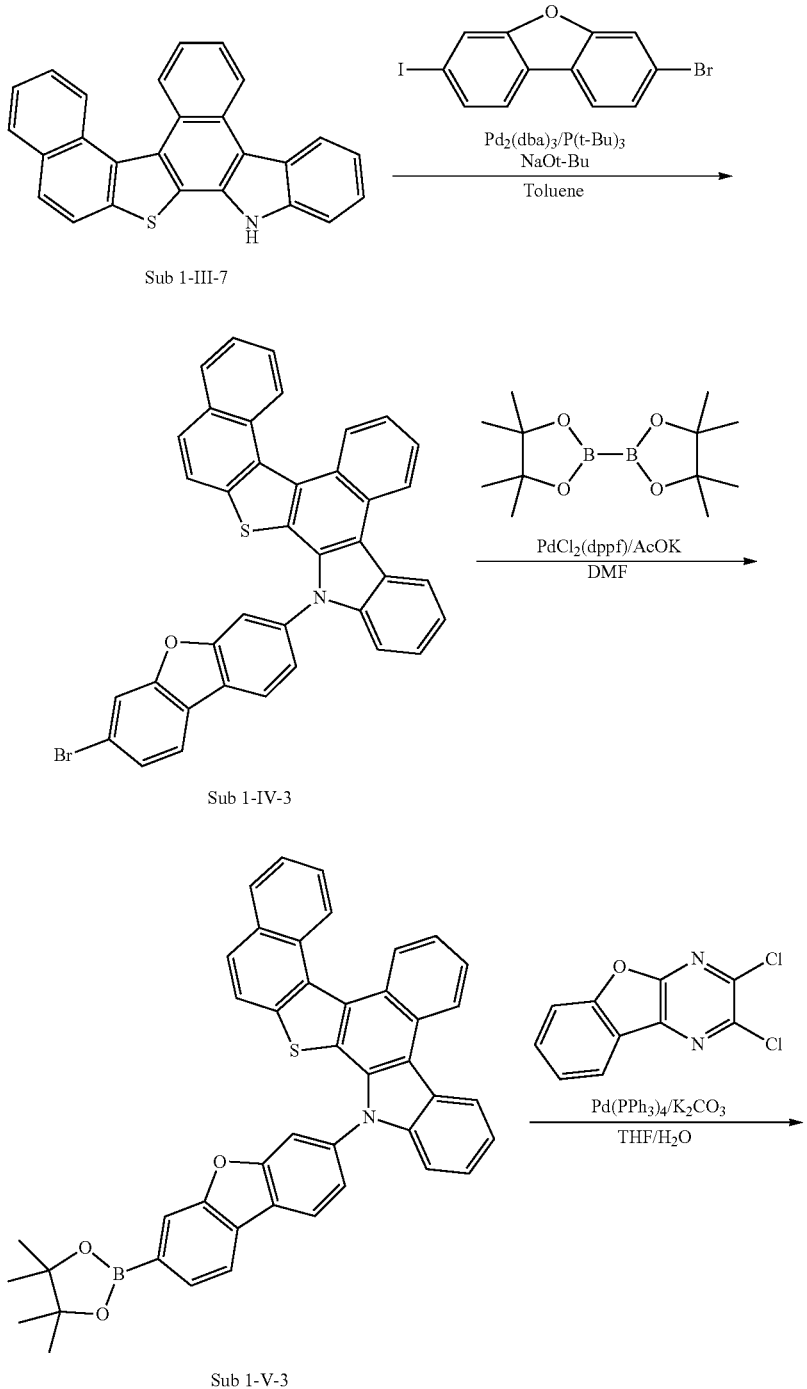

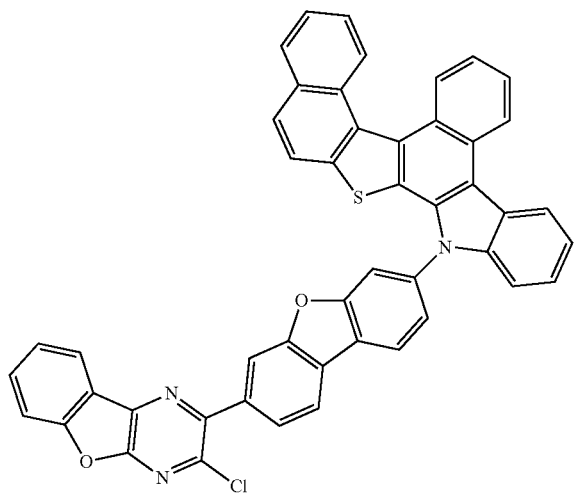

Sub 1-64

1) Synthesis of Sub 1-IV-3

3-bromo-7-iododibenzo[b,d]furan (38.95 g, 104.43 mmol), Pd$_2$(dba)$_3$ (1.43 g, 1.57 mmol), P(t-Bu)$_3$ (1.06 g, 5.22 mmol), NaOt-Bu (15.05 g, 156.64 mmol), toluene (1096 ml) were added to Sub 1-III-7 (39 g, 104.43 mmol) obtained in the above synthesis, and then 38.76 g (yield: 60%) of the product was obtained by carring out in the same manner as described above for the synthesis of Sub 1-1.

2) Synthesis of Sub 1-V-3

31.49 g (yield: 76%) of the product was obtained by using Sub 1-IV-3 (38.5 g, 62.24 mmol) obtained in the above synthesis, DMF (311 ml), Bis(pinacolato)diboron (17.39 g, 68.47 mmol), Pd(dppf)Cl$_2$ (1.37 g, 1.87 mmol), KOAc (18.33 g, 186.73 mmol) in the same manner as described above for the synthesis of Sub 1-V-1.

3) Synthesis of Sub 1-64

2,3-dichlorobenzofuro[2,3-b]pyrazine (11.13 g, 46.57 mmol), Pd(PPh$_3$)$_4$ (0.81 g, 0.70 mmol), K$_2$CO$_3$ (9.66 g, 69.86 mmol), THF (205 ml), water (102 ml) were added to Sub 1-V-3 (31 g, 46.57 mmol) obtained in the above synthesis, and then 11.06 g (yield: 32%) of the product was obtained by carring out in the same manner as described above for the synthesis of Sub 1-II-1.

10. Synthesis example of Sub 1-70

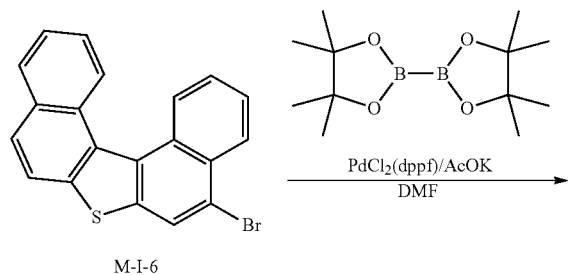

M-I-6

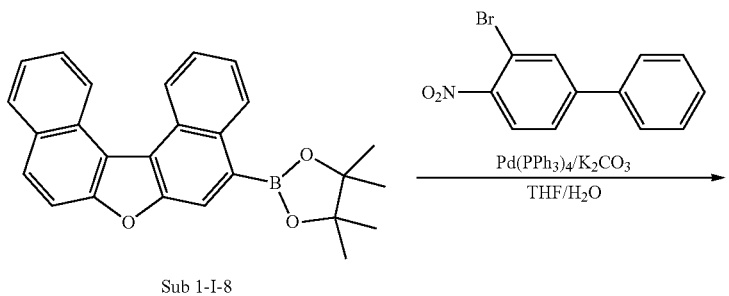

Sub 1-I-8

-continued

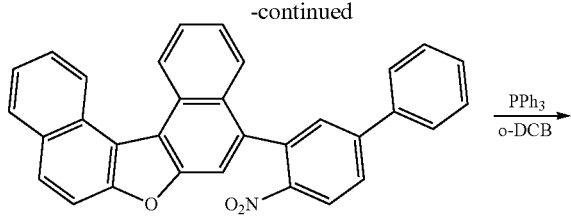
Sub 1-II-8

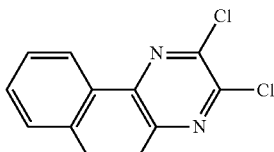

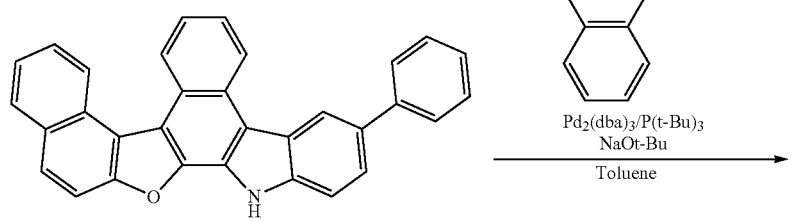
Sub 1-III-8

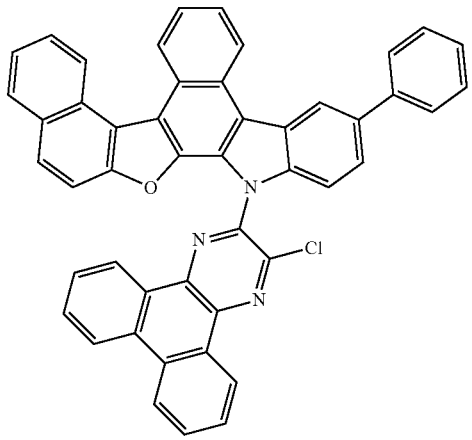
Sub 1-70

1) Synthesis of Sub 1-I-8

17.94 g (yield: 79%) of the product was obtained by using M-I-6 (20 g, 57.60 mmol) obtained in the above synthesis, DMF (288 ml), Bis(pinacolato)diboron (16.09 g, 63.36 mmol), Pd(dppf)Cl$_2$ (1.26 g, 1.73 mmol), KOAc (16.96 g, 172.81 mmol) in the same manner as described above for the synthesis of Sub 1-V-1.

2) Synthesis of Sub 1-II-8

3-bromo-4-nitro-1,1'-biphenyl (11.99 g, 43.12 mmol), Pd(PPh$_3$)$_4$ (1.49 g, 1.29 mmol), K$_2$CO$_3$ (17.88 g, 129.35 mmol), THF (189 ml), water (94 ml) were added to M-I-8 (17 g, 43.12 mmol) obtained in the above synthesis, and then 15.45 g (yield: 77%) of the product was obtained by carring out in the same manner as described above for the synthesis of Sub 1-II-1.

2) Synthesis of Sub 1-III-8

Triphenylphosphine (25.36 g, 96.67 mmol), o-dichlorobenzene (64 ml) were added to Sub 1-II-8 (15 g, 32.22 mmol) obtained in the above synthesis, and then 11.73 g (yield: 84%) of the product was obtained by carring out in the same manner as described above for the synthesis of Sub 1-III-1.

3) Synthesis of Sub 1-70

2,3-dichlorodibenzo[f,h]quinoxaline (7.59 g, 25.37 mmol), Pd$_2$(dba)$_3$ (0.35 g, 0.38 mmol), P(t-Bu)$_3$ (0.26 g, 1.27 mmol), NaOt-Bu (3.66 g, 38.06 mmol), toluene (266 ml) were added to Sub 1-III-8 (11 g, 25.37 mmol) obtained in the above synthesis, and then 11.13 g (yield: 63%) of the product was obtained by carring out in the same manner as described above for the synthesis of Sub 1-1.

Example of Sub 1
Sub 1-1
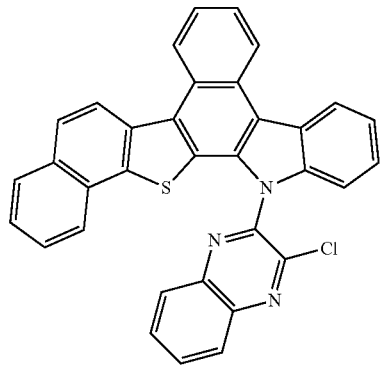
Sub 1-2
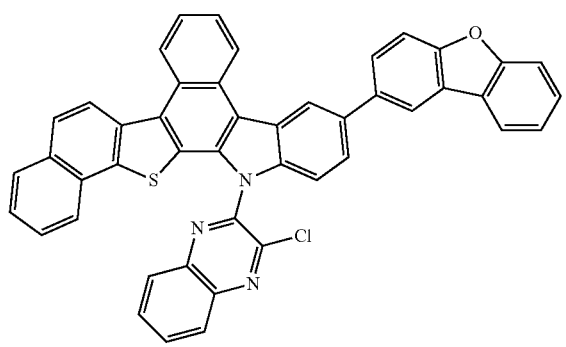
Sub 1-3
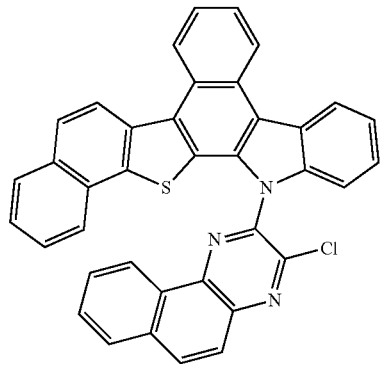
Sub 1-4
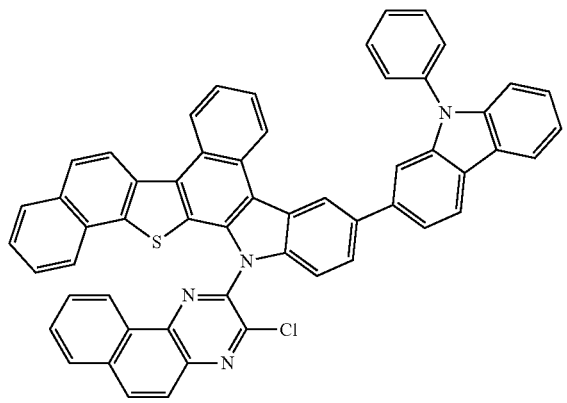
Sub 1-5
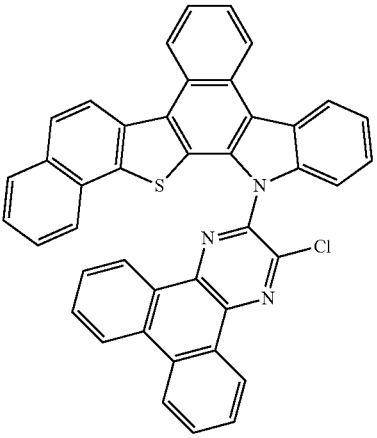
Sub 1-6
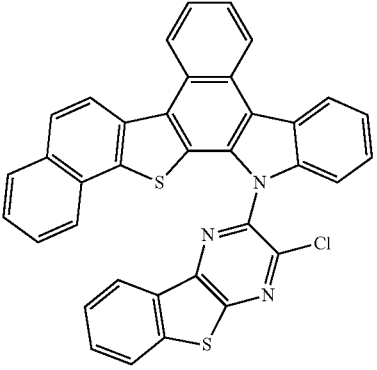
Sub 1-7
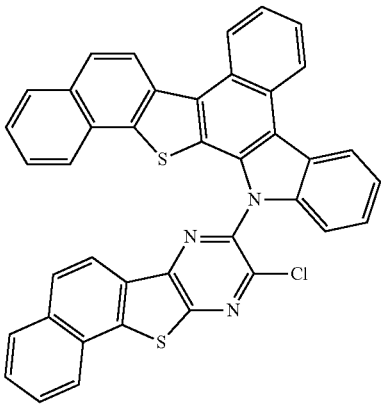
Sub 1-8
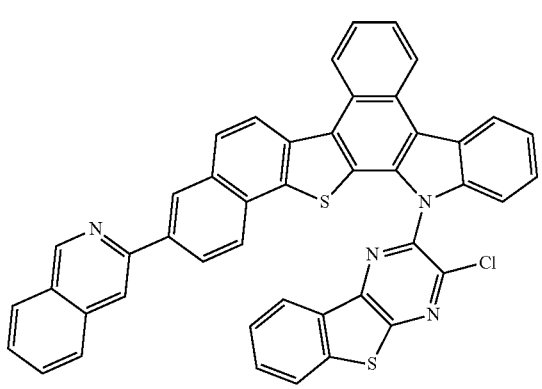

Sub 1-9
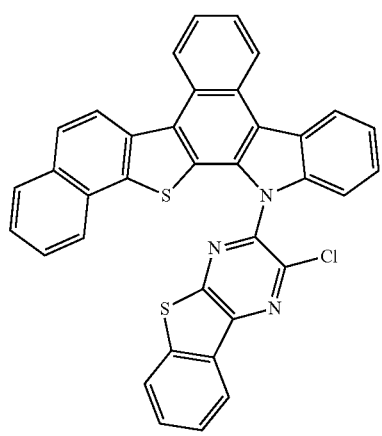
Sub 1-12
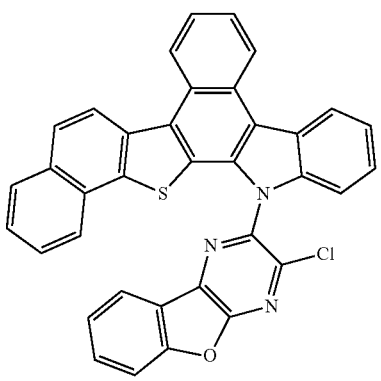
Sub 1-10
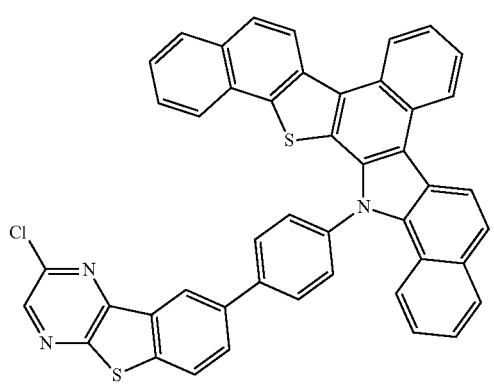
Sub 1-13
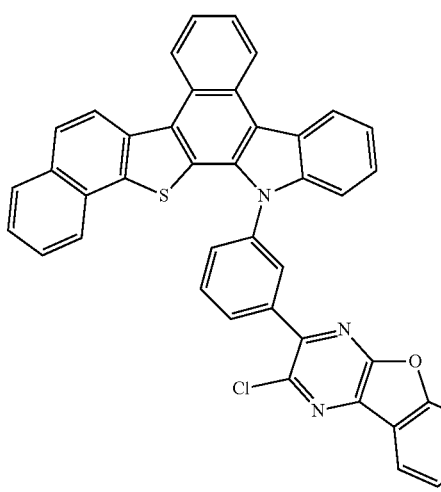
Sub 1-11
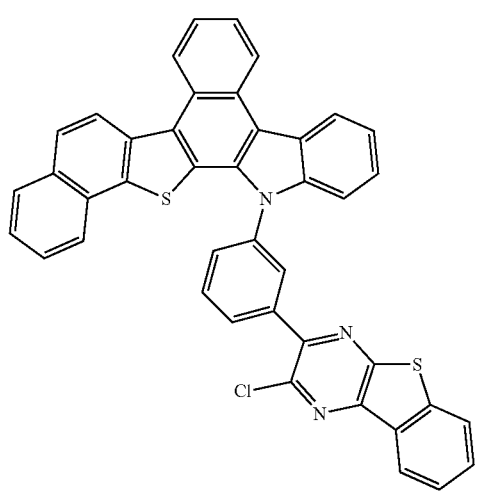
Sub 1-14
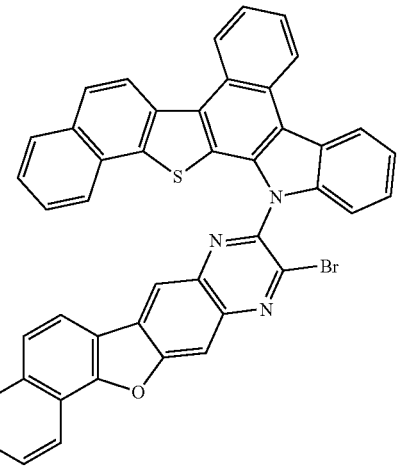

Sub 1-15
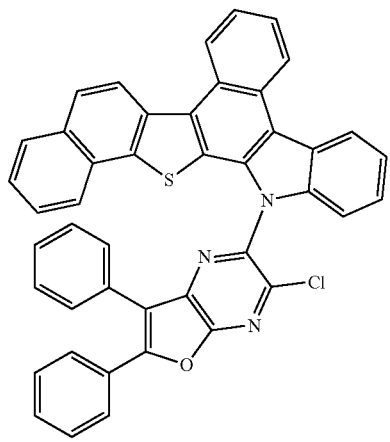
Sub 1-16
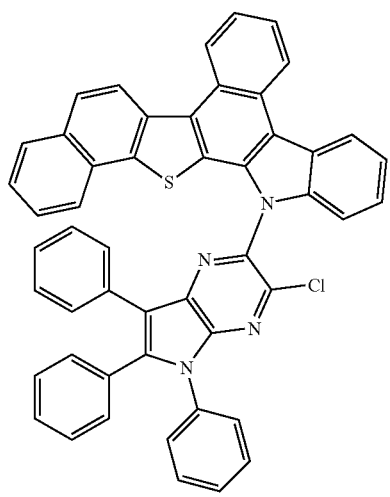
Sub 1-17
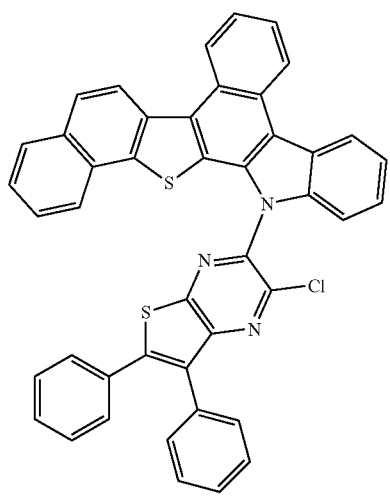
Sub 1-18
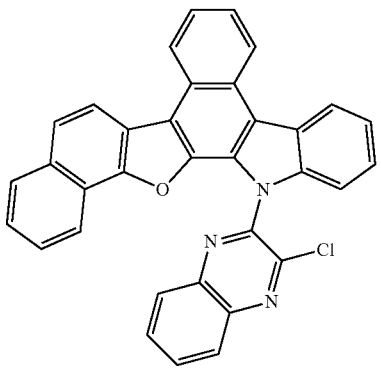
Sub 1-19
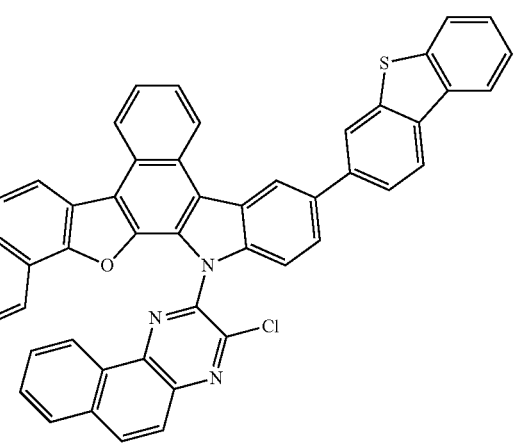
Sub 1-20
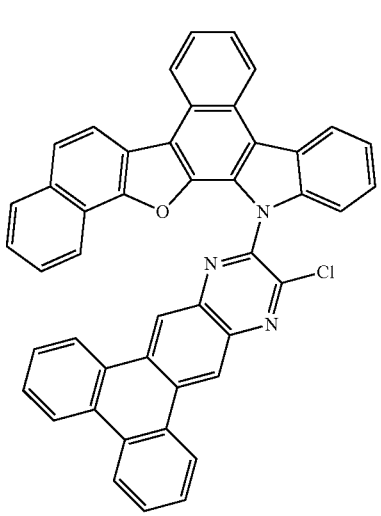

-continued
Sub 1-21
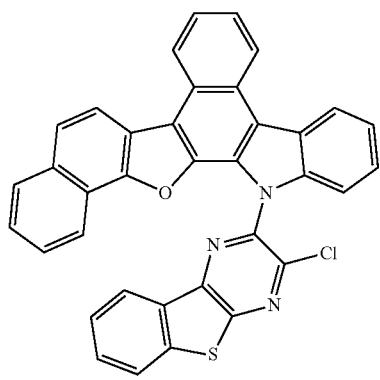
Sub 1-22
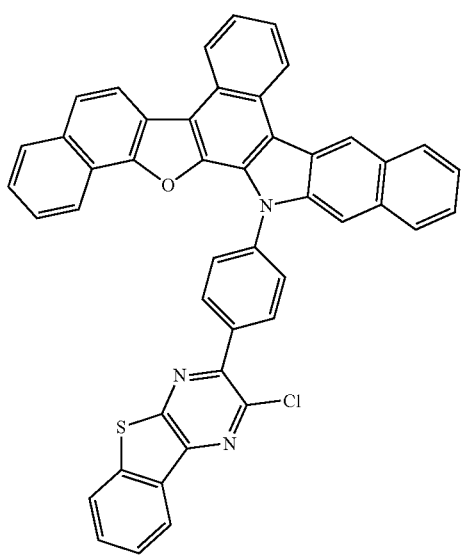
Sub 1-23
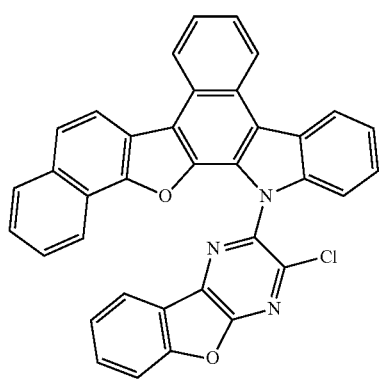
-continued
Sub 1-24
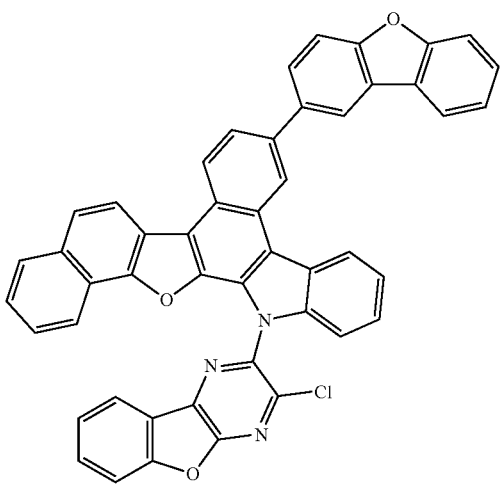
Sub 1-25
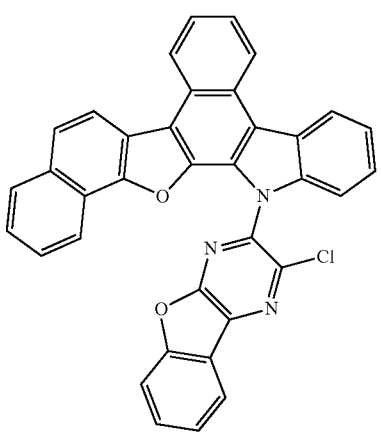
Sub 1-26
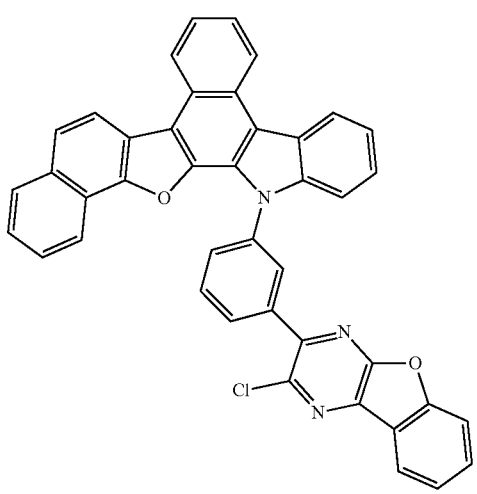

123
-continued
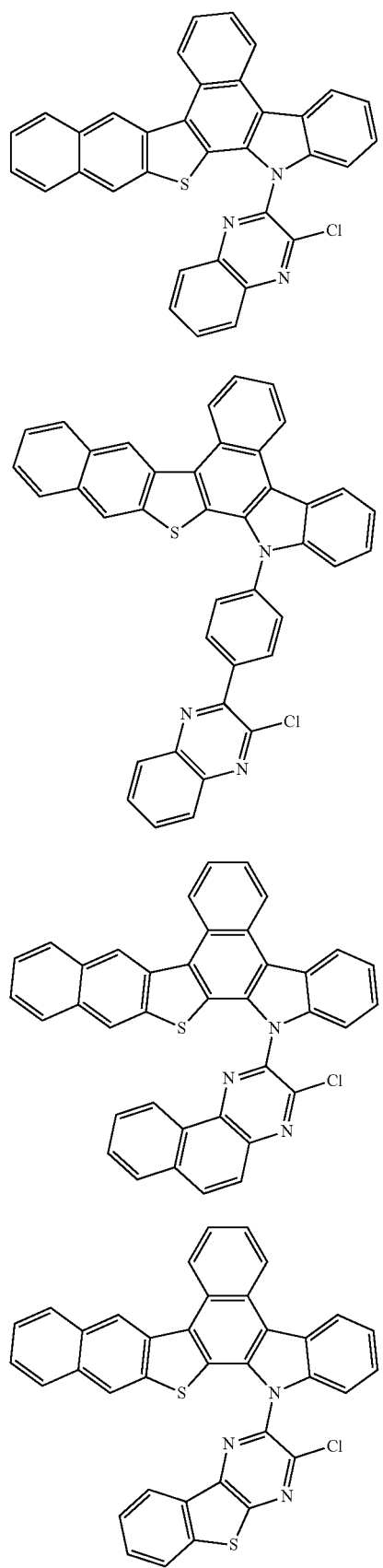
Sub 1-27
Sub 1-28
Sub 1-29
Sub 1-30
124
-continued
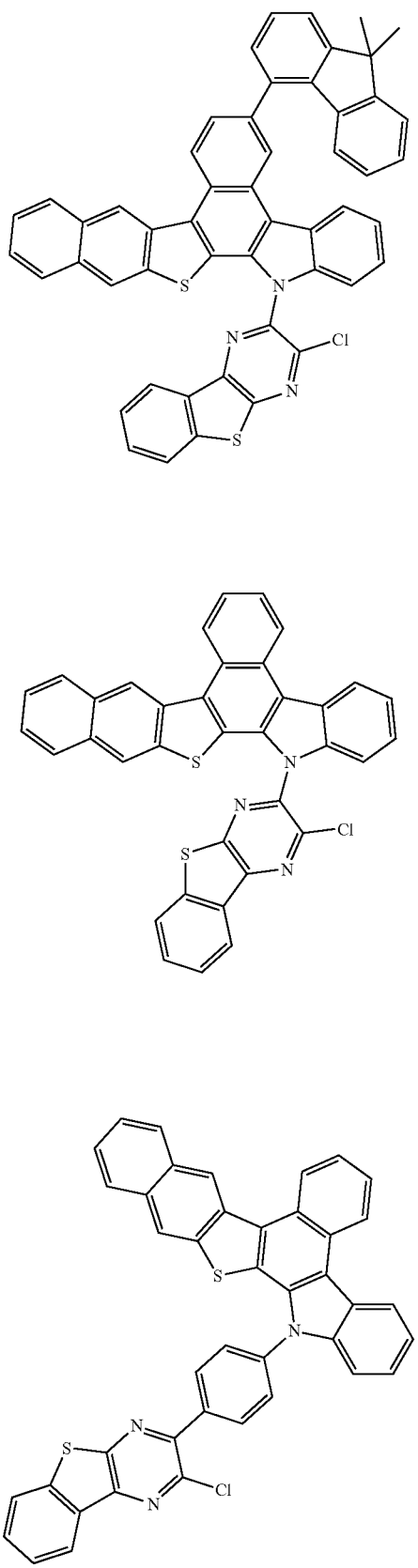
Sub 1-31
Sub 1-32
Sub 1-33

Sub 1-34
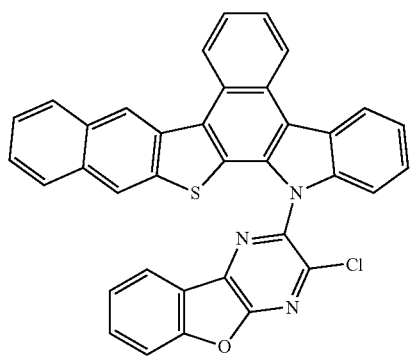
Sub 1-37
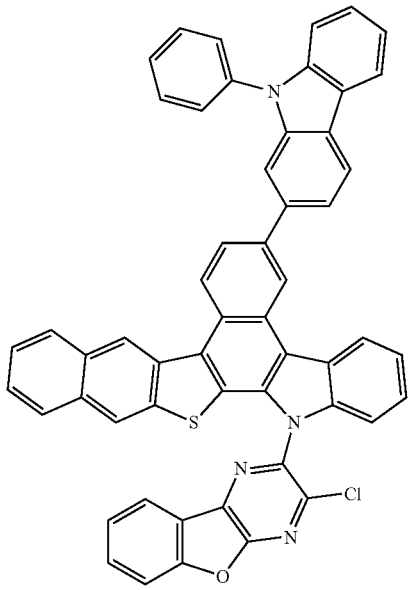
Sub 1-35
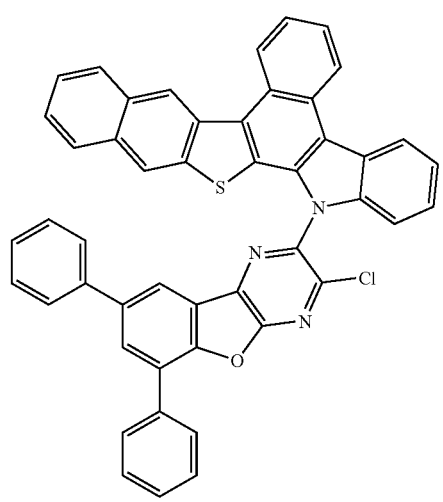
Sub 1-38
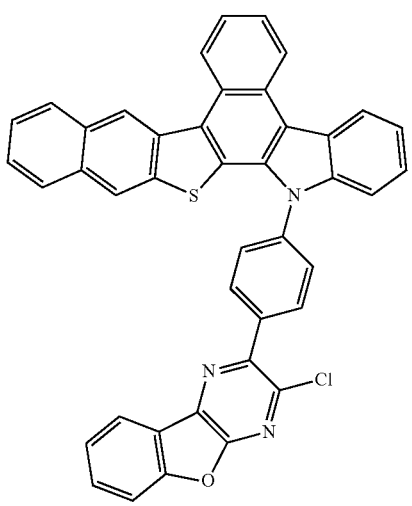
Sub 1-36
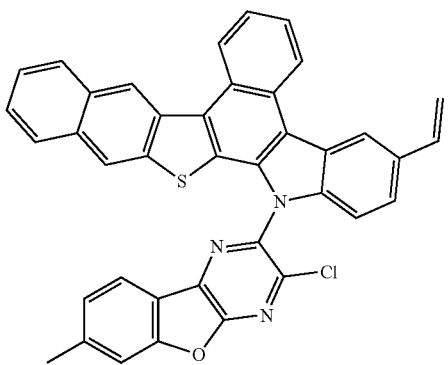
Sub 1-39
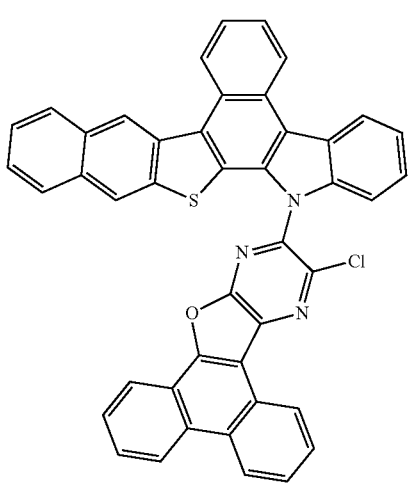

Sub 1-40
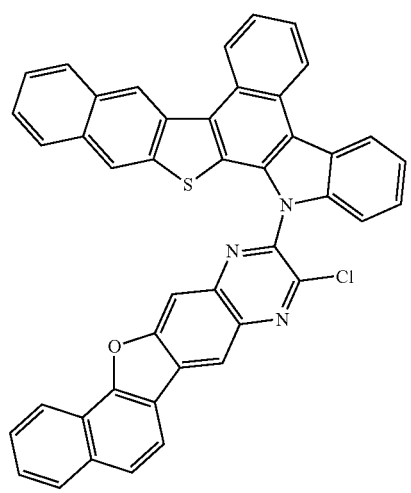
Sub 1-43
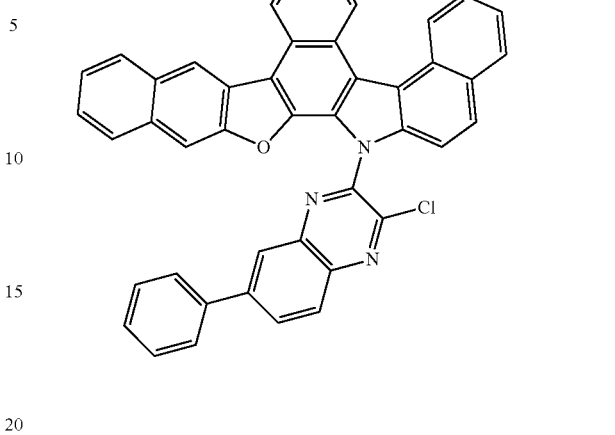
Sub 1-41
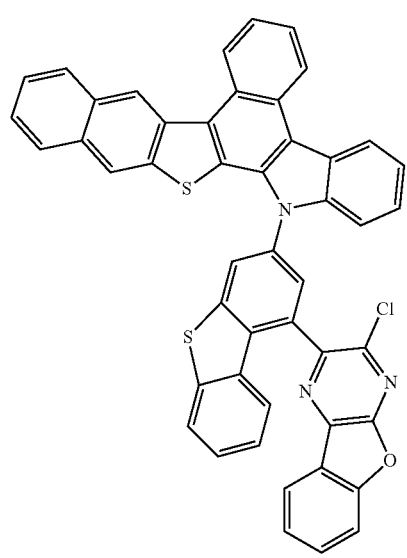
Sub 1-44
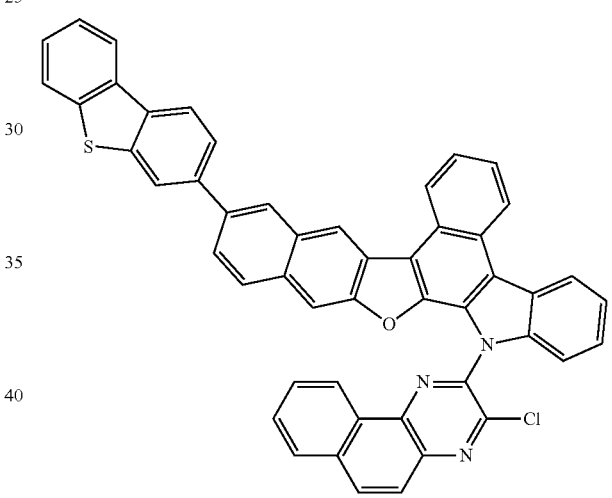
Sub 1-42
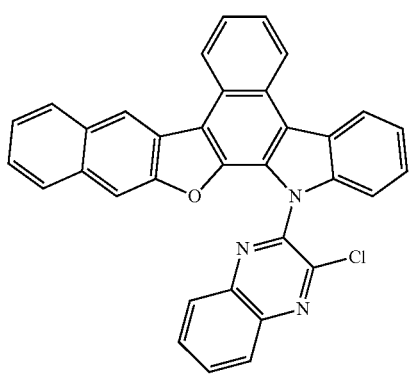
Sub 1-45
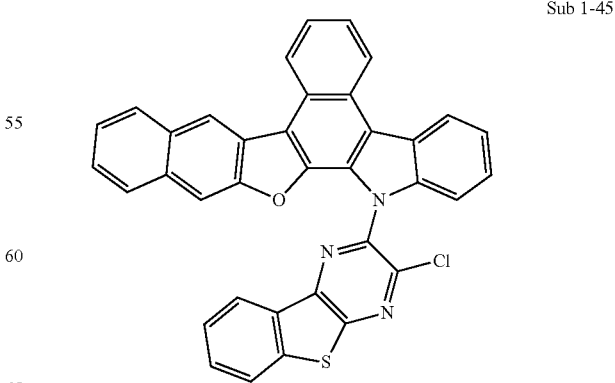

Sub 1-46
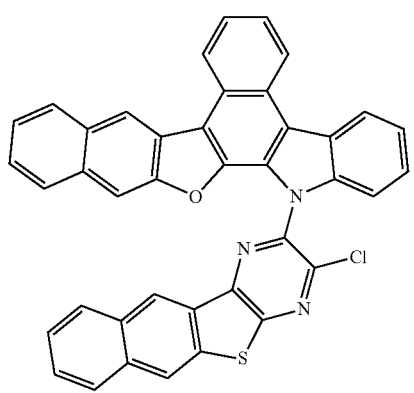
Sub 1-47
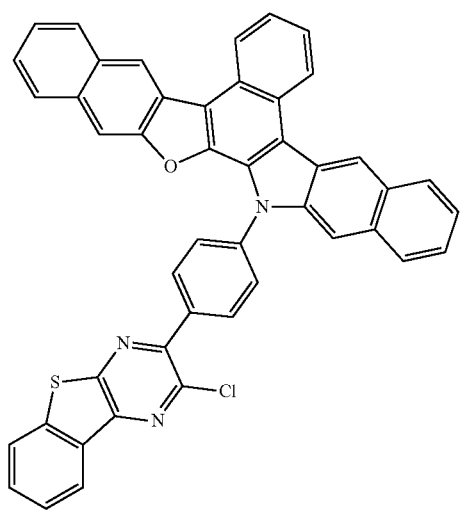
Sub 1-48
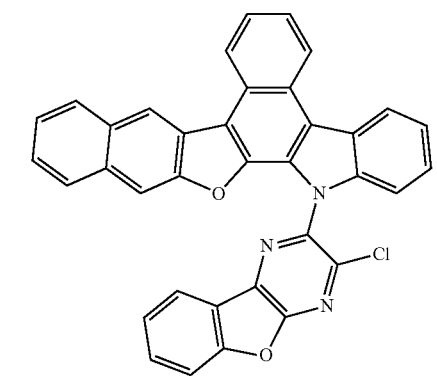
Sub 1-49
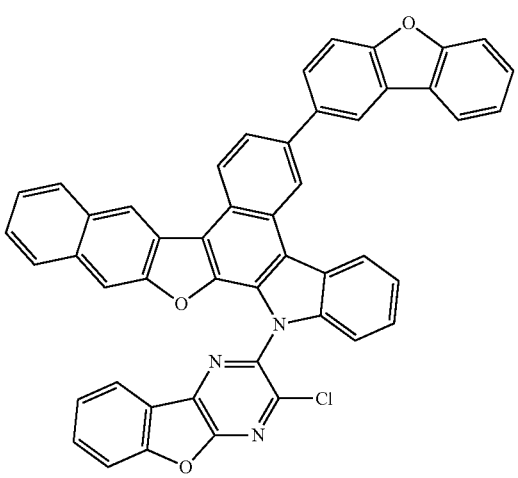
Sub 1-50
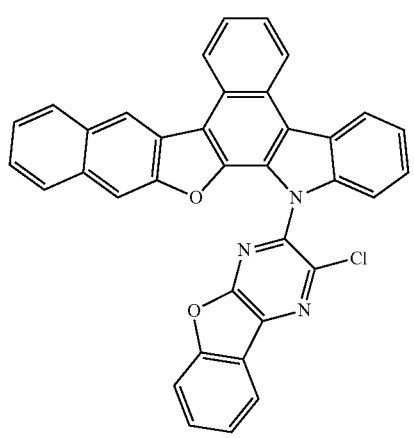
Sub 1-51
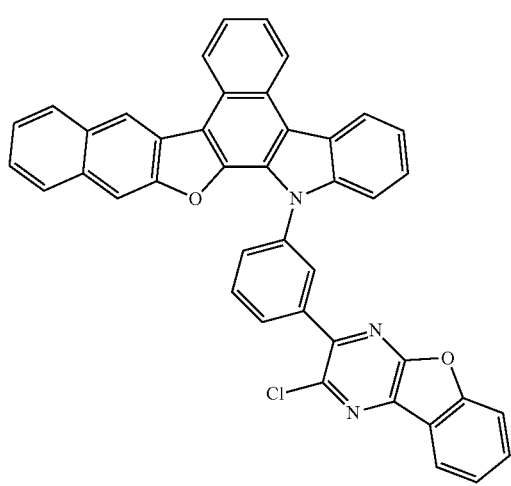

Sub 1-52
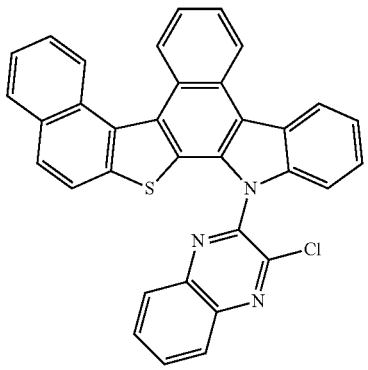
Sub 1-55
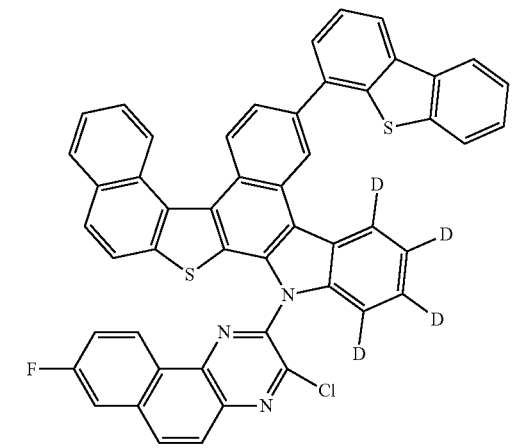
Sub 1-53
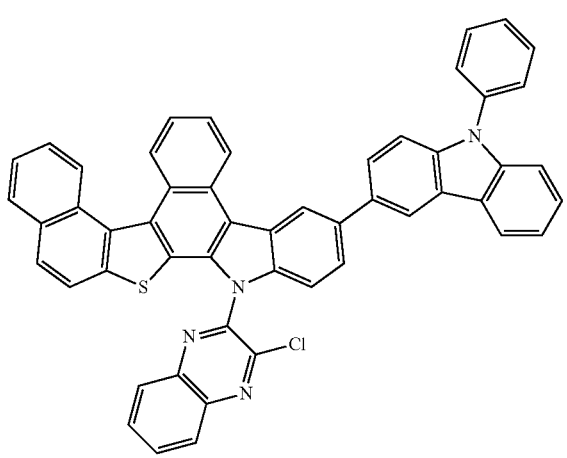
Sub 1-56
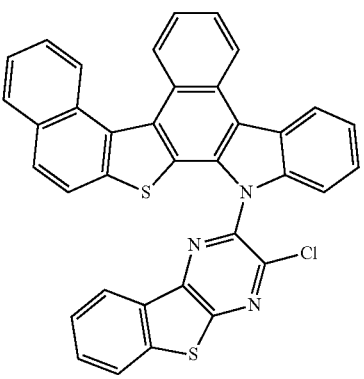
Sub 1-54
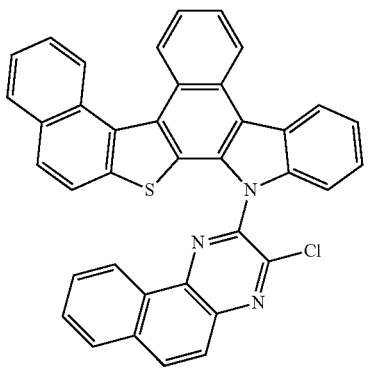
Sub 1-57
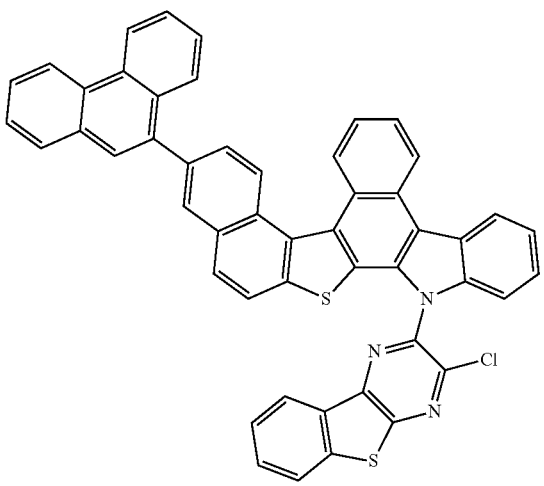

Sub 1-58
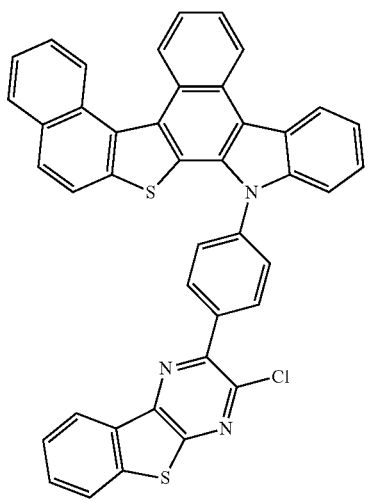
Sub 1-61
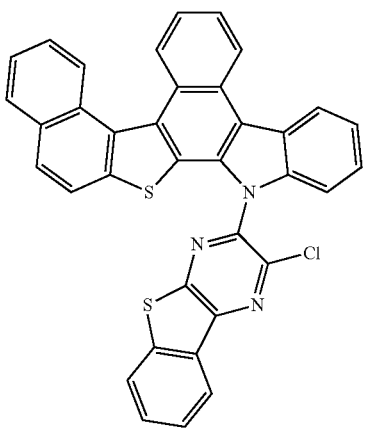
Sub 1-59
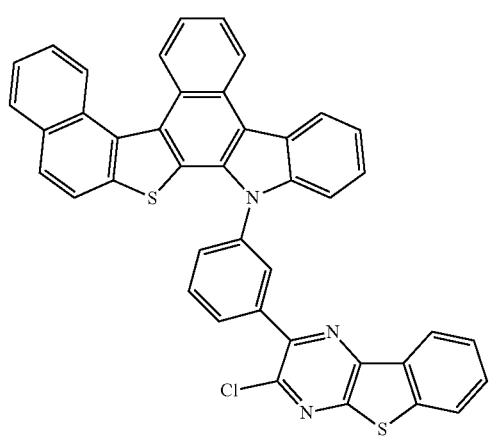
Sub 1-62
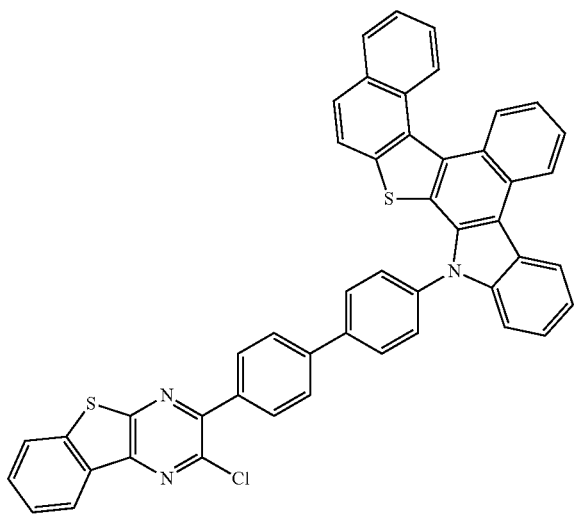
Sub 1-60
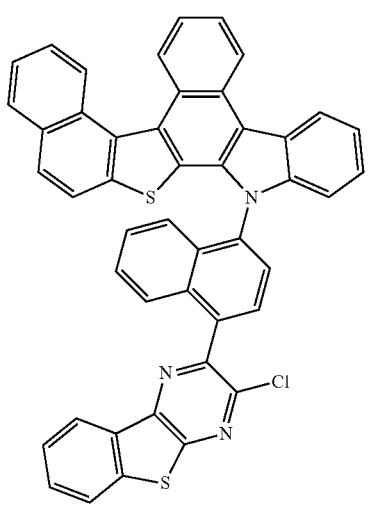
Sub 1-63
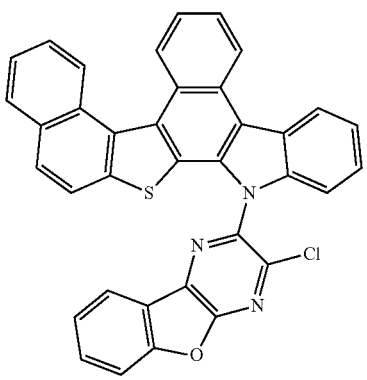

Sub 1-64
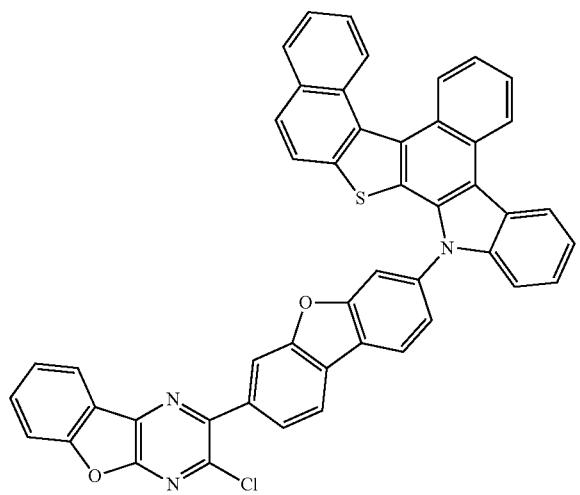
Sub 1-65
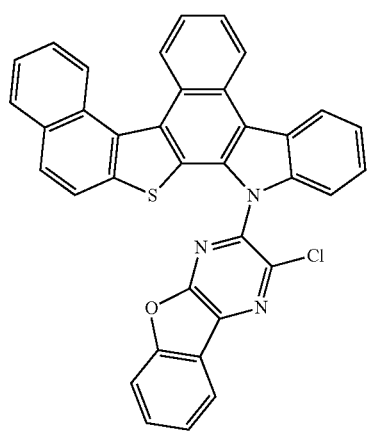
Sub 1-66
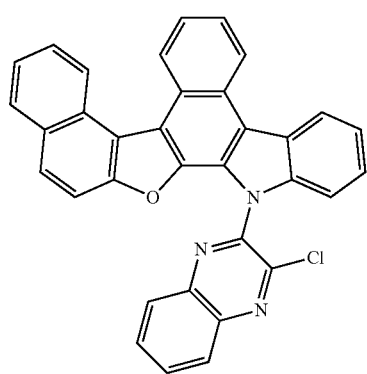
Sub 1-67
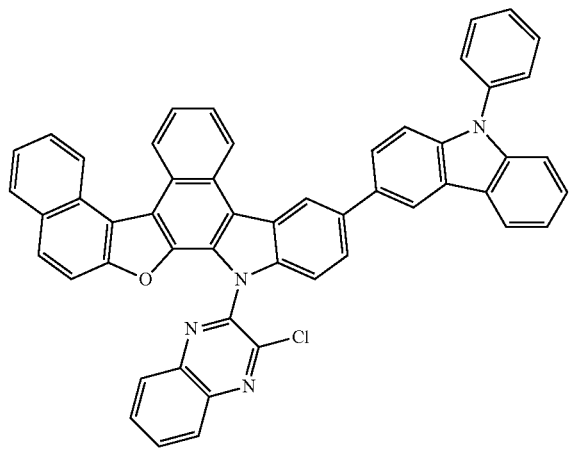
Sub 1-68
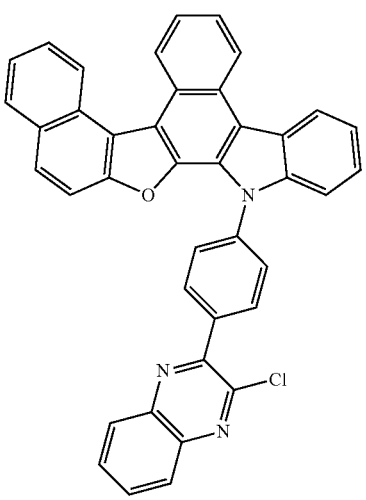
Sub 1-69
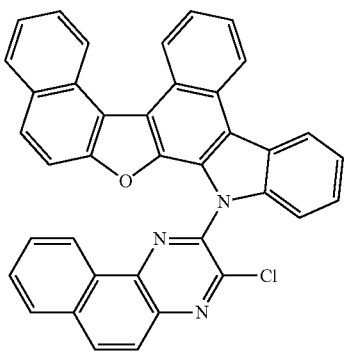

Sub 1-70
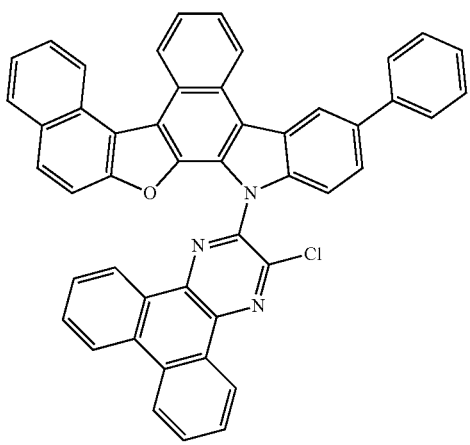
Sub 1-71
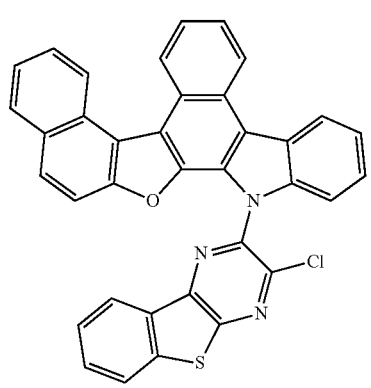
Sub 1-72
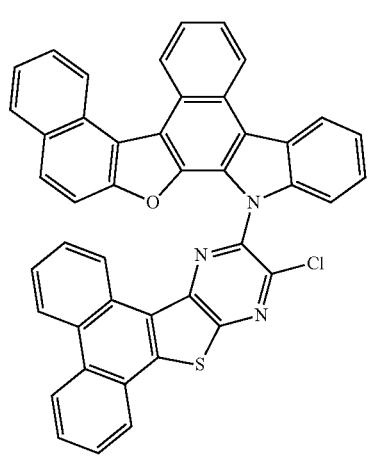
Sub 1-73
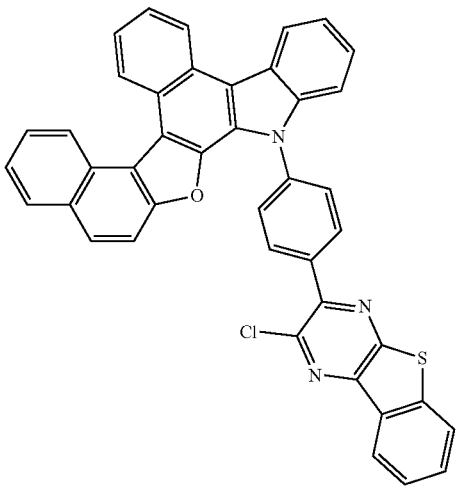
Sub 1-74
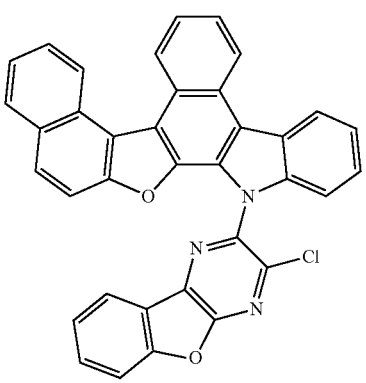
Sub 1-75
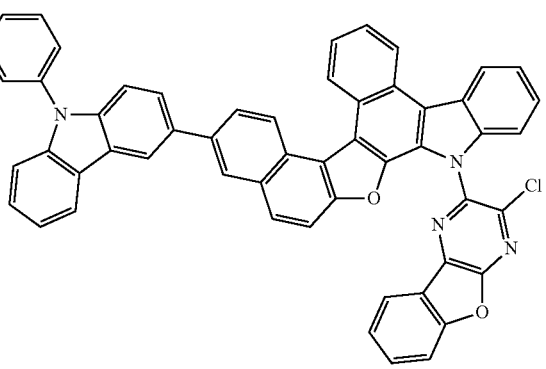
Sub 1-76
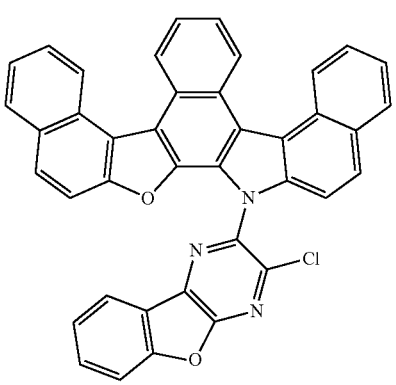

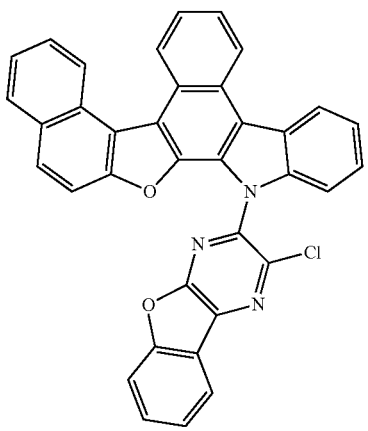

Sub 1-77

Sub 1-78

Sub 1-79

II. Synthesis of Sub 2

Sub 2 of the Reaction Scheme 1 can be synthesized according to, but not limited to, the reaction route of the following Reaction Scheme.

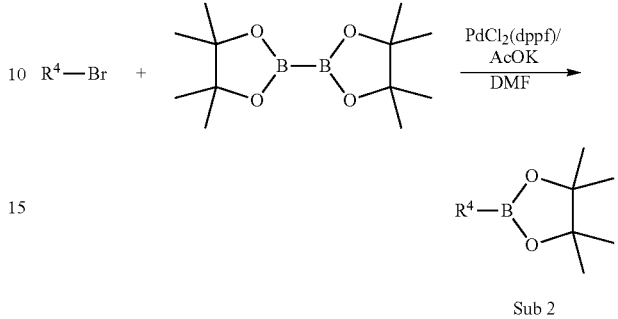

Sub 2

Synthesis Examples of compounds comprised in Sub 2 are as follows.

1. Synthesis example of Sub 2-1

<Reaction Scheme 24>

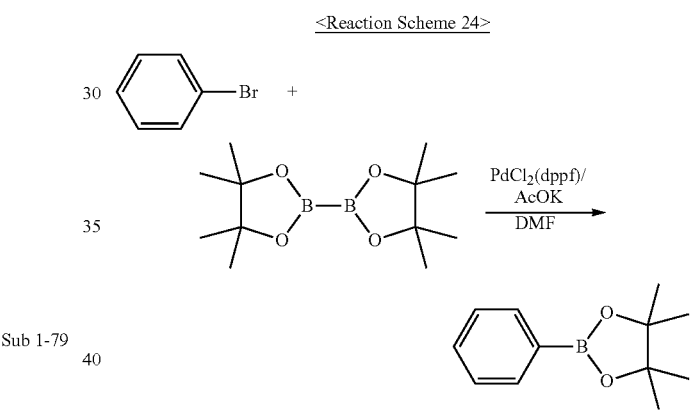

Sub 2-1

The starting material bromobenzene (29.16 g, 185.72 mmol) was dissolved in DMF (930 ml) in a round bottom flask, and then Bis(pinacolato)diboron (51.88 g, 204.29 mmol), Pd(dppf)Cl$_2$ (4.55 g, 5.57 mmol), KOAc (54.68 g, 557.16 mmol) were added and stirred at 90° C. When the reaction was completed, DMF was removed by distillation and the reaction product was extracted with CH$_2$Cl$_2$ and water. Then, the organic layer was dried with MgSO$_4$ and concentrated. Then, the concentrate was passed through silica gel column and recrystallized to obtain 31.84 g (yield: 84%) of the product.

TABLE 1

| Compound | FD-MS | Compound | FD-MS |
|---|---|---|---|
| Sub 1-1  | m/z = 541.05($C_{32}H_{16}ClN_3S_2$ = 542.07) | Sub 1-4  | m/z = 782.14($C_{50}H_{27}ClN_4S_2$ = 783.36) |
| Sub 1-10 | m/z = 717.11($C_{46}H_{24}ClN_3S_2$ = 718.29) | Sub 1-18 | m/z = 519.11($C_{34}H_{18}ClN_3O$ = 519.99) |
| Sub 1-24 | m/z = 725.15($C_{48}H_{24}ClN_3O_3$ = 726.19) | Sub 1-41 | m/z = 757.10($C_{48}H_{24}ClN_3OS_2$ = 758.31) |
| Sub 1-44 | m/z = 751.15($C_{50}H_{26}ClN_3OS$ = 752.29) | Sub 1-52 | m/z = 535.09($C_{34}H_{18}ClN_3S$ = 536.05) |
| Sub 1-64 | m/z = 741.13($C_{48}H_{24}ClN_3O_2S$ = 742.25) | Sub 1-70 | m/z = 695.18($C_{48}H_{26}ClN_3O$ = 696.21) |

2. Synthesis example of Sub 2-3

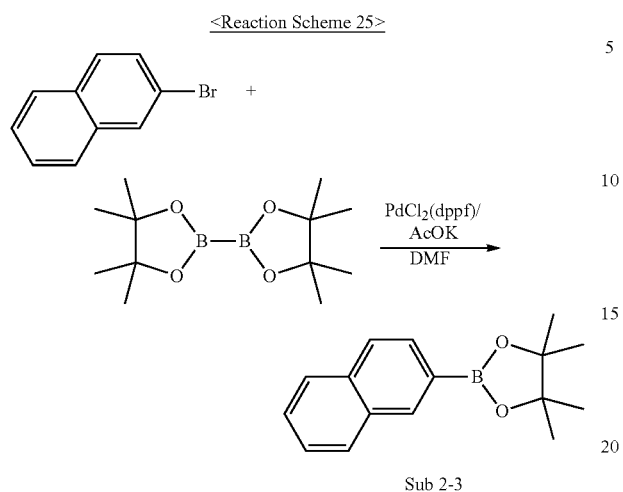

Sub 2-3

Bis(pinacolato)diboron (29.04 g, 114.37 mmol), Pd(dppf)Cl$_2$ (2.55 g, 3.12 mmol), KOAc (30.61 g, 311.92 mmol), DMF (520 ml) were added to 2-bromonaphthalene (21.53 g, 103.97 mmol) being starting material, and then 21.14 g (yield: 80%) of the product was obtained by carring out in the same manner as described above for the synthesis of Sub 2-1.

3. Synthesis example of Sub 2-5

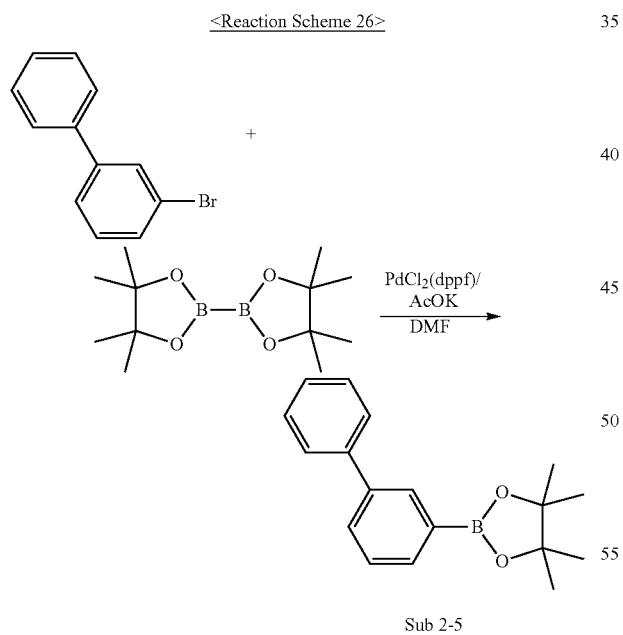

Sub 2-5

Bis(pinacolato)diboron (19.46 g, 76.63 mmol), Pd(dppf)Cl$_2$ (1.71 g, 2.09 mmol), KOAc (20.51 g, 209.00 mmol), DMF (350 ml) were added to 3-bromo-1,1'-biphenyl (16.24 g, 69.67 mmol) being starting material, and then 15.81 g (yield: 81%) of the product was obtained by carring out in the same manner as described above for the synthesis of Sub 2-1.

4. Synthesis example of Sub 2-12

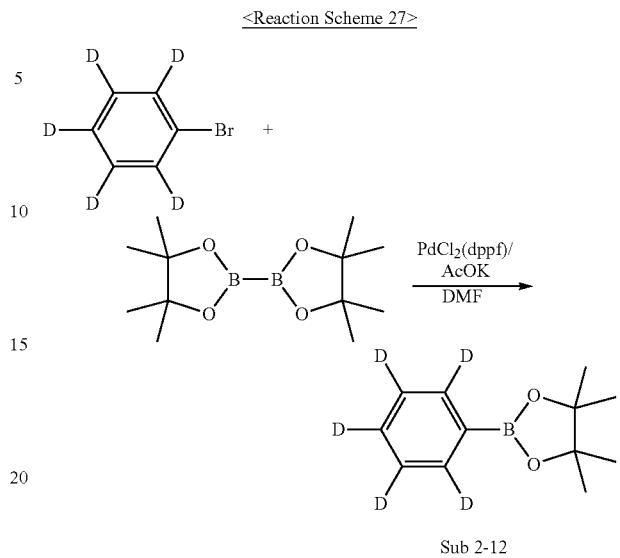

Sub 2-12

Bis(pinacolato)diboron (18.70 g, 73.65 mmol), Pd(dppf)Cl$_2$ (1.64 g, 2.01 mmol), KOAc (19.71 g, 200.88 mmol), DMF (335 ml) were added to 1-bromobenzene-2,3,4,5,6-d5 (10.85 g, 66.96 mmol) being starting material, and then 10.22 g (yield: 73%) of the product was obtained by carring out in the same manner as described above for the synthesis of Sub 2-1.

5. Synthesis example of Sub 2-21

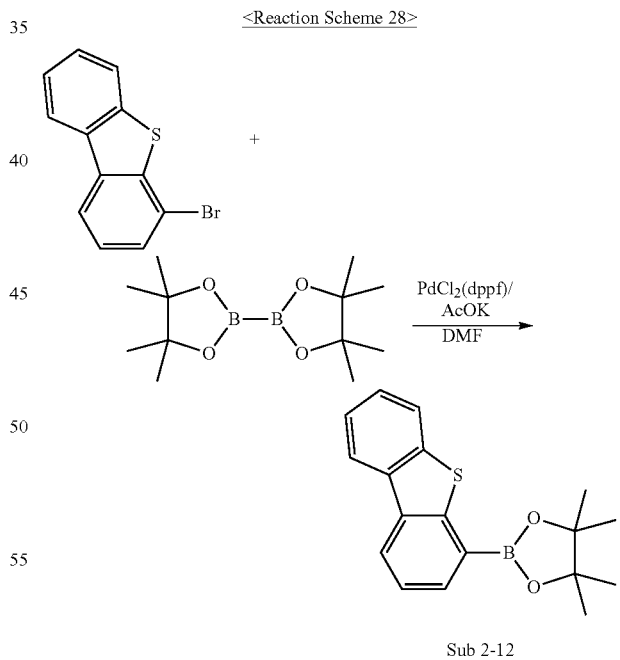

Sub 2-12

Bis(pinacolato)diboron (15.11 g, 59.48 mmol), Pd(dppf)Cl$_2$ (1.32 g, 1.62 mmol), KOAc (15.92 g, 162.23 mmol), DMF (270 ml) were added to 4-bromodibenzo[b,d]thiophene (14.23 g, 54.08 mmol) being starting material, and then 13.76 g (yield: 82%) of the product was obtained by carring out in the same manner as described above for the synthesis of Sub 2-1.

6. Synthesis example of Sub 2-28

<Reaction Scheme 29>

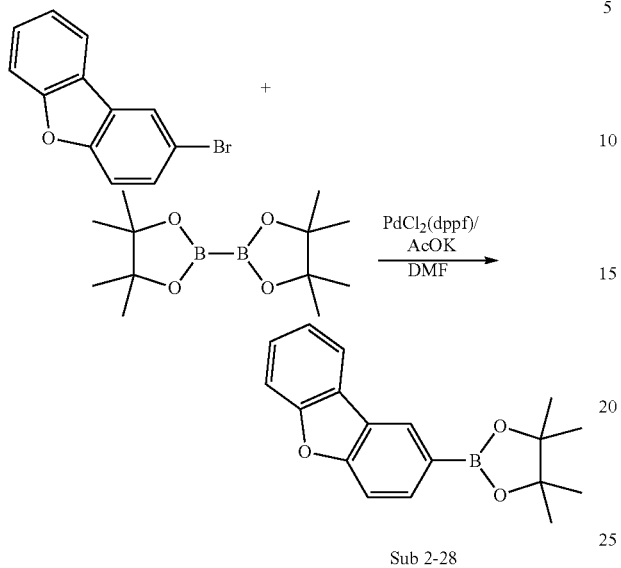

Sub 2-28

Bis(pinacolato)diboron (18.48 g, 72.79 mmol), Pd(dppf)Cl$_2$ (1.62 g, 1.99 mmol), KOAc (19.48 g, 198.51 mmol), DMF (330 ml) were added to 2-bromodibenzo[b,d]furan (16.35 g, 66.17 mmol) being starting material, and then 16.74 g (yield: 86%) of the product was obtained by carring out in the same manner as described above for the synthesis of Sub 2-1.

7. Synthesis example of Sub 2-32

<Reaction Scheme 30>

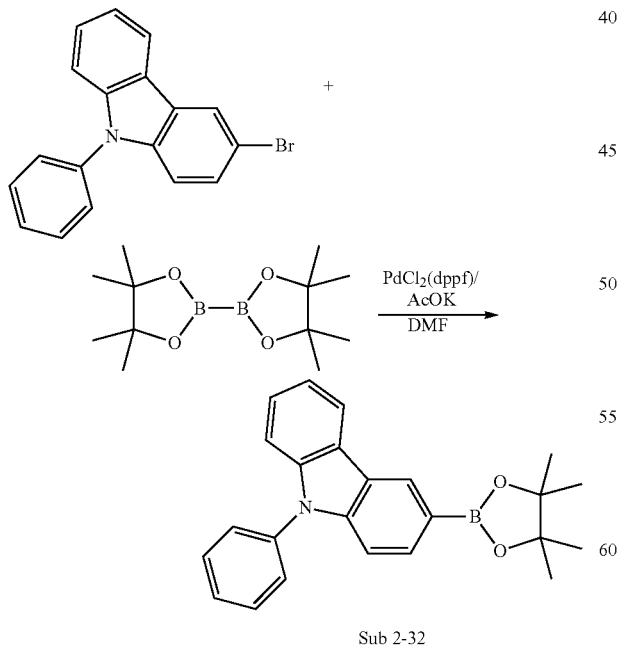

Sub 2-32

Bis(pinacolato)diboron (10.55 g, 41.55 mmol), Pd(dppf)Cl$_2$ (0.93 g, 1.13 mmol), KOAc (11.12 g, 113.31 mmol), DMF (190 ml) were added to 3-bromo-9-phenyl-9H-carbazole (12.17 g, 37.77 mmol) being starting material, and then 10.46 g (yield: 75%) of the product was obtained by carring out in the same manner as described above for the synthesis of Sub 2-1.

8. Synthesis example of Sub 2-27

<Reaction Scheme 31>

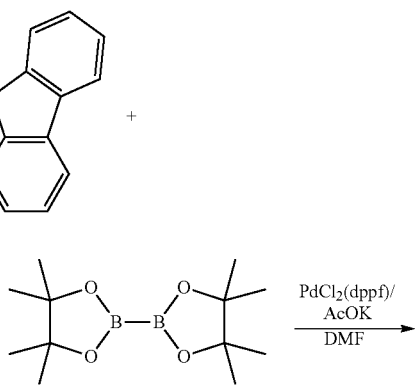

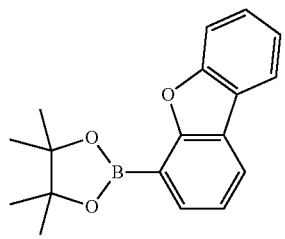

Sub 2-27

Bis(pinacolato)diboron (18.97 g, 74.70 mmol), Pd(dppf)Cl$_2$ (1.66 g, 2.04 mmol), KOAc (19.99 g, 203.73 mmol), DMF (340 ml) were added to 1-bromodibenzo[b,d]furan (16.78 g, 67.91 mmol) being starting material, and then 15.98 g (yield: 80%) of the product was obtained by carring out in the same manner as described above for the synthesis of Sub 2-1.

9. Synthesis example of Sub 2-36

<Reaction Scheme 32>

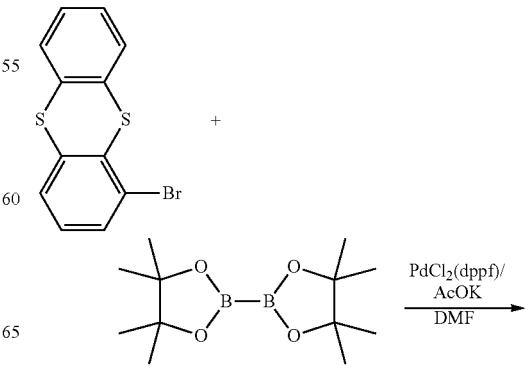

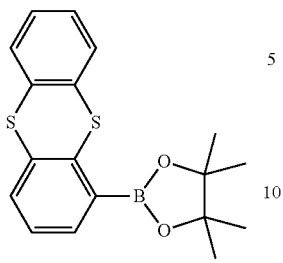

Sub 2-36

Bis(pinacolato)diboron (12.59 g, 49.60 mmol), Pd(dppf)Cl$_2$ (1.10 g, 1.35 mmol), KOAc (13.27 g, 135.26 mmol), DMF (225 ml) were added to 1-bromothianthrene (13.31 g, 45.09 mmol) being starting material, and then 10.34 g (yield: 67%) of the product was obtained by carring out in the same manner as described above for the synthesis of Sub 2-1.

The compound belonging to Sub 2 may be, but not limited to, the following compounds, and Table 2 shows FD-MS (Field Desorption-Mass Spectrometry) values of compounds belonging to Sub 2.

Sub 2-1

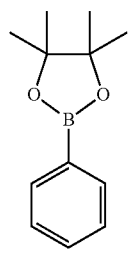

Sub 2-2

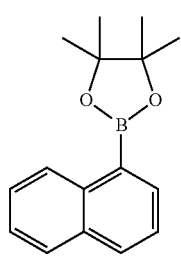

Sub 2-3

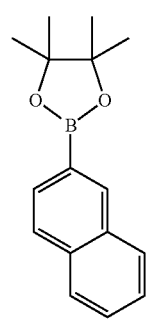

Sub 2-4

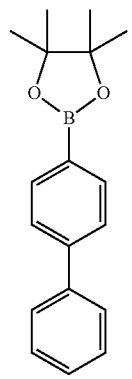

Sub 2-5

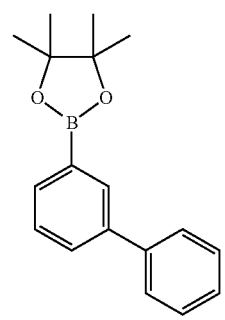

Sub 2-6

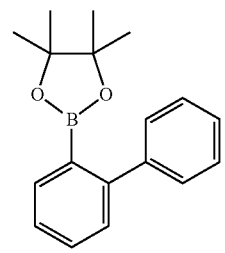

Sub 2-7

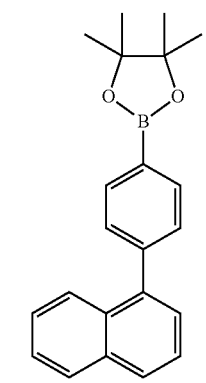

Sub 2-8
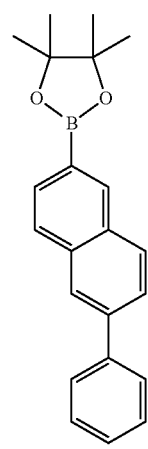
Sub 2-9
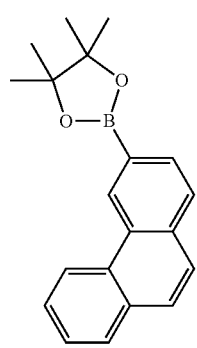
Sub 2-10
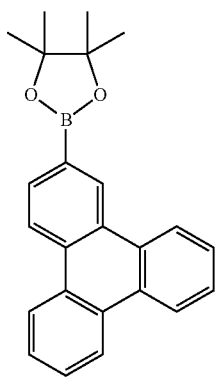
Sub 2-11
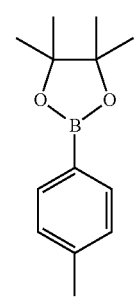
Sub 2-12
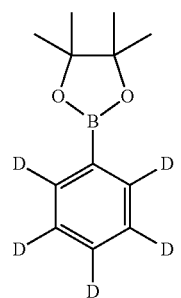
Sub 2-13
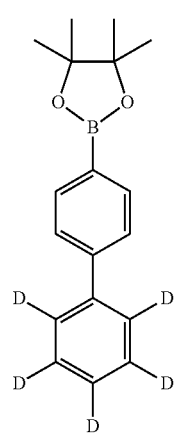
Sub 2-14
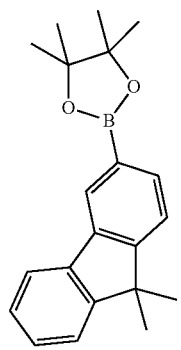
Sub 2-15
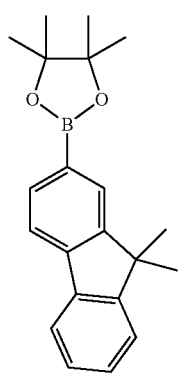

-continued
Sub 2-16
Sub 2-17
Sub 2-18
Sub 2-19
Sub 2-20
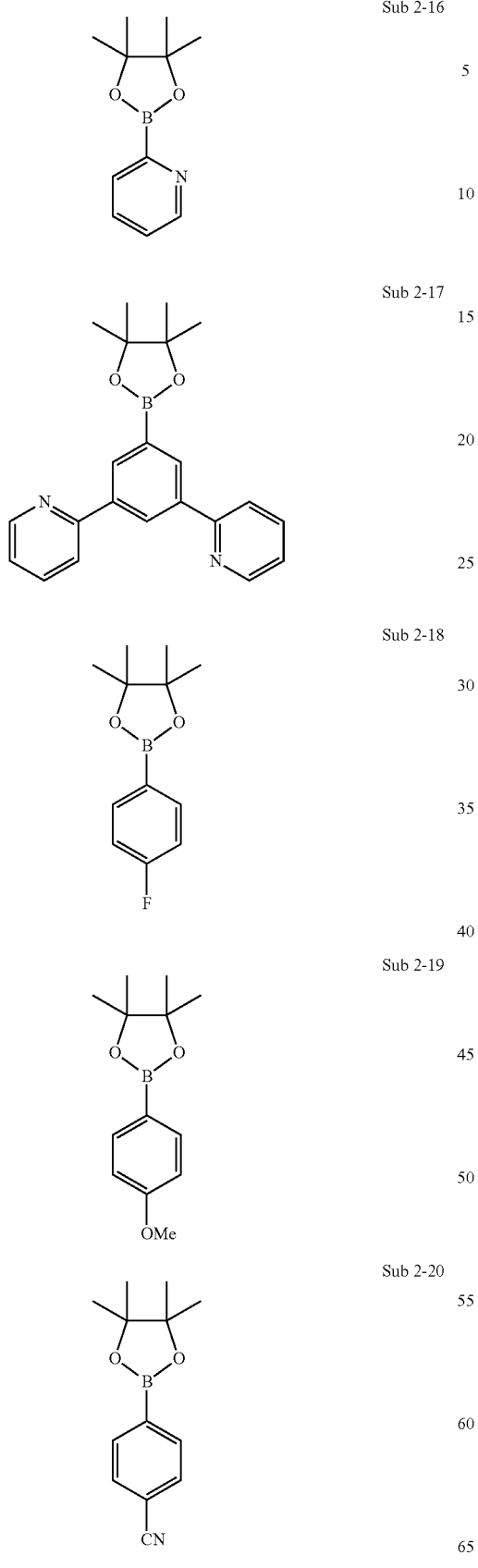
-continued
Sub 2-21
Sub 2-22
Sub 2-23
Sub 2-24
Sub 2-25
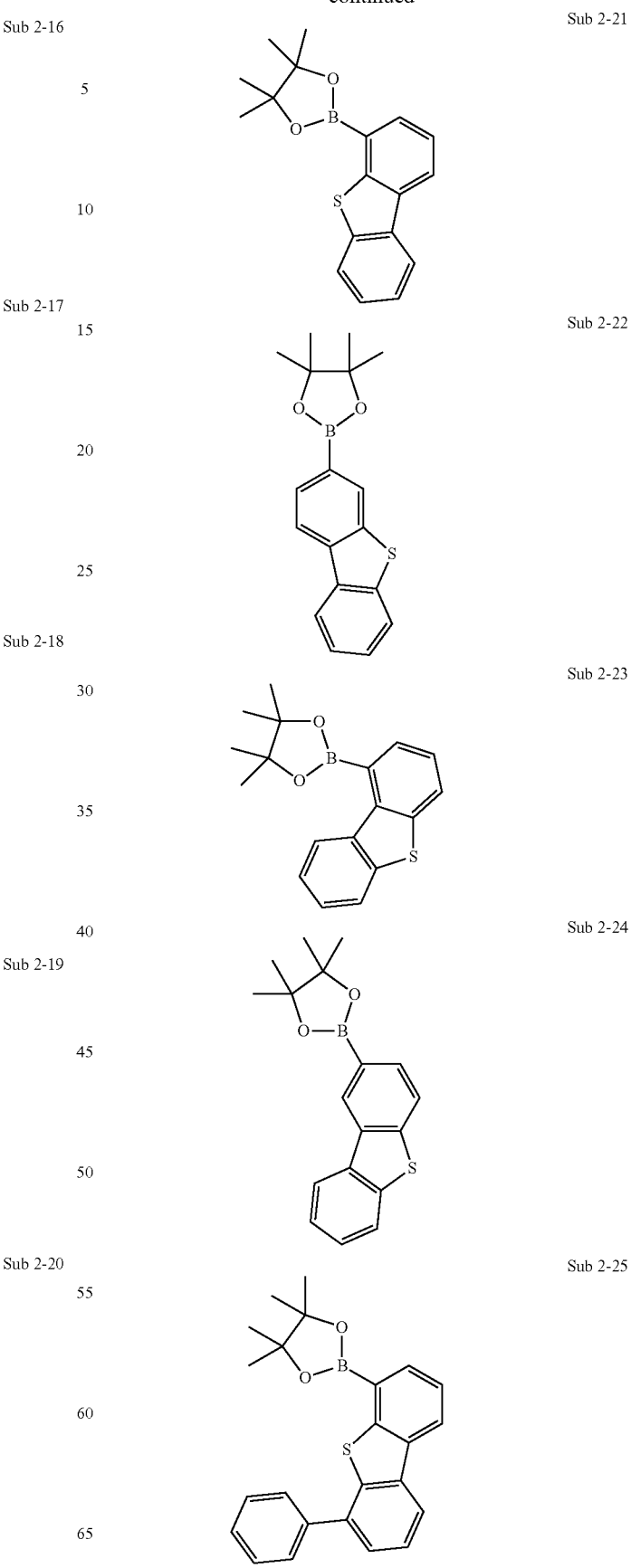

Sub 2-26
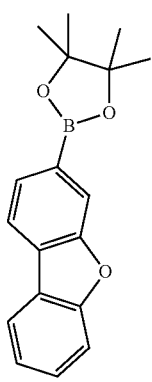
Sub 2-27
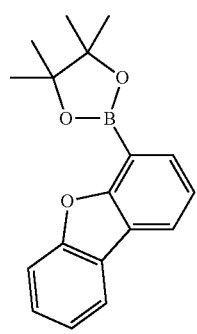
Sub 2-28
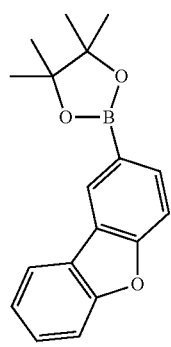
Sub 2-29
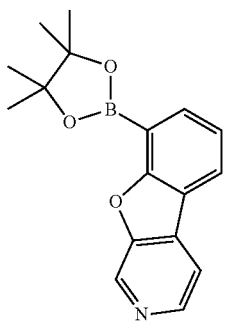
Sub 2-30
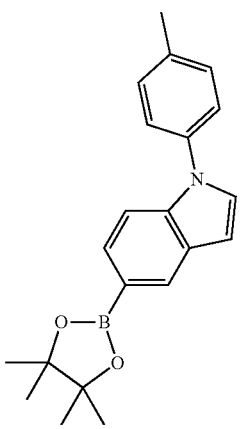
Sub 2-31
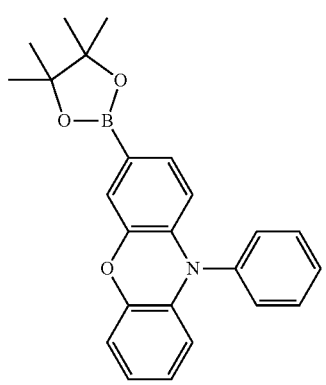
Sub 2-32
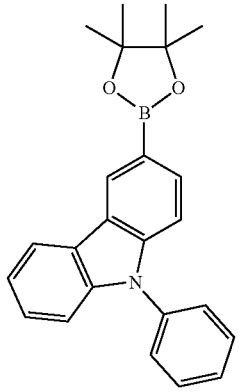
Sub 2-33
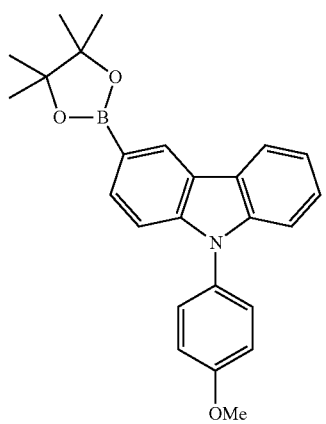

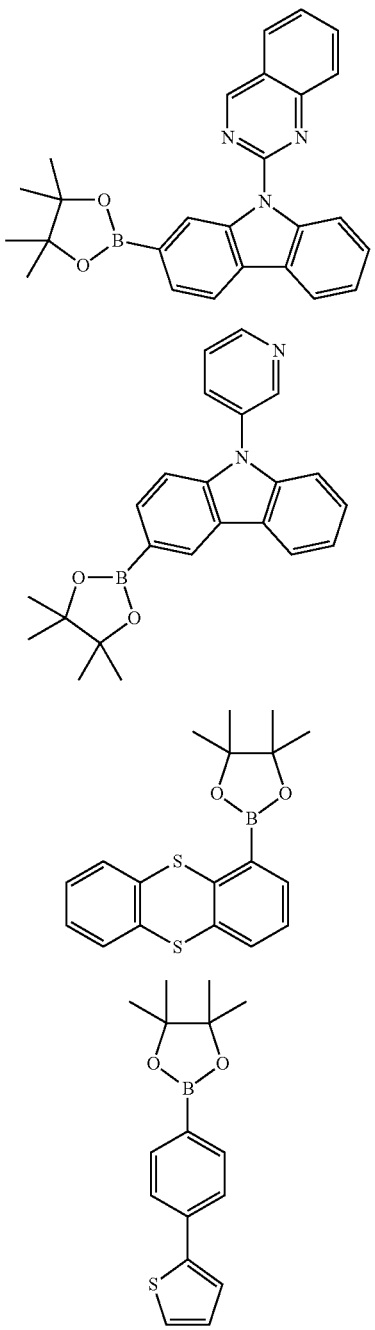

Sub 2-34

Sub 2-35

Sub 2-36

Sub 2-37

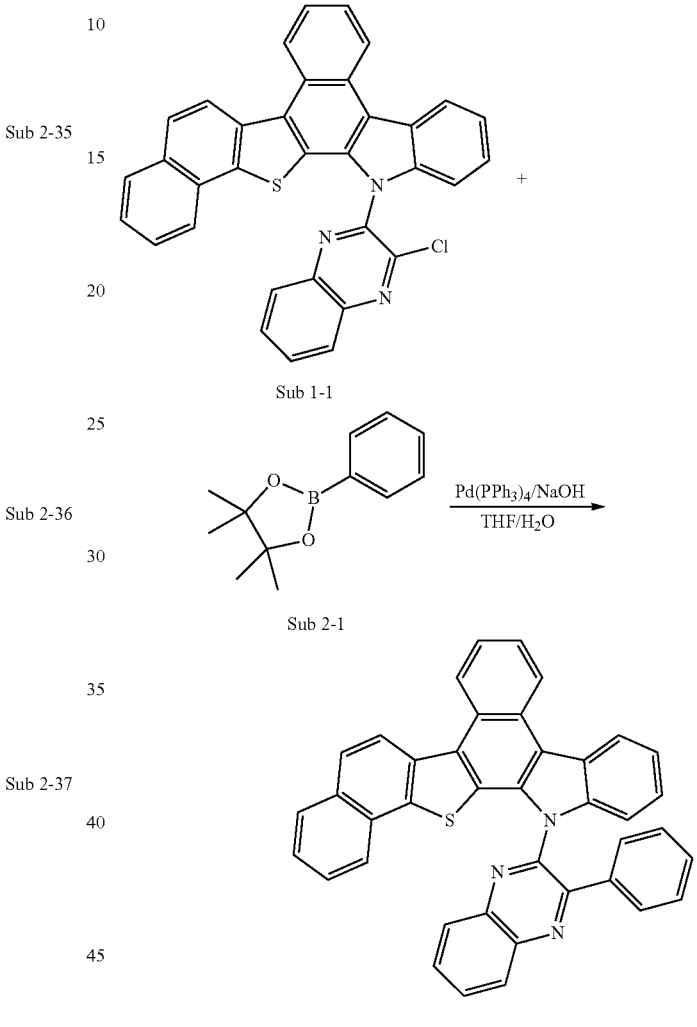

were added, then, stirring at 70° C. was followed. When the reaction was completed, the reaction product was extracted with CH$_2$Cl$_2$ and water, and then the organic layer was dried with MgSO$_4$ and concentrated. Then, the concentrate was passed through silica gel column and recrystallized to obtain final product.

Synthesis example of 1-1

Sub 1-1 (9 g, 16.79 mmol) was dissolved in THF (74 ml) in a round bottom flask, and Sub 2-1 (3.43 g, 16.79 mmol), Pd(PPh$_3$)$_4$ (0.78 g, 0.67 mmol), NaOH (2.01 g, 50.37 mmol) and water (37 ml) were added, then, stirring at 70° C. was

TABLE 2

| Compound | FD-MS | Compound | FD-MS |
|---|---|---|---|
| Sub 2-1 | m/z = 204.13(C$_{12}$H$_{17}$BO$_2$ = 204.08) | Sub 2-3 | m/z = 254.15(C$_{16}$H$_{19}$BO$_2$ = 254.14) |
| Sub 2-5 | m/z = 280.16(C$_{18}$H$_{21}$BO$_2$ = 280.17) | Sub 2-12 | m/z = 209.16(C$_{12}$H$_{12}$D$_5$BO$_2$ = 209.11) |
| Sub 2-21 | m/z = 310.12(C$_{18}$H$_{19}$BO$_2$S = 310.22) | Sub 2-28 | m/z = 294.14(C$_{18}$H$_{19}$BO$_3$ = 294.16) |
| Sub 2-32 | m/z = 369.19(C$_{24}$H$_{24}$BNO$_2$ = 369.27) | Sub 2-27 | m/z = 294.14(C$_{18}$H$_{19}$BO$_3$ = 294.16) |
| Sub 2-36 | m/z = 342.09(C$_{18}$H$_{19}$BO$_2$S$_2$ = 342.28) | | |

III. Synthesis of Product

Sub 1 (1 eq.) was dissolved in THF in a round bottom flask, and Pd(PPh$_3$)$_4$ (0.04 eq.), NaOH (3 eq.) and water followed. When the reaction was completed, the reaction product was extracted with CH$_2$Cl$_2$ and water, and then the organic layer was dried with MgSO$_4$ and concentrated.

Then, the concentrate was passed through silica gel column and recrystallized to obtain 7.47 g (yield: 77%) of product.

Synthesis example of 1-14

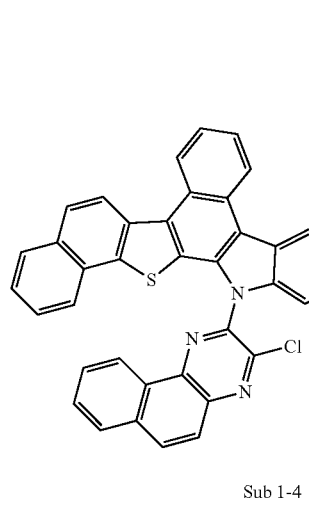

Sub 1-4

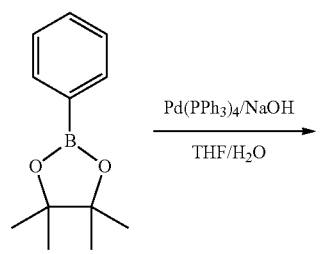

Sub 2-1

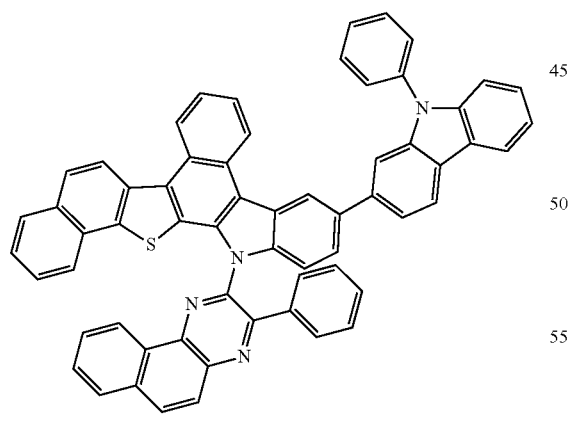

1-14

Synthesis example of 1-30

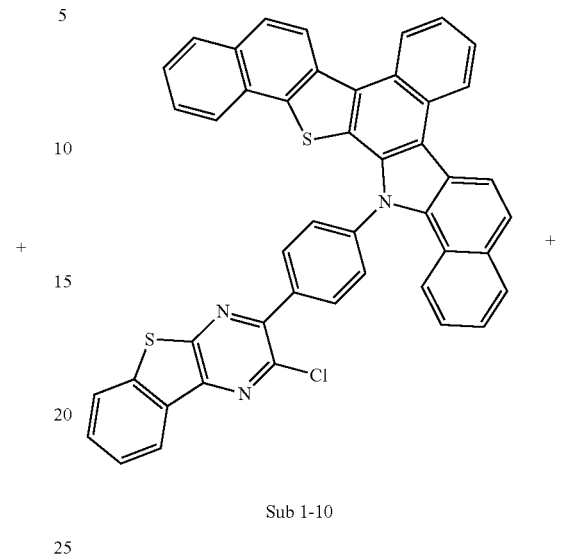

Sub 1-10

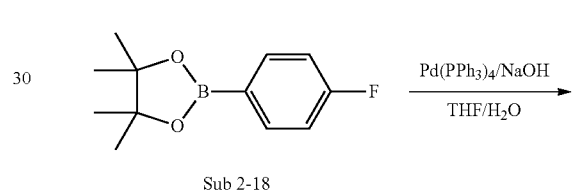

Sub 2-18

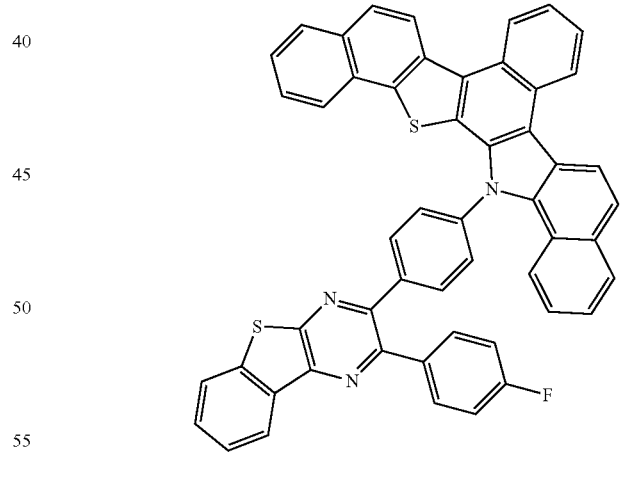

1-30

Sub 1-4 (9 g, 10.88 mmol), THF (48 ml), Sub 2-1 (2.22 g, 10.88 mmol), Pd(PPh$_3$)$_4$ (0.5 g, 0.44 mmol), NaOH (1.31 g, 32.63 mmol), water (24 ml) were carried out in the same manner as described above for the synthesis of the compound 1-1 to obtain 6.71 g of the product (yield: 71%).

Sub 1-10 (11 g, 15.31 mmol), THF (67 ml), Sub 2-18 (3.4 g, 15.31 mmol), Pd(PPh$_3$)$_4$ (0.71 g, 0.61 mmol), NaOH (1.84 g, 45.94 mmol), water (34 ml) were carried out in the same manner as described above for the synthesis of the compound 1-1 to obtain 7.51 g of the product (yield: 63%).

Synthesis example of 1-44

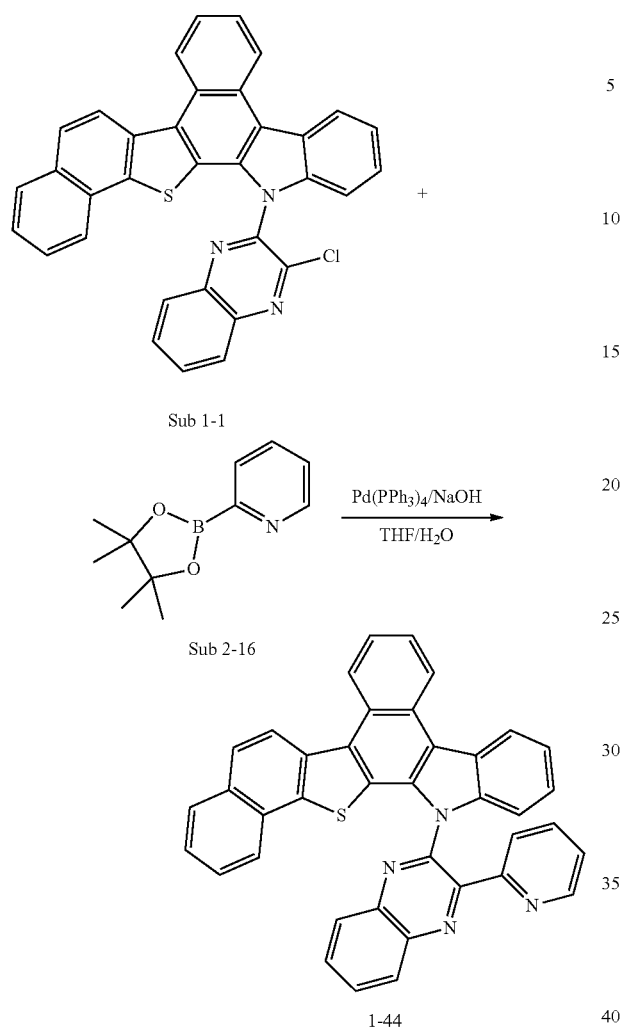

Sub 1-1 (11 g, 20.52 mmol), THF (90 ml), Sub 2-16 (4.21 g, 20.52 mmol), Pd(PPh$_3$)$_4$ (0.95 g, 0.82 mmol), NaOH (2.46 g, 61.56 mmol), water (45 ml) were carried out in the same manner as described above for the synthesis of the compound 1-1 to obtain 7.72 g of the product (yield: 65%).

Synthesis example of 1-45

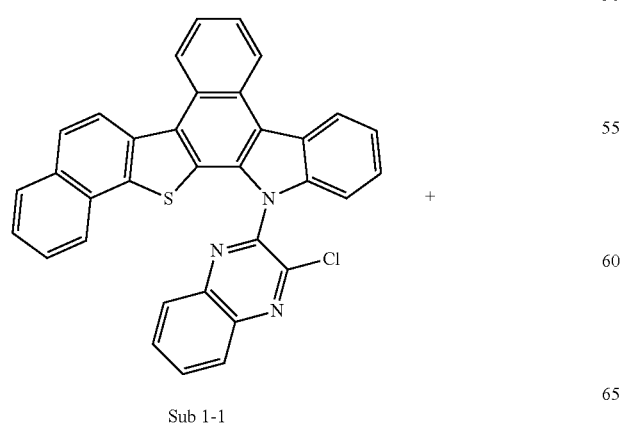

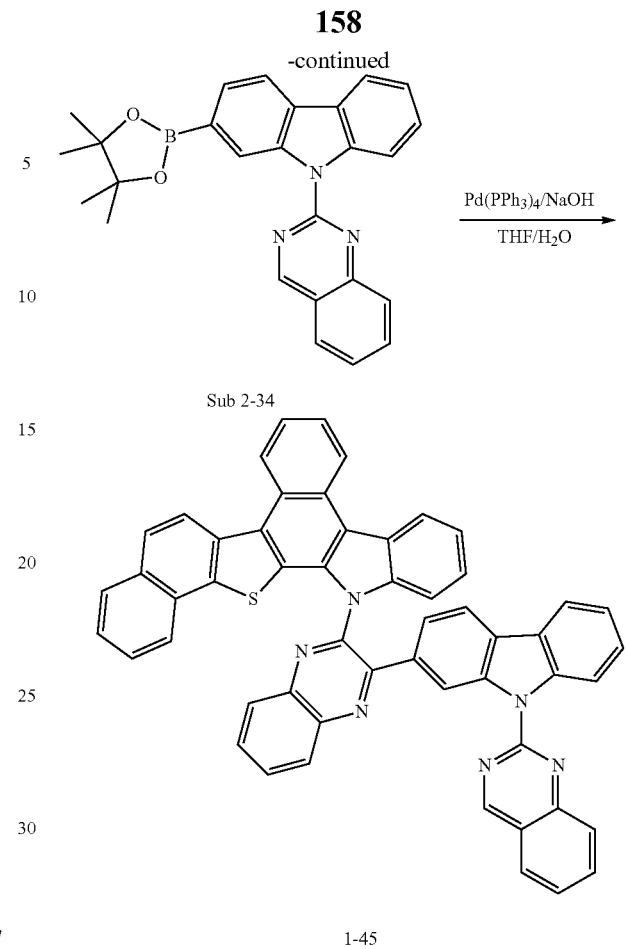

Sub 1-1 (11 g, 20.52 mmol), THF (90 ml), Sub 2-34 (8.65 g, 20.52 mmol), Pd(PPh$_3$)$_4$ (0.95 g, 0.82 mmol), NaOH (2.46 g, 61.56 mmol), water (45 ml) were carried out in the same manner as described above for the synthesis of the compound 1-1 to obtain 9.95 g of the product (yield: 61%).

Synthesis example of 2-7

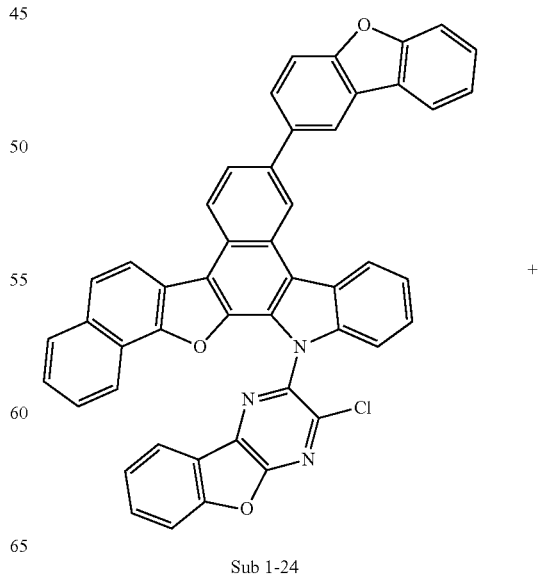

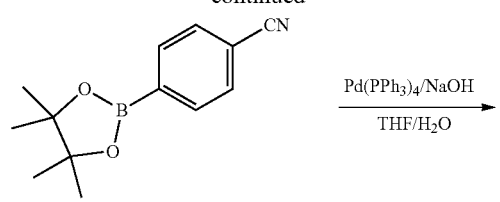
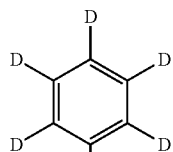

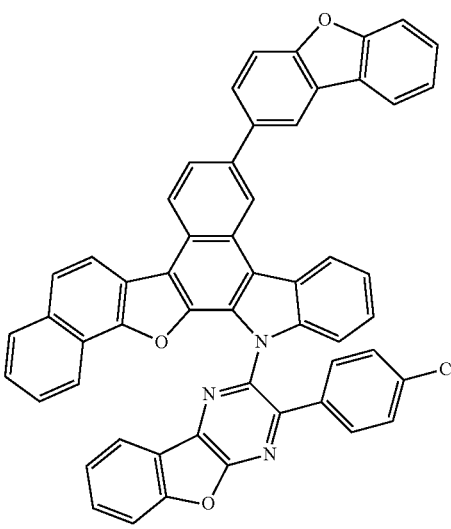

2-7

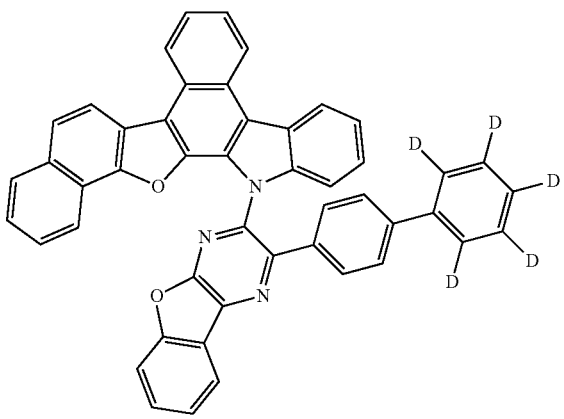

2-9

Sub 1-24 (11 g, 15.15 mmol), THF (66 ml), Sub 2-20 (3.47 g, 15.15 mmol), Pd(PPh$_3$)$_4$ (0.7 g, 0.61 mmol), NaOH (1.82 g, 45.44 mmol), water (33 ml) were carried out in the same manner as described above for the synthesis of the compound 1-1 to obtain 7.69 g of the product (yield: 64%).

Synthesis example of 2-9

Sub 1-25 (11 g, 19.64 mmol), THF (86 ml), Sub 2-13 (5.6 g, 19.64 mmol), Pd(PPh$_3$)$_4$ (0.91 g, 0.79 mmol), NaOH (2.36 g, 58.93 mmol), water (43 ml) were carried out in the same manner as described above for the synthesis of the compound 1-1 to obtain 9.92 g of the product (yield: 74%).

Synthesis example of 3-16

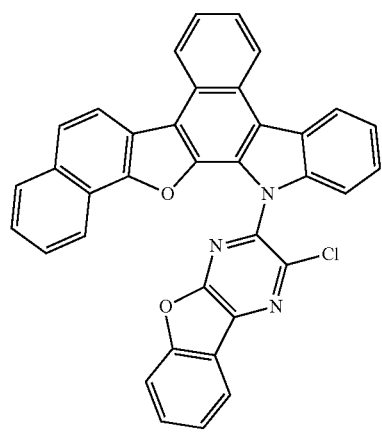

Sub 1-25

+

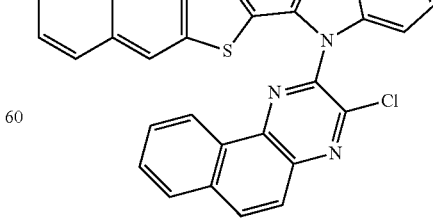

Sub 1-29

+

161
-continued

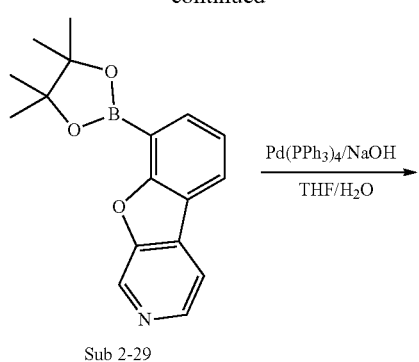
Sub 2-29

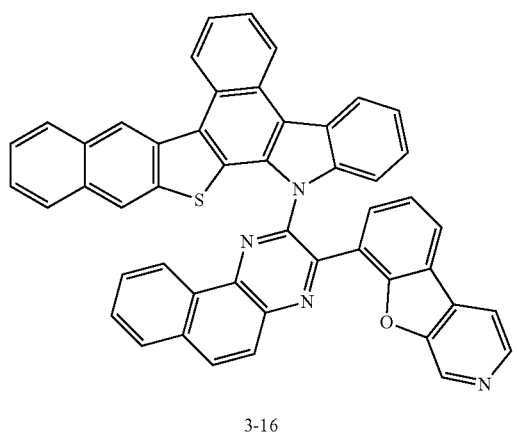
3-16

Sub 1-29 (11 g, 18.77 mmol), THF (82 ml), Sub 2-29 (5.54 g, 18.77 mmol), Pd(PPh$_3$)$_4$ (0.87 g, 0.75 mmol), NaOH (2.25 g, 56.30 mmol), water (41 ml) were carried out in the same manner as described above for the synthesis of the compound 1-1 to obtain 8.5 g of the product (yield: 63%).

Synthesis example of 4-3

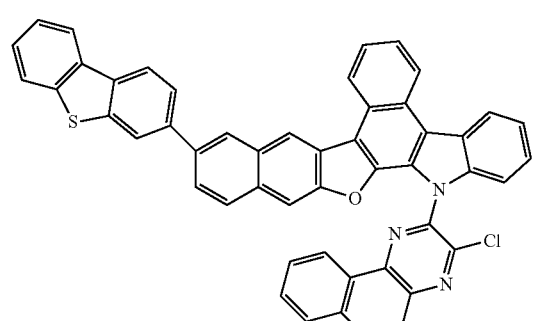
Sub 1-44

162
-continued

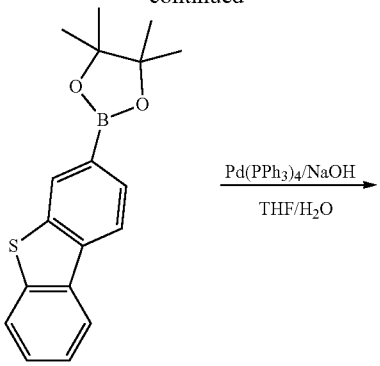
Sub 2-22

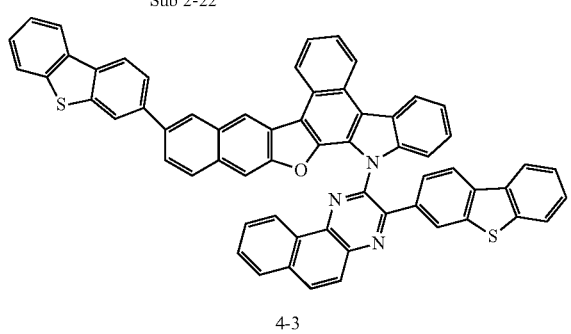
4-3

Sub 1-44 (11 g, 14.62 mmol), THF (64 ml), Sub 2-22 (4.54 g, 14.62 mmol), Pd(PPh$_3$)$_4$ (0.68 g, 0.58 mmol), NaOH (1.75 g, 43.87 mmol), water (32 ml) were carried out in the same manner as described above for the synthesis of the compound 1-1 to obtain 8.03 g of the product (yield: 61%).

Synthesis example of 5-9

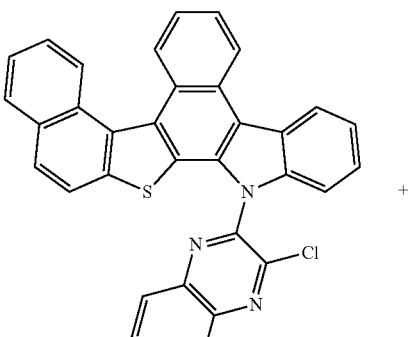
Sub 1-52

+

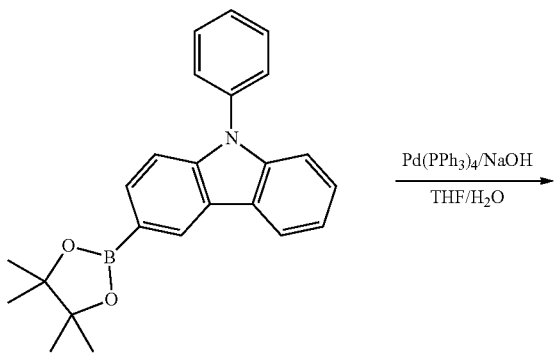
Sub 2-32

163

-continued

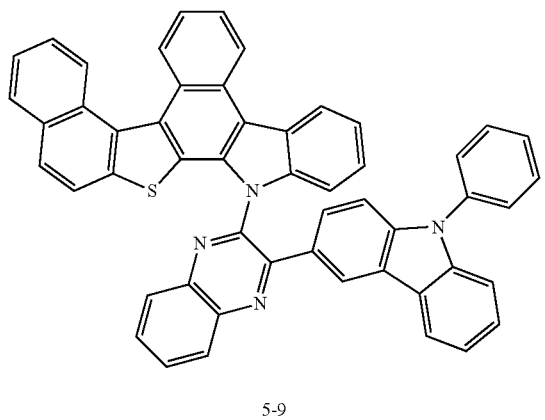

5-9

164

-continued

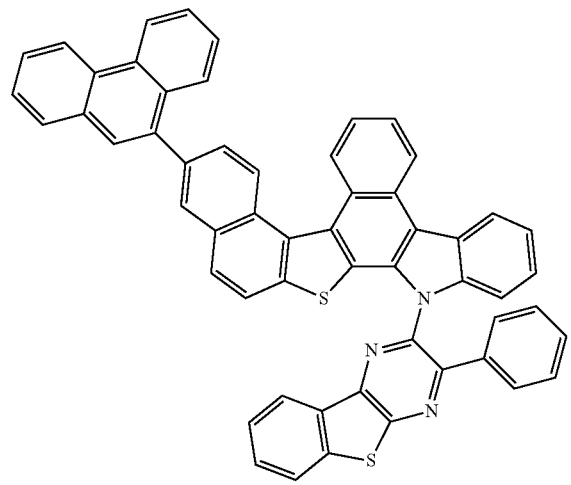

5-25

Sub 1-52 (11 g, 20.52 mmol), THF (90 ml), Sub 2-32 (7.58 g, 20.52 mmol), Pd(PPh$_3$)$_4$ (0.95 g, 0.82 mmol), NaOH (2.46 g, 61.56 mmol), water (45 ml) were carried out in the same manner as described above for the synthesis of the compound 1-1 to obtain 10.98 g of the product (yield: 72%).

Synthesis example of 5-25

Sub 1-57 (11 g, 14.32 mmol), THF (63 ml), Sub 2-1 (2.92 g, 14.32 mmol), Pd(PPh$_3$)$_4$ (0.66 g, 0.57 mmol), NaOH (1.72 g, 42.95 mmol), water (31 ml) were carried out in the same manner as described above for the synthesis of the compound 1-1 to obtain 8.35 g of the product (yield: 72%).

Synthesis example of 5-41

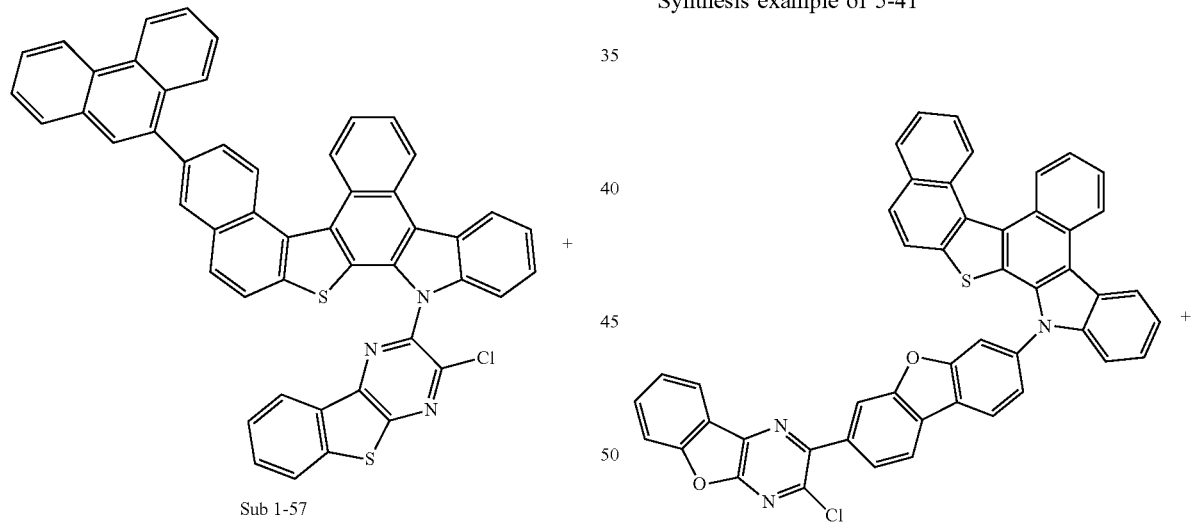

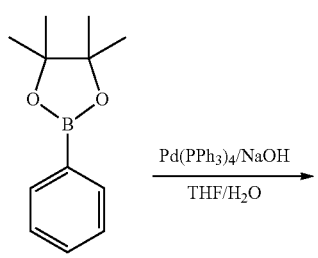

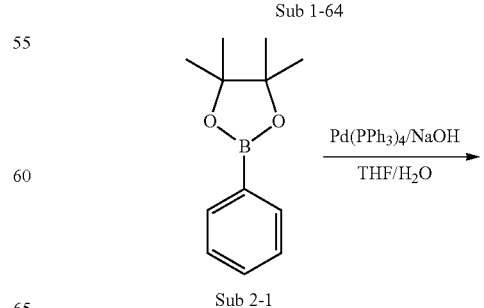

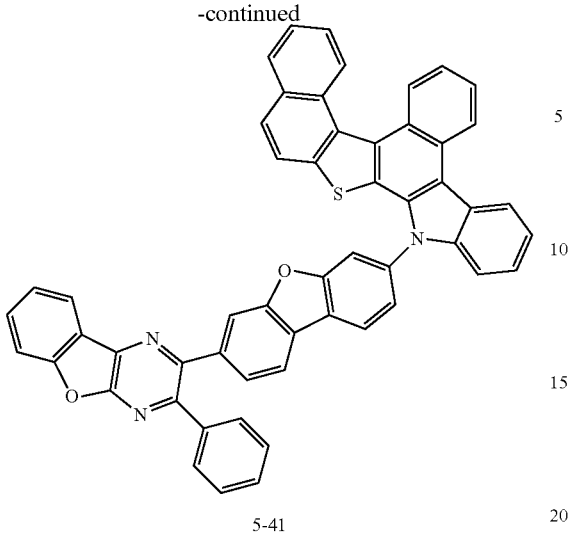

5-41

Sub 1-64 (11 g, 14.82 mmol), THF (65 ml), Sub 2-1 (3.02 g, 14.82 mmol), Pd(PPh$_3$)$_4$ (0.69 g, 0.59 mmol), NaOH (1.78 g, 44.46 mmol), water (32 ml) were carried out in the same manner as described above for the synthesis of the compound 1-1 to obtain 8.83 g of the product (yield: 76%).

Synthesis example of 6-15

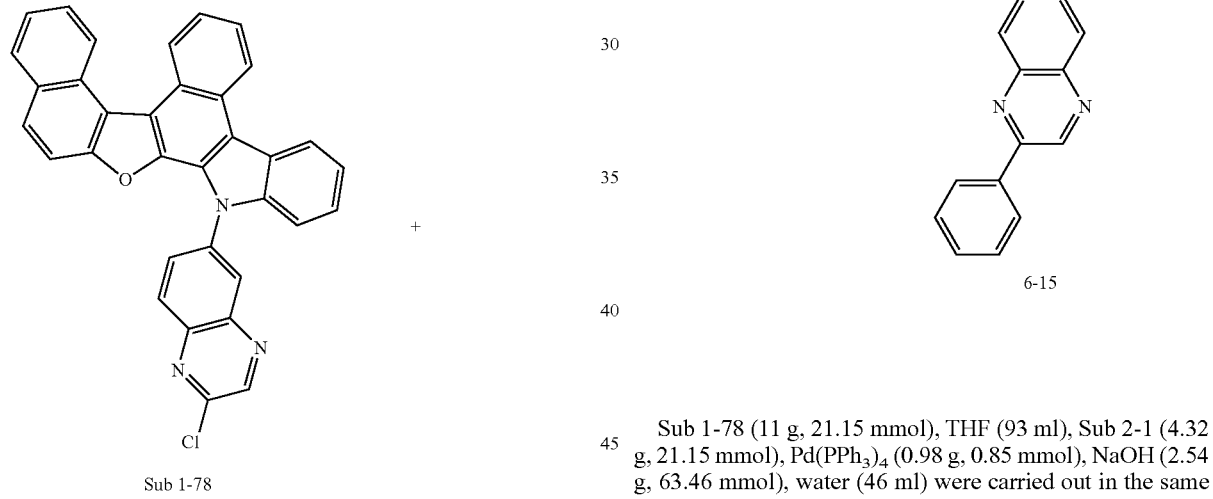

6-15

Sub 1-78 (11 g, 21.15 mmol), THF (93 ml), Sub 2-1 (4.32 g, 21.15 mmol), Pd(PPh$_3$)$_4$ (0.98 g, 0.85 mmol), NaOH (2.54 g, 63.46 mmol), water (46 ml) were carried out in the same manner as described above for the synthesis of the compound 1-1 to obtain 9.27 g of the product (yield: 78%).

TABLE 3

| Compound | FD-MS | Compound | FD-MS |
|---|---|---|---|
| 1-1 | m/z = 577.16(C$_{40}$H$_{23}$N$_3$S = 577.71) | 1-2 | m/z = 627.18(C$_{44}$H$_{25}$N$_3$S = 627.77) |
| 1-4 | m/z = 868.27(C$_{62}$H$_{36}$N$_4$S = 869.06) | 1-6 | m/z = 683.15(C$_{26}$H$_{25}$N$_3$S$_2$ = 683.85) |
| 1-8 | m/z = 627.18(C$_{44}$H$_{25}$N$_3$S = 627.77) | 1-14 | m/z = 868.27(C$_{62}$H$_{36}$N$_4$S = 869.06) |
| 1-16 | m/z = 633.13(C$_{42}$H$_{23}$N$_3$S$_2$ = 633.79) | 1-26 | m/z = 683.15(C$_{26}$H$_{25}$N$_3$S$_2$ = 683.85) |
| 1-30 | m/z = 777.17(C$_{52}$H$_{28}$FN$_3$S$_2$ = 777.94) | 1-34 | m/z = 667.17(C$_{46}$H$_{25}$N$_3$OS = 667.79) |
| 1-39 | m/z = 693.19(C$_{48}$H$_{27}$N$_3$—OS = 693.82) | 1-44 | m/z = 578.16(C$_{39}$H$_{22}$N$_4$O = 578.69) |
| 1-45 | m/z = 794.23(C$_{54}$H$_{30}$N$_6$S = 794.94) | 2-1 | m/z = 561.18(C$_{40}$H$_{23}$N$_3$O = 561.64) |
| 2-4 | m/z = 707.17(C$_{48}$H$_{25}$N$_3$—O$_2$S = 707.81) | 2-5 | m/z = 743.20(C$_{52}$H$_{29}$N$_3$—OS = 743.88) |
| 2-7 | m/z = 792.22(C$_{55}$H$_{28}$N$_4$—O$_3$ = 792.85) | 2-9 | m/z = 682.24(C$_{48}$H$_{22}$D$_5$N$_3$O$_2$ = 682.79) |
| 3-1 | m/z = 577.16(C$_{40}$H$_{23}$N$_3$S = 577.71) | 3-2 | m/z = 627.18(C$_{44}$H$_{25}$N$_3$S = 627.77) |
| 3-4 | m/z = 653.19(C$_{46}$H$_{27}$N$_3$S = 653.80) | 3-15 | m/z = 733.16(C$_{50}$H$_{27}$N$_3$S$_2$ = 733.91) |
| 3-16 | m/z = 718.18(C$_{49}$H$_{26}$N$_4$OS = 718.83) | 3-19 | m/z = 683.15(C$_{26}$H$_{25}$N$_3$S$_2$ = 683.85) |
| 3-36 | m/z = 693.19(C$_{48}$H$_{27}$N$_3$—OS = 693.82) | 3-44 | m/z = 717.19(C$_{50}$H$_{27}$N$_3$—OS = 717.85) |
| 3-45 | m/z = 799.18(C$_{54}$H$_{29}$N$_3$—OS$_2$ = 799.97) | 4-1 | m/z = 561.18(C$_{40}$H$_{23}$N$_3$O = 561.64) |
| 4-2 | m/z = 687.23(C$_{50}$H$_{29}$N$_3$O = 687.80) | 4-3 | m/z = 899.21(C$_{62}$H$_{33}$N$_3$OS$_2$ = 900.09) |
| 4-9 | m/z = 677.21(C$_{48}$H$_{27}$N$_3$O$_2$ = 677.76) | 5-1 | m/z = 577.16(C$_{40}$H$_{23}$N$_3$S = 577.71) |

TABLE 3-continued

| Compound | FD-MS | Compound | FD-MS |
|---|---|---|---|
| 5-2 | m/z = 627.18($C_{44}H_{25}N_3S$ = 627.77) | 5-7 | m/z = 632.21($C_{44}H_{20}D_5N_3S$ = 632.80) |
| 5-8 | m/z = 677.19($C_{48}H_{27}N_3S$ = 677.83) | 5-9 | m/z = 742.22($C_{52}H_{30}N_4S$ = 742.90) |
| 5-11 | m/z = 818.25($C_{58}H_{34}N_4S$ = 819.00) | 5-24 | m/z = 723.14($C_{48}H_{25}N_3OS_2$ = 723.87) |
| 5-25 | m/z = 809.20($C_{56}H_{31}N_3S_2$ = 810.01) | 5-26 | m/z = 709.16($C_{48}H_{27}N_3S_2$ = 709.89) |
| 5-31 | m/z = 683.15($C_{26}H_{25}N_3S_2$ = 683.85) | 5-41 | m/z = 783.20($C_{54}H_{279}N_3O_2S$ = 783.91) |
| 5-42 | m/z = 617.16($C_{42}H_{23}N_3OS$ = 617.73) | 5-44 | m/z = 733.22($C_{51}H_{31}N_3OS$ = 733.89) |
| 6-1 | m/z = 611.20($C_{44}H_{25}N_3O$ = 611.70) | 6-2 | m/z = 651.19($C_{46}H_{25}N_3O_2$ = 651.73) |
| 6-3 | m/z = 743.20($C_{52}H_{29}N_3OS$ = 743.88) | 6-5 | m/z = 713.25($C_{52}H_{31}N_3O$ = 713.84) |
| 6-7 | m/z = 737.25($C_{54}H_{31}N_3O$ = 737.86) | 6-12 | m/z = 918.30($C_{66}H_{38}N_4O_2$ = 919.06) |
| 6-15 | m/z = 561.18($C_{40}H_{23}N_3O$ = 561.64) | | |

In the above, even though an exemplary synthesis example of the present invention represented by the Formula 1 are described, all of them are based on Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), Grignard reaction, Cyclic Dehydration reaction and $PPh_3$-mediated reductive cyclization reaction (*J. Org. Chem.* 2005, 70, 5014.). Therefore, it will be understood by those skilled in the art that the above reaction proceeds even when other substituents (substituents of $R^1$, $R^2$, $R^3$, $R^4$, $L^1$, $L^2$, $Ar^1$ and the like) defined in Formula 1 are bonded, in addition to the substituents described in the specific synthesis example.

Fabrication and Evaluation of Organic Electronic Element

[Example 1] Red OLED (Phosphorescent Host)

Organic light emitting diodes (OLEDs) were fabricated according to a conventional method by using a compound obtained by synthesis as host material of a light emitting.

First, an ITO layer (anode) was formed on a glass substrate, and a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Then, 4,4-bis[N-(1-naphthyl)-N-phenylamino]biphenyl (hereinafter abbreviated as "NPD") was vacuum-deposited on the hole injection layer to form a hole transfer layer with a thickness of 60 nm.

Subsequently, a light emitting layer with a thickness of 30 nm was deposited on the hole transport layer by doping the hole transport layer with the compound 1-1 of the present invention as host material and bis-(1-phenylisoquinolyl) iridium(III)acetylacetonate (hereinafter abbreviated as "$(piq)_2Ir(acac)$") as a dopant material in a weight ratio of 95:5.

Next, a film of ((1,1'-bisphenyl)-4-olato)bis(2-methyl-8-quinolinolato)aluminum (hereinafter abbreviated as "BAlq") was vacuum-deposited with a thickness of 5 nm on the light emitting layer to form a hole blocking layer, and a film of Bis(10-hydroxybenzo[h]quinolinato)beryllium (hereinafter abbreviated as "$BeBq_2$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode.

[Example 2] to [Example 44]

OLEDs were manufactured in the same manner as described in Example 1, except that any one of the compounds of the present invention in the Table 4 below was used as host material of the light emitting layer, instead of the inventive compound 1-1.

[Comparative Example 1] to [Comparative Example 4]

OLEDs were manufactured in the same manner as described in Example 1, except that any one of comparative compounds 1 to 4 was used as host material of the light emitting layer, instead of the inventive compound 1-1.

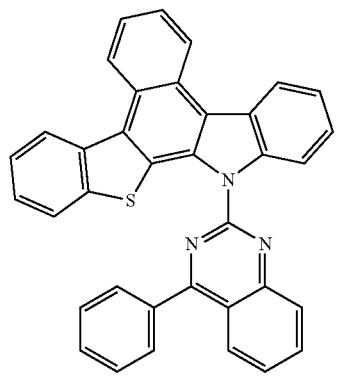

<comp. com. 1>

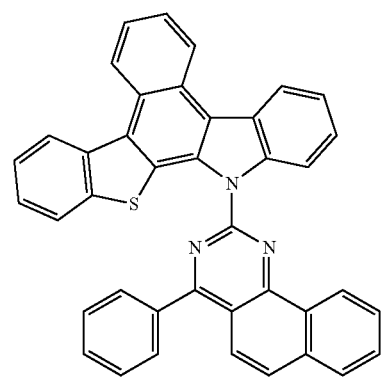

<comp. com. 2>

-continued

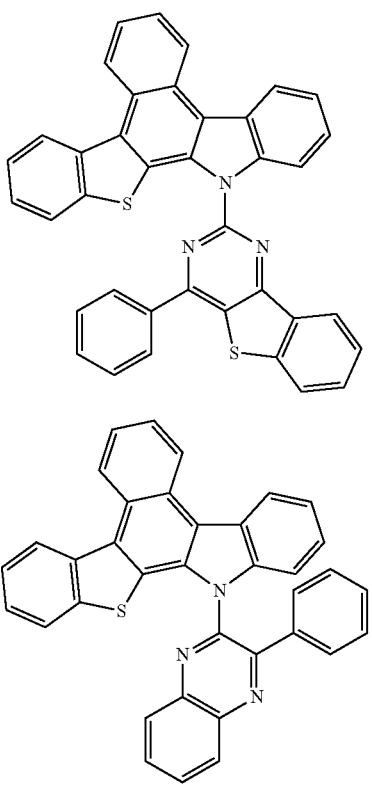

<comp. com. 3>

<comp. com. 4>

A forward bias DC voltage was applied to each of the OLEDs manufactured through the Examples 1 to 44 and Comparative Examples 1 to 4, and electro-luminescence (EL) characteristics of the OLED were measured by PR-650 (Photo research). T95 life span was measured by life span measuring equipment (Mc science) at reference brightness of 2500 cd/m². Table 4 below shows results of fabrication and evaluation of OLED.

TABLE 4

| Ex. (27) | Com. 3-36 | 5.3 | 14.0 | 2500 | 26.9 | 144.2 | 0.68 | 0.32 |
| Ex. (28) | Com. 3-44 | 5.3 | 14.1 | 2500 | 26.7 | 139.2 | 0.68 | 0.33 |
| Ex. (29) | Com. 3-45 | 5.3 | 14.0 | 2500 | 26.9 | 141.7 | 0.68 | 0.33 |
| Ex. (30) | Com. 2-1 | 5.3 | 14.6 | 2500 | 26.1 | 145.9 | 0.68 | 0.33 |
| Ex. (31) | Com. 2-4 | 5.2 | 14.4 | 2500 | 26.4 | 140.2 | 0.68 | 0.32 |
| Ex. (32) | Com. 2-5 | 5.2 | 14.3 | 2500 | 26.5 | 139.4 | 0.68 | 0.33 |
| Ex. (33) | Com. 2-9 | 5.3 | 14.0 | 2500 | 26.9 | 139.9 | 0.68 | 0.33 |
| Ex. (34) | Com. 6-1 | 5.4 | 14.5 | 2500 | 26.2 | 138.8 | 0.68 | 0.33 |
| Ex. (35) | Com. 6-2 | 5.4 | 14.5 | 2500 | 26.3 | 133.1 | 0.68 | 0.32 |
| Ex. (36) | Com. 6-3 | 5.4 | 14.6 | 2500 | 26.1 | 134.2 | 0.68 | 0.32 |
| Ex. (37) | Com. 6-5 | 5.4 | 14.4 | 2500 | 26.4 | 131.6 | 0.68 | 0.33 |
| Ex. (38) | Com. 6-7 | 5.3 | 14.7 | 2500 | 26.0 | 135.3 | 0.68 | 0.33 |
| Ex. (39) | Com. 6-9 | 5.2 | 14.8 | 2500 | 25.9 | 133.5 | 0.68 | 0.33 |
| Ex. (40) | Com. 6-12 | 5.4 | 14.5 | 2500 | 26.3 | 131.4 | 0.68 | 0.32 |
| Ex. (41) | Com. 6-15 | 5.6 | 15.0 | 2500 | 25.7 | 129.2 | 0.68 | 0.33 |
| Ex. (42) | Com. 4-1 | 5.5 | 15.5 | 2500 | 25.1 | 133.1 | 0.68 | 0.33 |
| Ex. (43) | Com. 4-2 | 5.5 | 16.4 | 2500 | 24.2 | 130.5 | 0.68 | 0.33 |
| Ex. (44) | Com. 4-9 | 5.5 | 14.8 | 2500 | 25.9 | 130.2 | 0.68 | 0.32 |

As can be seen from the results of Table 4, it was confirmed that in case of Examples 1 to 44 using compound according to one embodiment of the present invention as a phosphorescent host, the driving voltage, luminescent efficiency, life span and color purity were significantly improved as compared to Comparative Examples 1 to 4.

At present, the present inventors are studying to lower power consumption, increase efficiency and color purity, and a sub-substituent having excellent electron mobility is required. Therefore, the fused pyrazine type substituent which has better electron transfer properties than the substituents of the fused pyrimidine type used in conventional phosphorescent red host was introduced. In fact, it was confirmed that the introduction of a specific substituent (fused pyrazine type) such as comparative compound 4 is excellent in the electron mobility and thus the efficiency is increased and the driving voltage is lowered.

TABLE 5

| Fused pyrazine type (The present invention) | Fused pyrimidine |
|---|---|
| (pyrazine structure with B ring) | (pyrimidine structure with B ring) |
| Quinoxaline, benzoquinoxaline, dibenzoquinoxaline, benzothienopyrazine, benzofuropyrazine, etc. | Quinazoline, benzoquinazoline, dibenzoquinazoline, benzothienopyrimidine, benzofuropyrimidine, etc. |

(The definition of the B ring is the same as the B ring of claim 1)

Comparing Comparative Examples 1 to 3 with Comparative Example 4, it was confirmed that Comparative Example 4 having quinoxaline (a fused pyrazine) as a sub substituent showed the improved efficiency and remarkably improved driving voltage, compared with Comparative Compounds 1 to 3 in which fused pyrimidine was bonded as a sub substituent having a different N substitution position. It can be explained that the energy band gap is changed and electron mobility becomes high due to the binding of specific substituents even if the core is the same.

That is, in the case of the compound of the present invention in which fused pyrazine is introduced as a sub-substituent instead of fused pyrimidine, electron injection from the ETL into a light emitting layer becomes easier as the LUMO level becomes lower and the charge balance in a light emitting layer is improved, and thus it is considered that the driving voltage and the lifetime are improved.

In addition, it seems that efficiency is improved because the conjugation length becomes longer and the charge transfer to the dopant becomes easy as benzene being more fused at a specific position of the 6-ring heterocyclic core. It can be confirmed that the PL wavelength is red shifted when a benzene ring is formed at a specific position of the core (Comparison of PL data of Comparative Compound 4 and the inventive Compound 1-1: long wavelength from 527 nm to 555 nm). It can be confirmed that the efficiency and color purity are improved because the charge transfer to the dopant is facilitated by making the wavelength of the host longer wavelength.

It is considered that as a result, HOMO/LUMO, T1 value and energy band gap are optimized so that the charge transfer from the host to the dopant can be smoothly performed as the effect of the fused pyrazine type substituent (high charge carrier mobility, improved driving voltage) and the formation of additional benzene rings at specific positions of the core (7 ring), thereby improving the performance of the device as a whole.

TABLE 6

| <PL data of comparative compounds 1 to 4 and compound 1-1 of the present invention> | | | | |
|---|---|---|---|---|
| comp. Com 1 | comp. Com 2 | comp. Com 3 | comp. Com 4 | The inventive Com. 1-1 |
| PL (nm) 515 | 497 | 507 | 527 | 555 |

Figure 4:
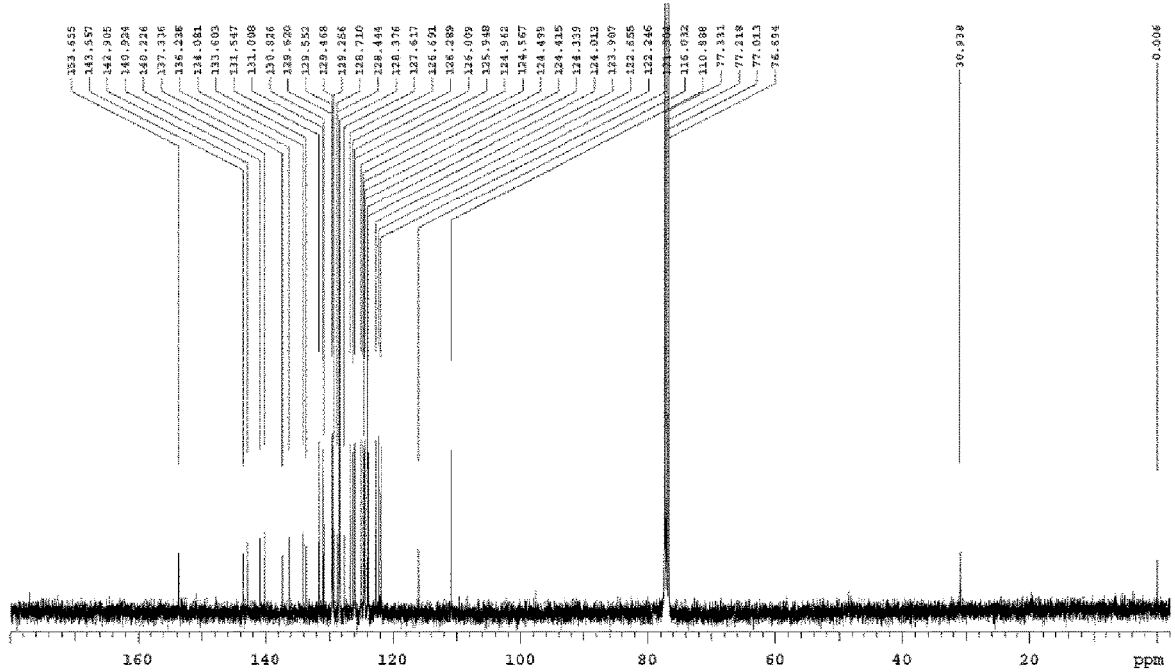
FIG. 4 shows the 13C NMR results of compound 1-1 of the present invention.

Refer to FIG. 4.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1 below:

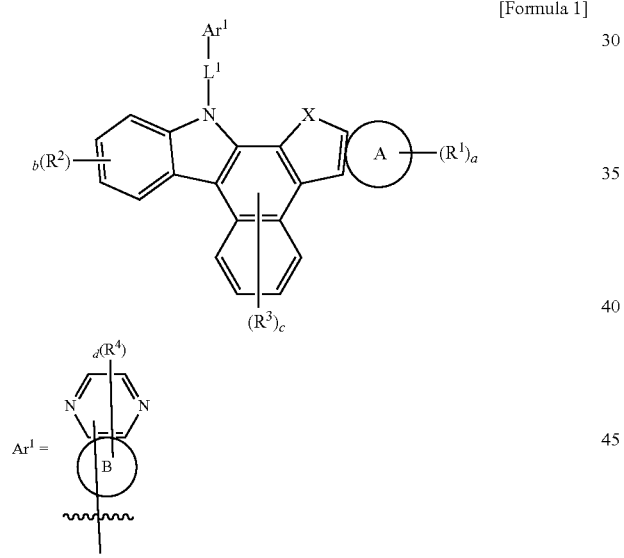

[Formula 1]

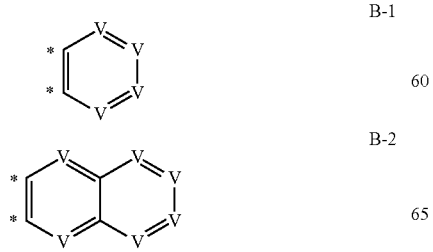

wherein,
1) A ring is $C_{10}$ aryl group,
2) B ring is selected from the group consisting of the following formulas B-1 to B-16:

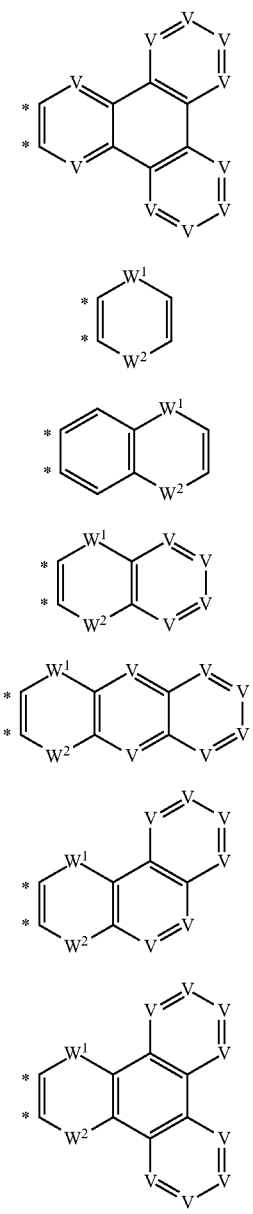

in formulas B-1 to B-16, "*" indicates the position to be condensed with pyrazine comprising two Ns, 3) $W^1$ and $W^2$ are each independently a single bond, S or O,
4) V is N or C,
5) X is O or S,
6) a is an integer of 0 to 6, b and c are each an integer of 0 to 4, d is an integer of 0 to 11,
7) $R^1$, $R^2$, $R^3$ and $R^4$ are the same or different from each other, and are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxyl group and -L'-N($R^a$)($R^b$), or when a, b and c are 2 or more, $R^1$, $R^2$ and $R^3$ are each in plural and are the same or different, and a plurality of $R^1$, a plurity of $R^2$, or a plurality of $R^3$ may be bonded to each other to form a ring, 8) L' is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group, and $R^a$ and $R^b$ are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, 9) $L^1$ is each independently selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group and the aryl group, fluorenyl group, arylene group, heterocyclic group, fused ring group, alkyl group, alkenyl group, alkoxyl group, and aryloxy group may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, -L'-N($R^a$)($R^b$), a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group, and these substituents may be linked each other to form a ring, wherein 'ring' comprises a $C_3$-$C_{60}$ aliphatic ring, a $C_6$-$C_{60}$ aromatic ring, a $C_2$-$C_{60}$ heterocyclic group or the combination thereof.

2. The compound of claim 1, wherein Formula 1 above is represented by any one of Formulas 2 to 4 below:

[Formula 2]

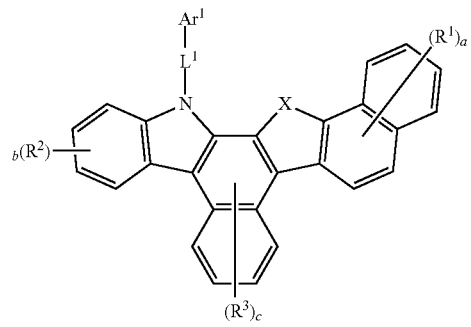

[Formula 3]

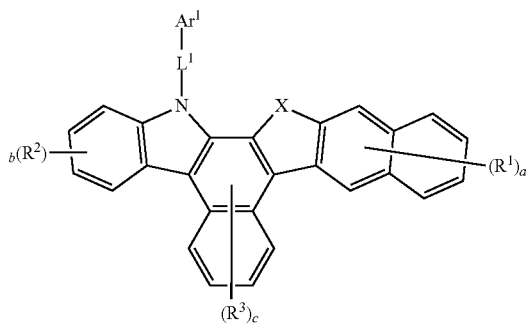

175
-continued

[Formula 4]

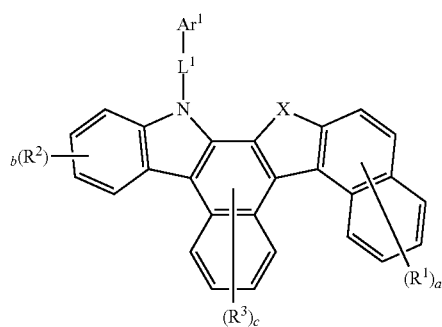

in Formulas 2 to 4, X, $L^1$, $Ar^1$, $R^1$, $R^2$, $R^3$, a, b and c are the same as defined in claim 1.

3. The compound of claim 1, wherein Formula 1 above is represented by any one of Formulas 5 to 7 below:

[Formula 5]

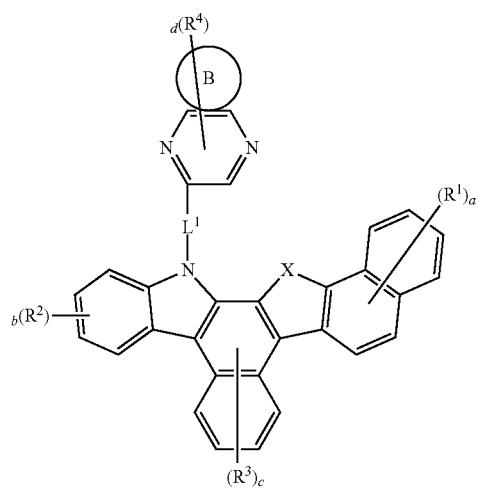

[Formula 6]

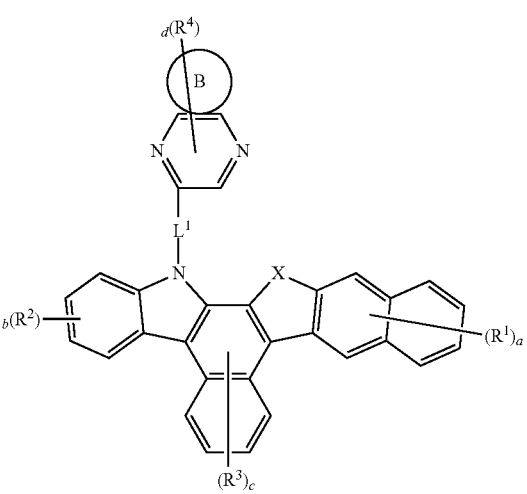

176
-continued

[Formula 7]

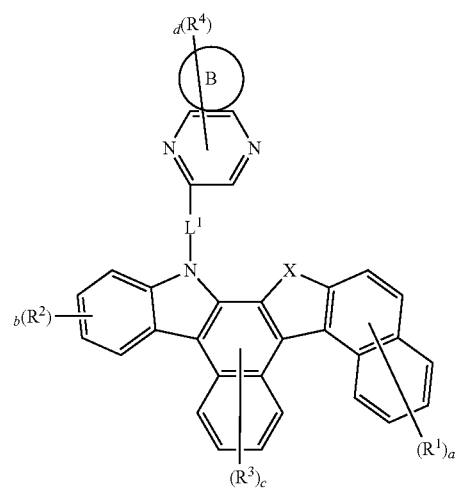

in Formulas 5 to 7, X, $L^1$, $Ar^1$, $R^1$, $R^2$, $R^3$, $R^4$, a, b, c, d and B ring are the same as defined in claim 1.

4. The compound of claim 1, wherein the chemical structure $Ar'$ of the formula 1 comprising the pyrazine is represented by any one of the following Formulas C-1 to C-22:

C-1

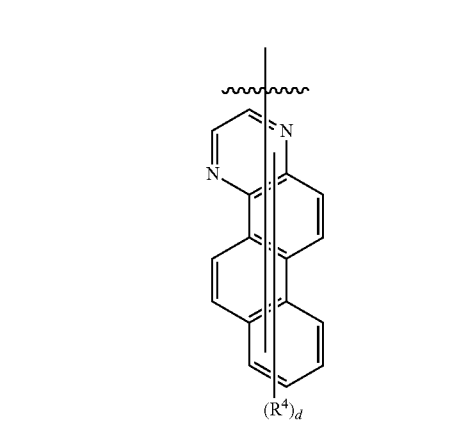

C-2

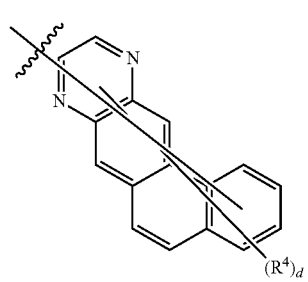

C-3

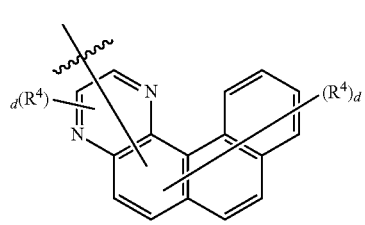

-continued
C-4
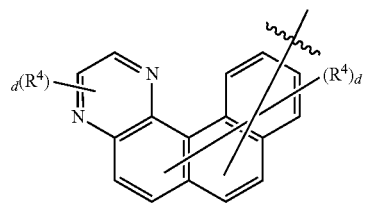
C-5
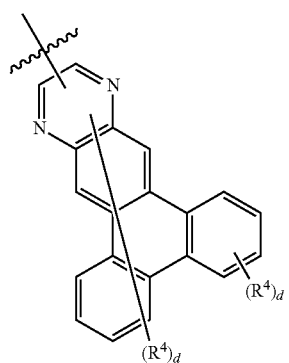
C-6
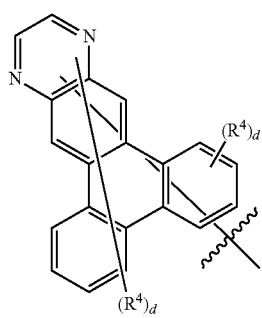
C-7
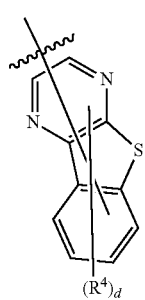
C-8
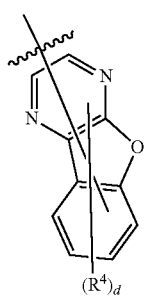
-continued
C-9
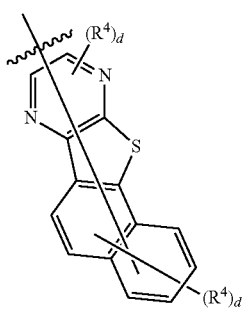
C-10
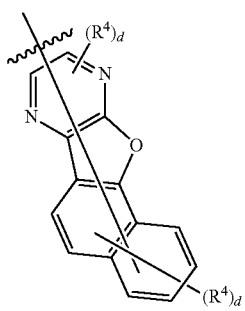
C-11
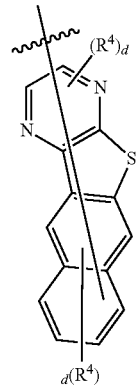
C-12
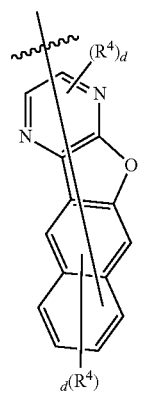

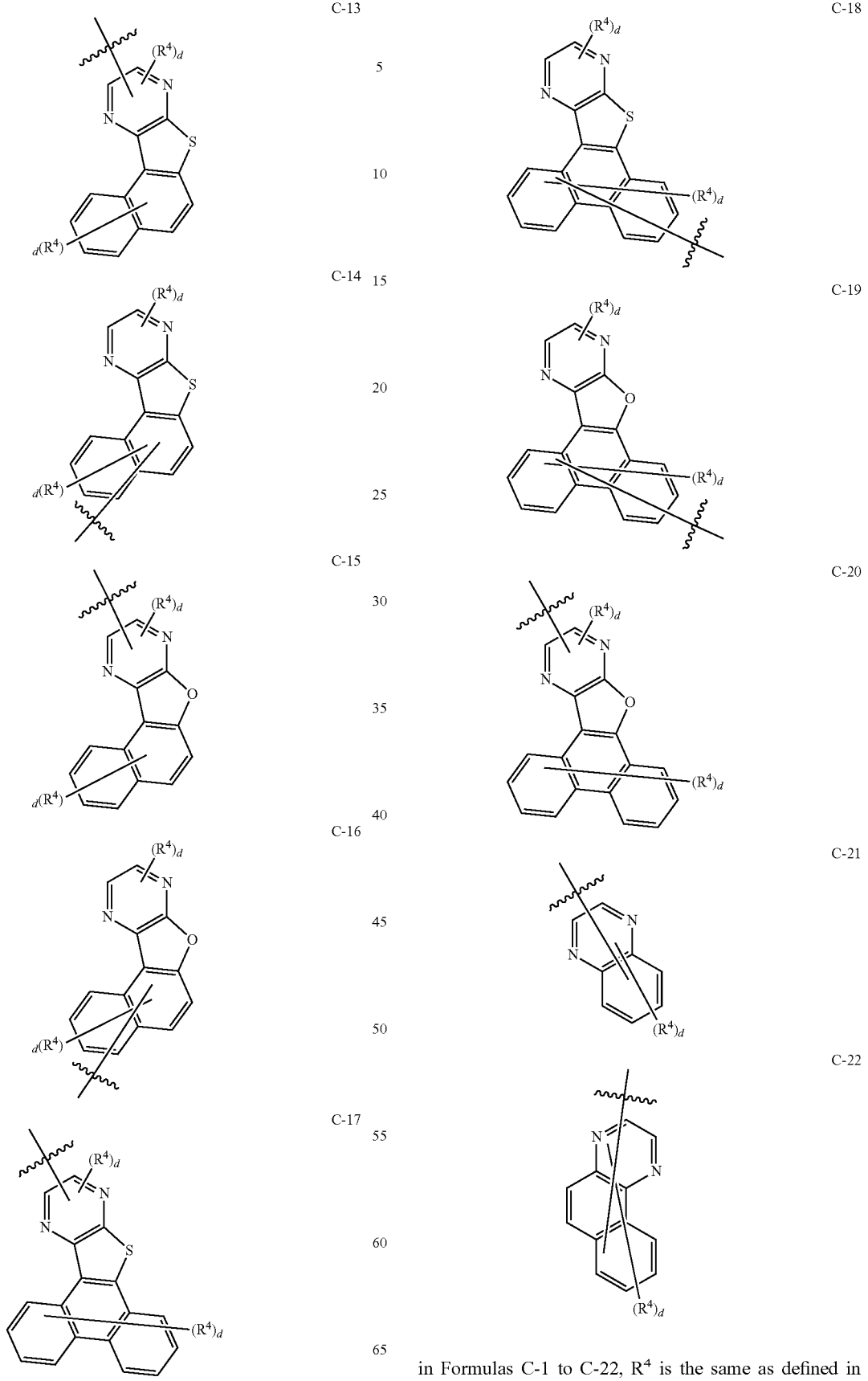
in Formulas C-1 to C-22, $R^4$ is the same as defined in claim 1, and d is an integer of 0 to 11.

5. The compound of claim 1, wherein $R^4$ of Formula 1 is represented by any one of the following formulas R-1 to R-10:

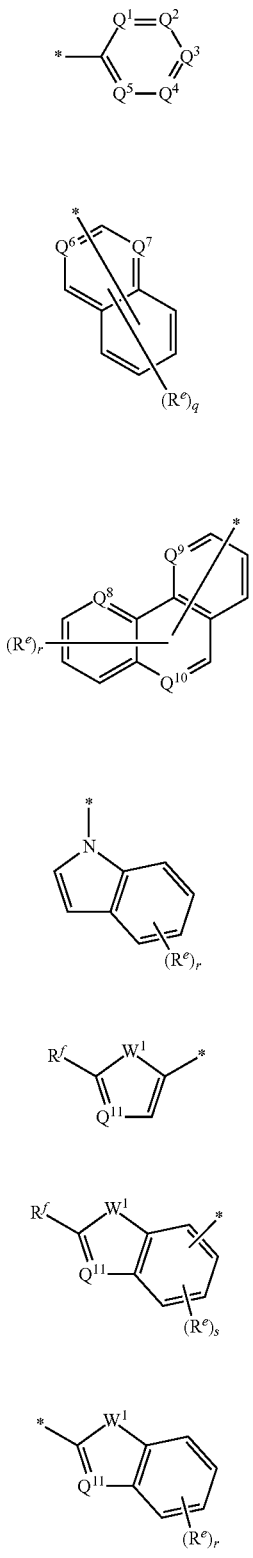

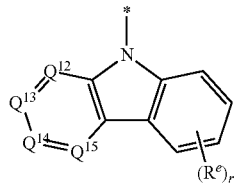

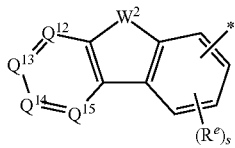

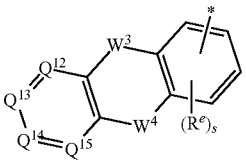

in Formulas R-1 to R-10,
1) $Q^1$ to $Q^{15}$ are each independently $CR^g$ or N,
2) $W^1$ is S, O or $NR^h$,
3) $W^2$ to $W^4$ are each independently S, O, $NR^h$ or $CR^iR^j$,
4) $R^e$ is selected from the group consisting of hydrogen, deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, and when these substituents are adjacent, they may be linked each other to form a ring,
5) $R^f$ and $R^g$ are each independently selected from the group consisting of hydrogen, deuterium, a $C_6$-$C_{20}$ aryl group, a fluorenyl group, a fused ring group of a $C_3$-$C_{20}$ aliphatic ring and a $C_6$-$C_{20}$ aromatic ring, a $C_2$-$C_{20}$ heterocyclic group containing at least one heteroatom selected from O, N, S, Si, and P, a $C_1$-$C_{20}$ alkyl group, a $C_2$-$C_{20}$ alkenyl group, a $C_2$-$C_{20}$ alkynyl group, and a $C_1$-$C_{30}$ alkoxyl group,
6) $R^h$, $R^i$ and $R^j$ are each independently selected from the group consisting of a $C_6$-$C_{20}$ aryl group, a $C_2$-$C_{20}$ heterocyclic group containing at least one heteroatom selected from O, N, S, Si, and P, a $C_1$-$C_{20}$ alkyl group, a $C_2$-$C_{20}$ alkenyl group, a $C_1$-$C_{20}$ alkoxyl group and a fluorenyl group, $R^i$ and $R^j$ may be linked each other to form a spiro compound together with C to which they are bonded,
7) q is each independently an integer of 0 to 5,
8) r is each independently an integer of 0 to 4,
9) s is each independently an integer of 0 to 3,
when q, r and s are each 2 or more, $R^e$ is each the same or different, and * indicates the position to be bonded.

6. The compound of claim 1, wherein Formula 1 is any one of the compounds below:

183 184
1-1 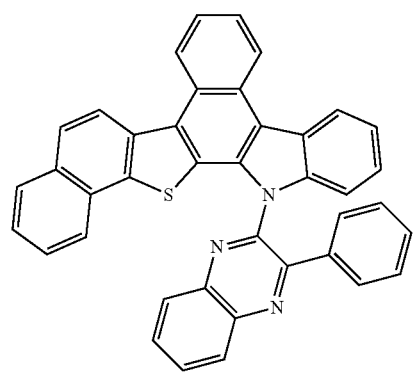
1-2 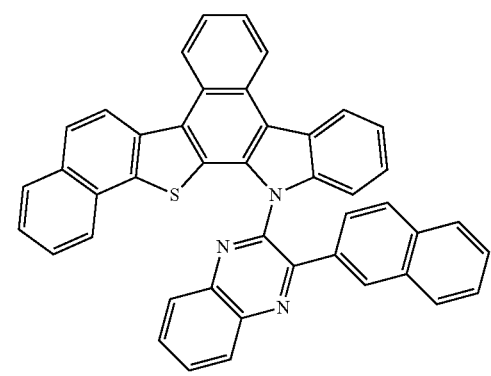
1-3 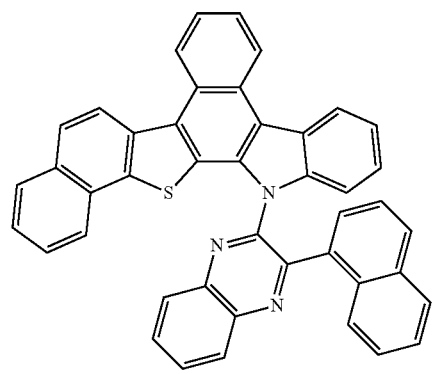
1-4 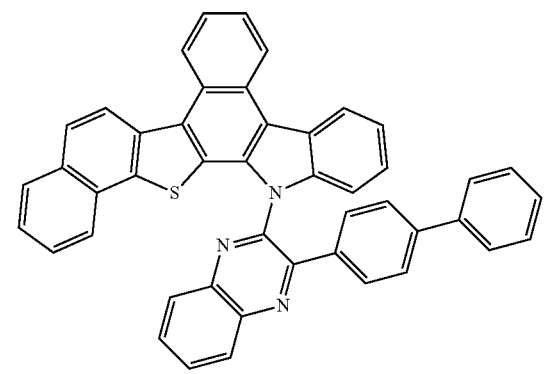
1-5 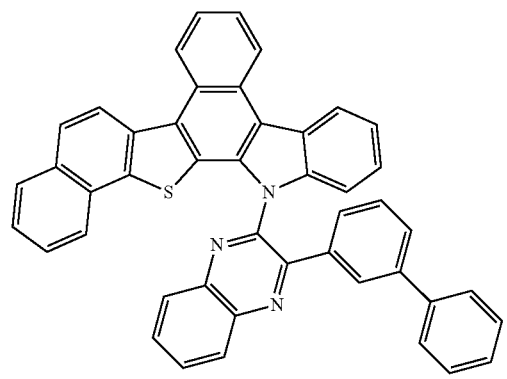
1-6 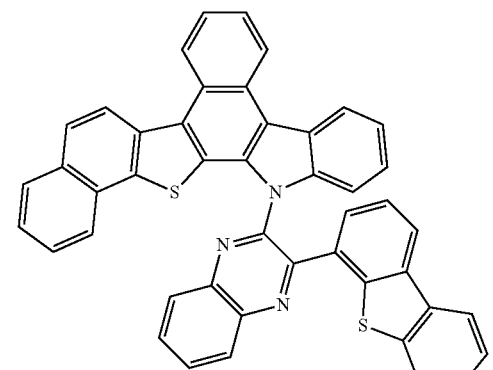
1-7 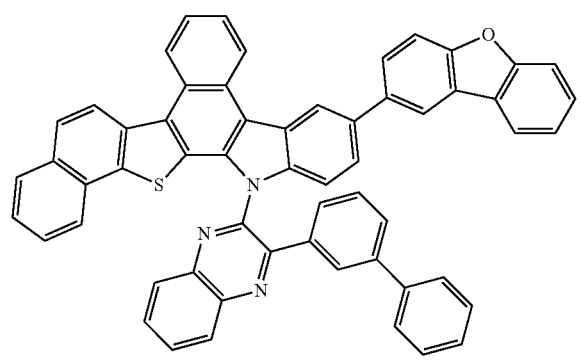
1-8 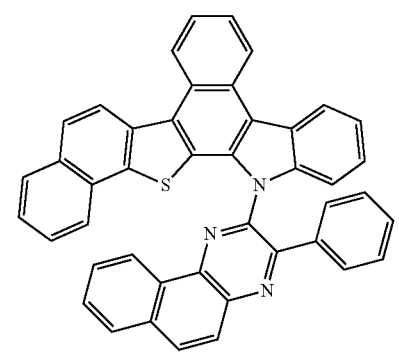

-continued
1-9
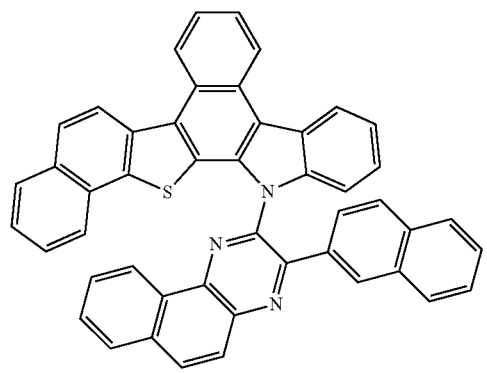
1-10
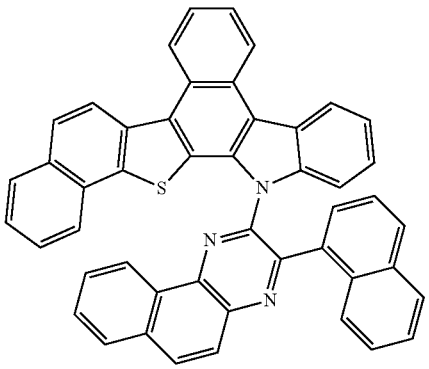
1-11
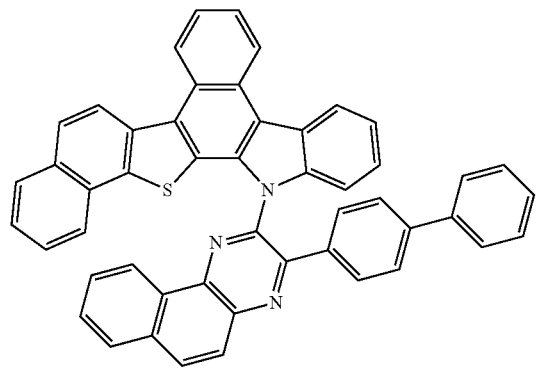
1-12
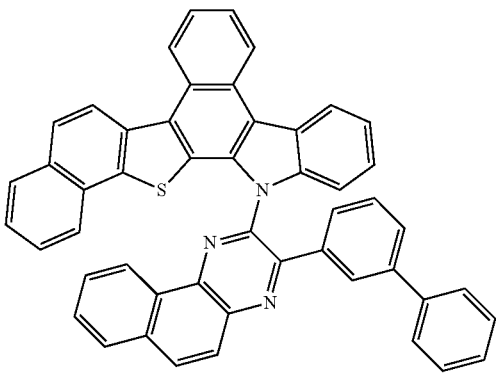
1-13
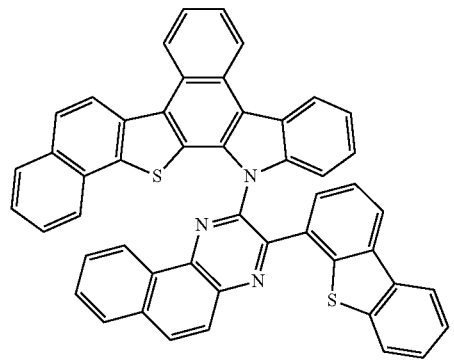
1-14
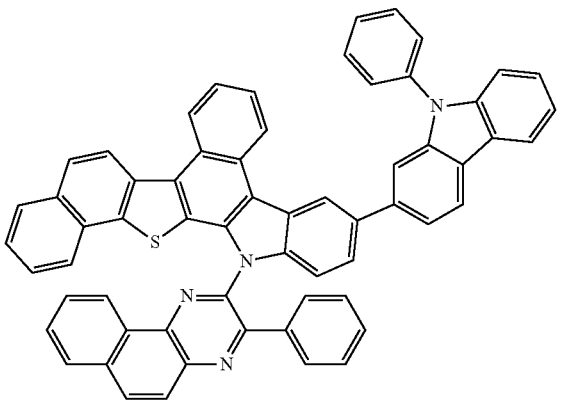
1-15
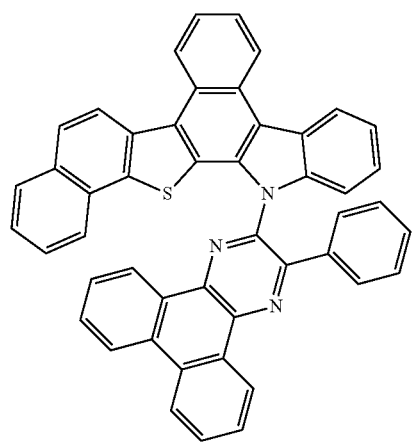
1-16
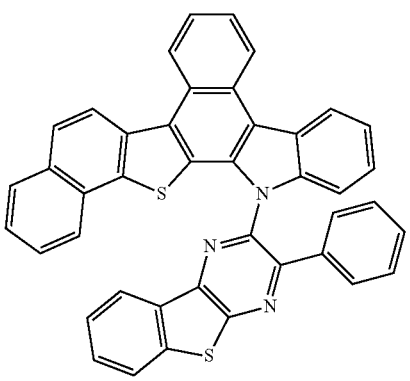

-continued
1-17
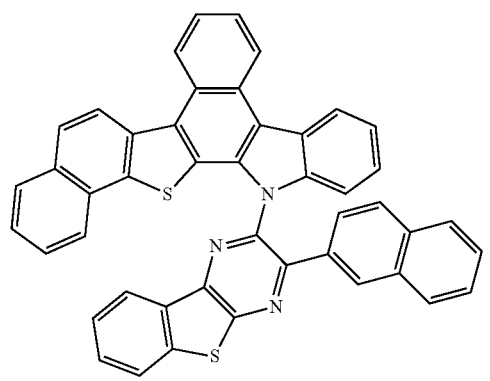
1-18
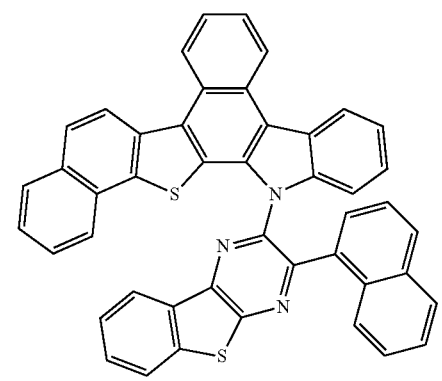
1-19
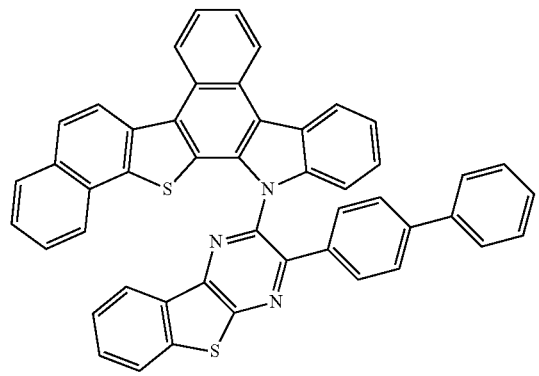
1-20
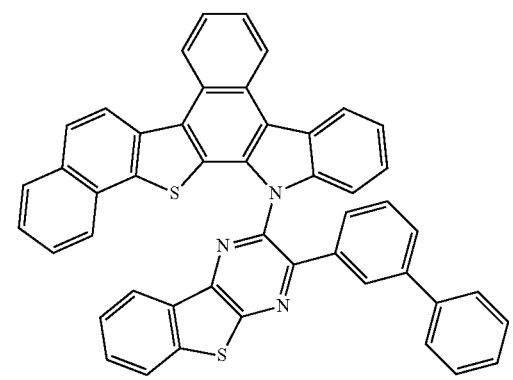
1-21
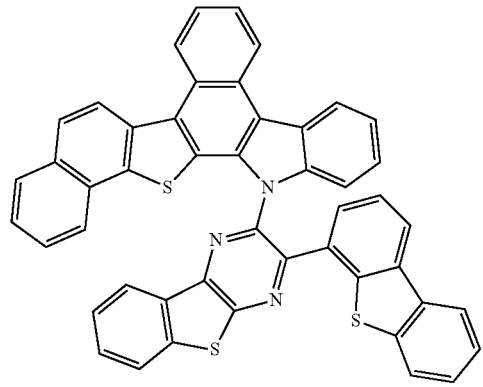
1-22
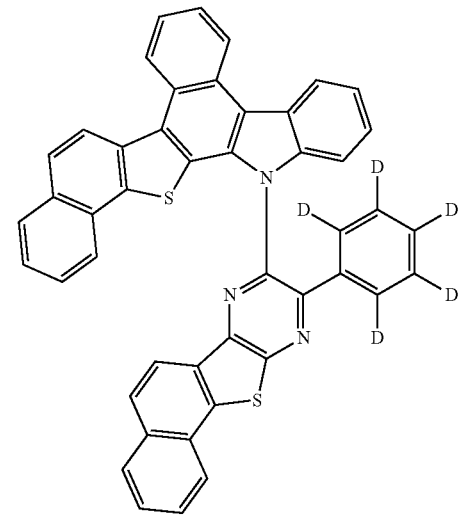
1-23
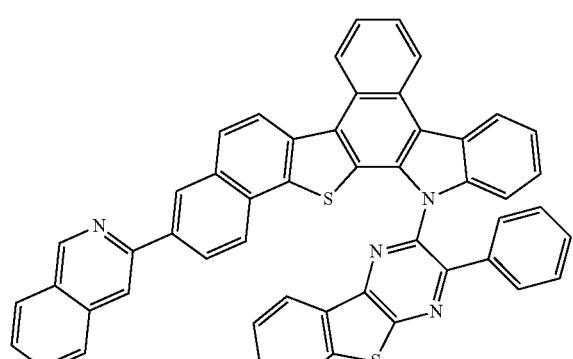
1-24
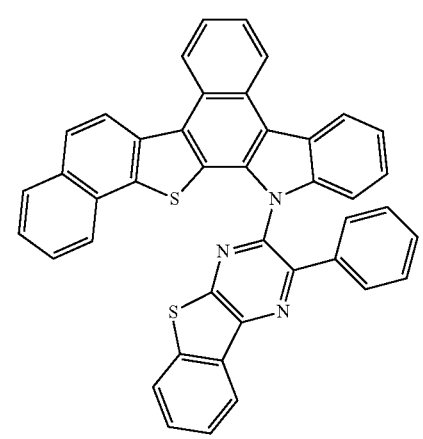

-continued
1-25
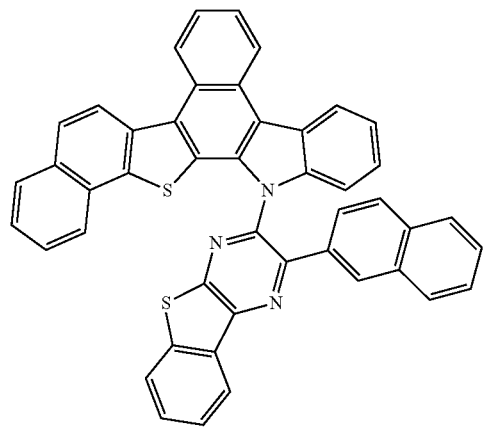
1-26
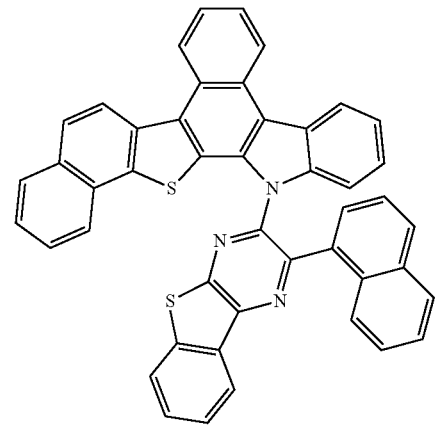
1-27
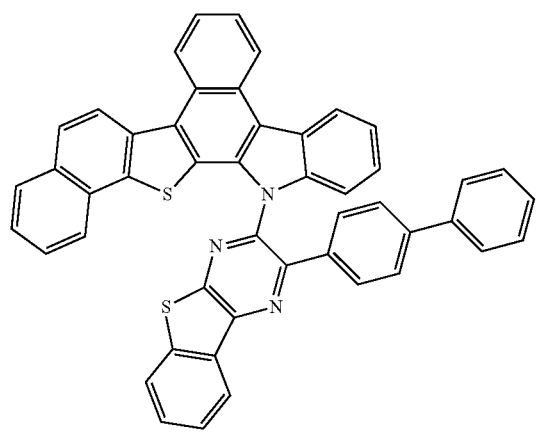
1-28
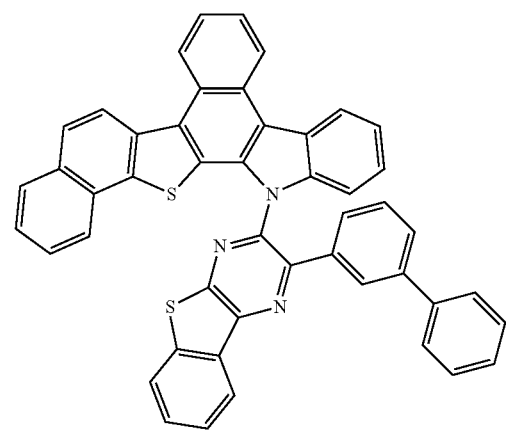
1-29
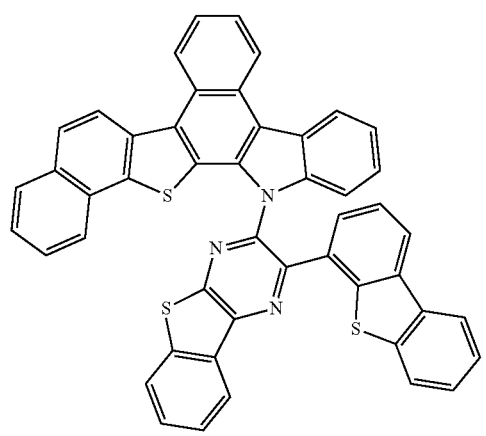
1-30
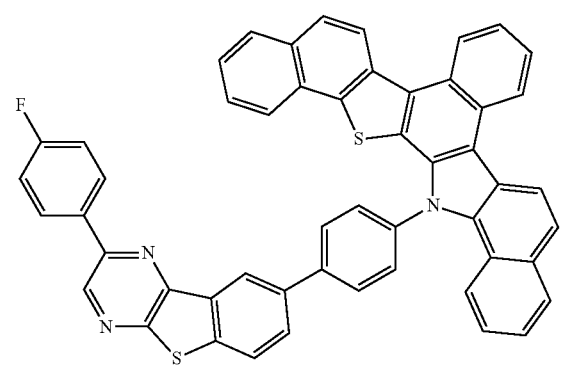

-continued
1-31
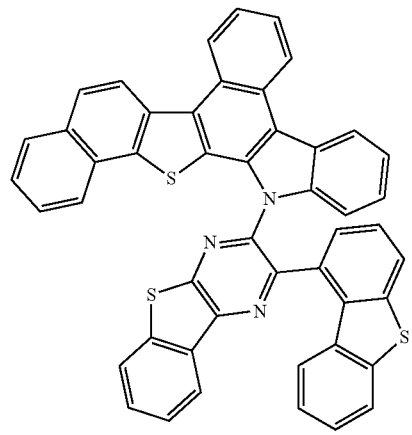
1-32
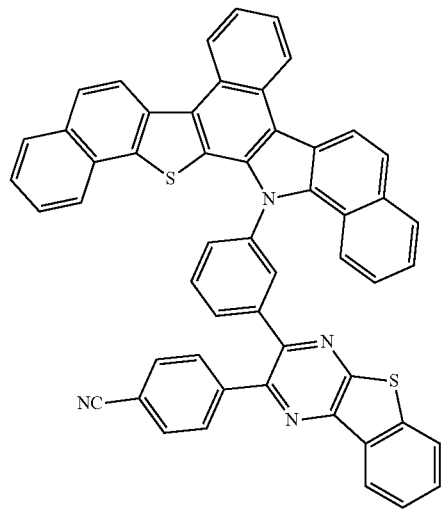
1-33
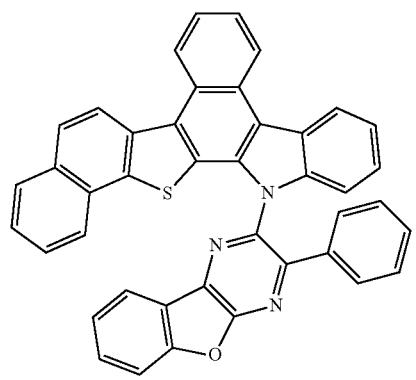
1-34
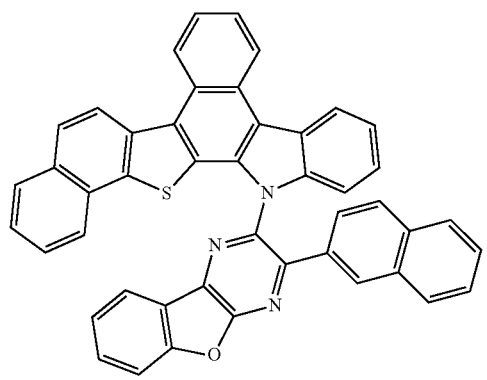
1-35
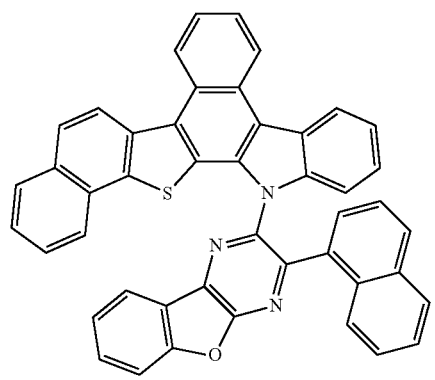
1-36
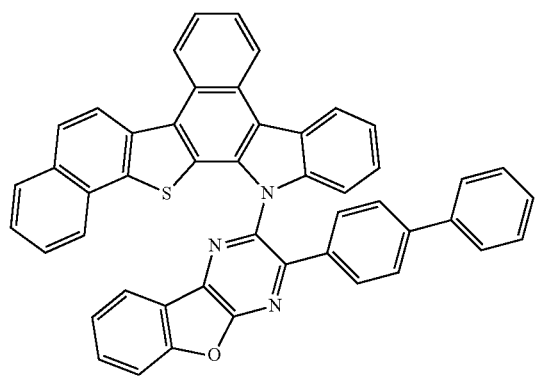
1-37
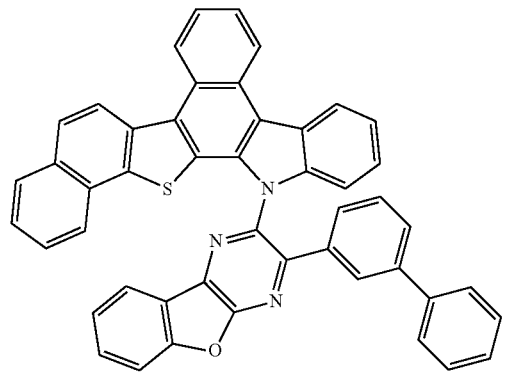
1-38
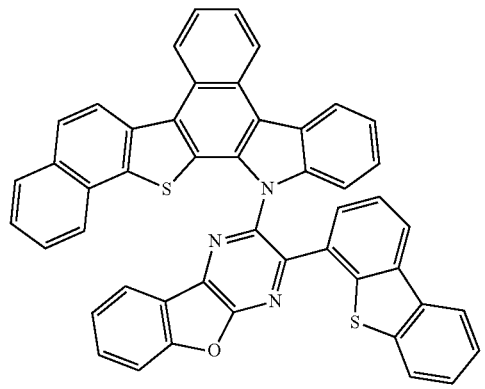

-continued
1-39
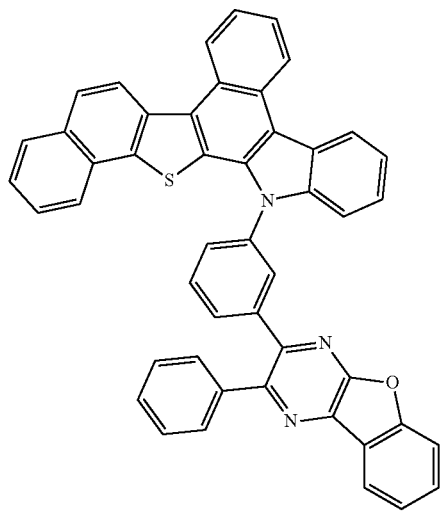
1-40
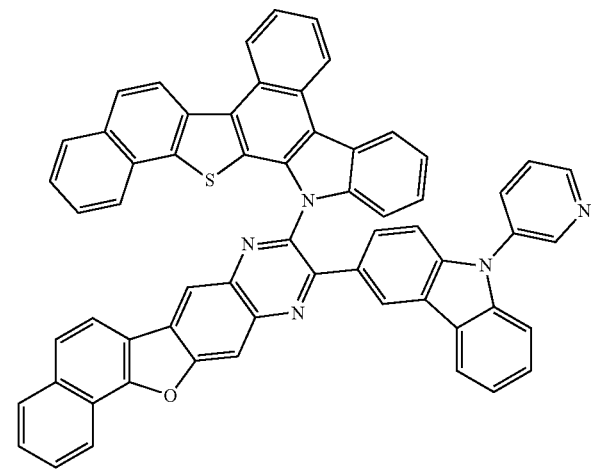
1-41
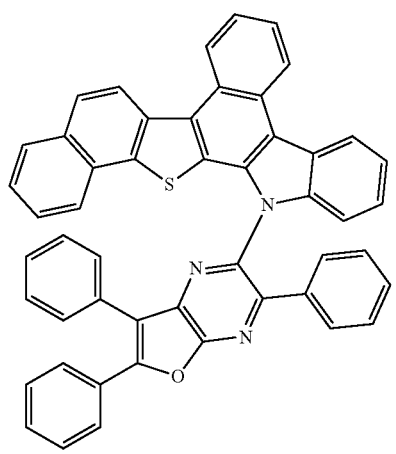
1-42
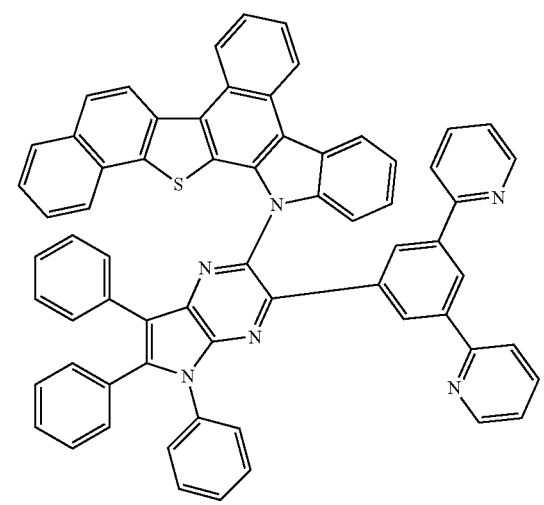
1-43
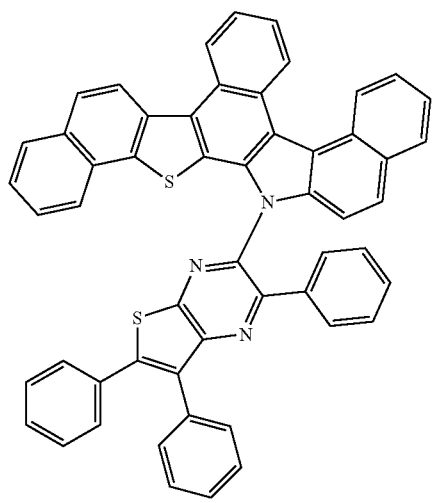
1-44
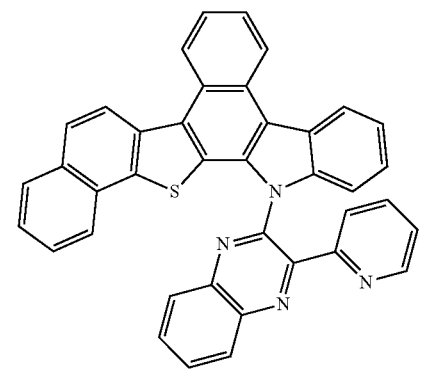

195
-continued
1-45
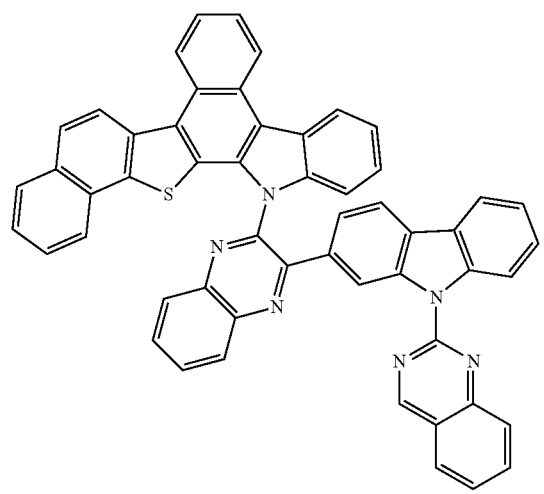
196
2-1
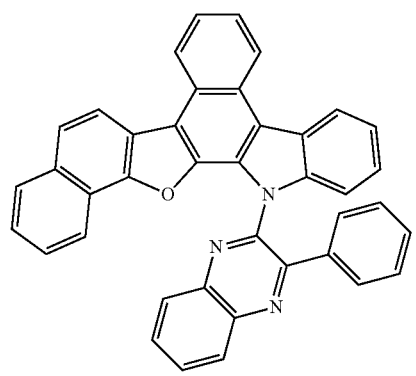
2-2
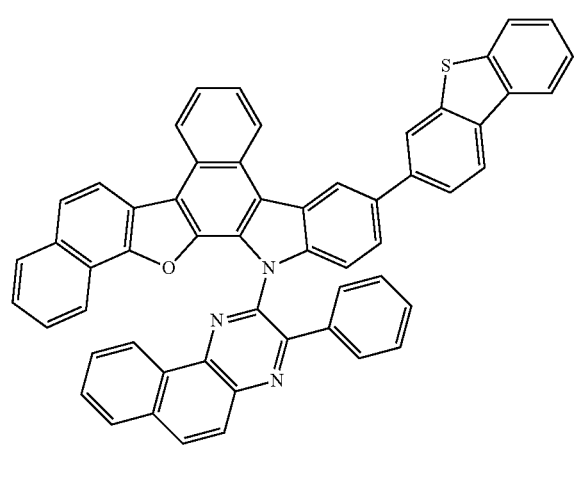
2-3
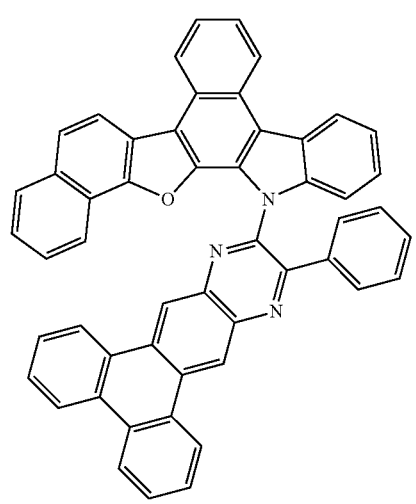
2-4
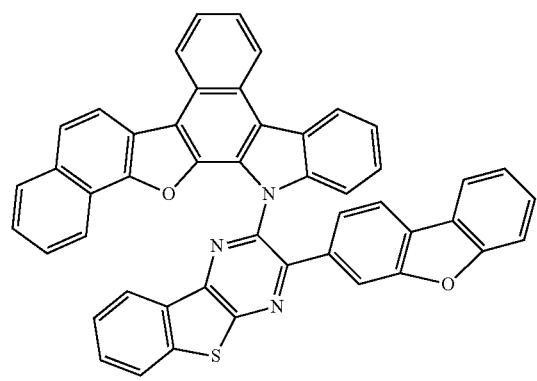
2-5
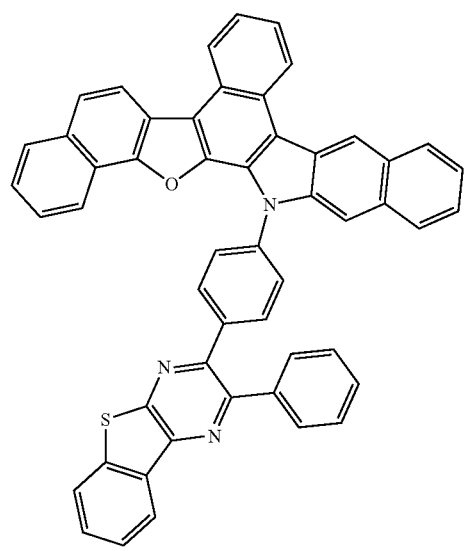

-continued
2-6
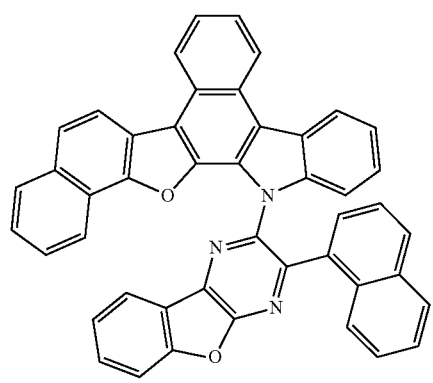
2-7
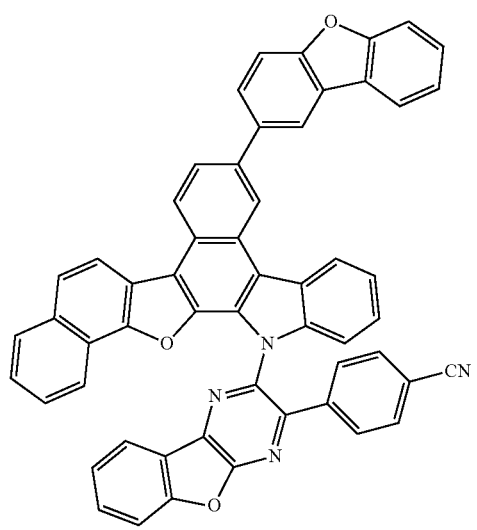
2-8
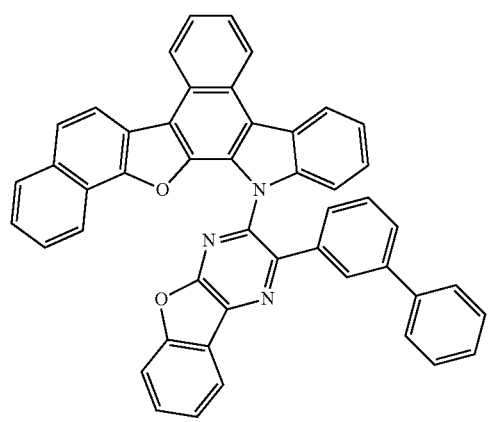
2-9
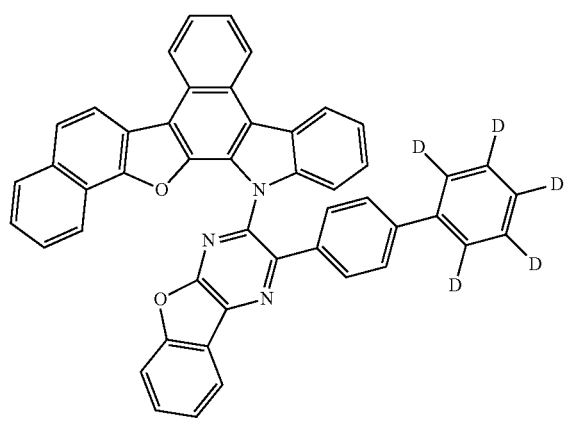
2-10
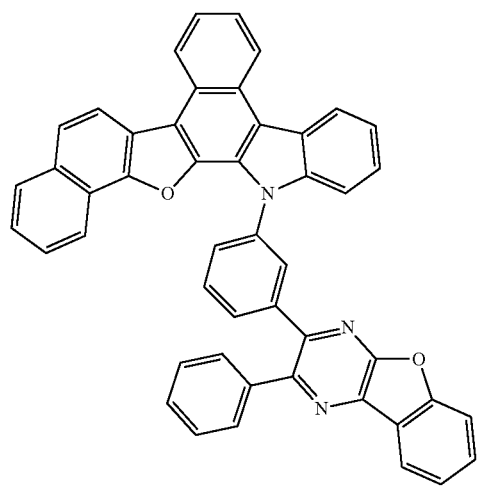
3-1
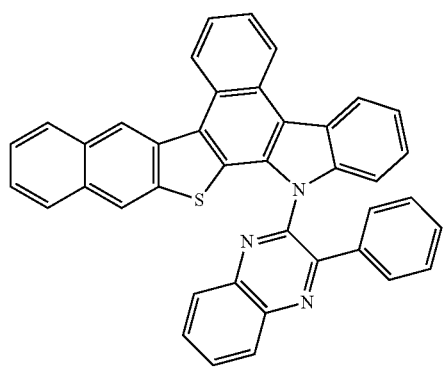

-continued
3-2
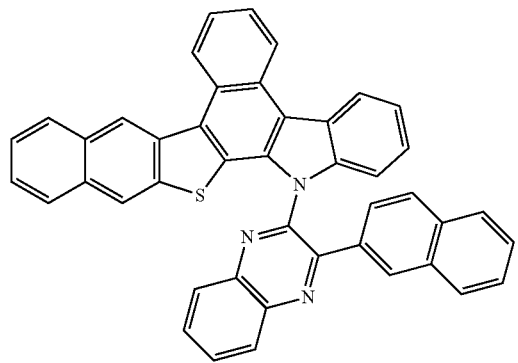
3-3
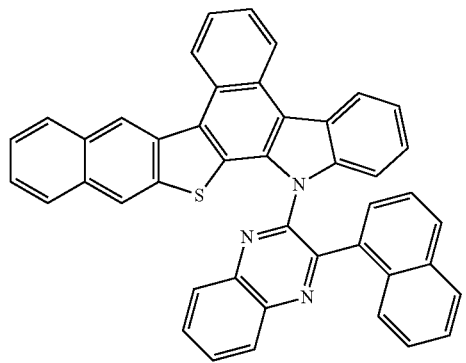
3-4
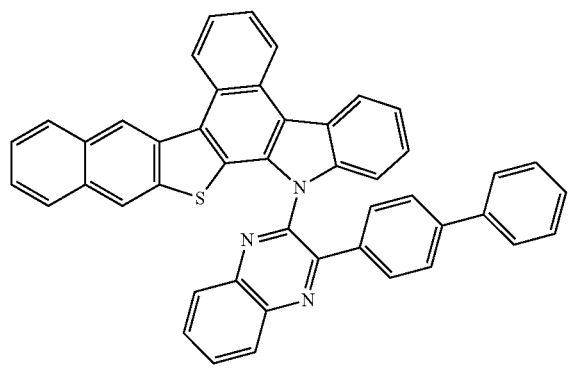
3-5
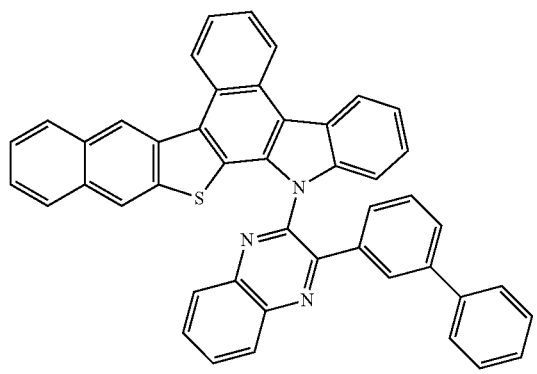
3-6
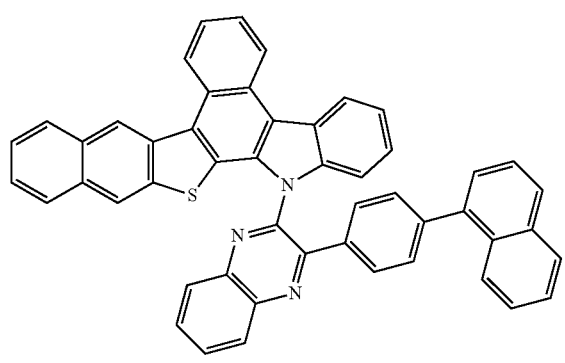
3-7
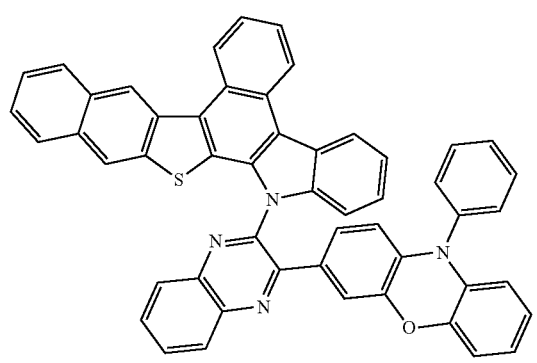
3-8
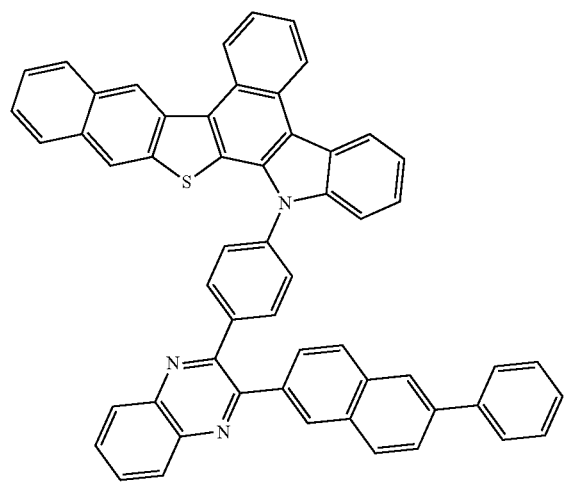
3-9
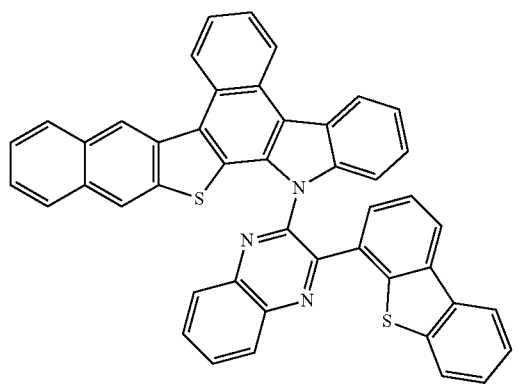

-continued
3-10
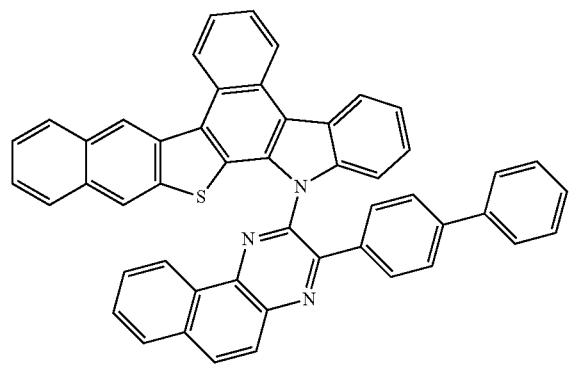
3-11
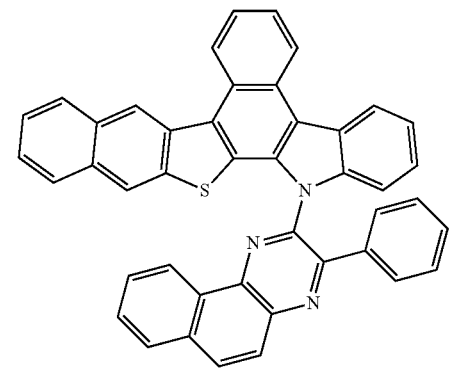
3-12
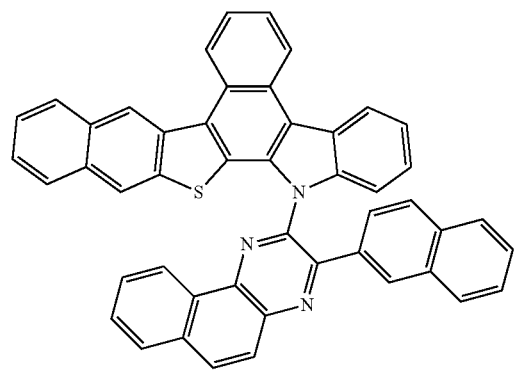
3-13
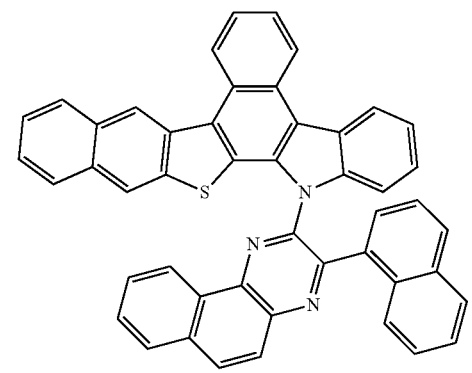
3-14
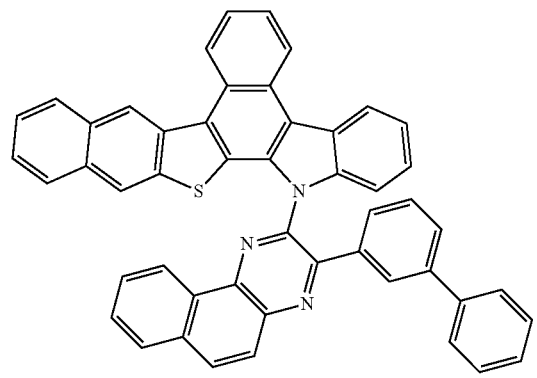
3-15
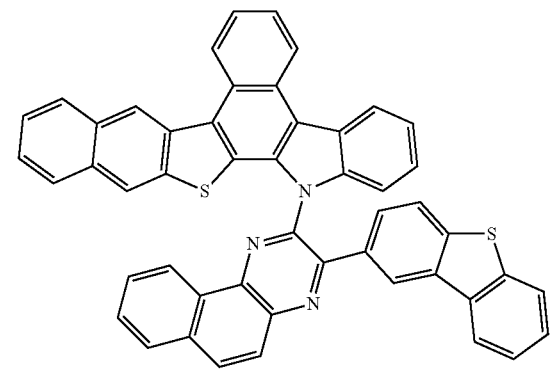
3-16
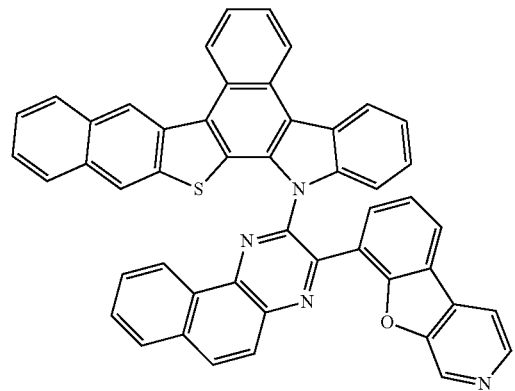
3-17
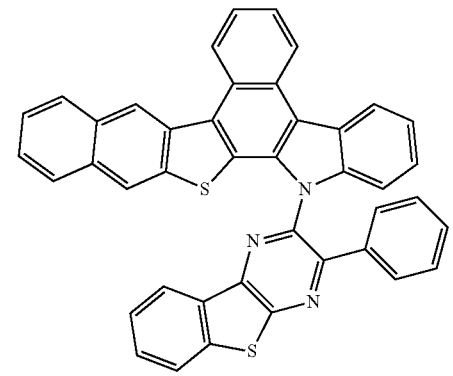

-continued
3-18
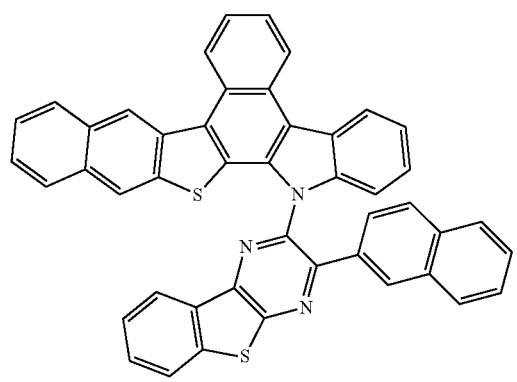
3-19
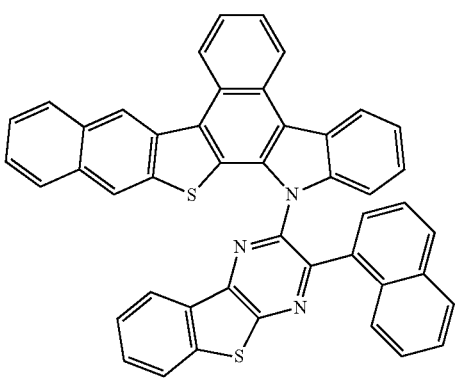
3-20
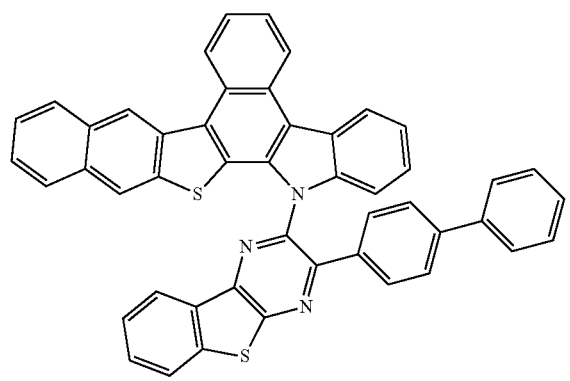
3-21
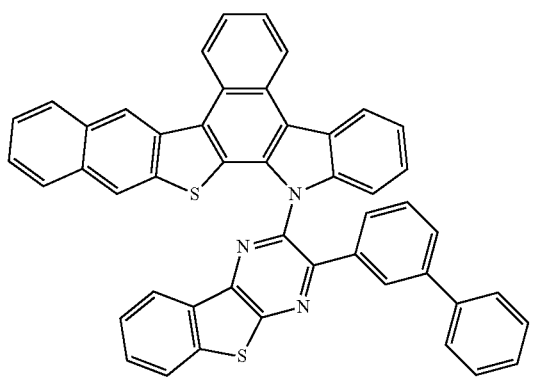
3-22
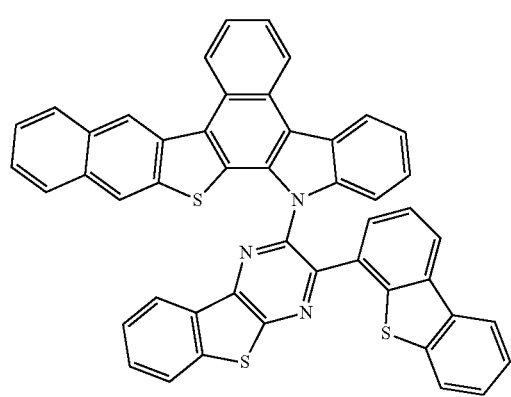
3-23
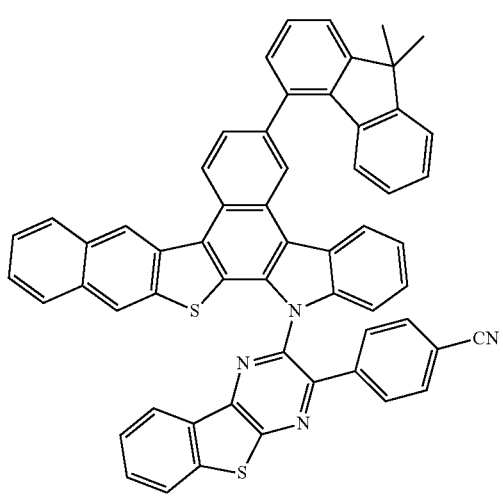

-continued
3-24
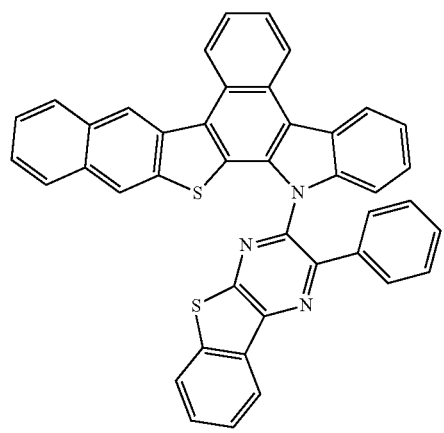
3-25
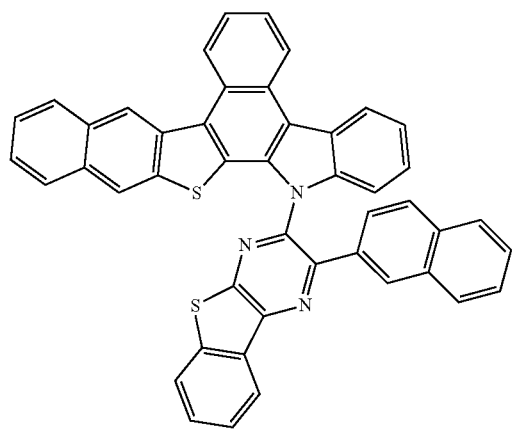
3-26
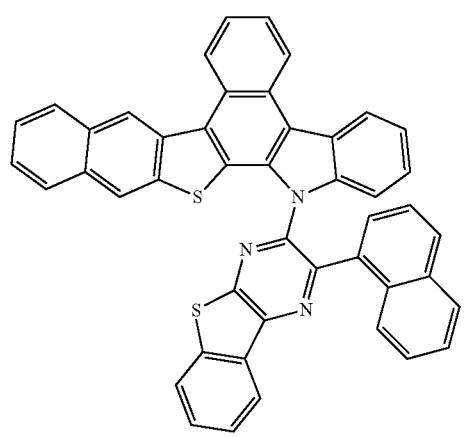
3-27
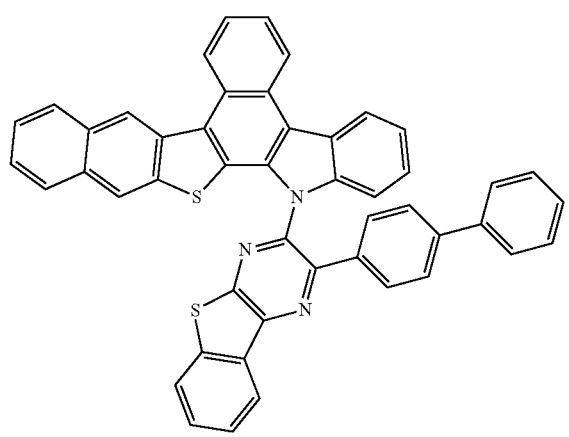
3-28
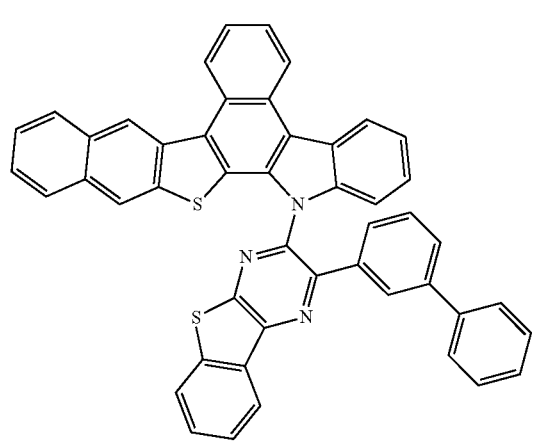
3-29
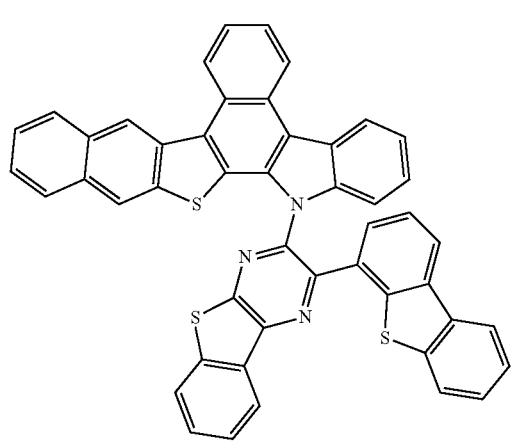

-continued
3-30
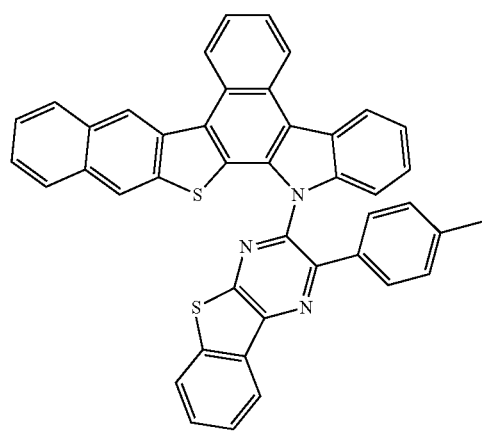
3-31
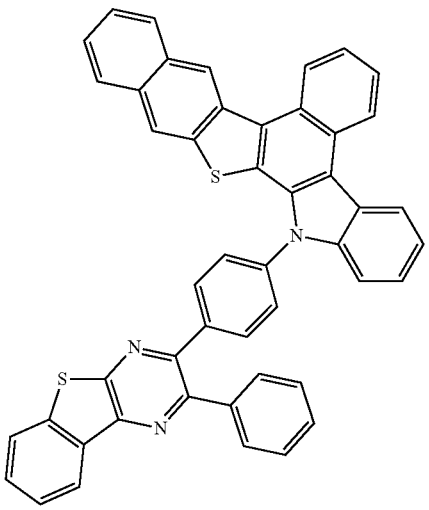
3-32
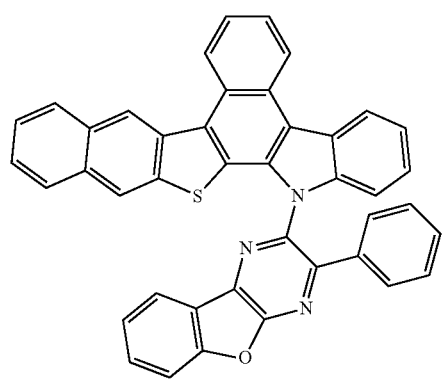
3-33
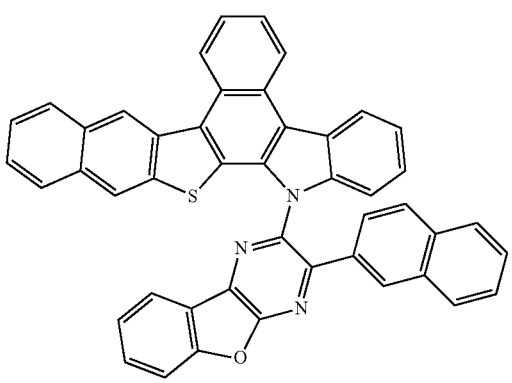
3-34
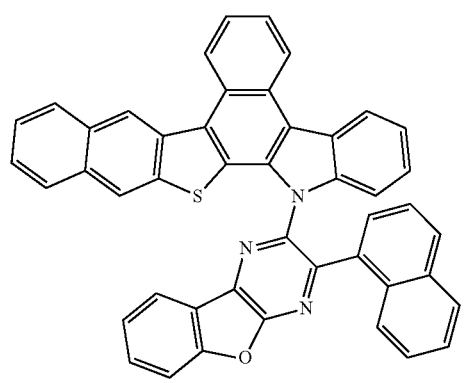
3-35
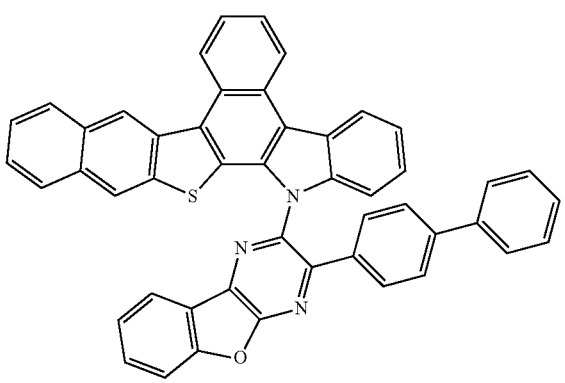

-continued
3-36
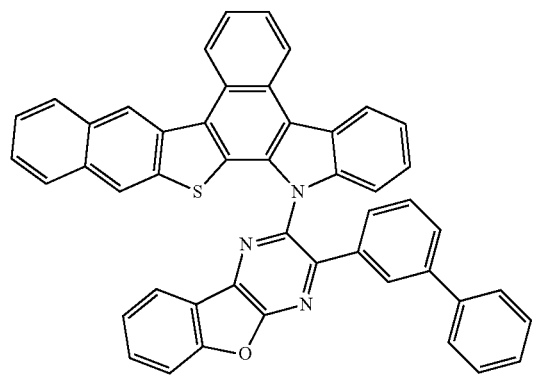
3-37
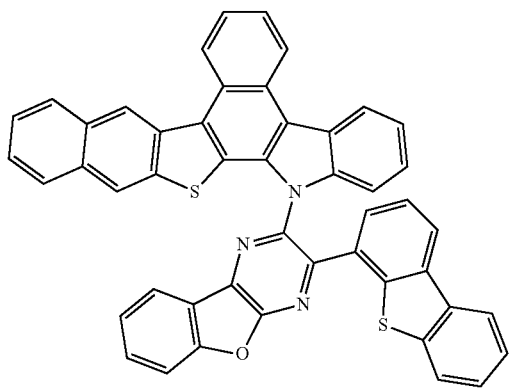
3-38
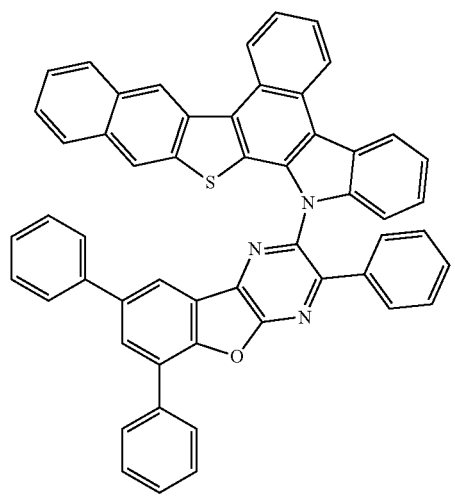
3-39
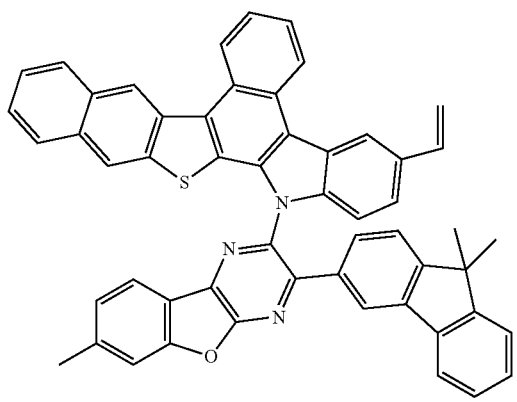
3-40
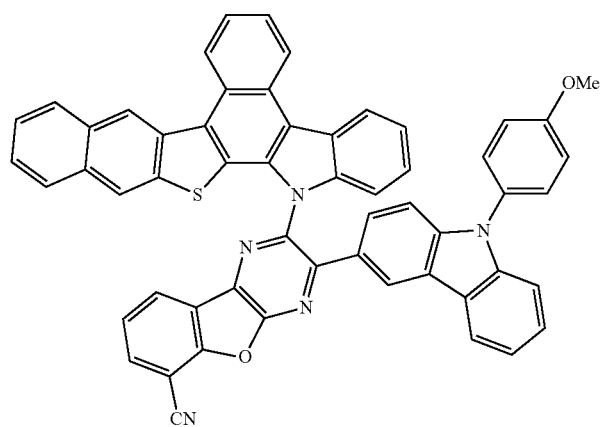

3-41
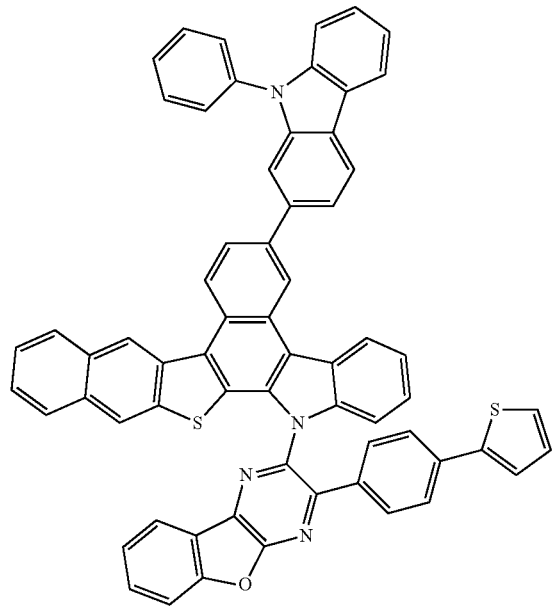
3-42
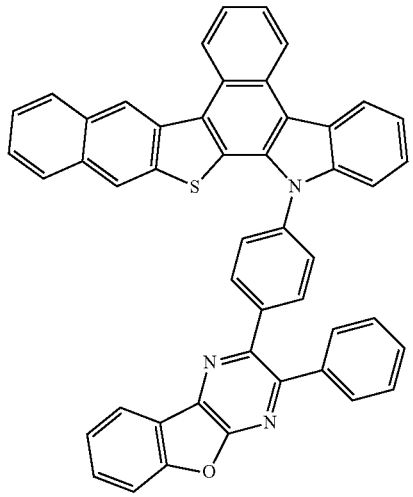
3-43
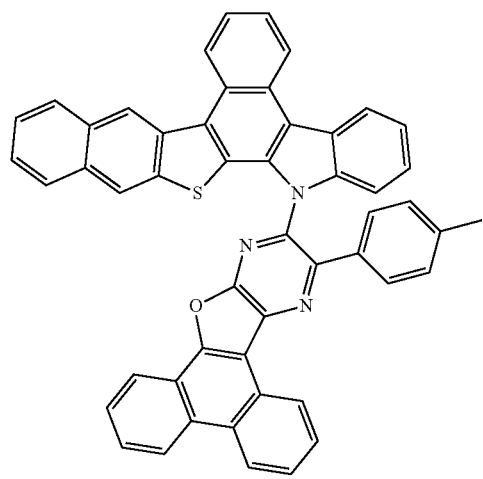
3-44
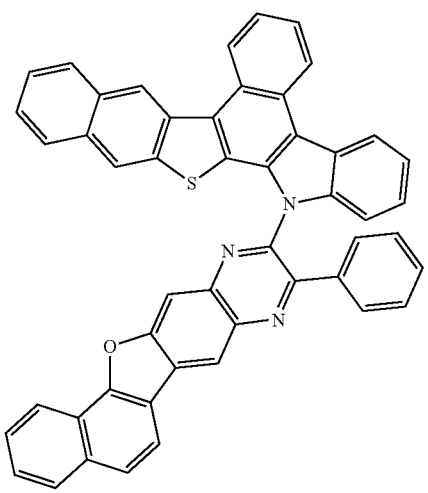
3-45
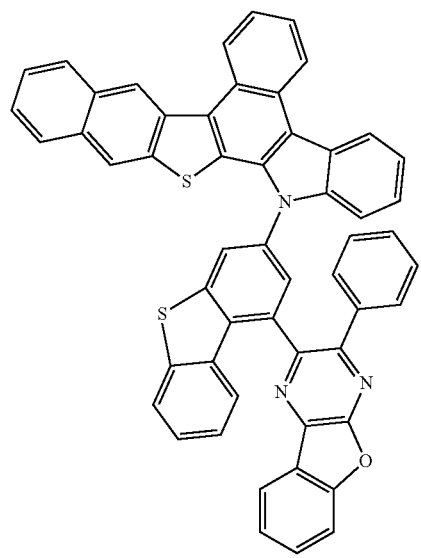
4-1
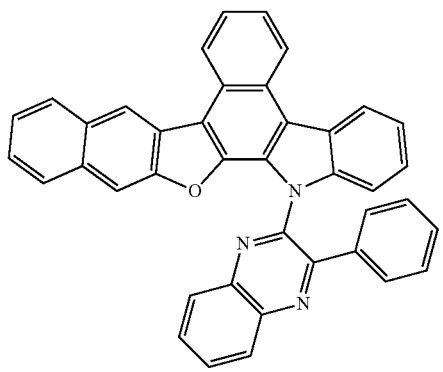

-continued
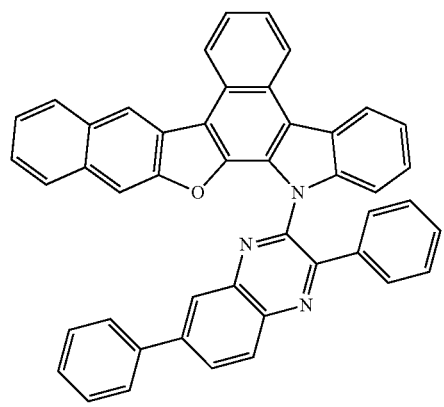
4-2
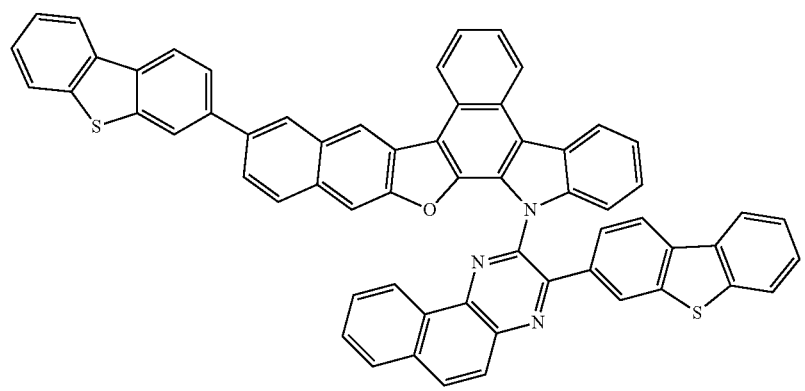
4-3
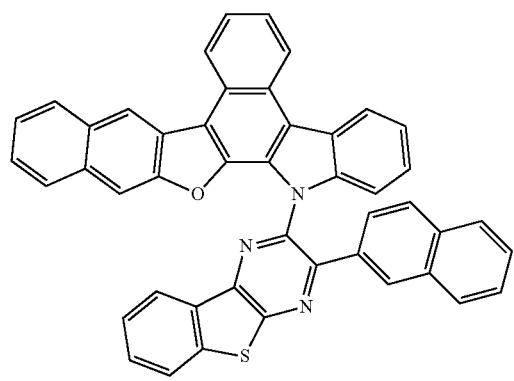
4-4
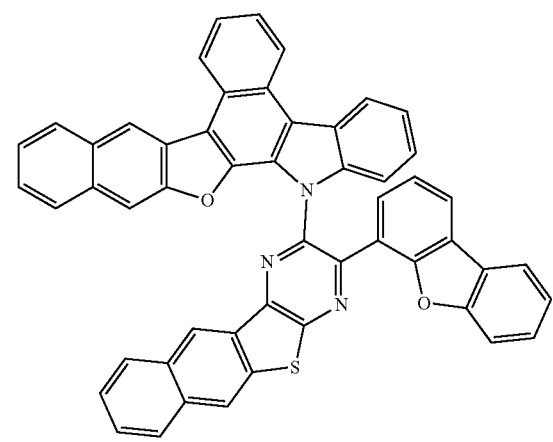
4-5

-continued
4-6
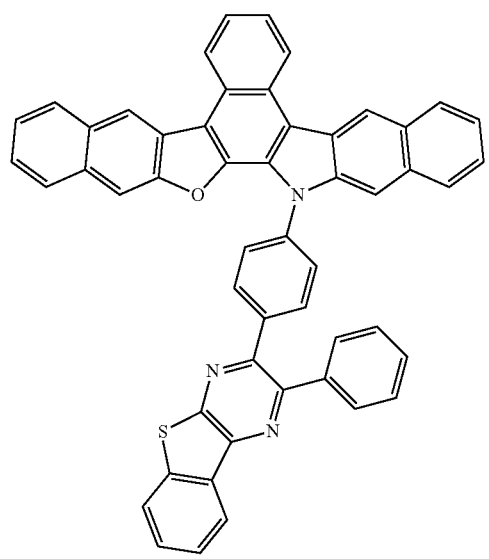
4-7
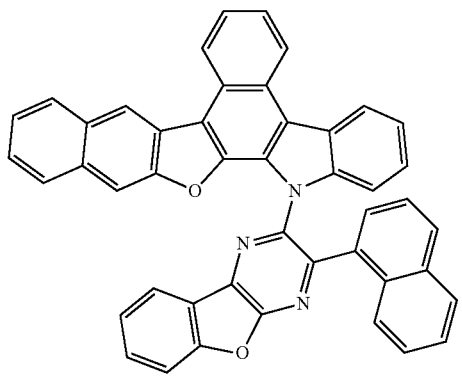
4-8
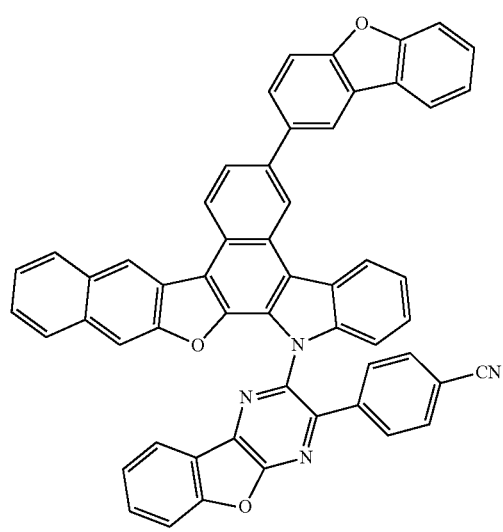
4-9
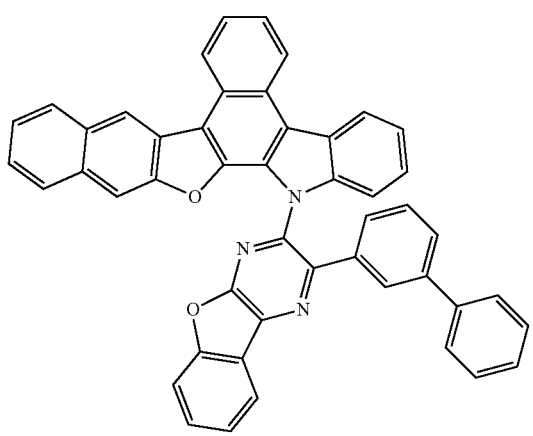
4-10
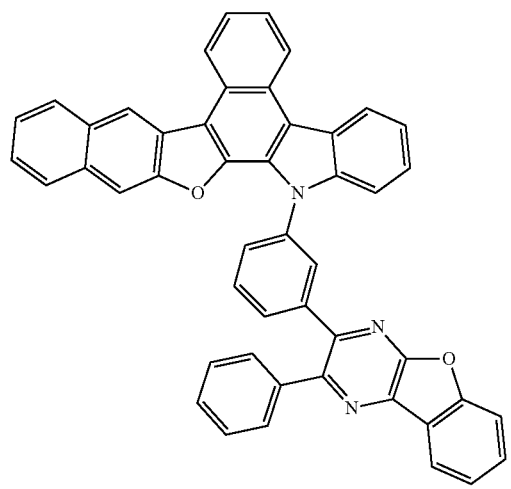
5-1
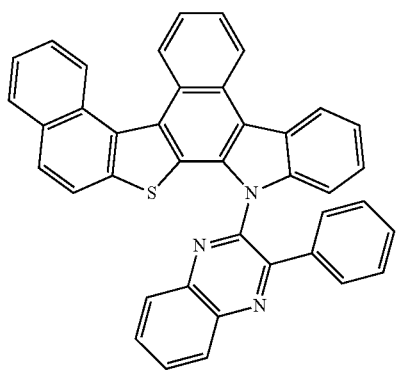

-continued
5-2
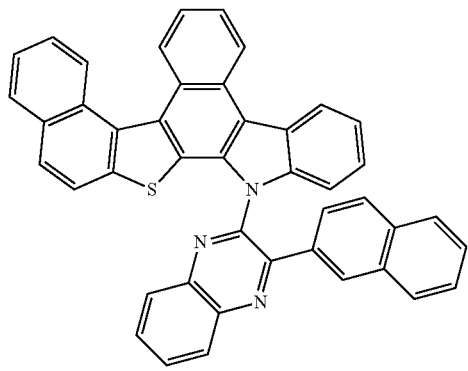
5-3
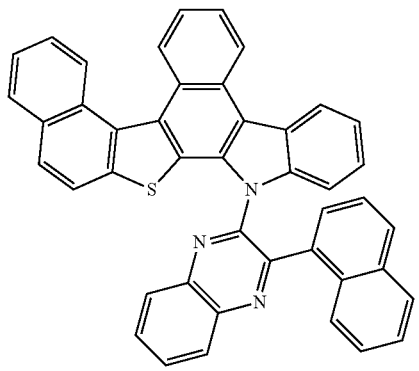
5-4
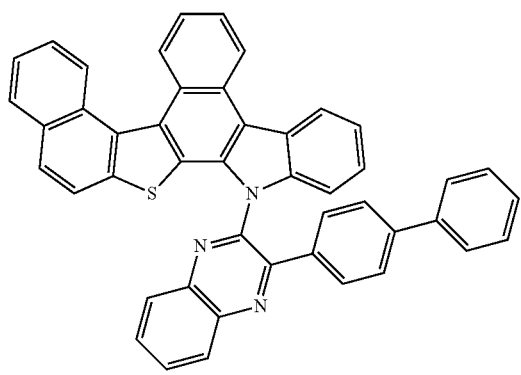
5-5
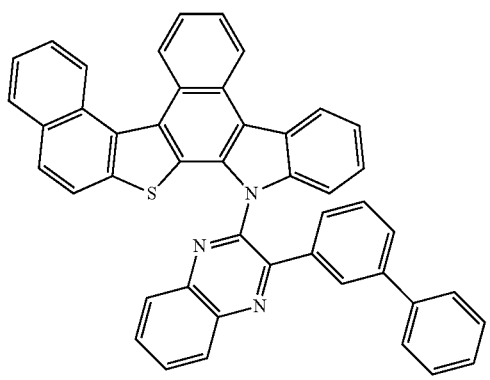
5-6
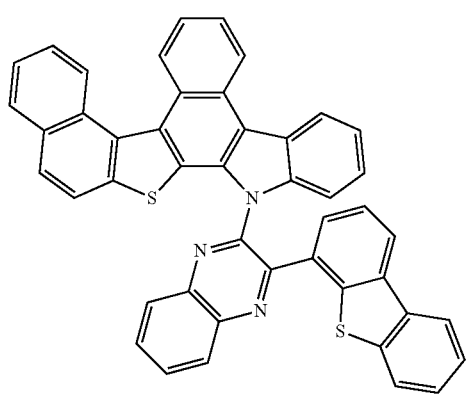
5-7
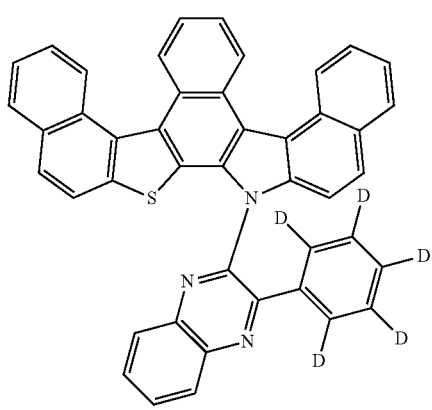
5-8
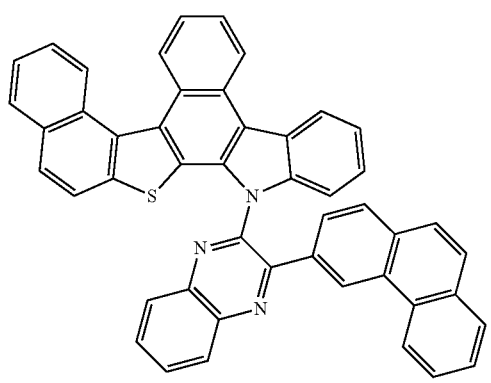
5-9
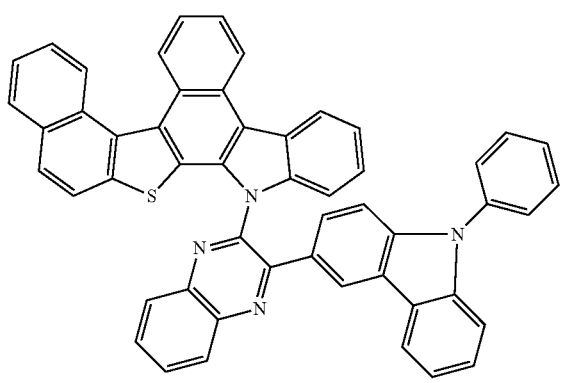

-continued
5-10
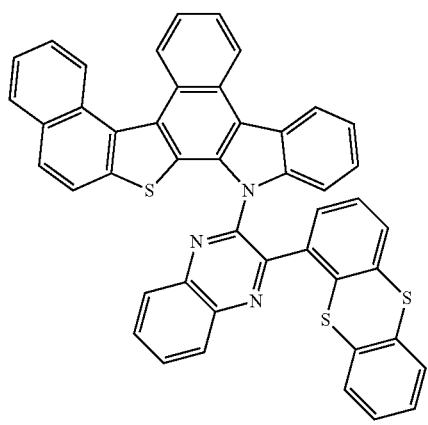
5-11
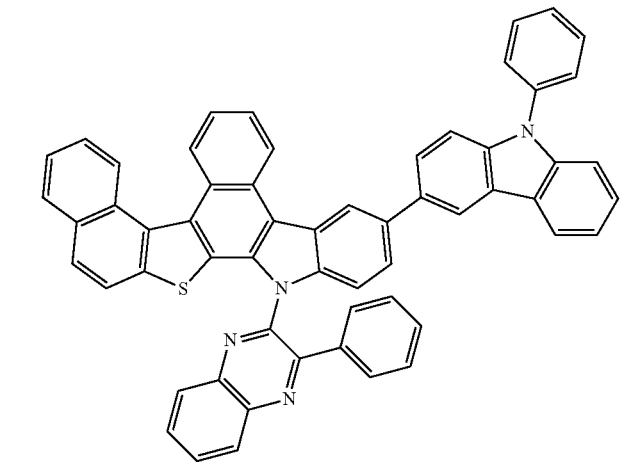
5-12
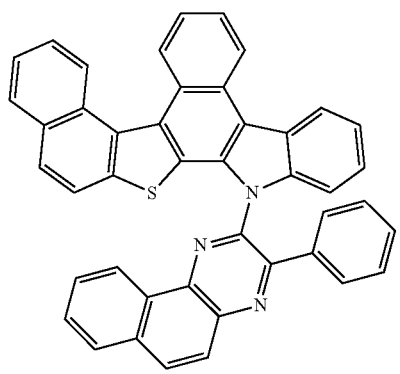
5-13
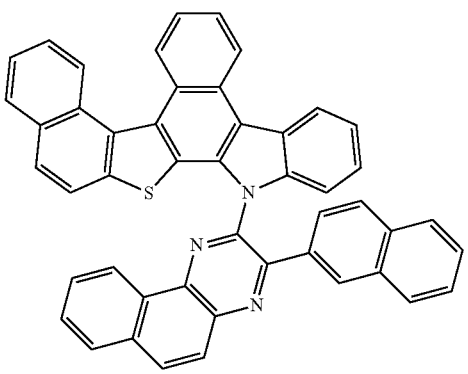
5-14
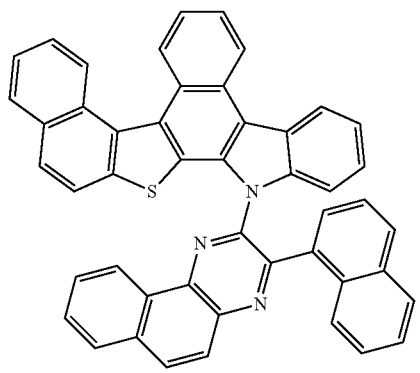
5-15
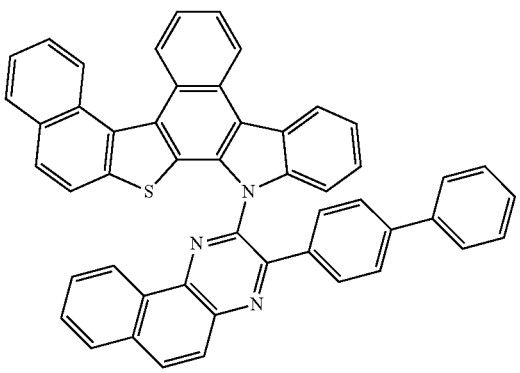
5-16
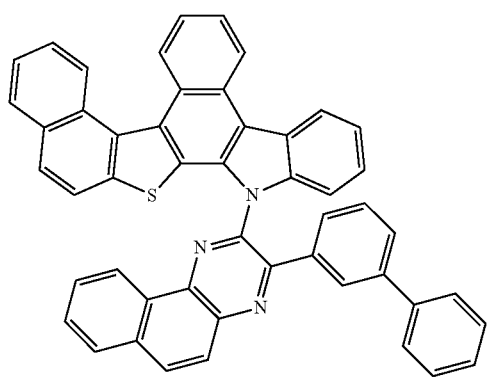
5-17
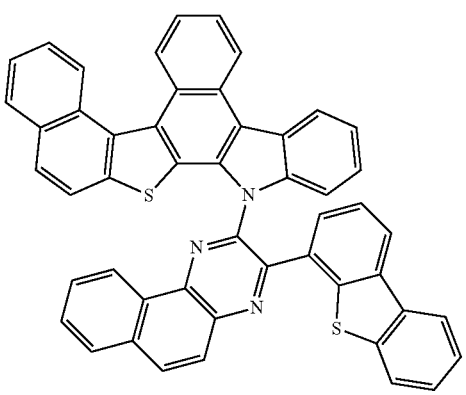

-continued
5-18
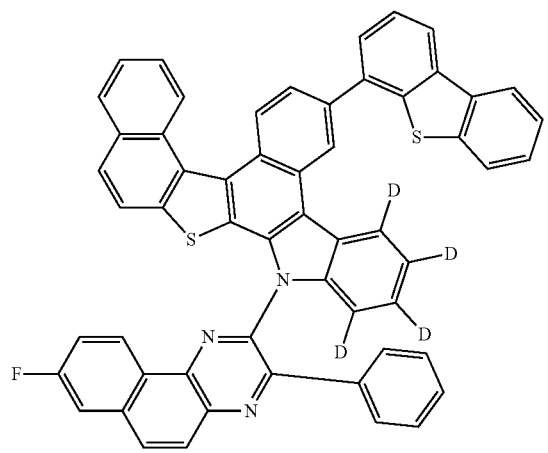
5-19
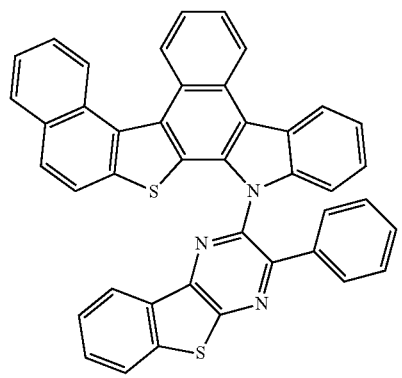
5-20
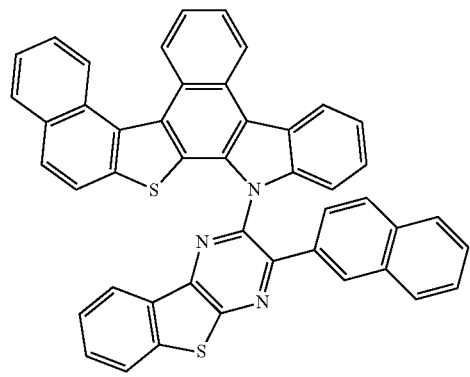
5-21
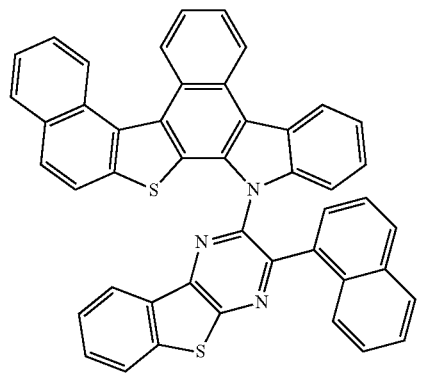
5-22
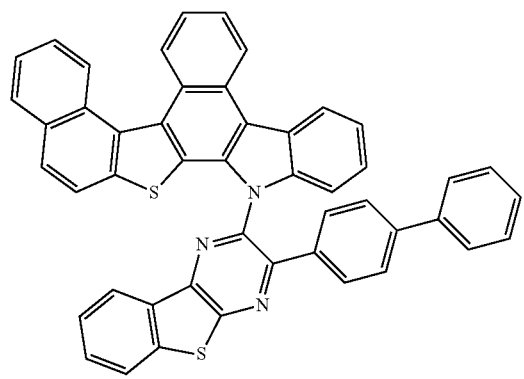
5-23
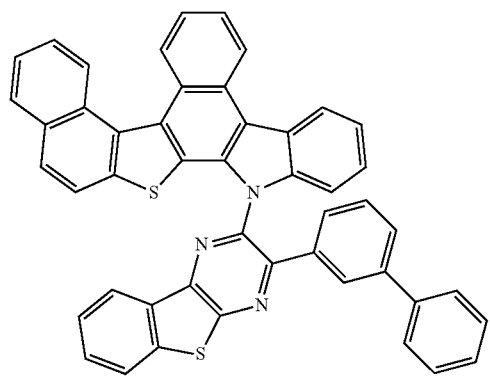

-continued
5-24
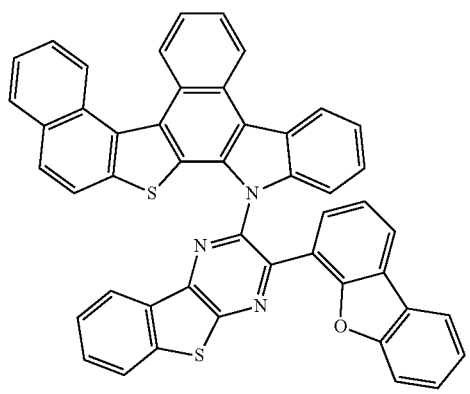
5-25
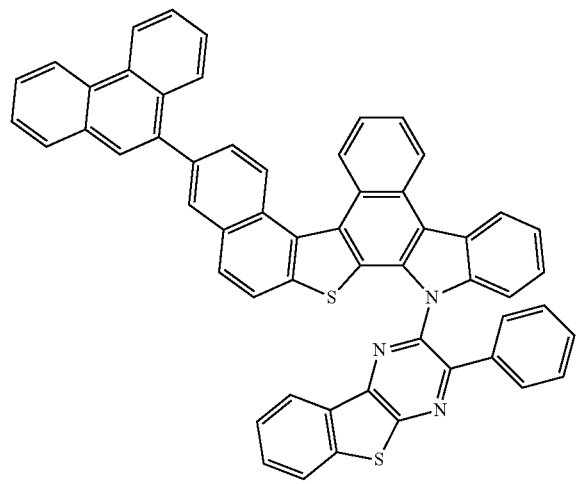
5-26
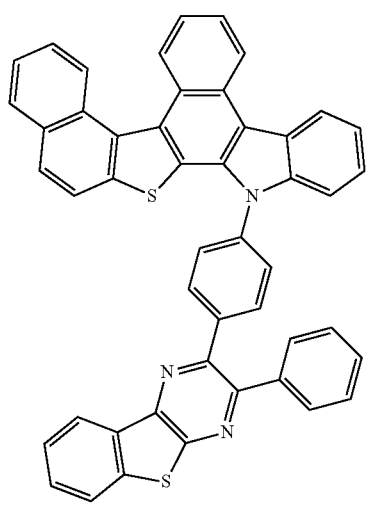
5-27
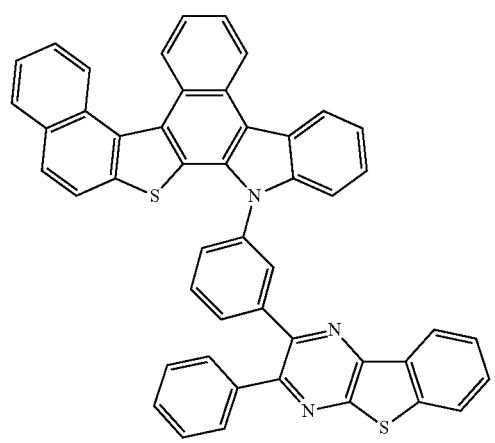
5-28
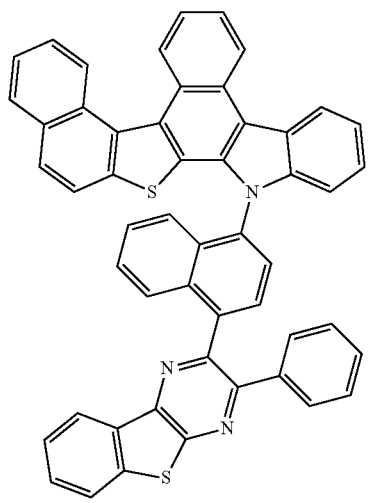
5-29
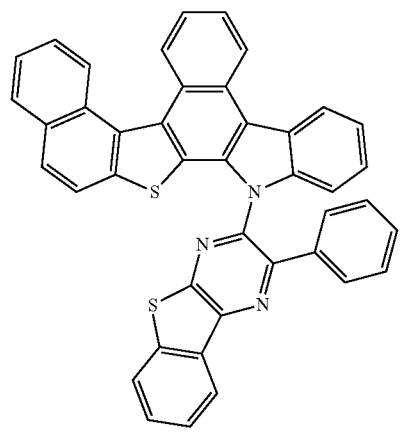

-continued
5-30
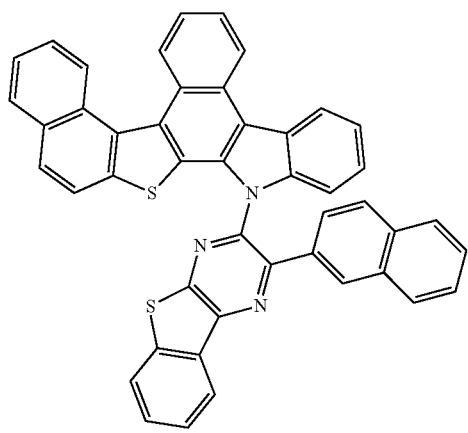
5-31
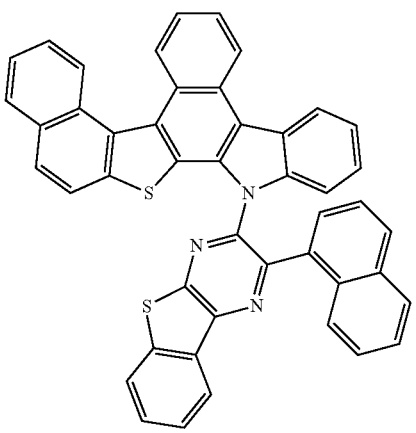
5-32
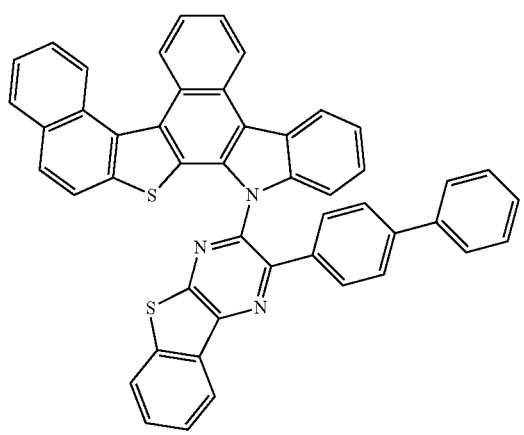
5-33
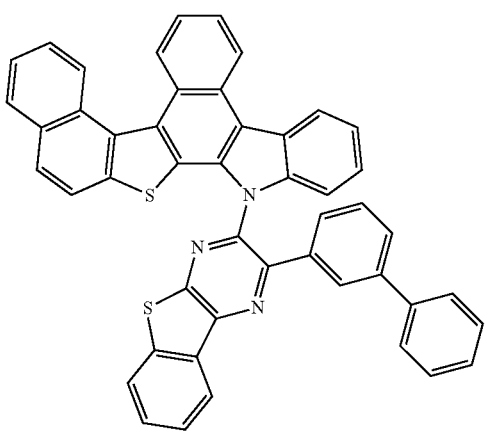
5-34
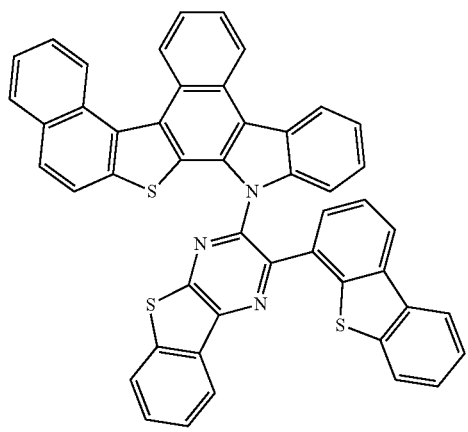
5-35
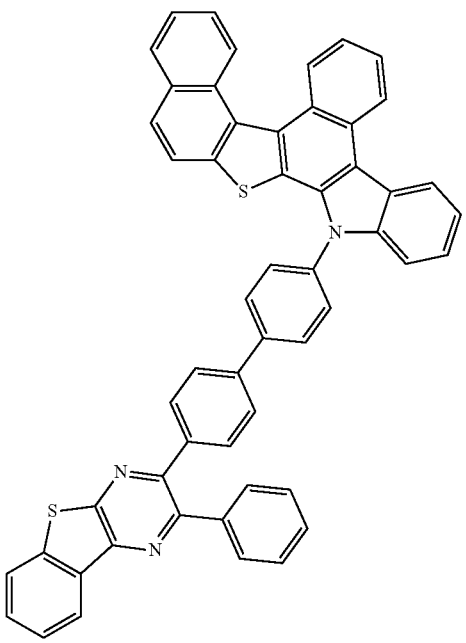

-continued
5-36
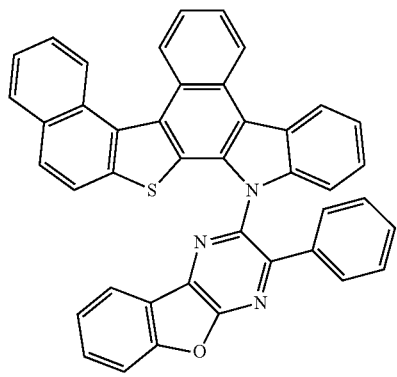
5-37
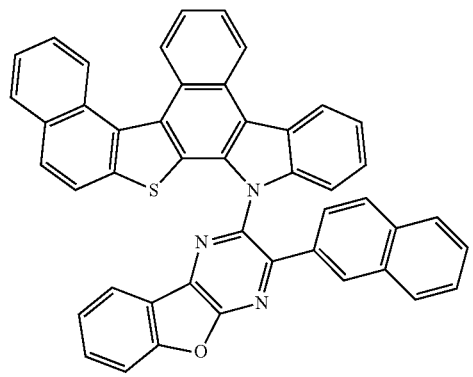
5-39
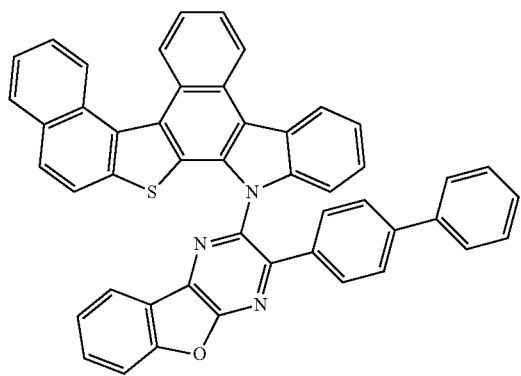
5-40
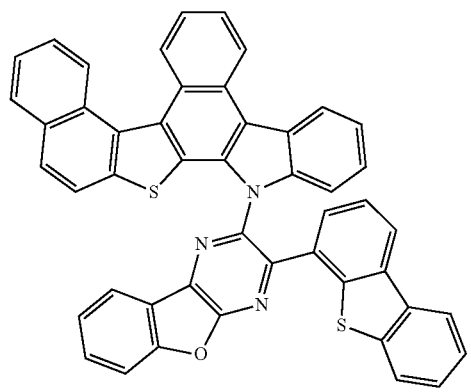
5-41
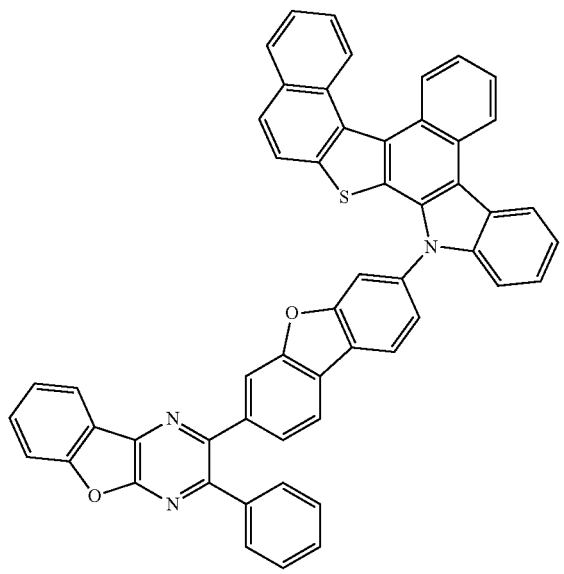
5-42
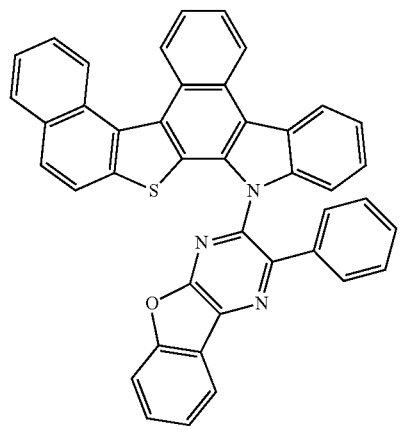

-continued
5-43
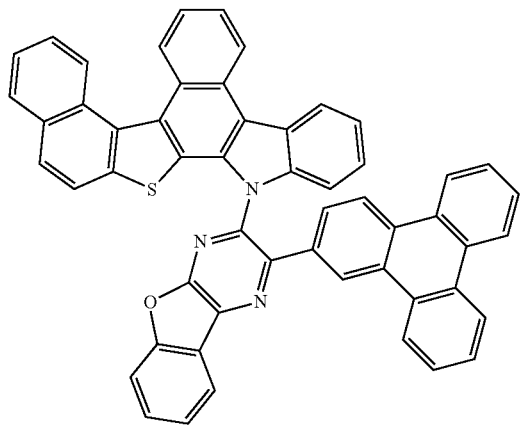
5-44
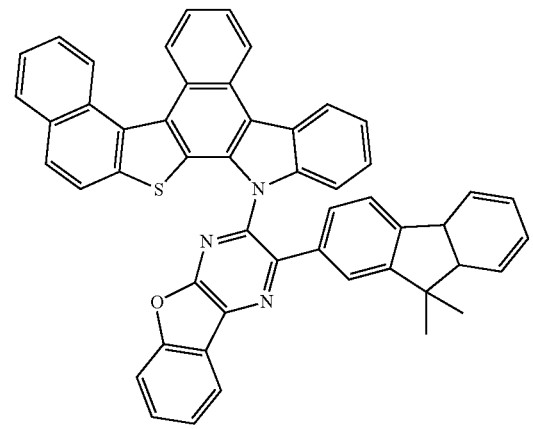
5-45
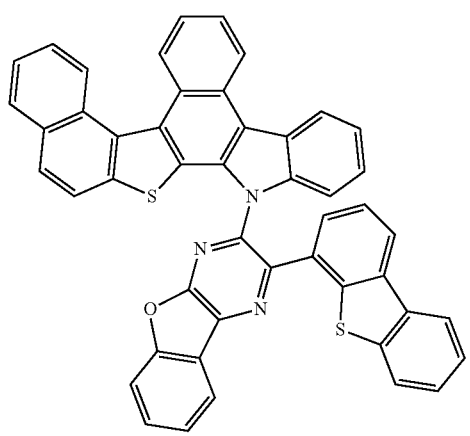
6-1
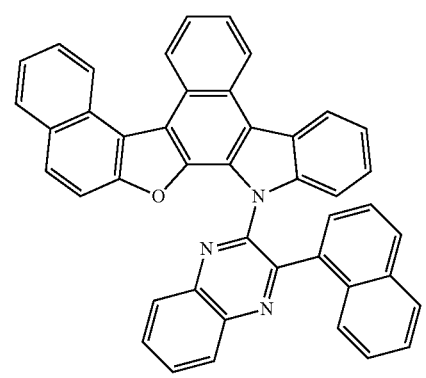
6-2
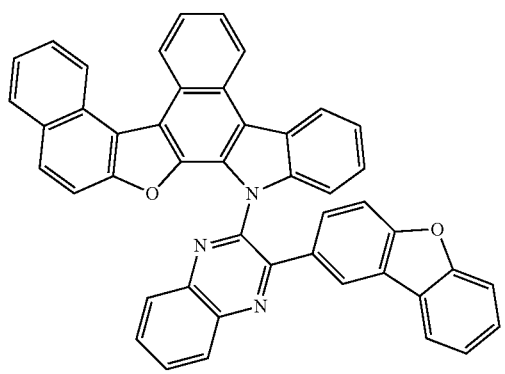
6-3
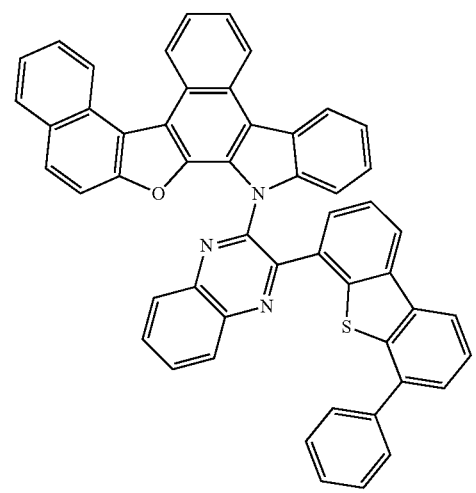

-continued
6-4
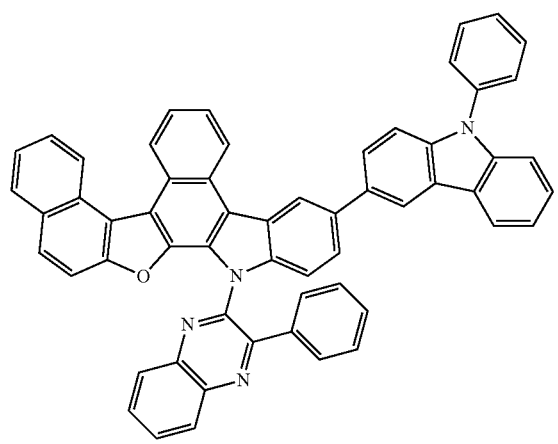
6-5
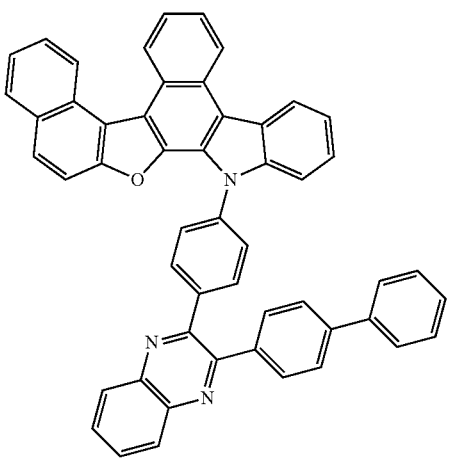
6-6
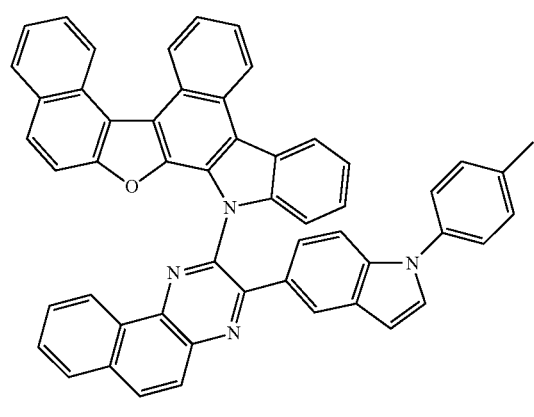
6-7
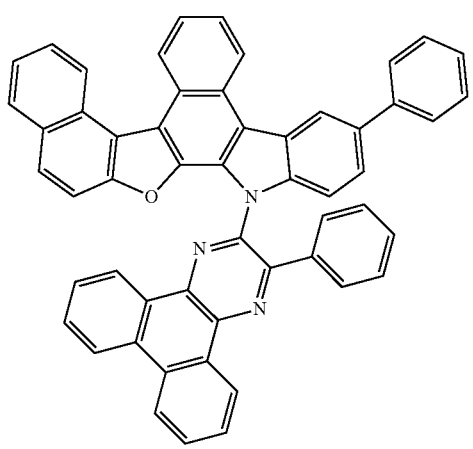
6-8
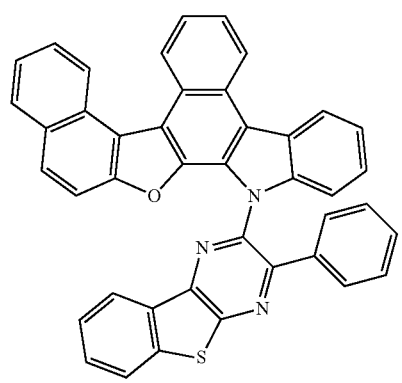
6-9
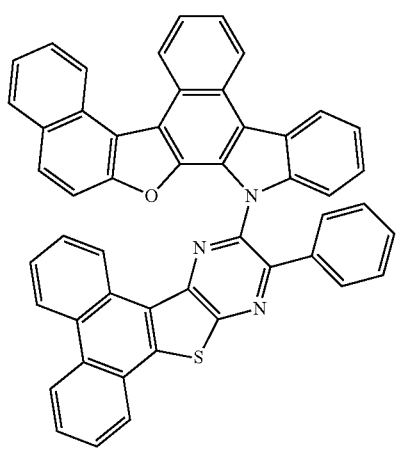

6-10
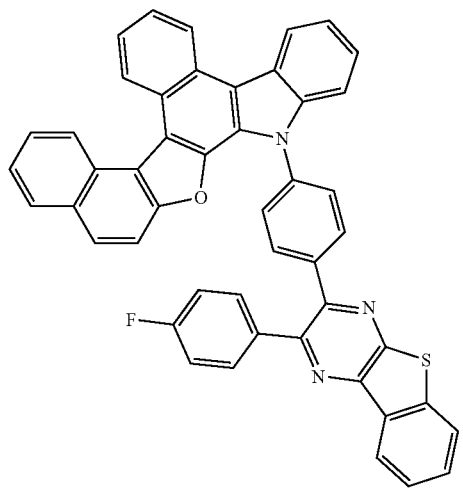

6-11
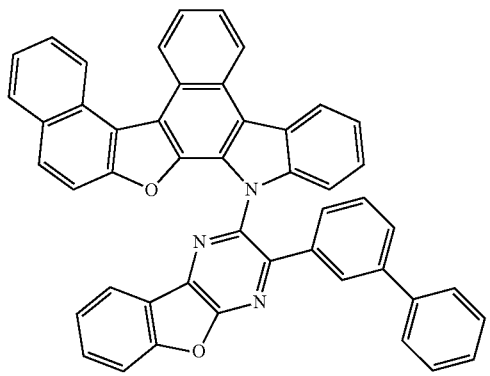

6-12
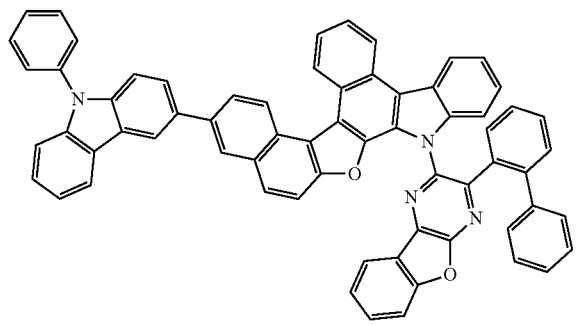

6-13
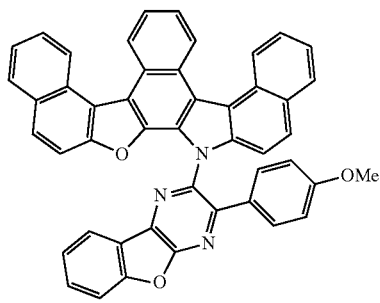

6-14
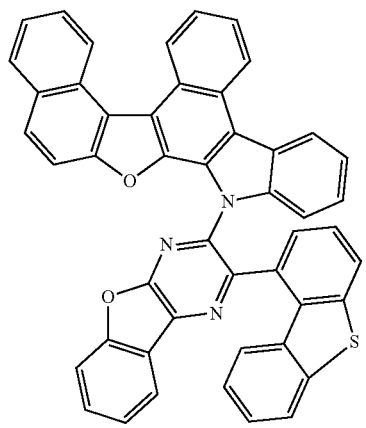

6-15
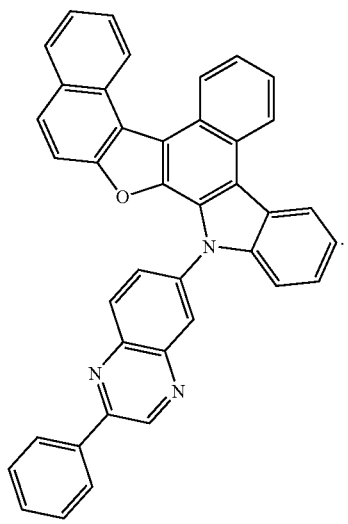

7. An organic electric element comprising a first electrode, a second electrode, and an organic material layer formed between the first electrode and the second electrode, wherein the organic material layer comprises the compound of claim 1.

8. The organic electric element of claim 7, wherein the compound is comprised in at least one layer of a hole injection layer, a hole transport layer, an emission-auxiliary layer, an electron transport-auxiliary layer, an electron transport layer and an light emitting layer, and the compound is comprised as a single compound or a mixture of two or more different kinds.

9. The organic electric element of claim 7, wherein the compound is used as a phosphorescent host material of the light emitting layer.

10. The organic electric element of claim 7, wherein the organic material layer is formed by any one of the processes of spin coating, nozzle printing, inkjet printing, slot coating, dip coating or roll-to-roll.

11. An electronic device comprising a display device and a control unit for driving the display device, wherein the display device comprises the organic electric element of claim 7.

12. The electronic device of claim 11, wherein the organic electric element is selected from the group consisting of an organic light emitting diode, an organic solar cell, an organic photo conductor, an organic transistor, and an element for monochromatic or white illumination.

* * * * *